US008049070B2

(12) United States Patent
Damude et al.

(10) Patent No.: US 8,049,070 B2
(45) **Date of Patent: *Nov. 1, 2011**

(54) DELTA-5 DESATURASE AND ITS USE IN MAKING POLYUNSATURATED FATTY ACIDS

(75) Inventors: Howard G. Damude, Hockessin, DE (US); Quinn Qun Zhu, West Chester, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 1049 days.

This patent is subject to a terminal disclaimer.

(21) Appl. No.: 11/749,859

(22) Filed: May 17, 2007

(65) Prior Publication Data

US 2008/0286436 A1 Nov. 20, 2008

Related U.S. Application Data

(60) Provisional application No. 60/801,119, filed on May 17, 2006.

(51) Int. Cl.
*A01H 5/00* (2006.01)
*C12N 15/82* (2006.01)
*C07H 21/04* (2006.01)

(52) U.S. Cl. ..... 800/298; 800/281; 435/419; 435/252.3; 536/23.2

(58) Field of Classification Search ........................ None
See application file for complete search history.

(56) References Cited

U.S. PATENT DOCUMENTS

| | | | |
|---|---|---|---|
| 5,968,809 A | 10/1999 | Knutzon et al. | |
| 5,972,664 A | 10/1999 | Knutzon et al. | |
| 6,051,754 A | 4/2000 | Knutzon | |
| 6,075,183 A | 6/2000 | Knutzon et al. | |
| 6,136,574 A | 10/2000 | Knutzon et al. | |
| 6,403,349 B1 | 6/2002 | Mukerji et al. | |
| 6,410,288 B1 | 6/2002 | Knutzon et al. | |
| 6,677,145 B2 | 1/2004 | Mukerji et al. | |
| 6,825,017 B1 | 11/2004 | Browse et al. | |
| 7,125,672 B2 | 10/2006 | Picataggio et al. | |
| 7,189,559 B2 | 3/2007 | Damude et al. | |
| 7,192,762 B2 | 3/2007 | Macool et al. | |
| 7,198,937 B2 | 4/2007 | Xue et al. | |
| 7,202,356 B2 | 4/2007 | Pollak et al. | |
| 7,537,920 B2 * | 5/2009 | Renz et al. | 435/194 |
| 2003/0196217 A1 | 10/2003 | Mukerji et al. | |
| 2004/0049805 A1 | 3/2004 | Lerchl et al. | |
| 2004/0172682 A1 | 9/2004 | Kinney et al. | |
| 2005/0132442 A1 | 6/2005 | Yadav et al. | |
| 2005/0136519 A1 | 6/2005 | Picataggio et al. | |
| 2005/0273885 A1 | 12/2005 | Singh et al. | |
| 2006/0174376 A1 | 8/2006 | Renz et al. | |

FOREIGN PATENT DOCUMENTS

| | | |
|---|---|---|
| WO | WO 98/46763 A1 | 10/1998 |
| WO | WO 98/46764 A1 | 10/1998 |
| WO | WO 00/12720 A2 | 3/2000 |
| WO | WO 00/34439 A1 | 6/2000 |
| WO | WO 00/40705 A2 | 7/2000 |
| WO | WO 02/00905 A2 | 1/2002 |
| WO | WO 02/08269 A2 | 1/2002 |
| WO | WO 02/08401 A2 | 1/2002 |
| WO | WO 02/057464 A2 | 7/2002 |
| WO | WO 02/077213 A2 | 10/2002 |
| WO | WO 02/081668 A2 | 10/2002 |
| WO | WO 02/090493 A2 | 11/2002 |
| WO | WO 2004/057001 A2 | 7/2004 |
| WO | WO 2004/071467 A2 | 8/2004 |
| WO | WO 2004/087902 A2 | 10/2004 |
| WO | WO 2004/101753 | 11/2004 |
| WO | WO 2004/101757 A2 | 11/2004 |
| WO | WO 2005/003310 A2 | 1/2005 |
| WO | WO 2005/047479 A2 | 5/2005 |
| WO | WO 2005/047480 A2 | 5/2005 |
| WO | WO 2005/047485 | 5/2005 |
| WO | WO 2005/049805 A2 | 6/2005 |
| WO | WO 2005/103253 A1 | 11/2005 |
| WO | WO 2006/012325 A1 | 2/2006 |
| WO | WO 2006/012326 A1 | 2/2006 |
| WO | WO 2006/052870 A2 | 5/2006 |
| WO | WO 2006/052871 A2 | 5/2006 |
| WO | WO 2006/055322 A2 | 5/2006 |

OTHER PUBLICATIONS

Sequence alignment of SEQ ID No. 1 with Renz et al, US Patent 7,537,920—SEQ ID No. 13, run date Jun. 6, 2010.*
Fourgoux-Nicol et al, Plant Mol Biol 40: 857-872, 1999.*
U.S. Appl. No. 60/795,810, filed Apr. 28, 2006, Howard Glenn Damude et al.
U.S. Appl. No. 10/840,579, filed May 6, 2004, Stephen K. Pictaggio et al.
U.S. Appl. No. 10/840,325, filed May 6, 2004, Narendra S. Yadav et al.
U.S. Appl. No. 10/869630, filed Jun. 16, 2004, Stephen K. Pictaggio et al.
U.S. Appl. No. 10/882,760, filed Jul. 1, 2004, Narendra S. Yadav et al.
U.S. Appl. No. 10/985,254, filed Nov. 10, 2004, Narendra S. Yadav et al.
U.S. Appl. No. 10/985,691, filed Nov. 10, 2004, Narendra S. Yadav et al.
U.S. Appl. No. 11/024,544, filed Dec. 29, 2004, Narendra S. Yadav et al.
U.S. Appl. No. 11/166,993, filed Jun. 24, 2005, Howard Glenn Damude et al.
U.S. Appl. No. 11/183,664, filed Jul. 18, 2005, Stephen K. Pictaggio et al.
U.S. Appl. No. 11/185,301, filed Jul. 20, 2005, Zhixiong Xue et al.
U.S. Appl. No. 11/190,750, filed Jul. 27, 2005, Stephen K. Pictaggio et al.
U.S. Appl. No. 11/198,975, filed Aug. 8, 2005, Quinn Qun Zhu et al.
U.S. Appl. No. 11/225,354, filed Sep. 13, 2005, Zhixiong Xue et al.
U.S. Appl. No. 11/253,882, filed Oct. 19, 2005, Daniel Joseph Macool et al.
National Center for Biotechnology Information General Identifier No. 34221933, Jul. 28, 2004, E. Sakuradani et al., Gene Cloning and Functional Analysis of a Second Delta 6-Fatty Acid Desaturase from an Arachidonic Acid-Producing *Mortierella* Fungus, AB070557.

(Continued)

*Primary Examiner* — Elizabeth McElwain

(57) ABSTRACT

Isolated nucleic acid fragments and recombinant constructs comprising such fragments encoding delta-5 desaturase along with a method of making long chain polyunsaturated fatty acids (PUFAs) using this delta-5 desaturase in plants and oleaginous yeast are disclosed.

22 Claims, 15 Drawing Sheets

OTHER PUBLICATIONS

Pereira et al., Identification of Two Novel Microalgal Enzymes Involved in the Conversion of the 3-Fatty Acid, Eicosapentaenoic Acid, Into Docosahexaenoic Aicid, Biochem. J., 2004, vol. 384:357-366.

National Center for Biotechnology Information General Identifier No. 173245, Jul. 14, 1993, P. Fournier et al., Colocalization of Centromeric and Replicative Functions on Autonomously Replicating Sequences Isolated from the Yeast *Yarrowia lipolytica* M91600.

National Center for Biotechnology Information General Identifier No. 4003522, Accession No. AF078796, Dec. 11, 1998, Michaelson,L.V. et al., Functional Identification of a Fatty Acid Delta5 Desaturase Gene From *Caenorhabditis elegans*.

Sakuradani & Shimizu, Biosci Biotechnol. Biochem, Gene Cloning and Functional Analysis of a Second Delta6-Fatty Acid Desaturase from an Arachidonic Acid-Producing *Mortierella* Fungus. vol. 67, pp. 704-711 (2003).

T. Nakahara et al., Linolenic acid from genus *Mortierella*. In: Kyle DJ, Ratledge C (eds). Industrial applications of single cell oils. American Oil Chemists Society, Champaign, Ill., pp. 61-97, (1992).

National Center for Biotechnology Information General Identifier No. 3859487, Nov. 11, 1998, D.S Knutzon et al., Identificaton of Delta5-Desaturase from *Mortierella alpina* by Heterologous Expression in Bakers' Yeast and Canola, AF067654.

National Center for Biotechnology Information General Identifier No. 4150955, Apr. 17, 2003, T. Saito et al., A Second Functional Delta5 Fatty Acid Desaturase in the Cellular Slime Mould *Dictyostelium discoideum*, AB022097.

National Center for Biotechnology Information General Identifier No. 16033740, Mar. 24, 2005, H. Hong et al., Isolation and Characterization of a Delta5 FA Desaturase from *Pythium irregulare* by Heterologous Expression in *Saccharmoyces serevisiae* and Oil Seed Crops, AAL13311.

National Center for Biotechnology Information General Identifier No. 23894018, Apr. 15, 2005, E. Hornung et al., Specific Formation of Arachidonic Acid by a Front-End Delta5-Desaturase from *Phytophthora megasperma,* CAD53323.

National Center for Biotechnology Information General Identifier No. 19879687, F. Domergue et al., Cloning and Functional Characterization of *Phaeoactylum tricornutum* Front-End Desaturases Involved in Eicosapentaenoic Acid Biosynthesis, AAL92562.

National Center for Biotechnology Information General Identifier No. 66812304, Aug. 17, 2006, L. Eichinger et al., The Genome of the Social Amoeba *Dictyostelium discoideum*, XP_640331.

National Center for Biotechnology Information General Identifier No. 60172920, Jul. 16, 2005, T. Tonon et al., Fatty Acid Desaturases from the Microalga *Thalassiosira pseudonana,* AAX14502.

National Center for Biotechnology Information General Identifier No. 60499699, Nov. 1, 2005, H. Lu et al., Identification and characterization of a Novel 6-Fatty Acid Desaturase Gene from *Rhizopus nigricans,* AAX22052.

National Center for Biotechnology Information General Identifier No. 83027409, Dec. 7, 2005, Y.B. Zhang et al., Identification and Characterization of a Novel 6-Fatty Acid Desaturase Gene from *Rhizopus stolonifer,* ABB96724.

Sayanova et al., The Alternative Pathway C20 8-Desaturase From the Non-Photosynthetic Organism *Acanthamoebe castellanii* is an Atypical cytochrome B5-Fusion Desaturase, FEBS Lett., 2006, vol. 580:1946-1952.

National Center for Biotechnology Information General Identifier No. 17226122, Mar. 9, 2006, B. Qi et al., Identification of a CDNA Encoding a Novel C18-Delta (9) Polyunsaturated Fatty Acid-Specific Elongating Activity from Docosahexaenoic Acid (DHR) -Producing Microalga, *Isochrysis galbana,* AF390174.

U.S. Appl. No. 11/264,784, filed Nov. 1, 2005, Howard Glenn Damude et al.

U.S. Appl. No. 11/264,737, filed Nov. 1, 2005, Howard Glenn Damude et al.

U.S. Appl. No. 11/265,761, filed Nov. 2, 2005, Howard Glenn Damude et al.

U.S. Appl. No. 11/737,772, filed Apr. 20, 2007, Howard Glenn Damude et al.

U.S. Appl. No. 11/787,772, filed Apr. 18, 2007, Zhixiong Xue et al.

U.S. Appl. No. 11/740,298, filed Apr. 26, 2007, Narendra S. Yadav et al.

U.S. Appl. No. 60/801,172, filed May 17, 2006, Howard Glenn Damude et al.

U.S. Appl. No. 60/801,119, filed May 17, 2006, Howard Glenn Damude.

U.S. Appl. No. 60/853,563, filed Oct. 23, 2006, Howard Glenn Damude.

U.S. Appl. No. 60/855,177, filed Oct. 30, 2006, Zhixiong Xue et al.

U.S. Appl. No. 11/601,563, filed Nov. 16, 2006, Howard Glenn Damude et al.

U.S. Appl. No. 11/601,564, filed Nov. 16, 2006, Howard Glenn Damude et al.

U.S. Appl. No. 11/635,258, filed Dec. 7, 2006, Howard Glenn Damude et al.

U.S. Appl. No. 11/613,420, filed Dec. 20, 2006, John E Seip et al.

U.S. Appl. No. 60/909,790, filed Apr. 3, 2007, Howard Glenn Damude et al.

U.S. Appl. No. 60/911,925, filed Apr. 16, 2007, Howard Glenn Damuse et al.

U.S. Appl. No. 60/910,831, filed Apr. 10, 2007, Howard Glenn Damude et al.

U.S. Appl. No. 60/915,733, filed May 3, 2007, Howard Glenn Damude et al.

National Center for Biotechnology Information General Identifier No. 21245143, May 29, 2002, Titorenko et al., PEX20p of the Yeast *Yarrowia lipolytica* is Required for the Oligomerization of Thiolase in the Cytosol and for its Targeting to the Peroxisome, AF054613.

National Center for Biotechnology Information General Identifier No. 513915, Apr. 19, 1994, P. Fournier et al., ARS Sequence Useful for *Yarrowia* Lipolytics, and its Preparation, A17608.

National Center for Biotechnology Information General Identifier No. 13160443, Apr. 15, 2005, S. Mauersberger et al., Insertional Mutagenesis in the N-Alkane-Assimilating Yeast *Yarrowia lipolytica*:Generation of Tagged Mutations in Genes Involved in Hydrophobic Substrate Utilization, AJ306421.

National Center for Biotechnology Information General Identifier No. 21899501, Jul. 16, 2002, P. Mukerji et al., Elogase Genes and Uses Thereof, AX464731.

National Center for Biotechnology Information General Identifer No. 21245143, May 29, 2002, V.I Titorenko et al., PEX20P of The Yeast *Yarrowia lipolytica* is Required for the Oligomerization of Thiolase in the Cytosol and for its Targeting to the Peroxisome, AF054613.

National Center for Biotechnology Information General Identifier No. 2996001, Oct. 16, 1998, S. Muller et al., Comparison of Expression System in The Yeasts *Saccharmyces cerevisiae, Hansenula polymorpha, Klyveromyces lactis, Schizosaccharomyces pombe* and *Yarrowia lipolytica*. Cloning of Two Novel Promoters From *Yarrowia lipolytica,* AF054508.

National Center for Biotechnology Information General Identifier No. 18483174, Feb. 4, 2002, L. Liu et al., Cloning and Sequence Analysis of the Delta 6 Fatty Acid Desaturase Gene From *Mortierella aplina* ATCC16266, AF465281.

National Center for Biotechnology Information General Identifier No. 1246861, Apr. 18, 2005, F. Gonzalez, Thesis (1996) Department of Microbiologia Y Genetica, Z50020.

National Center for Biotechnology Information General Identifier No. 7801377, Jun. 12, 2006, G. Pignede et al., Characterization of an Extracellular Lipase Encoded by LIP2 in *Yarrowia lipolytica,* AJ012632.

National Center for Biotechnology Information General Identifier No. 173242, Apr. 27, 1993, L.S. Davidow et al., Cloning and Sequencing of the Alkaline Extracellular Protease Gene of *Yarrowia lipolytica,* M17741.

National Center for Biotechnology Information General Identifier No. 34221934, Jul. 28, 2004, E. Sakuradani et al., Gene Cloning and Functional Analysis of a Second Delta 6-Fatty Acid Desaturase From an Arachidonic Acid-Producing *Mortierella* Fungus, BAC82361.

J. Dyerberg et al., Fatty Acid Composition of the Plasma Lipids in Grrenland Eskimos, Amer. J. Clin. Nutr., 1975, vol. 28:958-966.

J. Dyerberg et al., Eicosapentaenoic Acid and Prevention of Thrombosis and Atherosclerosis, Lancet., 1978, vol. 2:117-119.

H. Shimokawa, Beneficial Effects of Eicosapentaenoic Acid on Endothelial Vasodilator Functions in Animals and Humans, World Rev. Nutr. Diet, 2001, vol. 88:100-108.

C. Schacky et al., 3 Fatty Acids From Eskimos to Clinical Cardiology—What Took Us So Long?, J. World Rev. Nutr. Diet, 2001, vol. 88:90-99.

National Center for Biotechnology Information General Identifier No. 6842049, Jun. 21, 2000, H.P. Cho et al., Cloning Expression, and Fatty Acid Regulation of the Human Delta-5 Desaturase, AF199596.

National Center for Biotechnology Information General Identifier No. 7861969, May 17, 2000, A.E. Leonard et al., CDNA Cloning and Characterization of Human Delta5-Desaturase Involved in the Biosynthesis of Arachidonic Acid, AF226273.

National Center for Biotechnology Information General Identifier No. 11386008, Aug. 13, 2001, R. Zolfaghari et al., Fatty Acid Delta (5)-Desaturase MRNA is Regulated by Dietary Vitamin A and Exogenous Retinoic Acid in Liver of Adult Rats, AF320509.

National Center for Biotechnology Information General Identifier No. 16151828, Oct. 16, 2001, T. Matsuzaka et al., Dual Gene Regulation of Mouse Delta-5 and -6 Desaturasesd By SREBP-1 and PPAR Alpha, AB072976.

National Center for Biotechnology Information General Identifier No. 20069122, Apr. 8, 2002, X. Qiu et al., Identification of a Delta 4 Fatty Acid Desaturase From *Thraustochytrium* Sp. Involved in the Biosynthesis of Docosahexanoic Acid by Heterologous Expression in *Saccharomyces cerevisiae* and *Brassica juncea,* AF489588.

National Center for Biotechnology Information General Identifier No. 23894017, Apr. 15, 2005, E. Hornung et al., Specific Formation of Arachidonic Acid by a Front-End Delta5-Desaturase From *Phytophthora megasperman,* AJ510244.

National Center for Biotechnology Information General Identifier No. 16033739, Mar. 24, 2005, H. Hong et al., Isolation and Characterization of a Delta5 FA Desaturase from *Pythium irregulare* by Heterologous Expression in *Saccharomyces cerevisiae* and Oilseed Crops, AF419297.

Shamsudin, L., Lipid and Fatty Acid Contents in Red Tides from Tropical Fish Ponds of the Coastal Water of South China Sea, Archives of Physiology and Biochemistry, vol. 104, No. 1, pp. 36-42, 1996.

Chen, Chih-Yu et al., Screening of Red Algae Filaments as a Potential Alternative Source of Eicosapentaenoic Acid, Marine Biotechnology, vol. 4, No. 2, pp. 189-192, Mar. 2002.

* cited by examiner

Figure 3

Conserved Region 1

```
205 WQEQHWT-HHAYTNHAEMDPDSFGAEPMLLFND--YPLDH SEQ ID NO:14
225 WLNQHVVGHHIYTNVAGADPD-LPVDFKSDVR---RIVYR SEQ ID NO:13
204 WLNQHVVGHHIYTNVAGADPD-LPVDFESDVR---RIVHR SEQ ID NO:12
207 WCHQHVIGHHLYTNVRNADPD-LGQG-EIDFR---VVTPY SEQ ID NO:15
178 WKDRHNA-HHSATNVQGHDPD-IDNLPLLAWSEDDVTRAS SEQ ID NO:16
205 WRARHNT-HHVCTNEDGSDPD-IKTAPLLIYVRENPSIAK SEQ ID NO:18

242 PARTWLHRFQAFFYMPVLAGYWLSAVFNPQILD-LQQRGA SEQ ID NO:14
261 QVLLPIYKYQ-HLYLPPLYGVLG---LKFRVQDVFETFVT SEQ ID NO:13
340 QVLLPIYKFQ-HIYLPPLYGVLG---LKFRIQDVFETFVS SEQ ID NO:12
242 QARSWYHKYQ-HIYAPILYGVYA---LKYRIQD-HEIFTK SEQ ID NO:15
216 PISRKLIQFQ-QYYFLVICILR---FIWCFQSVLTVRSL SEQ ID NO:16
243 RLN-FFQRWQ-QYYVVPTMAILD---LYWRLESIAYVAVR SEQ ID NO:18

281 LSVGIRLDNAFIHSRRKYAVFWRAVYIAVNVIAPFYTNSG SEQ ID NO:14
297 LTNGPLRVNPLSVGDWAEMILSKAFWVFYRIYLPLAVLQV SEQ ID NO:13
276 LTNGPVRVNPHPVSDWVQMIFAKAFWTFYRIYIPLVWLKI SEQ ID NO:12
277 KSNGAIRYSPISTIDTAIFILGKLVFIISRFILPLIYNHS SEQ ID NO:15
252 KD-----RDNQFYRSQYKKEAIGLALHWTLKTLFHLFFMPS SEQ ID NO:16
278 ---------------LPKMWMQAAALAAHYAL--LCWVFAAHL SEQ ID NO:18
```

Conserved Region 2

```
321 -LEWSWRVFGNIMLMGVAESLALAVLFSLSHNFESADRDP SEQ ID NO:14
337 DPARFWGVF---FLAEFSTGWYLAFNFQVSHVSTACEYPG SEQ ID NO:13
316 TPSTFWGVF---FLAEFTTGWYLAFNFQVSHVSTECEYPC SEQ ID NO:12
317 -FSHLICFF---LISELVLGWYLAISFQVSHVVEDLQFMA SEQ ID NO:15
288 ILTSLLVFF----VSELVGGFGIAIVVFMNHYPLEKIGDS SEQ ID NO:16
304 NLIPLMMVA----R-----GFATGIVVFATHYGEDILDRE SEQ ID NO:18
```

+1
ATG
+631
+1192
+1389-1392
Stop Codon
RD5
SEQ ID NOs:1 and 2
(1392 bp; 463 AA)
Conserved
Region 1
Conserved
Region 2
PCR fragment: pT-12-D5
SEQ ID NOs:4 and 5
(563 bp; 187 AA)
5' RACE #1: pT-RD5-5'C2
SEQ ID NO:6 (693 bp)
5' RACE #2:
pT-RD5-5'2nd
SEQ ID NO:8 (358 bp)
3' RACE: pT-RD5-3'
SEQ ID NO:10 (299 bp)

A
pKUNF12T6E
12649 bp
PacI (1)
XPR2
EL2Syn
TEF pro
ClaI (1459)
Lip2-3'
F. D12
FBA1
PmeI (4207)
BglII (4221)
TEF
D6S
Lip1-3'
SwaI (6380)
Fba1 + Intron
EL1S
Pex20-3'
BsiWI (8629)
Ura5'-784
AscI (9420)
Amp
SphI (12128)
Ura3'-516
B
pRD5S
4112 bp
EcoRI (397)
NcoI (433)
BamHI (1094)
RD5S(626)
BamHI (1493)
NotI (1828)
BamHI (1838)
SphI (1872)
Ori
Amp
C
pZURD5S
8480 bp
NcoI (1)
BamHI (662)
RD5S(626)
BamHI (1061)
NotI (1396)
Pex20-3'
BsiWI (1713)
ColE1
Amp
f1 ori
EcoRI (4509)
ARS 18
SphI (5855)
ClaI (5905)
PacI (5925)
Ura3
EcoRI (7436)
EcoRI (7458)
FBAIN

Figure 7A

```
1   ATGGCTCCAGATGCGGACAAGTTGAGACAGCGCAAGGCGCAATCGATTCAAGACACGGCT SEQ ID NO:1
1   ATGGCTCCCGACGCCGACAAGCTGCGACAGCGAAAGGCTCAGTCCATCCAGGACACTGCC SEQ ID NO:3

61  GATTCGCAAGCTACCGAACTCAAGATTGGCACCCTGAAGGGCTTGCAGGGGACAGAAATC SEQ ID NO:1
61  GATTCTCAGGCTACCGAGCTCAAGATTGGCACCCTGAAGGGTCTCCAAGGCACCGAGATC SEQ ID NO:3

121 GTCATTGATGGAGACATTTACGATATAAAAGACTTTGATCACCCCGGTGGTGAATCCATC SEQ ID NO:1
121 GTCATTGATGGCGACATCTACGACATCAAAGACTTCGATCACCCTGGAGGCGAATCCATC SEQ ID NO:3

181 ATGACTTTTGGGGGAAACGATGTCACCGCCACGTACAAGATGATCCACCCCTACCACTCT SEQ ID NO:1
181 ATGACCTTTGGTGGCAACGACGTTACTGCCACCTACAAGATGATTCATCCCTACCACTCG SEQ ID NO:3

241 AAGCACCATTTGGAGAAGATGAAGAAAGTGGGACGAGTTCCGGACTACACCTCGGAATAC SEQ ID NO:1
241 AAGCATCACCTGGAGAAGATGAAAAAGGTCGGTCGAGTGCCCGACTACACCTCCGAGTAC SEQ ID NO:3

301 AAGTTTGATACTCCCTTTGAGCGTGAAATCAAGCAAGAGGTCTTCAAGATTGTGCGACGA SEQ ID NO:1
301 AAGTTCGATACTCCCTTCGAACGAGAGATCAAACAGGAGGTCTTCAAGATTGTGCGAAGA SEQ ID NO:3

361 GGCCGCGAGTTTGGAACACCTGGATACTTCTTCCGGGCTTTCTGCTACATTGGACTTTTC SEQ ID NO:1
361 GGTCGAGAGTTTGGAACACCTGGCTACTTCTTTCGAGCCTTCTGCTACATCGGTCTCTTC SEQ ID NO:3

421 TTTTACTTGCAGTATTTGTGGGTCACGACTCCCACTACCTTTGCCTTGGCGATCTTCTAT SEQ ID NO:1
421 TTTTACCTGCAGTATCTCTGGGTTACCACTCCTACCACTTTCGCCCTTGCTATCTTCTAC SEQ ID NO:3

481 GGTGTTTCGCAAGCTTTCATTGGTTTGAACGTACAACATGATGCCAACCACGGAGCTGCC SEQ ID NO:1
481 GGTGTGTCTCAGGCCTTCATTGGCCTGAACGTCCAGCACGACGCCAACCACGGAGCTGCC SEQ ID NO:3

541 TCCAAGAAGCCTTGGATCAATAACTTGCTAGGATTGGGGGCTGACTTTATCGGAGGTTCC SEQ ID NO:1
541 TCCAAAAAGCCCTGGATCAACAATTTGCTCGGCCTGGGTGCCGACTTTATCGGAGGCTCC SEQ ID NO:3

601 AAATGGTTGTGGATGAACCAGCACTGGACGCACCACACATACACCAACCACCATGAGAAG SEQ ID NO:1
601 AAGTGGCTCTGGATGAACCAGCACTGGACCCATCACACTTACACCAACCATCACGAGAAG SEQ ID NO:3

661 GATCCCGATGCCTTGGGCGCTGAACCAATGTTGTTGTTCAATGATTATCCCTTGGGTCAC SEQ ID NO:1
661 GATCCCGACGCCCTGGGTGCAGAGCCTATGCTGCTCTTCAACGACTATCCCTTGGGTCAC SEQ ID NO:3
```

Figure 7B

```
721  CCAAAGCGTACTTTGATTCACCACTTCCAGGCCTTCTATTACCTTTTCGTCTTGGCCGGCA SEQ ID NO:1
721  CCCAAGCGAACCCTCATTCATCACTTCCAAGCCTTCTACTATCTGTTTGTCCTTGCTGGC SEQ ID NO:3

781  TACTGGTCTCTTCGGTCTTCAACCCTCAAATTTTGGACTTGCAACACCGCGGTCCTCAA SEQ ID NO:1
781  TACTGGTGTCTTCGGTGTTCAACCCTCAGATCCTGGACCTCCAGCACCGAGGTGCCCAG SEQ ID NO:3

841  GCGGTTGGAATGAAAATGGAGAACGATTACATTGCCAAAAGCCGAAAGTATGCCATCTTC SEQ ID NO:1
841  GCTGTCGGCATGAAGATGGAGAACGACTACATTGCCAAGTCTCGAAAGTACGCTATCTTC SEQ ID NO:3

901  TTGCGTCTCTTGTATATTTACACCAACATTGTCGCTCCGATCCAAAACCAAGGCTTCTCG SEQ ID NO:1
901  CTGCCACTCCTGTACATCTACACCAACATTGTGGCTCCCATCCAGAACCAAGGCTTTTCG SEQ ID NO:3

961  TTGACCGTGGTCGCCCACATTTTGACCATGGGCGTCGCTTCCAGTTTGACTTTGGCGACT SEQ ID NO:1
961  CTCACCGTCGTTGCTCACATTCTTACTATGGGTGTCGCCTCCAGCCTGACCCTCGCTACT SEQ ID NO:3

1021 CTTTTTGCCTTGTCGCACAATTTTGAAAACGCGGATCGCGATCCCACTTACGAGGCCCGC SEQ ID NO:1
1021 CTGTTCGCCCTCTCCCACAACTTCGAGAACGCAGATCGGGATCCCACCTACGAGGCTCGA SEQ ID NO:3

1081 AAGGGAGGAGAGCCTGTTTGTTGGTTCAAGTCGCAAGTCGAAACCTCGTCAACTTACGGA SEQ ID NO:1
1081 AAGGGAGGCGAGCCTGTCTGTTGGTTCAAGTCGCAGGTGGAAACCTCCTCTACTTACGGT SEQ ID NO:3

1141 GGTTTCATCTCGGGTTGCTTGACGGGCGGACTCAACTTCCAAGTGGAACACCACTTGTTC SEQ ID NO:1
1141 GGCTTCATTTCCGGTTGCCTTACAGGCGGACTCAACTTTCAGGTCGAGCATCACCTGTTT SEQ ID NO:3

1201 CCTCGTATGAGTTCGGCCTGGTACCCCTACATTGCCCCTACTGTTCGAGAGGTTTGCAAA SEQ ID NO:1
1201 CCTCCAATGTCCTCTGCCTGGTACCCCTACATCGCTCCTACCGTTCGAGAGGTCTGCAAA SEQ ID NO:3

1261 AAGCACGGAGTCAAGTACGCATACTATCCCTGGGTCTGGCAAAACTTGATTTCAACTGTC SEQ ID NO:1
1261 AAGCACGGCGTCAAGTACGCCTACTATCCCTGGGTGTGGCAGAACCTCATCTCGACCGTC SEQ ID NO:3

1321 AAGTATCTGCATCAAAGCGGAACTGGATCCAACTGGAAGAATGGCGCCAACCCCTACTCG SEQ ID NO:1
1321 AAGTACCTGCATCAGTCCGGAACTGGCTCGAACTGGAAGAACGGTGCCAATCCCTACTCT SEQ ID NO:3

1381 GGAAAATTGTAA                                                 SEQ ID NO:1
1381 GGCAAGCTGTAA                                                 SEQ ID NO:3
```

Figure 8A

```
                10         20         30         40
1    MGKGGDGGAQAVSGTDASL----AEVSSVDSKSVHVVLYG  SEQ ID NO:18 (Pavlova lutheri).pro
1    MGRGGDSSGQAHPAAELAVPSDRAEVSNADSKALHIVLYG  SEQ ID NO:66 (Pavlova salina).pro
1    MK----S-KRQALP------------------------LTID  SEQ ID NO:16 (Euglena gracilis).pro
1    MS----TLDRQSIFTIKELESISQRIHDGDEEAMKFIIID  SEQ ID NO:65 (Rhizopus stolonifer).pro
1    MS----TLDRQSIFTIKELESISQRIHDGDEEAMKFIIID  SEQ ID NO:53 (Rhizopus stolonifer).pro

                50         60         70         80
37   KRV-DVTKFQKAHPGGSKVFRIFQERDATEQFESYHSPKA  SEQ ID NO:18 (Pavlova lutheri).pro
41   KRV-DVTKFQRTHPGGSKVFRIFQDRDATEQFESYHSKRA  SEQ ID NO:66 (Pavlova salina).pro
14   GTTYDVSAWVNFHPGGAEIIENYQGRDATDAFMVMHSQEA  SEQ ID NO:16 (Euglena gracilis).pro
37   KKVYDVTEFIEDHPGGAQVLLTHVGKDASDVFHAMHPESA  SEQ ID NO:65 (Rhizopus stolonifer).pro
37   KKVYDVTEFIEDHPGGAQVLLTHVGKDASDVFHAMHPESA  SEQ ID NO:53 (Rhizopus stolonifer).pro

                90        100        110        120
76   IKMMEGMLKKSEDAPASVPLPSRSTMGTEFKEMIERHKRA  SEQ ID NO:18 (Pavlova lutheri).pro
80   IKMMEGMLKKSEDAPADTPLPSQSPMGKDFKAMIERHVAA  SEQ ID NO:66 (Pavlova salina).pro
54   FDKLKR-MPKINPSSELPPQAAVNEAQEDFRKLREELIAT  SEQ ID NO:16 (Euglena gracilis).pro
77   YEVLNNYFVGDVQETVVTEKSSSAQFAVEMRQLRDQLKKE  SEQ ID NO:65 (Rhizopus stolonifer).pro
77   YEVLNNYFVGDVQETVVTEKSSSAQFAVEMRQLRDQLKKE  SEQ ID NO:53 (Rhizopus stolonifer).pro

               130        140        150        160
116  GLYDPCPLDELFKLTIVLAPIFVGAYLV----RSGV-SPL  SEQ ID NO:18 (Pavlova lutheri).pro
120  GYYDPCPLDELFKLSLVLLPTFAGMYML----KAGVGSPL  SEQ ID NO:66 (Pavlova salina).pro
93   GMFDASPLWYSYKISTTLGLGVLGYFLMVQYQM-----YF  SEQ ID NO:16 (Euglena gracilis).pro
117  GYFHSSKLFYAYKVLSTLAICIAGLSPLYAYGRTSTLAVV  SEQ ID NO:65 (Rhizopus stolonifer).pro
117  GYFHSSKLFYAYKVLSTLAICIAGLSLLYAYGRTSTLAVV  SEQ ID NO:53 (Rhizopus stolonifer).pro

               170        180        190        200
151  AGALSMGFGFYLDGWLAHDYLHHAVFKGSVNTLVKANNAM  SEQ ID NO:18 (Pavlova lutheri).pro
156  CGALMVSFGWYLDGWLAHDYLHHSVFKGSVARTVGWNNAA  SEQ ID NO:66 (Pavlova salina).pro
128  IGAVLLGMHYQQMGWLSHDICHHQTFKNR-----NWNNLV  SEQ ID NO:16 (Euglena gracilis).pro
157  ASAITVGIFWQQCGWLAHDFGHHQCFEDR-----TWNDVL  SEQ ID NO:65 (Rhizopus stolonifer).pro
157  ASAITVGIFWQQCGWLAHDFGHHQCFEDR-----TWNDVL  SEQ ID NO:53 (Rhizopus stolonifer).pro

               210        220        230        240
191  GYALG-FLQGYDVAWWRARHNTHHVCTNEDGSDPDIKTAP  SEQ ID NO:18 (Pavlova lutheri).pro
196  GYFLG-FVQGYAVEWWRARHNTHHVCTNEDGSDPDIKTAP  SEQ ID NO:66 (Pavlova salina).pro
163  GLVFGNGLQGFSVTWWKDRHNAHHSATNVQGHDPDIDNLP  SEQ ID NO:16 (Euglena gracilis).pro
192  VVFLGNFCQGFSLSWWKNKHNTHHASTNVHGQDPDIDTAP  SEQ ID NO:65 (Rhizopus stolonifer).pro
192  VVFLGNFCQGFSLSWWKNKHNTHHASTNVHGQDPDIDTAP  SEQ ID NO:53 (Rhizopus stolonifer).pro
```

Figure 8B

```
                250        260        270        280
230  LLIY-----------VRENPSIAKRL---NFFQRWQQYYY  SEQ ID NO:18 (Pavlova lutheri).pro
235  LLIY-----------VRNKPSIAKRL---NAFQRYQQYYY  SEQ ID NO:66 (Pavlova salina).pro
203  LLAWSE-------DDVTRASPISRKLIQFQ------QYYF  SEQ ID NO:16 (Euglena gracilis).pro
232  VLLWDEYASAAYYASLDQEPTMVSRFLAEQVLPHQTRYFF  SEQ ID NO:65 (Rhizopus stolonifer).pro
232  VLLWDEYASAAYYASLDQEPTMVSRFLAEQVLPHQTRYFF  SEQ ID NO:53 (Rhizopus stolonifer).pro

                290        300        310        320
256  VPTMAILDLYWRLESIAYVAVR--LPKMWMQAA-------  SEQ ID NO:18 (Pavlova lutheri).pro
261  VPVMAILDLYWRLESIAYVAMR--LPKMLPQAL-------  SEQ ID NO:66 (Pavlova salina).pro
230  LVICILLRFIWCFQSV---LTVRSL-KDRDNQFYRSQYKK  SEQ ID NO:16 (Euglena gracilis).pro
272  FIL-AFARLSWALQSLSYSFKKESINKSRQLNLF------  SEQ ID NO:65 (Rhizopus stolonifer).pro
272  FIL-AFARLSWALQSLSYSFKKESINKSRQLNLF------  SEQ ID NO:53 (Rhizopus stolonifer).pro

                330        340        350        360
287  ---------ALAAHYALLCWVFAAHLNLIPLMM--VARGF  SEQ ID NO:18 (Pavlova lutheri).pro
292  ---------ALVAHYAIVAWVFAGNYHLLPLVT--VLRGF  SEQ ID NO:66 (Pavlova salina).pro
266  EAIGLALHWTLKTLFHLF-FMPSILTSLLVFFVSELVGGF  SEQ ID NO:16 (Euglena gracilis).pro
305  ERVCIVGHWALSA-FCIYSWCSNVYHMVLFFLVSQATTGY  SEQ ID NO:65 (Rhizopus stolonifer).pro
305  ERVCIVGHWALFA-FCIYSWCSNVYHMVLFFLVSQATTGY  SEQ ID NO:53 (Rhizopus stolonifer).pro

                370        380        390        400
316  ATGIVVFATHYGEDILDREHVEGMTLVEQTAKTSRNITGG  SEQ ID NO:18 (Pavlova lutheri).pro
321  GTGITVFATHYGEDILDADQVRHMTLVEQTALTSRNISGG  SEQ ID NO:66 (Pavlova salina).pro
305  GIAIVVFMNHYPLEKIGDSVWDGHGFSVGQIHETMNIRRG  SEQ ID NO:16 (Euglena gracilis).pro
344  TLALVFALNHNGMPVITEEKAESMEFFEIQVITGRDVTLS  SEQ ID NO:65 (Rhizopus stolonifer).pro
344  TLALVFALNHNGMPVITEEKAESMEFFEIQVITGRDVTLS  SEQ ID NO:53 (Rhizopus stolonifer).pro

                410        420        430        440
356  WLVNVLTGFISLQTEHHLFPMMPTGNLMTIQPEVRDFFKK  SEQ ID NO:18 (Pavlova lutheri).pro
361  WLVNVLTGFISLQTEHHLFPMMPTGNLMTIQPEVRAFFKK  SEQ ID NO:66 (Pavlova salina).pro
345  IITDWFFGGLNYQIEHHLWPTLPRHNLTAVSYQVEQLCQK  SEQ ID NO:16 (Euglena gracilis).pro
384  PLGDWFMGGLNYQIEHHVFPNMPRHNLPTVKPMVKSLCQK  SEQ ID NO:65 (Rhizopus stolonifer).pro
384  PLGDWFMGGLNYQIEHHVFPNMPRHNLPTVKPMVKSLCQK  SEQ ID NO:53 (Rhizopus stolonifer).pro

                450        460        470
396  HGLEYREGNLFQCVHQNIKALAFEHLLH              SEQ ID NO:18 (Pavlova lutheri).pro
401  HGLEYREGNLIECVRQNIRALAFEHLL               SEQ ID NO:66 (Pavlova salina).pro
365  HNLPYRNPLPHEGLVILLRYLAVFARMAEKQPAGKAL     SEQ ID NO:16 (Euglena gracilis).pro
424  YDINYHDTGFLKGTLEVLQTLDITSKLSL-QLSKKSF     SEQ ID NO:65 (Rhizopus stolonifer).pro
424  YDINYHDTGFLKGTLEVLQTLDITSKLSL-QLSKKSF     SEQ ID NO:53 (Rhizopus stolonifer).pro
```

| Fatty Acid | Clone | Gene | Fatty acid composition (wt.%) 16:0 | 16:1 | 18:0 | 18:1 | LA | GLA | ALA | STA | EDA | SCI | DGLA | ARA | ETrA | JUP | ETA | EPA |
|---|---|---|---|---|---|---|---|---|---|---|---|---|---|---|---|---|---|---|
| None | pY98 | MaD5 | 9.5 | 9.5 | 0.7 | 37.4 | 42.8 | 0.0 | 0.0 | 0.0 | 0.0 | 0.0 | 0.0 | 0.0 | 0.0 | 0.0 | 0.0 | 0.0 |
| | pDMW368 | RD5 | 10.0 | 9.3 | 0.8 | 39.4 | 40.5 | 0.0 | 0.0 | 0.0 | 0.0 | 0.0 | 0.0 | 0.0 | 0.0 | 0.0 | 0.0 | 0.0 |
| EDA | pY98 | MaD5 | 9.8 | 8.2 | 0.8 | 39.7 | 34.1 | 0.0 | 0.0 | 0.0 | 7.1 | 0.2 | 0.0 | 0.0 | 0.0 | 0.0 | 0.0 | 0.0 |
| | pDMW368 | RD5 | 8.9 | 8.2 | 1.1 | 41.2 | 32.7 | 0.0 | 0.0 | 0.0 | 5.4 | 2.6 | 0.0 | 0.0 | 0.0 | 0.0 | 0.0 | 0.0 |
| DGLA | pY98 | MaD5 | 12.0 | 6.8 | 1.4 | 38.8 | 19.3 | 0.6 | 0.0 | 0.0 | 0.0 | 0.0 | 18.2 | 3.0 | 0.0 | 0.0 | 0.0 | 0.0 |
| | pDMW368 | RD5 | 12.1 | 7.0 | 1.2 | 40.3 | 18.3 | 0.6 | 0.0 | 0.0 | 0.0 | 0.0 | 10.2 | 10.3 | 0.0 | 0.0 | 0.0 | 0.0 |
| ETrA | pY98 | MaD5 | 8.9 | 7.2 | 1.0 | 41.2 | 17.2 | 0.0 | 12.1 | 0.0 | 0.0 | 0.0 | 0.0 | 0.0 | 11.7 | 0.6 | 0.0 | 0.0 |
| | pDMW368 | RD5 | 8.1 | 7.3 | 0.9 | 42.3 | 16.1 | 0.0 | 12.1 | 0.0 | 0.0 | 0.0 | 0.0 | 0.0 | 10.1 | 3.1 | 0.0 | 0.0 |
| ETA | pY98 | MaD5 | 11.9 | 6.5 | 0.8 | 38.5 | 12.2 | 0.0 | 0.0 | 0.4 | 0.0 | 0.0 | 0.0 | 0.0 | 0.0 | 0.0 | 26.1 | 3.6 |
| | pDMW368 | RD5 | 11.9 | 6.4 | 0.8 | 40.0 | 11.1 | 0.0 | 0.0 | 0.4 | 0.0 | 0.0 | 0.0 | 0.0 | 0.0 | 0.0 | 18.8 | 10.5 |

B

| Fatty Acid | Clone | Gene | % delta-5 desat | Ratio Desat R/Ma | Ratio Prod/By-Prod | Ratio Prod/By-Prod R/Ma | Ratio n-6/n-3 |
|---|---|---|---|---|---|---|---|
| None | pY98 | MaD5 | | | | | |
| | pDMW368 | RD5 | | | | | |
| EDA | pY98 | MaD5 | 3.4 | 9.7 | | | 0.68 |
| | pDMW368 | RD5 | 32.6 | | | | 1.40 |
| DGLA | pY98 | MaD5 | 14.0 | 3.6 | 4.17 | 0.37 | 1.17 |
| | pDMW368 | RD5 | 50.3 | | 1.54 | | 1.40 |
| ETrA | pY98 | MaD5 | 4.9 | 4.7 | | | |
| | pDMW368 | RD5 | 23.2 | | | | |
| ETA | pY98 | MaD5 | 12.0 | 3.0 | 2.44 | 0.63 | |
| | pDMW368 | RD5 | 35.9 | | 1.55 | | |

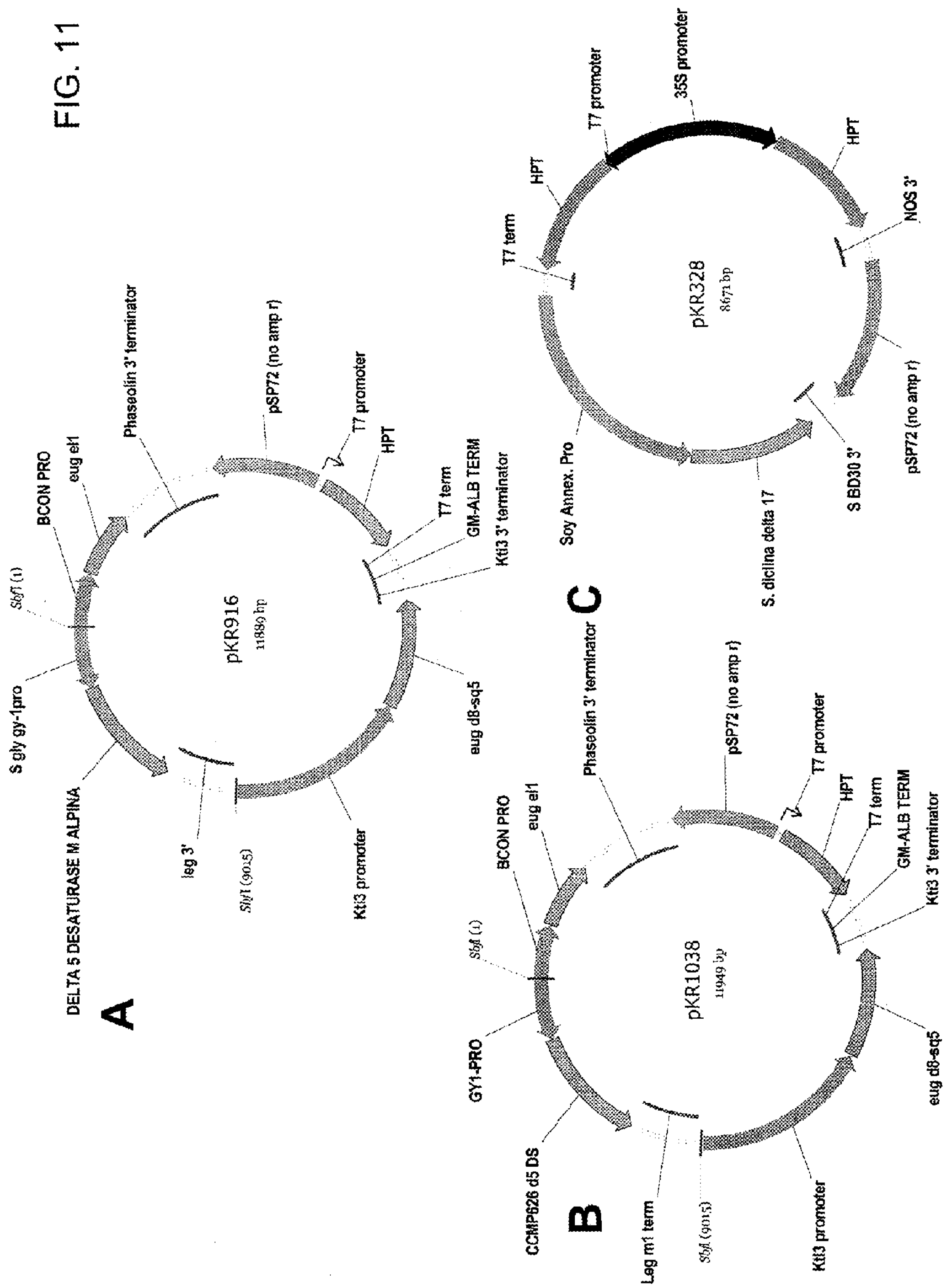
FIG. 11
A
pKR916
11889 bp
DELTA 5 DESATURASE M ALPINA
S gly gy-1pro
SbfI (1)
BCON PRO
eug el1
Phaseolin 3' terminator
pSP72 (no amp r)
T7 promoter
HPT
T7 term
GM-ALB TERM
Kti3 3' terminator
eug d8-sq5
Kti3 promoter
SbfI (9015)
leg 3'
B
pKR1038
11949 bp
GY1-PRO
SbfI (1)
BCON PRO
eug el1
Phaseolin 3' terminator
pSP72 (no amp r)
T7 promoter
HPT
T7 term
GM-ALB TERM
Kti3 3' terminator
eug d8-sq5
Kti3 promoter
SbfI (9015)
Leg m1 term
CCMP626 d5 DS
C
pKR328
8671 bp
T7 promoter
35S promoter
HPT
NOS 3'
pSP72 (no amp r)
S BD30 3'
S. diclina delta 17
Soy Annex. Pro
T7 term
HPT

FIG. 12A

| Event | 16:0 | 18:0 | 18:1 | LA | ALA | EDA | SCI | DGLA | ARA | ERA | JUP | ETA | EPA | Other | Correct % delta-5 desat | Wrong % delta-5 desat |
|---|---|---|---|---|---|---|---|---|---|---|---|---|---|---|---|---|
| | Average Fatty acid composition (wt.%) | | | | | | | | | | | | | | | |
| 2010-5-4-1 | 13.4 | 2.7 | 8.1 | 25.9 | 13.8 | 4.9 | 5.1 | 0.0 | 0.8 | 1.7 | 8.9 | 0.0 | 9.0 | 5.7 | 100.0 | 67.7 |
| 2010-5-12-1 | 17.2 | 5.0 | 14.3 | 28.4 | 12.5 | 5.7 | 0.8 | 0.3 | 0.0 | 2.1 | 4.8 | 0.4 | 6.0 | 2.6 | 89.3 | 41.5 |
| 2010-13-2-1 | 14.6 | 4.5 | 17.6 | 25.0 | 6.6 | 9.9 | 1.7 | 1.1 | 0.5 | 1.7 | 3.8 | 0.5 | 8.8 | 3.7 | 85.2 | 32.0 |
| 2010-9-10-1 | 17.2 | 4.3 | 14.7 | 22.1 | 7.1 | 7.1 | 0.7 | 0.8 | 0.1 | 3.4 | 5.9 | 1.7 | 10.5 | 4.4 | 80.6 | 38.8 |
| 2010-13-3-1 | 15.9 | 4.5 | 15.0 | 28.5 | 9.2 | 7.6 | 0.1 | 2.1 | 0.5 | 1.3 | 2.2 | 0.6 | 9.5 | 3.0 | 78.1 | 20.8 |
| 2010-6-2-1 | 17.9 | 3.4 | 10.1 | 18.8 | 9.4 | 8.1 | 0.8 | 0.3 | 0.1 | 6.6 | 15.1 | 1.3 | 4.9 | 3.3 | 76.4 | 52.0 |
| 2010-6-1-1 | 16.9 | 3.2 | 9.8 | 22.5 | 7.6 | 19.2 | 2.1 | 3.5 | 6.5 | 2.7 | 0.8 | 0.5 | 2.6 | 2.0 | 69.5 | 11.8 |
| 2010-12-8-1 | 16.0 | 3.9 | 14.9 | 17.2 | 5.2 | 18.2 | 0.3 | 1.9 | 0.0 | 7.0 | 2.2 | 1.9 | 8.4 | 2.9 | 68.8 | 9.2 |
| 2010-9-13-1 | 16.6 | 3.6 | 8.6 | 26.3 | 13.1 | 7.4 | 0.8 | 7.2 | 7.6 | 1.6 | 0.2 | 1.0 | 4.2 | 1.7 | 59.0 | 10.2 |
| 2010-12-4-1 | 15.7 | 4.2 | 27.6 | 17.2 | 4.7 | 6.7 | 0.0 | 3.5 | 0.0 | 1.6 | 0.0 | 6.8 | 7.2 | 4.9 | 41.2 | 0.0 |

FIG. 12B

| Event | 16:0 | 18:0 | 18:1 | LA | ALA | EDA | SCI | DGLA | ARA | ERA | JUP | ETA | EPA | Other | Correct % delta-5 desat | Wrong % delta-5 desat |
|---|---|---|---|---|---|---|---|---|---|---|---|---|---|---|---|---|
| | Average Fatty acid composition (wt.%) | | | | | | | | | | | | | | | |
| 2033-5-5-1 | 18.6 | 4.7 | 15.7 | 36.3 | 17.0 | 2.1 | 0.7 | 0.1 | 1.7 | 0.4 | 0.7 | 0.0 | 0.4 | 1.4 | 94.7 | 37.1 |
| 2033-1-1-1 | 18.5 | 4.3 | 14.3 | 32.5 | 14.7 | 5.3 | 1.1 | 0.7 | 3.9 | 1.0 | 0.7 | 0.1 | 1.7 | 1.4 | 87.6 | 21.8 |
| 2033-1-2-1 | 18.6 | 5.5 | 16.1 | 22.8 | 9.4 | 9.9 | 4.9 | 0.8 | 4.3 | 1.7 | 2.3 | 0.0 | 1.4 | 2.4 | 87.2 | 38.1 |
| 2033-7-5-1 | 17.4 | 4.1 | 12.7 | 26.0 | 13.5 | 7.9 | 1.8 | 1.7 | 7.4 | 1.3 | 1.1 | 0.4 | 3.5 | 1.2 | 84.2 | 23.8 |
| 2033-6-2-1 | 17.1 | 4.5 | 17.6 | 25.2 | 10.8 | 7.8 | 0.2 | 0.6 | 0.0 | 2.1 | 2.8 | 1.2 | 9.0 | 1.0 | 83.8 | 23.5 |
| 2033-7-6-1 | 15.7 | 4.4 | 17.4 | 24.0 | 9.0 | 9.2 | 0.4 | 0.5 | 0.1 | 3.2 | 5.1 | 1.1 | 7.6 | 2.4 | 83.1 | 30.3 |
| 2033-1-3-1 | 16.4 | 5.0 | 18.3 | 25.6 | 11.8 | 6.6 | 0.5 | 2.6 | 2.5 | 1.1 | 0.5 | 0.8 | 6.2 | 1.8 | 72.1 | 11.7 |
| 2033-3-2-1 | 16.7 | 4.1 | 15.6 | 22.6 | 10.8 | 11.4 | 3.0 | 2.0 | 1.2 | 2.2 | 2.4 | 0.9 | 4.9 | 2.1 | 68.1 | 28.2 |
| 1998-4-1-1 | 14.8 | 3.0 | 10.9 | 28.4 | 6.0 | 25.9 | 0.8 | 1.7 | 1.8 | 3.8 | 0.1 | 0.4 | 0.6 | 1.9 | 52.1 | 2.9 |
| 2033-6-1-1 | 16.2 | 4.7 | 23.5 | 23.5 | 10.2 | 7.5 | 0.0 | 0.3 | 0.0 | 4.5 | 0.4 | 4.8 | 2.9 | 1.6 | 36.4 | 3.2 |

SEQUENCE LISTING

```
<160> NUMBER OF SEQ ID NOS: 94

<210> SEQ ID NO 1
<211> LENGTH: 1392
<212> TYPE: DNA
<213> ORGANISM: Peridinium sp. CCMP626
<220> FEATURE:
<221> NAME/KEY: misc_feature
<223> OTHER INFORMATION: delta-5 desaturase

<400> SEQUENCE: 1

atggctccag atgcggacaa gttgagacag cgcaaggcgc aatcgattca agacacggct     60

gattcgcaag ctaccgaact caagattggc accctgaagg gcttgcaggg gacagaaatc    120

gtcattgatg gagacattta cgatataaaa gactttgatc accccggtgg tgaatccatc    180

atgacttttg ggggaaacga tgtcaccgcc acgtacaaga tgatccaccc ctaccactct    240

aagcaccatt tggagaagat gaagaaagtg ggacgagttc cggactacac ctcggaatac    300

aagtttgata ctccctttga gcgtgaaatc aagcaagagg tcttcaagat tgtgcgacga    360

ggccgcgagt ttggaacacc tggatacttc ttccgggctt tctgctacat tggacttttc    420

ttttacttgc agtatttgtg ggtcacgact cccactacct ttgccttggc gatcttctat    480

ggtgtttcgc aagctttcat tggtttgaac gtacaacatg atgccaacca cggagctgcc    540

tccaagaagc cttggatcaa taacttgcta ggattggggg ctgactttat cggaggttcc    600

aaatggttgt ggatgaacca gcactggacg caccacacat acaccaacca ccatgagaag    660

gatcccgatg ccttgggcgc tgaaccaatg ttgttgttca atgattatcc cttgggtcac    720

ccaaagcgta ctttgattca ccacttccag gccttctatt accttttcgt cttggccgga    780

tactgggtct cttcggtctt caaccctcaa attttggact tgcaacaccg cggtgctcaa    840

gcggttggaa tgaaaatgga gaacgattac attgccaaaa gccgaaagta tgccatcttc    900

ttgcgtctct tgtatattta caccaacatt gtcgctccga tccaaaacca aggcttctcg    960
```

```
ttgaccgtgg tcgcccacat tttgaccatg ggcgtcgctt ccagtttgac tttggcgact   1020

ctttttgcct tgtcgcacaa ttttgaaaac gcggatcgcg atcccactta cgaggcccgc   1080

aagggaggag agcctgtttg ttggttcaag tcgcaagtcg aaacctcgtc aacttacgga   1140

ggtttcatct cgggttgctt gacgggcgga ctcaacttcc aagtggaaca ccacttgttc   1200

cctcgtatga gttcggcctg gtacccctac attgccccta ctgttcgaga ggtttgcaaa   1260

aagcacggag tcaagtacgc atactatccc tgggtctggc aaaacttgat ttcaactgtc   1320

aagtatctgc atcaaagcgg aactggatcc aactggaaga atggcgccaa cccctactcg   1380

ggaaaattgt aa                                                       1392
```

<210> SEQ ID NO 2
<211> LENGTH: 463
<212> TYPE: PRT
<213> ORGANISM: Peridinium sp. CCMP626

<400> SEQUENCE: 2

```
Met Ala Pro Asp Ala Asp Lys Leu Arg Gln Arg Lys Ala Gln Ser Ile
1               5                   10                  15

Gln Asp Thr Ala Asp Ser Gln Ala Thr Glu Leu Lys Ile Gly Thr Leu
            20                  25                  30

Lys Gly Leu Gln Gly Thr Glu Ile Val Ile Asp Gly Asp Ile Tyr Asp
        35                  40                  45

Ile Lys Asp Phe Asp His Pro Gly Gly Glu Ser Ile Met Thr Phe Gly
    50                  55                  60

Gly Asn Asp Val Thr Ala Thr Tyr Lys Met Ile His Pro Tyr His Ser
65                  70                  75                  80

Lys His His Leu Glu Lys Met Lys Lys Val Gly Arg Val Pro Asp Tyr
                85                  90                  95

Thr Ser Glu Tyr Lys Phe Asp Thr Pro Phe Glu Arg Glu Ile Lys Gln
            100                 105                 110

Glu Val Phe Lys Ile Val Arg Arg Gly Arg Glu Phe Gly Thr Pro Gly
        115                 120                 125

Tyr Phe Phe Arg Ala Phe Cys Tyr Ile Gly Leu Phe Phe Tyr Leu Gln
    130                 135                 140

Tyr Leu Trp Val Thr Thr Pro Thr Thr Phe Ala Leu Ala Ile Phe Tyr
145                 150                 155                 160

Gly Val Ser Gln Ala Phe Ile Gly Leu Asn Val Gln His Asp Ala Asn
                165                 170                 175

His Gly Ala Ala Ser Lys Lys Pro Trp Ile Asn Asn Leu Leu Gly Leu
            180                 185                 190

Gly Ala Asp Phe Ile Gly Gly Ser Lys Trp Leu Trp Met Asn Gln His
        195                 200                 205

Trp Thr His His Thr Tyr Thr Asn His His Glu Lys Asp Pro Asp Ala
    210                 215                 220

Leu Gly Ala Glu Pro Met Leu Leu Phe Asn Asp Tyr Pro Leu Gly His
225                 230                 235                 240

Pro Lys Arg Thr Leu Ile His His Phe Gln Ala Phe Tyr Tyr Leu Phe
                245                 250                 255

Val Leu Ala Gly Tyr Trp Val Ser Ser Val Phe Asn Pro Gln Ile Leu
            260                 265                 270

Asp Leu Gln His Arg Gly Ala Gln Ala Val Gly Met Lys Met Glu Asn
        275                 280                 285

Asp Tyr Ile Ala Lys Ser Arg Lys Tyr Ala Ile Phe Leu Arg Leu Leu
```

```
    290                 295                 300

Tyr Ile Tyr Thr Asn Ile Val Ala Pro Ile Gln Asn Gln Gly Phe Ser
305                 310                 315                 320

Leu Thr Val Val Ala His Ile Leu Thr Met Gly Val Ala Ser Ser Leu
                325                 330                 335

Thr Leu Ala Thr Leu Phe Ala Leu Ser His Asn Phe Glu Asn Ala Asp
            340                 345                 350

Arg Asp Pro Thr Tyr Glu Ala Arg Lys Gly Gly Glu Pro Val Cys Trp
        355                 360                 365

Phe Lys Ser Gln Val Glu Thr Ser Ser Thr Tyr Gly Gly Phe Ile Ser
    370                 375                 380

Gly Cys Leu Thr Gly Gly Leu Asn Phe Gln Val Glu His His Leu Phe
385                 390                 395                 400

Pro Arg Met Ser Ser Ala Trp Tyr Pro Tyr Ile Ala Pro Thr Val Arg
                405                 410                 415

Glu Val Cys Lys Lys His Gly Val Lys Tyr Ala Tyr Tyr Pro Trp Val
            420                 425                 430

Trp Gln Asn Leu Ile Ser Thr Val Lys Tyr Leu His Gln Ser Gly Thr
        435                 440                 445

Gly Ser Asn Trp Lys Asn Gly Ala Asn Pro Tyr Ser Gly Lys Leu
    450                 455                 460


<210> SEQ ID NO 3
<211> LENGTH: 1392
<212> TYPE: DNA
<213> ORGANISM: Peridinium sp. CCMP626
<220> FEATURE:
<221> NAME/KEY: misc_feature
<223> OTHER INFORMATION: synthetic delta-5 desaturase (codon-optimized)
      for Yarrowia lipolytica

<400> SEQUENCE: 3

atggctcccg acgccgacaa gctgcgacag cgaaaggctc agtccatcca ggacactgcc     60

gattctcagg ctaccgagct caagattggc accctgaagg gtctccaagg caccgagatc    120

gtcattgatg gcgacatcta cgacatcaaa gacttcgatc accctggagg cgaatccatc    180

atgacctttg gtggcaacga cgttactgcc acctacaaga tgattcatcc ctaccactcg    240

aagcatcacc tggagaagat gaaaaaggtc ggtcgagtgc ccgactacac ctccgagtac    300

aagttcgata ctcccttcga acgagagatc aaacaggagg tcttcaagat tgtgcgaaga    360

ggtcgagagt ttggaacacc tggctacttc tttcgagcct tctgctacat cggtctcttc    420

ttttacctgc agtatctctg ggttaccact cctaccactt tcgcccttgc tatcttctac    480

ggtgtgtctc aggccttcat tggcctgaac gtccagcacg acgccaacca cggagctgcc    540

tccaaaaagc cctggatcaa caatttgctc ggcctgggtg ccgactttat cggaggctcc    600

aagtggctct ggatgaacca gcactggacc catcacactt acaccaacca tcacgagaag    660

gatcccgacg ccctgggtgc agagcctatg ctgctcttca acgactatcc cttgggtcac    720

cccaagcgaa ccctcattca tcacttccaa gccttctact atctgtttgt ccttgctggc    780

tactgggtgt cttcggtgtt caaccctcag atcctggacc tccagcaccg aggtgcccag    840

gctgtcggca tgaagatgga gaacgactac attgccaagt ctcgaaagta cgctatcttc    900

ctgcgactcc tgtacatcta caccaacatt gtggctccca tccagaacca aggcttttcg    960

ctcaccgtcg ttgctcacat tcttactatg ggtgtcgcct ccagcctgac cctcgctact   1020

ctgttcgccc tctcccacaa cttcgagaac gcagatcggg atcccaccta cgaggctcga   1080
```

```
aagggaggcg agcctgtctg ttggttcaag tcgcaggtgg aaacctcctc tacttacggt   1140

ggcttcattt ccggttgcct tacaggcgga ctcaactttc aggtcgagca tcacctgttt   1200

cctcgaatgt cctctgcctg gtacccctac atcgctccta ccgttcgaga ggtctgcaaa   1260

aagcacggcg tcaagtacgc ctactatccc tgggtgtggc agaacctcat ctcgaccgtc   1320

aagtacctgc atcagtccgg aactggctcg aactggaaga acggtgccaa tccctactct   1380

ggcaagctgt aa                                                       1392
```

<210> SEQ ID NO 4
<211> LENGTH: 563
<212> TYPE: DNA
<213> ORGANISM: Artificial Sequence
<220> FEATURE:
<223> OTHER INFORMATION: 563 bp fragment of pT-12-D5

<400> SEQUENCE: 4

```
ggtcatcatg tttataccaa ccaccatgag aaggatcccg atgccttggg cgctgaacca     60

atgttgttgt tcaatgatta tcccttgggt cacccaaagc gtactttgat tcaccacttc    120

caggccttct attacctttt cgtcttggcc ggatactggg tctcttcggt cttcaaccct    180

caaattttgg acttgcaaca ccgcggtgct caagcggttg gaatgaaaat ggagaacgat    240

tacattgcca aaagccgaaa gtatgccatc ttcttgcgtc tcttgtatat ttacaccaac    300

attgtcgctc cgatccaaaa ccaaggcttc tcgttgaccg tggtcgccca catttgacc    360

atgggcgtcg cttccagttt gactttggcg actctttttg cctcgtcgca caattttgaa    420

aacgcggatc gcgatcccac ttacgaggcc cgcaaggggg gagagcctgt ttgttggttc    480

aagtcgcaag tcgaaacctc gtcaacttac ggaggtttca tctcgggttg cttgacgggc    540

ggactcaact tccaagtatc aca                                            563
```

<210> SEQ ID NO 5
<211> LENGTH: 187
<212> TYPE: PRT
<213> ORGANISM: Artificial Sequence
<220> FEATURE:
<223> OTHER INFORMATION: translation of 563 bp fragment of pT-12-D5

<400> SEQUENCE: 5

```
Gly His His Val Tyr Thr Asn His His Glu Lys Asp Pro Asp Ala Leu
1               5                   10                  15

Gly Ala Glu Pro Met Leu Leu Phe Asn Asp Tyr Pro Leu Gly His Pro
            20                  25                  30

Lys Arg Thr Leu Ile His His Phe Gln Ala Phe Tyr Tyr Leu Phe Val
        35                  40                  45

Leu Ala Gly Tyr Trp Val Ser Ser Val Phe Asn Pro Gln Ile Leu Asp
    50                  55                  60

Leu Gln His Arg Gly Ala Gln Ala Val Gly Met Lys Met Glu Asn Asp
65                  70                  75                  80

Tyr Ile Ala Lys Ser Arg Lys Tyr Ala Ile Phe Leu Arg Leu Leu Tyr
                85                  90                  95

Ile Tyr Thr Asn Ile Val Ala Pro Ile Gln Asn Gln Gly Phe Ser Leu
            100                 105                 110

Thr Val Val Ala His Ile Leu Thr Met Gly Val Ala Ser Ser Leu Thr
        115                 120                 125

Leu Ala Thr Leu Phe Ala Ser Ser His Asn Phe Glu Asn Ala Asp Arg
    130                 135                 140

Asp Pro Thr Tyr Glu Ala Arg Lys Gly Gly Glu Pro Val Cys Trp Phe
```

```
145                 150                 155                 160

Lys Ser Gln Val Glu Thr Ser Ser Thr Tyr Gly Gly Phe Ile Ser Gly
                165                 170                 175

Cys Leu Thr Gly Gly Leu Asn Phe Gln Val Ser
            180                 185


<210> SEQ ID NO 6
<211> LENGTH: 693
<212> TYPE: DNA
<213> ORGANISM: Artificial Sequence
<220> FEATURE:
<223> OTHER INFORMATION: 693 bp fragment of pT-RD5-5'C2
<220> FEATURE:
<221> NAME/KEY: misc_feature
<222> LOCATION: (10)..(10)
<223> OTHER INFORMATION: n is a, c, g, or t

<400> SEQUENCE: 6

aatcgtcatn gatggagaca tttacgatat aaaagacttt gatcaccccg gtggtgaatc     60

catcatgact tttgggggaa acgatgtcac cgccacgtac aagatgatcc acccctacca    120

ctctaagcac catttggaga agatgaagaa agtgggacga gttccggact acacctcgga    180

atacaagttt gatactccct ttgagcgtga aatcaagyaa gaggtcttca agattgtgcg    240

acgaggccgc gagtttggaa cacctggata cttcttccgg gctttctgct acattggact    300

tttcttttac ttgcagtatt tgtgggtcac gactcccact acctttgcct tggcgatctt    360

ctatggtgtt tcgcaagctt tcattggttt gaacgtacaa catgatgcca accacggagc    420

tgcctccaag aagccttgga tcaataactt gctaggattg gggggctgact ttatcggagg   480

ttccaaatgg ttgtggatga accagcactg gacgcaccac acatacacca accaccatga    540

gaaggatccc gatgccttgg gcgctgaacc aatgttgttg ttcaatgatt atcccttggg    600

tcacccaaag cgtactttga ttcaccactt ccaggccttc tattaccttt tcgtcttggc    660

cggatactgg gtctcttcgg tcttcaaccc tca                                  693


<210> SEQ ID NO 7
<211> LENGTH: 511
<212> TYPE: DNA
<213> ORGANISM: Artificial Sequence
<220> FEATURE:
<223> OTHER INFORMATION: 511 bp 5' extended fragment of pT-RD5-5'C2

<400> SEQUENCE: 7

aatcgtcatt gatggagaca tttacgatat aaaagacttt gatcaccccg gtggtgaatc     60

catcatgact tttgggggaa acgatgtcac cgccacgtac aagatgatcc acccctacca    120

ctctaagcac catttggaga agatgaagaa agtgggacga gttccggact acacctcgga    180

atacaagttt gatactccct ttgagcgtga aatcaagyaa gaggtcttca agattgtgcg    240

acgaggccgc gagtttggaa cacctggata cttcttccgg gctttctgct acattggact    300

tttcttttac ttgcagtatt tgtgggtcac gactcccact acctttgcct tggcgatctt    360

ctatggtgtt tcgcaagctt tcattggttt gaacgtacaa catgatgcca accacggagc    420

tgcctccaag aagccttgga tcaataactt gctaggattg gggctgact ttatcggagg     480

ttccaaatgg ttgtggatga accagcactg g                                    511


<210> SEQ ID NO 8
<211> LENGTH: 358
<212> TYPE: DNA
<213> ORGANISM: Artificial Sequence
<220> FEATURE:
```

<223> OTHER INFORMATION: 358 bp fragment of pT-RD5-5'2nd

<400> SEQUENCE: 8
gatttctttc gttggcattt ttcgttggga aagactcttg caacgatggc tccagatgcg 60
gacaagttga gacagcgcaa ggcgcaatcg attcaagaca cggctgattc gcaagctacc 120
gaactcaaga ttggcaccct gaagggcttg caggggacag aaatcgtcat tgatggagac 180
atttacgata taaaagactt tgatcacccc ggtggtgaat ccatcatgac ttttggagga 240
aacgatgtca ctgccacgta caagatgatc cacccctacc actctaagca ccatttggag 300
aagatgaaga aagtgggacg agttctggac tacacctcgg aatacaagtt tgatactc 358

<210> SEQ ID NO 9
<211> LENGTH: 161
<212> TYPE: DNA
<213> ORGANISM: Artificial Sequence
<220> FEATURE:
<223> OTHER INFORMATION: 161 bp 5' extended fragment of pT-RD5-5'2nd

<400> SEQUENCE: 9
gatttctttc gttggcattt ttcgttggga aagactcttg caacgatggc tccagatgcg 60
gacaagttga gacagcgcaa ggcgcaatcg attcaagaca cggctgattc gcaagctacc 120
gaactcaaga ttggcaccct gaagggcttg caggggacag a 161

<210> SEQ ID NO 10
<211> LENGTH: 299
<212> TYPE: DNA
<213> ORGANISM: Artificial Sequence
<220> FEATURE:
<223> OTHER INFORMATION: 299 bp fragment of pT-RD5-3'

<400> SEQUENCE: 10
gaggtttcat ctcgggttgt ttgacgggcg gactcaactt tcaagtggaa caccacttgt 60
tccctcgtat gagttcggcc tggtacccct acattgcccc tgctgttcga gaggtttgca 120
aaaagcacgg agtcaagtac gcatactatc cctgggtctg gcaaaacttg atttcaactg 180
tcaagtatct gcatcaaagc ggaactggat ccaactggaa gaatggcgcc aacccctact 240
cgggaaaatt gtaaatgaat tctagtcaag atgggtcact gcattcaaaa aaaaaaaaa 299

<210> SEQ ID NO 11
<211> LENGTH: 247
<212> TYPE: DNA
<213> ORGANISM: Artificial Sequence
<220> FEATURE:
<223> OTHER INFORMATION: 247 bp of 3' downstream sequence of pT-RD5-3'

<400> SEQUENCE: 11
ccacttgttc cctcgtatga gttcggcctg gtacccctac attgcccctg ctgttcgaga 60
ggtttgcaaa aagcacggag tcaagtacgc atactatccc tgggtctggc aaaacttgat 120
ttcaactgtc aagtatctgc atcaaagcgg aactggatcc aactggaaga atggcgccaa 180
cccctactcg ggaaaattgt aaatgaattc tagtcaagat gggtcactgc attcaaaaaa 240
aaaaaaa 247

<210> SEQ ID NO 12
<211> LENGTH: 456
<212> TYPE: PRT
<213> ORGANISM: Pythium irregulare (GenBank Accession No. AAL13311)
<220> FEATURE:
<221> NAME/KEY: MISC_FEATURE
<223> OTHER INFORMATION: delta-5 desaturase

<400> SEQUENCE: 12

```
Met Gly Thr Asp Gln Gly Lys Thr Phe Thr Trp Gln Glu Val Ala Lys
1               5                   10                  15

His Asn Thr Ala Lys Ser Ala Trp Val Ile Ile Arg Gly Glu Val Tyr
            20                  25                  30

Asp Val Thr Glu Trp Ala Asp Lys His Pro Gly Gly Ser Glu Leu Ile
        35                  40                  45

Val Leu His Ser Gly Arg Glu Cys Thr Asp Thr Phe Tyr Ser Tyr His
    50                  55                  60

Pro Phe Ser Asn Arg Ala Asp Lys Ile Leu Ala Lys Tyr Lys Ile Gly
65                  70                  75                  80

Lys Leu Val Gly Gly Tyr Glu Phe Pro Val Phe Lys Pro Asp Ser Gly
                85                  90                  95

Phe Tyr Lys Glu Cys Ser Glu Arg Val Ala Glu Tyr Phe Lys Thr Asn
            100                 105                 110

Asn Leu Asp Pro Lys Ala Ala Phe Ala Gly Leu Trp Arg Met Val Phe
        115                 120                 125

Val Phe Ala Val Ala Ala Leu Ala Tyr Met Gly Met Asn Glu Leu Ile
    130                 135                 140

Pro Gly Asn Val Tyr Ala Gln Tyr Ala Trp Gly Val Val Phe Gly Val
145                 150                 155                 160

Phe Gln Ala Leu Pro Leu Leu His Val Met His Asp Ser Ser His Ala
                165                 170                 175

Ala Cys Ser Ser Ser Pro Ala Met Trp Gln Ile Ile Gly Arg Gly Val
            180                 185                 190

Met Asp Trp Phe Ala Gly Ala Ser Met Val Ser Trp Leu Asn Gln His
        195                 200                 205

Val Val Gly His His Ile Tyr Thr Asn Val Ala Gly Ala Asp Pro Asp
    210                 215                 220

Leu Pro Val Asp Phe Glu Ser Asp Val Arg Arg Ile Val His Arg Gln
225                 230                 235                 240

Val Leu Leu Pro Ile Tyr Lys Phe Gln His Ile Tyr Leu Pro Pro Leu
                245                 250                 255

Tyr Gly Val Leu Gly Leu Lys Phe Arg Ile Gln Asp Val Phe Glu Thr
            260                 265                 270

Phe Val Ser Leu Thr Asn Gly Pro Val Arg Val Asn Pro His Pro Val
        275                 280                 285

Ser Asp Trp Val Gln Met Ile Phe Ala Lys Ala Phe Trp Thr Phe Tyr
    290                 295                 300

Arg Ile Tyr Ile Pro Leu Val Trp Leu Lys Ile Thr Pro Ser Thr Phe
305                 310                 315                 320

Trp Gly Val Phe Phe Leu Ala Glu Phe Thr Thr Gly Trp Tyr Leu Ala
                325                 330                 335

Phe Asn Phe Gln Val Ser His Val Ser Thr Glu Cys Glu Tyr Pro Cys
            340                 345                 350

Gly Asp Ala Pro Ser Ala Glu Val Gly Asp Glu Trp Ala Ile Ser Gln
        355                 360                 365

Val Lys Ser Ser Val Asp Tyr Ala His Gly Ser Pro Leu Ala Ala Phe
    370                 375                 380

Leu Cys Gly Ala Leu Asn Tyr Gln Val Thr His His Leu Tyr Pro Gly
385                 390                 395                 400

Ile Ser Gln Tyr His Tyr Pro Ala Ile Ala Pro Ile Ile Ile Asp Val
                405                 410                 415
```

```
Cys Lys Lys Tyr Asn Ile Lys Tyr Thr Val Leu Pro Thr Phe Thr Glu
            420                 425                 430

Ala Leu Leu Ala His Phe Lys His Leu Lys Asn Met Gly Glu Leu Gly
        435                 440                 445

Lys Pro Val Glu Ile His Met Gly
    450                 455


<210> SEQ ID NO 13
<211> LENGTH: 477
<212> TYPE: PRT
<213> ORGANISM: Phytophthora megasperma (GenBank Accession No. CAD53323)
<220> FEATURE:
<221> NAME/KEY: MISC_FEATURE
<223> OTHER INFORMATION: delta-5 desaturase

<400> SEQUENCE: 13

Met Ala Pro Ile Glu Thr Val Lys Asp Ala Asn Glu Gly Leu His Gln
1               5                   10                  15

Arg Lys Gly Ala Ala Ala Ala Ser Lys Asp Thr Thr Thr Phe Thr Trp
            20                  25                  30

Gln Asp Val Ala Lys His Asn Thr Ala Lys Ser Ala Trp Val Thr Ile
        35                  40                  45

Arg Gly Val Val Tyr Asp Val Thr Glu Trp Ala Asp Arg His Pro Gly
    50                  55                  60

Gly Arg Glu Leu Val Leu Leu His Ser Gly Arg Glu Cys Thr Asp Thr
65                  70                  75                  80

Phe Asp Ser Tyr His Pro Phe Ser Asp Arg Ala Asp Lys Ile Leu Ala
                85                  90                  95

Lys Tyr Ala Ile Gly Lys Leu Val Gly Gly Ser Glu Phe Pro Thr Tyr
            100                 105                 110

Lys Pro Asp Thr Gly Phe Tyr Lys Glu Cys Cys Asp Arg Val Asn Gln
        115                 120                 125

Tyr Phe Lys Asp Asn Lys Leu Asp Pro Arg Ser Pro Tyr Ser Gly Leu
    130                 135                 140

Trp Arg Met Ile Leu Val Ala Ile Val Gly Ala Val Ala Tyr Met Gly
145                 150                 155                 160

Met Asn Gln Leu Leu Pro Gly Asn Ile Tyr Ala His Tyr Ala Trp Gly
                165                 170                 175

Ala Leu Phe Gly Val Cys Gln Ala Leu Pro Leu Leu His Val Met His
            180                 185                 190

Asp Ala Ser His Ala Ala Ile Thr Ser Ser Pro Thr Gly Trp Arg Leu
        195                 200                 205

Ile Gly Arg Leu Ala Met Asp Trp Val Ala Gly Ala Asn Met Val Ser
    210                 215                 220

Trp Leu Asn Gln His Val Val Gly His His Ile Tyr Thr Asn Val Ala
225                 230                 235                 240

Gly Ala Asp Pro Asp Leu Pro Val Asp Phe Lys Ser Asp Val Arg Arg
                245                 250                 255

Ile Val Tyr Arg Gln Val Leu Leu Pro Ile Tyr Lys Tyr Gln His Leu
            260                 265                 270

Tyr Leu Pro Pro Leu Tyr Gly Val Leu Gly Leu Lys Phe Arg Val Gln
        275                 280                 285

Asp Val Phe Glu Thr Phe Val Thr Leu Thr Asn Gly Pro Leu Arg Val
    290                 295                 300

Asn Pro Leu Ser Val Gly Asp Trp Ala Glu Met Ile Leu Ser Lys Ala
305                 310                 315                 320
```

```
Phe Trp Val Phe Tyr Arg Ile Tyr Leu Pro Leu Ala Val Leu Gln Val
                325                 330                 335

Asp Pro Ala Arg Phe Trp Gly Val Phe Phe Leu Ala Glu Phe Ser Thr
            340                 345                 350

Gly Trp Tyr Leu Ala Phe Asn Phe Gln Val Ser His Val Ser Thr Ala
        355                 360                 365

Cys Glu Tyr Pro Gly Gly Asp Glu Glu Val Thr Ser Ile Asp Asp Glu
    370                 375                 380

Trp Ala Ile Ser Gln Val Lys Ser Ser Val Asp Tyr Gly His Gly Ser
385                 390                 395                 400

Phe Ile Thr Thr Phe Leu Thr Gly Ala Leu Asn Tyr Gln Val Thr His
                405                 410                 415

His Leu Phe Pro Gly Val Ser Gln Tyr His Tyr Pro Ala Ile Ala Pro
            420                 425                 430

Leu Ile Leu Asp Val Cys His Lys Tyr Lys Val Lys Tyr Asn Val Leu
        435                 440                 445

Pro Asp Phe Thr Ala Ala Met Ala Gly His Phe Asp His Leu Val Ile
    450                 455                 460

Met Gly Lys Met Gly Lys Arg Val Thr Ile His Met Gly
465                 470                 475


<210> SEQ ID NO 14
<211> LENGTH: 469
<212> TYPE: PRT
<213> ORGANISM: Phaeodactylum tricornutum (GenBank Accession No.
      AAL92562)
<220> FEATURE:
<221> NAME/KEY: MISC_FEATURE
<223> OTHER INFORMATION: delta-5 desaturase

<400> SEQUENCE: 14

Met Ala Pro Asp Ala Asp Lys Leu Arg Gln Arg Gln Thr Thr Ala Val
1               5                   10                  15

Ala Lys His Asn Ala Ala Thr Ile Ser Thr Gln Glu Arg Leu Cys Ser
            20                  25                  30

Leu Ser Ser Leu Lys Gly Glu Glu Val Cys Ile Asp Gly Ile Ile Tyr
        35                  40                  45

Asp Leu Gln Ser Phe Asp His Pro Gly Gly Glu Thr Ile Lys Met Phe
    50                  55                  60

Gly Gly Asn Asp Val Thr Val Gln Tyr Lys Met Ile His Pro Tyr His
65                  70                  75                  80

Thr Glu Lys His Leu Glu Lys Met Lys Arg Val Gly Lys Val Thr Asp
                85                  90                  95

Phe Val Cys Glu Tyr Lys Phe Asp Thr Glu Phe Glu Arg Glu Ile Lys
            100                 105                 110

Arg Glu Val Phe Lys Ile Val Arg Arg Gly Lys Asp Phe Gly Thr Leu
        115                 120                 125

Gly Trp Phe Phe Arg Ala Phe Cys Tyr Ile Ala Ile Phe Phe Tyr Leu
    130                 135                 140

Gln Tyr His Trp Val Thr Thr Gly Thr Ser Trp Leu Leu Ala Val Ala
145                 150                 155                 160

Tyr Gly Ile Ser Gln Ala Met Ile Gly Met Asn Val Gln His Asp Ala
                165                 170                 175

Asn His Gly Ala Thr Ser Lys Arg Pro Trp Val Asn Asp Met Leu Gly
            180                 185                 190

Leu Gly Ala Asp Phe Ile Gly Gly Ser Lys Trp Leu Trp Gln Glu Gln
```

```
        195                 200                 205

His Trp Thr His His Ala Tyr Thr Asn His Ala Glu Met Asp Pro Asp
    210                 215                 220

Ser Phe Gly Ala Glu Pro Met Leu Leu Phe Asn Asp Tyr Pro Leu Asp
225                 230                 235                 240

His Pro Ala Arg Thr Trp Leu His Arg Phe Gln Ala Phe Phe Tyr Met
                245                 250                 255

Pro Val Leu Ala Gly Tyr Trp Leu Ser Ala Val Phe Asn Pro Gln Ile
            260                 265                 270

Leu Asp Leu Gln Gln Arg Gly Ala Leu Ser Val Gly Ile Arg Leu Asp
        275                 280                 285

Asn Ala Phe Ile His Ser Arg Arg Lys Tyr Ala Val Phe Trp Arg Ala
    290                 295                 300

Val Tyr Ile Ala Val Asn Val Ile Ala Pro Phe Tyr Thr Asn Ser Gly
305                 310                 315                 320

Leu Glu Trp Ser Trp Arg Val Phe Gly Asn Ile Met Leu Met Gly Val
                325                 330                 335

Ala Glu Ser Leu Ala Leu Ala Val Leu Phe Ser Leu Ser His Asn Phe
            340                 345                 350

Glu Ser Ala Asp Arg Asp Pro Thr Ala Pro Leu Lys Lys Thr Gly Glu
        355                 360                 365

Pro Val Asp Trp Phe Lys Thr Gln Val Glu Thr Ser Cys Thr Tyr Gly
    370                 375                 380

Gly Phe Leu Ser Gly Cys Phe Thr Gly Gly Leu Asn Phe Gln Val Glu
385                 390                 395                 400

His His Leu Phe Pro Arg Met Ser Ser Ala Trp Tyr Pro Tyr Ile Ala
                405                 410                 415

Pro Lys Val Arg Glu Ile Cys Ala Lys His Gly Val His Tyr Ala Tyr
            420                 425                 430

Tyr Pro Trp Ile His Gln Asn Phe Leu Ser Thr Val Arg Tyr Met His
        435                 440                 445

Ala Ala Gly Thr Gly Ala Asn Trp Arg Gln Met Ala Arg Glu Asn Pro
    450                 455                 460

Leu Thr Gly Arg Ala
465


<210> SEQ ID NO 15
<211> LENGTH: 467
<212> TYPE: PRT
<213> ORGANISM: Dictyostelium discoideum (GenBank Accession No.
      XP_640331)
<220> FEATURE:
<221> NAME/KEY: MISC_FEATURE
<223> OTHER INFORMATION: delta-5 desaturase

<400> SEQUENCE: 15

Met Met Glu Thr Asn Asn Glu Asn Lys Glu Lys Leu Lys Leu Tyr Thr
1               5                   10                  15

Trp Asp Glu Val Ser Lys His Asn Gln Lys Asn Asp Leu Trp Ile Ile
            20                  25                  30

Val Asp Gly Lys Val Tyr Asn Ile Thr Lys Trp Val Pro Leu His Pro
        35                  40                  45

Gly Gly Glu Asp Ile Leu Leu Leu Ser Ala Gly Arg Asp Ala Thr Asn
    50                  55                  60

Leu Phe Glu Ser Tyr His Pro Met Thr Asp Lys His Tyr Ser Leu Ile
65                  70                  75                  80
```

```
Lys Gln Tyr Glu Ile Gly Tyr Ile Ser Ser Tyr Glu His Pro Lys Tyr
                85                  90                  95

Val Glu Lys Ser Glu Phe Tyr Ser Thr Leu Lys Gln Arg Val Arg Lys
            100                 105                 110

His Phe Gln Thr Ser Ser Gln Asp Pro Lys Val Ser Val Gly Val Phe
        115                 120                 125

Thr Arg Met Val Leu Ile Tyr Leu Phe Leu Phe Val Thr Tyr Tyr Leu
    130                 135                 140

Ser Gln Phe Ser Thr Asp Arg Phe Trp Leu Asn Cys Ile Phe Ala Val
145                 150                 155                 160

Leu Tyr Gly Val Ala Asn Ser Leu Phe Gly Leu His Thr Met His Asp
                165                 170                 175

Ala Cys His Thr Ala Ile Thr His Asn Pro Met Thr Trp Lys Ile Leu
            180                 185                 190

Gly Ala Thr Phe Asp Leu Phe Ala Gly Ala Ser Phe Tyr Ala Trp Cys
        195                 200                 205

His Gln His Val Ile Gly His His Leu Tyr Thr Asn Val Arg Asn Ala
    210                 215                 220

Asp Pro Asp Leu Gly Gln Gly Glu Ile Asp Phe Arg Val Val Thr Pro
225                 230                 235                 240

Tyr Gln Ala Arg Ser Trp Tyr His Lys Tyr Gln His Ile Tyr Ala Pro
                245                 250                 255

Ile Leu Tyr Gly Val Tyr Ala Leu Lys Tyr Arg Ile Gln Asp His Glu
            260                 265                 270

Ile Phe Thr Lys Lys Ser Asn Gly Ala Ile Arg Tyr Ser Pro Ile Ser
        275                 280                 285

Thr Ile Asp Thr Ala Ile Phe Ile Leu Gly Lys Leu Val Phe Ile Ile
    290                 295                 300

Ser Arg Phe Ile Leu Pro Leu Ile Tyr Asn His Ser Phe Ser His Leu
305                 310                 315                 320

Ile Cys Phe Phe Leu Ile Ser Glu Leu Val Leu Gly Trp Tyr Leu Ala
                325                 330                 335

Ile Ser Phe Gln Val Ser His Val Val Glu Asp Leu Gln Phe Met Ala
            340                 345                 350

Thr Pro Glu Ile Phe Asp Gly Ala Asp His Pro Leu Pro Thr Thr Phe
        355                 360                 365

Asn Gln Asp Trp Ala Ile Leu Gln Val Lys Thr Thr Gln Asp Tyr Ala
    370                 375                 380

Gln Asp Ser Val Leu Ser Thr Phe Phe Ser Gly Gly Leu Asn Leu Gln
385                 390                 395                 400

Val Ile His His Cys Phe Pro Thr Ile Ala Gln Asp Tyr Tyr Pro Gln
                405                 410                 415

Ile Val Pro Ile Leu Lys Glu Val Cys Lys Glu Tyr Asn Val Thr Tyr
            420                 425                 430

His Tyr Lys Pro Thr Phe Thr Glu Ala Ile Lys Ser His Ile Asn Tyr
        435                 440                 445

Leu Tyr Lys Met Gly Asn Asp Pro Asp Tyr Val Arg Lys Pro Val Asn
    450                 455                 460

Lys Asn Asp
465
```

<210> SEQ ID NO 16
<211> LENGTH: 421
<212> TYPE: PRT
<213> ORGANISM: Euglena gracilis
<220> FEATURE:
<221> NAME/KEY: MISC_FEATURE
<223> OTHER INFORMATION: delta-8 desaturase
<300> PUBLICATION INFORMATION:
<302> TITLE: DELTA-8 DESATURASE AND ITS USE IN MAKING POLYUNSATURATED FATTY ACIDS
<310> PATENT DOCUMENT NUMBER: WO2006012325
<311> PATENT FILING DATE: 2005-06-24
<312> PUBLICATION DATE: 2006-02-02
<313> RELEVANT RESIDUES IN SEQ ID NO: (1)..(421)
<300> PUBLICATION INFORMATION:
<302> TITLE: DELTA-8 DESATURASE AND ITS USE IN MAKING POLYUNSATURATED FATTY ACIDS
<310> PATENT DOCUMENT NUMBER: WO2006012326
<311> PATENT FILING DATE: 2005-06-24
<312> PUBLICATION DATE: 2006-02-02
<313> RELEVANT RESIDUES IN SEQ ID NO: (1)..(421)

<400> SEQUENCE: 16

```
Met Lys Ser Lys Arg Gln Ala Leu Pro Leu Thr Ile Asp Gly Thr Thr
1               5                   10                  15

Tyr Asp Val Ser Ala Trp Val Asn Phe His Pro Gly Gly Ala Glu Ile
            20                  25                  30

Ile Glu Asn Tyr Gln Gly Arg Asp Ala Thr Asp Ala Phe Met Val Met
        35                  40                  45

His Ser Gln Glu Ala Phe Asp Lys Leu Lys Arg Met Pro Lys Ile Asn
    50                  55                  60

Pro Ser Ser Glu Leu Pro Pro Gln Ala Ala Val Asn Glu Ala Gln Glu
65                  70                  75                  80

Asp Phe Arg Lys Leu Arg Glu Glu Leu Ile Ala Thr Gly Met Phe Asp
                85                  90                  95

Ala Ser Pro Leu Trp Tyr Ser Tyr Lys Ile Ser Thr Thr Leu Gly Leu
            100                 105                 110

Gly Val Leu Gly Tyr Phe Leu Met Val Gln Tyr Gln Met Tyr Phe Ile
        115                 120                 125

Gly Ala Val Leu Leu Gly Met His Tyr Gln Gln Met Gly Trp Leu Ser
    130                 135                 140

His Asp Ile Cys His His Gln Thr Phe Lys Asn Arg Asn Trp Asn Asn
145                 150                 155                 160

Leu Val Gly Leu Val Phe Gly Asn Gly Leu Gln Gly Phe Ser Val Thr
                165                 170                 175

Trp Trp Lys Asp Arg His Asn Ala His His Ser Ala Thr Asn Val Gln
            180                 185                 190

Gly His Asp Pro Asp Ile Asp Asn Leu Pro Leu Leu Ala Trp Ser Glu
        195                 200                 205

Asp Asp Val Thr Arg Ala Ser Pro Ile Ser Arg Lys Leu Ile Gln Phe
    210                 215                 220

Gln Gln Tyr Tyr Phe Leu Val Ile Cys Ile Leu Leu Arg Phe Ile Trp
225                 230                 235                 240

Cys Phe Gln Ser Val Leu Thr Val Arg Ser Leu Lys Asp Arg Asp Asn
                245                 250                 255

Gln Phe Tyr Arg Ser Gln Tyr Lys Lys Glu Ala Ile Gly Leu Ala Leu
            260                 265                 270

His Trp Thr Leu Lys Thr Leu Phe His Leu Phe Phe Met Pro Ser Ile
        275                 280                 285

Leu Thr Ser Leu Leu Val Phe Phe Val Ser Glu Leu Val Gly Gly Phe
    290                 295                 300

Gly Ile Ala Ile Val Val Phe Met Asn His Tyr Pro Leu Glu Lys Ile
305                 310                 315                 320
```

```
Gly Asp Ser Val Trp Asp Gly His Gly Phe Ser Val Gly Gln Ile His
                325                 330                 335

Glu Thr Met Asn Ile Arg Arg Gly Ile Ile Thr Asp Trp Phe Phe Gly
            340                 345                 350

Gly Leu Asn Tyr Gln Ile Glu His His Leu Trp Pro Thr Leu Pro Arg
        355                 360                 365

His Asn Leu Thr Ala Val Ser Tyr Gln Val Glu Gln Leu Cys Gln Lys
    370                 375                 380

His Asn Leu Pro Tyr Arg Asn Pro Leu Pro His Glu Gly Leu Val Ile
385                 390                 395                 400

Leu Leu Arg Tyr Leu Ala Val Phe Ala Arg Met Ala Glu Lys Gln Pro
                405                 410                 415

Ala Gly Lys Ala Leu
            420


<210> SEQ ID NO 17
<211> LENGTH: 1269
<212> TYPE: DNA
<213> ORGANISM: Pavlova lutheri CCMP459
<220> FEATURE:
<221> NAME/KEY: misc_feature
<223> OTHER INFORMATION: delta-8 desaturase

<400> SEQUENCE: 17

atgggcaagg gtggagacgg cggcgcgcag gcggtgagcg ggaccgacgc gtctctcgct      60

gaggtgagct ccgtcgatag caagagcgtg cacgtcgtgc tctacggcaa gcgcgtggat     120

gtcacaaagt tccagaaggc acacccgggc gggagcaagg tgttccgcat cttccaggag     180

cgcgacgcga cggagcagtt cgagtcttac cactcgccca aggccatcaa gatgatggag     240

ggcatgctca agaagtcgga ggatgcgccc gcttccgtgc cctgccctc gcggtccacc     300

atgggcacgg agttcaagga gatgattgag cgccacaaga gggctggtct ctacgaccct     360

tgcccgttgg acgagctgtt caagctcacc atcgtccttg cgcccatctt cgtgggcgcc     420

tatctcgtgc ggagcggcgt ctcgccccctc gcgggcgcgc tctccatggg ctttggcttc     480

tacctcgacg gctggcttgc tcacgactac ctgcatcacg cagtcttcaa gggctcggtc     540

aacacgctcg tcaaggcgaa caacgccatg ggatacgccc tcggcttcct ccagggctac     600

gacgtggcct ggtggcgcgc gcgccataac acgcaccacg tgtgcaccaa cgaggatggt     660

tcggacccgg acatcaagac ggcgcccctg ctcatctacg tgcgagagaa cccgtccatt     720

gccaagcggc tcaacttctt ccagcgctgg cagcagtact actatgtgcc gaccatggcc     780

atcctcgacc tctactggcg cctggagtcc atcgcgtacg tggctgtgcg cctgcctaag     840

atgtggatgc aggccgccgc tcttgccgct cactacgcgc tcctgtgctg ggtcttcgca     900

gcgcatctca acctcatccc tctcatgatg gttgcacgcg gcttcgcgac gggcatcgtt     960

gtctttgcaa cccactatgg tgaggacatc ctcgaccgcg agcacgtcga gggcatgacg    1020

ctcgtcgagc agaccgccaa gacctcccgt aacatcacgg gcggctggct agtgaacgtg    1080

ctcacgggct tcatctccct gcagaccgag catcacctct tccccatgat gcccaccggc    1140

aacctaatga ctatccagcc cgaggtacgc gacttcttca agaagcatgg cctcgagtac    1200

cgcgagggca acctcttcca gtgcgtgcac cagaacatca aggctctcgc cttcgagcac    1260

ctcctccac                                                            1269

<210> SEQ ID NO 18
<211> LENGTH: 423
<212> TYPE: PRT
```

<213> ORGANISM: Pavlova lutheri CCMP459

<400> SEQUENCE: 18

```
Met Gly Lys Gly Gly Asp Gly Gly Ala Gln Ala Val Ser Gly Thr Asp
1               5                   10                  15

Ala Ser Leu Ala Glu Val Ser Ser Val Asp Ser Lys Ser Val His Val
            20                  25                  30

Val Leu Tyr Gly Lys Arg Val Asp Val Thr Lys Phe Gln Lys Ala His
        35                  40                  45

Pro Gly Gly Ser Lys Val Phe Arg Ile Phe Gln Glu Arg Asp Ala Thr
    50                  55                  60

Glu Gln Phe Glu Ser Tyr His Ser Pro Lys Ala Ile Lys Met Met Glu
65                  70                  75                  80

Gly Met Leu Lys Lys Ser Glu Asp Ala Pro Ala Ser Val Pro Leu Pro
                85                  90                  95

Ser Arg Ser Thr Met Gly Thr Glu Phe Lys Glu Met Ile Glu Arg His
            100                 105                 110

Lys Arg Ala Gly Leu Tyr Asp Pro Cys Pro Leu Asp Glu Leu Phe Lys
        115                 120                 125

Leu Thr Ile Val Leu Ala Pro Ile Phe Val Gly Ala Tyr Leu Val Arg
    130                 135                 140

Ser Gly Val Ser Pro Leu Ala Gly Ala Leu Ser Met Gly Phe Gly Phe
145                 150                 155                 160

Tyr Leu Asp Gly Trp Leu Ala His Asp Tyr Leu His His Ala Val Phe
                165                 170                 175

Lys Gly Ser Val Asn Thr Leu Val Lys Ala Asn Asn Ala Met Gly Tyr
            180                 185                 190

Ala Leu Gly Phe Leu Gln Gly Tyr Asp Val Ala Trp Trp Arg Ala Arg
        195                 200                 205

His Asn Thr His His Val Cys Thr Asn Glu Asp Gly Ser Asp Pro Asp
    210                 215                 220

Ile Lys Thr Ala Pro Leu Leu Ile Tyr Val Arg Glu Asn Pro Ser Ile
225                 230                 235                 240

Ala Lys Arg Leu Asn Phe Phe Gln Arg Trp Gln Gln Tyr Tyr Tyr Val
                245                 250                 255

Pro Thr Met Ala Ile Leu Asp Leu Tyr Trp Arg Leu Glu Ser Ile Ala
            260                 265                 270

Tyr Val Ala Val Arg Leu Pro Lys Met Trp Met Gln Ala Ala Ala Leu
        275                 280                 285

Ala Ala His Tyr Ala Leu Leu Cys Trp Val Phe Ala Ala His Leu Asn
    290                 295                 300

Leu Ile Pro Leu Met Met Val Ala Arg Gly Phe Ala Thr Gly Ile Val
305                 310                 315                 320

Val Phe Ala Thr His Tyr Gly Glu Asp Ile Leu Asp Arg Glu His Val
                325                 330                 335

Glu Gly Met Thr Leu Val Glu Gln Thr Ala Lys Thr Ser Arg Asn Ile
            340                 345                 350

Thr Gly Gly Trp Leu Val Asn Val Leu Thr Gly Phe Ile Ser Leu Gln
        355                 360                 365

Thr Glu His His Leu Phe Pro Met Met Pro Thr Gly Asn Leu Met Thr
    370                 375                 380

Ile Gln Pro Glu Val Arg Asp Phe Phe Lys Lys His Gly Leu Glu Tyr
385                 390                 395                 400

Arg Glu Gly Asn Leu Phe Gln Cys Val His Gln Asn Ile Lys Ala Leu
```

```
                405                 410                 415

Ala Phe Glu His Leu Leu His
            420


<210> SEQ ID NO 19
<211> LENGTH: 7
<212> TYPE: PRT
<213> ORGANISM: Artificial Sequence
<220> FEATURE:
<223> OTHER INFORMATION: Conserved Region 1
<220> FEATURE:
<221> NAME/KEY: MISC_FEATURE
<222> LOCATION: (4)..(4)
<223> OTHER INFORMATION: Xaa = Ile or Val

<400> SEQUENCE: 19

Gly His His Xaa Tyr Thr Asn
1               5


<210> SEQ ID NO 20
<211> LENGTH: 7
<212> TYPE: PRT
<213> ORGANISM: Artificial Sequence
<220> FEATURE:
<223> OTHER INFORMATION: Conserved Region 2
<220> FEATURE:
<221> NAME/KEY: MISC_FEATURE
<222> LOCATION: (4)..(4)
<223> OTHER INFORMATION: Xaa = Val or Ala
<220> FEATURE:
<221> NAME/KEY: MISC_FEATURE
<222> LOCATION: (5)..(5)
<223> OTHER INFORMATION: Xaa = Ser or Asn

<400> SEQUENCE: 20

Asn Phe Gln Xaa Xaa His Val
1               5


<210> SEQ ID NO 21
<211> LENGTH: 476
<212> TYPE: PRT
<213> ORGANISM: Thalassiosira pseudonana (GenBank Accession No.
      AAX14502)
<220> FEATURE:
<221> NAME/KEY: MISC_FEATURE
<223> OTHER INFORMATION: delta-8 desaturase

<400> SEQUENCE: 21

Met Pro Pro Asn Ala Asp Ile Ser Arg Ile Arg Asn Arg Ile Pro Thr
1               5                   10                  15

Lys Thr Gly Thr Val Ala Ser Ala Asp Asn Asn Asp Pro Ala Thr Gln
            20                  25                  30

Ser Val Arg Thr Leu Lys Ser Leu Lys Gly Asn Glu Val Val Ile Asn
        35                  40                  45

Gly Thr Ile Tyr Asp Ile Ala Asp Phe Val His Pro Gly Gly Glu Val
    50                  55                  60

Val Lys Phe Phe Gly Gly Asn Asp Val Thr Ile Gln Tyr Asn Met Ile
65                  70                  75                  80

His Pro Tyr His Thr Gly Lys His Leu Glu Lys Met Lys Ala Val Gly
                85                  90                  95

Lys Val Val Asp Trp Gln Ser Asp Tyr Lys Phe Asp Thr Pro Phe Glu
            100                 105                 110

Arg Glu Ile Lys Ser Glu Val Phe Lys Ile Val Arg Arg Gly Arg Glu
        115                 120                 125

Phe Gly Thr Thr Gly Tyr Phe Leu Arg Ala Phe Phe Tyr Ile Ala Leu
```

```
    130                 135                 140

Phe Phe Thr Met Gln Tyr Thr Phe Ala Thr Cys Thr Thr Phe Thr Thr
145                 150                 155                 160

Tyr Asp His Trp Tyr Gln Ser Gly Val Phe Ile Ala Ile Val Phe Gly
                165                 170                 175

Ile Ser Gln Ala Phe Ile Gly Leu Asn Val Gln His Asp Ala Asn His
            180                 185                 190

Gly Ala Ala Ser Lys Arg Pro Trp Val Asn Asp Leu Leu Gly Phe Gly
        195                 200                 205

Thr Asp Leu Ile Gly Ser Asn Lys Trp Asn Trp Met Ala Gln His Trp
    210                 215                 220

Thr His His Ala Tyr Thr Asn His Ser Glu Lys Asp Pro Asp Ser Phe
225                 230                 235                 240

Ser Ser Glu Pro Met Phe Ala Phe Asn Asp Tyr Pro Ile Gly His Pro
                245                 250                 255

Lys Arg Lys Trp Trp His Arg Phe Gln Gly Gly Tyr Phe Leu Phe Met
            260                 265                 270

Leu Gly Leu Tyr Trp Leu Pro Thr Val Phe Asn Pro Gln Phe Ile Asp
        275                 280                 285

Leu Arg Gln Arg Gly Ala Gln Tyr Val Gly Ile Gln Met Glu Asn Asp
    290                 295                 300

Phe Ile Val Lys Arg Arg Lys Tyr Ala Val Ala Leu Arg Met Met Tyr
305                 310                 315                 320

Ile Tyr Leu Asn Ile Val Ser Pro Phe Met Asn Asn Gly Leu Ser Trp
                325                 330                 335

Ser Thr Phe Gly Ile Ile Met Leu Met Gly Ile Ser Glu Ser Leu Thr
            340                 345                 350

Leu Ser Val Leu Phe Ser Leu Ser His Asn Phe Ile Asn Ser Asp Arg
        355                 360                 365

Asp Pro Thr Ala Asp Phe Lys Lys Thr Gly Glu Gln Val Cys Trp Phe
    370                 375                 380

Lys Ser Gln Val Glu Thr Ser Ser Thr Tyr Gly Gly Phe Ile Ser Gly
385                 390                 395                 400

Cys Leu Thr Gly Gly Leu Asn Phe Gln Val Glu His His Leu Phe Pro
                405                 410                 415

Arg Met Ser Ser Ala Trp Tyr Pro Tyr Ile Ala Pro Thr Val Arg Glu
            420                 425                 430

Val Cys Lys Lys His Gly Met Ser Tyr Ala Tyr Tyr Pro Trp Ile Gly
        435                 440                 445

Gln Asn Leu Val Ser Thr Phe Lys Tyr Met His Arg Ala Gly Ser Gly
    450                 455                 460

Ala Asn Trp Glu Leu Lys Pro Leu Ser Gly Ser Ala
465                 470                 475
```

<210> SEQ ID NO 22
<211> LENGTH: 8165
<212> TYPE: DNA
<213> ORGANISM: Artificial Sequence
<220> FEATURE:
<223> OTHER INFORMATION: Plasmid pZUF17

<400> SEQUENCE: 22

```
gtacgagccg gaagcataaa gtgtaaagcc tggggtgcct aatgagtgag ctaactcaca     60

ttaattgcgt tgcgctcact gcccgctttc cagtcgggaa acctgtcgtg ccagctgcat    120

taatgaatcg gccaacgcgc ggggagaggc ggtttgcgta ttgggcgctc ttccgcttcc    180
```

```
tcgctcactg actcgctgcg ctcggtcgtt cggctgcggc gagcggtatc agctcactca    240
aaggcggtaa tacggttatc cacagaatca ggggataacg caggaaagaa catgtgagca    300
aaaggccagc aaaaggccag gaaccgtaaa aaggccgcgt tgctggcgtt tttccatagg    360
ctccgccccc ctgacgagca tcacaaaaat cgacgctcaa gtcagaggtg gcgaaacccg    420
acaggactat aaagatacca ggcgtttccc cctggaagct ccctcgtgcg ctctcctgtt    480
ccgaccctgc cgcttaccgg atacctgtcc gcctttctcc cttcgggaag cgtggcgctt    540
tctcatagct cacgctgtag gtatctcagt tcggtgtagg tcgttcgctc caagctgggc    600
tgtgtgcacg aaccccccgt tcagcccgac cgctgcgcct tatccggtaa ctatcgtctt    660
gagtccaacc cggtaagaca cgacttatcg ccactggcag cagccactgg taacaggatt    720
agcagagcga ggtatgtagg cggtgctaca gagttcttga agtggtggcc taactacggc    780
tacactagaa ggacagtatt tggtatctgc gctctgctga agccagttac cttcggaaaa    840
agagttggta gctcttgatc cggcaaacaa accaccgctg gtagcggtgg tttttttgtt    900
tgcaagcagc agattacgcg cagaaaaaaa ggatctcaag aagatccttt gatcttttct    960
acggggtctg acgctcagtg gaacgaaaac tcacgttaag ggattttggt catgagatta   1020
tcaaaaagga tcttcaccta gatcctttta aattaaaaat gaagttttaa atcaatctaa   1080
agtatatatg agtaaacttg gtctgacagt taccaatgct taatcagtga ggcacctatc   1140
tcagcgatct gtctatttcg ttcatccata gttgcctgac tccccgtcgt gtagataact   1200
acgatacggg agggcttacc atctggcccc agtgctgcaa tgataccgcg agacccacgc   1260
tcaccggctc cagatttatc agcaataaac cagccagccg gaagggccga gcgcagaagt   1320
ggtcctgcaa ctttatccgc ctccatccag tctattaatt gttgccggga agctagagta   1380
agtagttcgc cagttaatag tttgcgcaac gttgttgcca ttgctacagg catcgtggtg   1440
tcacgctcgt cgtttggtat ggcttcattc agctccggtt cccaacgatc aaggcgagtt   1500
acatgatccc ccatgttgtg caaaaaagcg gttagctcct tcggtcctcc gatcgttgtc   1560
agaagtaagt tggccgcagt gttatcactc atggttatgg cagcactgca taattctctt   1620
actgtcatgc catccgtaag atgcttttct gtgactggtg agtactcaac caagtcattc   1680
tgagaatagt gtatgcggcg accgagttgc tcttgcccgg cgtcaatacg ggataatacc   1740
gcgccacata gcagaacttt aaaagtgctc atcattggaa aacgttcttc ggggcgaaaa   1800
ctctcaagga tcttaccgct gttgagatcc agttcgatgt aacccactcg tgcacccaac   1860
tgatcttcag catcttttac tttcaccagc gtttctgggt gagcaaaaac aggaaggcaa   1920
aatgccgcaa aaaagggaat aagggcgaca cggaaatgtt gaatactcat actcttcctt   1980
tttcaatatt attgaagcat ttatcagggt tattgtctca tgagcggata catatttgaa   2040
tgtatttaga aaaataaaca aataggggtt ccgcgcacat ttccccgaaa agtgccacct   2100
gacgcgccct gtagcggcgc attaagcgcg gcgggtgtgg tggttacgcg cagcgtgacc   2160
gctacacttg ccagcgccct agcgcccgct cctttcgctt tcttcccttc ctttctcgcc   2220
acgttcgccg gctttccccg tcaagctcta aatcgggggc tccctttagg gttccgattt   2280
agtgctttac ggcacctcga ccccaaaaaa cttgattagg gtgatggttc acgtagtggg   2340
ccatcgccct gatagacggt ttttcgccct ttgacgttgg agtccacgtt ctttaatagt   2400
ggactcttgt tccaaactgg aacaacactc aaccctatct cggtctattc ttttgattta   2460
taagggattt tgccgatttc ggcctattgg ttaaaaaatg agctgattta acaaaaattt   2520
aacgcgaatt ttaacaaaat attaacgctt acaatttcca ttcgccattc aggctgcgca   2580
```

```
actgttggga agggcgatcg gtgcgggcct cttcgctatt acgccagctg gcgaaagggg   2640
gatgtgctgc aaggcgatta agttgggtaa cgccagggtt ttcccagtca cgacgttgta   2700
aaacgacggc cagtgaattg taatacgact cactataggg cgaattgggt accgggcccc   2760
ccctcgaggt cgatggtgtc gataagcttg atatcgaatt catgtcacac aaaccgatct   2820
tcgcctcaag gaaacctaat tctacatccg agagactgcc gagatccagt ctacactgat   2880
taattttcgg gccaataatt taaaaaaatc gtgttatata atattatatg tattatatat   2940
atacatcatg atgatactga cagtcatgtc ccattgctaa atagacagac tccatctgcc   3000
gcctccaact gatgttctca atatttaagg ggtcatctcg cattgtttaa taataaacag   3060
actccatcta ccgcctccaa atgatgttct caaaatatat tgtatgaact tatttttatt   3120
acttagtatt attagacaac ttacttgctt tatgaaaaac acttcctatt taggaaacaa   3180
tttataatgg cagttcgttc atttaacaat ttatgtagaa taaatgttat aaatgcgtat   3240
gggaaatctt aaatatggat agcataaatg atatctgcat tgcctaattc gaaatcaaca   3300
gcaacgaaaa aaatcccttg tacaacataa atagtcatcg agaaatatca actatcaaag   3360
aacagctatt cacacgttac tattgagatt attattggac gagaatcaca cactcaactg   3420
tctttctctc ttctagaaat acaggtacaa gtatgtacta ttctcattgt tcatacttct   3480
agtcatttca tcccacatat tccttggatt tctctccaat gaatgacatt ctatcttgca   3540
aattcaacaa ttataataag atataccaaa gtagcggtat agtggcaatc aaaaagcttc   3600
tctggtgtgc ttctcgtatt tatttttatt ctaatgatcc attaaaggta tatatttatt   3660
tcttgttata taatcctttt gtttattaca tgggctggat acataaaggt attttgattt   3720
aatttttttgc ttaaattcaa tccccccctcg ttcagtgtca actgtaatgg taggaaatta   3780
ccatactttt gaagaagcaa aaaaaatgaa agaaaaaaaa aatcgtattt ccaggttaga   3840
cgttccgcag aatctagaat gcggtatgcg gtacattgtt cttcgaacgt aaaagttgcg   3900
ctccctgaga tattgtacat ttttgctttt acaagtacaa gtacatcgta caactatgta   3960
ctactgttga tgcatccaca acagtttgtt ttgttttttt ttgttttttt tttttctaat   4020
gattcattac cgctatgtat acctacttgt acttgtagta agccgggtta ttggcgttca   4080
attaatcata gacttatgaa tctgcacggt gtgcgctgcg agttactttt agcttatgca   4140
tgctacttgg gtgtaatatt gggatctgtt cggaaatcaa cggatgctca atcgatttcg   4200
acagtaatta attaagtcat acacaagtca gctttcttcg agcctcatat aagtataagt   4260
agttcaacgt attagcactg tacccagcat ctccgtatcg agaaacacaa caacatgccc   4320
cattggacag atcatgcgga tacacaggtt gtgcagtatc atacatactc gatcagacag   4380
gtcgtctgac catcatacaa gctgaacaag cgctccatac ttgcacgctc tctatataca   4440
cagttaaatt acatatccat agtctaacct ctaacagtta atcttctggt aagcctccca   4500
gccagccttc tggtatcgct tggcctcctc aataggatct cggttctggc cgtacagacc   4560
tcggccgaca attatgatat ccgttccggt agacatgaca tcctcaacag ttcggtactg   4620
ctgtccgaga gcgtctccct tgtcgtcaag acccaccccg gggtcagaa taagccagtc   4680
ctcagagtcg cccttaggtc ggttctgggc aatgaagcca accacaaact cggggtcgga   4740
tcgggcaagc tcaatggtct gcttggagta ctcgccagtg gccagagagc ccttgcaaga   4800
cagctcggcc agcatgagca gacctctggc cagcttctcg ttgggagagg ggactaggaa   4860
ctccttgtac tgggagttct cgtagtcaga gacgtcctcc ttcttctgtt cagagacagt   4920
ttcctcggca ccagctcgca ggccagcaat gattccggtt ccgggtacac cgtgggcgtt   4980
```

```
ggtgatatcg gaccactcgg cgattcggtg acaccggtac tggtgcttga cagtgttgcc   5040
aatatctgcg aactttctgt cctcgaacag gaagaaaccg tgcttaagag caagttcctt   5100
gagggggagc acagtgccgg cgtaggtgaa gtcgtcaatg atgtcgatat gggttttgat   5160
catgcacaca taaggtccga ccttatcggc aagctcaatg agctccttgg tggtggtaac   5220
atccagagaa gcacacaggt tggttttctt ggctgccacg agcttgagca ctcgagcggc   5280
aaaggcggac ttgtggacgt tagctcgagc ttcgtaggag ggcattttgg tggtgaagag   5340
gagactgaaa taaatttagt ctgcagaact tttatcgga accttatctg gggcagtgaa   5400
gtatatgtta tggtaatagt tacgagttag ttgaacttat agatagactg gactatacgg   5460
ctatcggtcc aaattagaaa gaacgtcaat ggctctctgg gcgtcgcctt tgccgacaaa   5520
aatgtgatca tgatgaaagc cagcaatgac gttgcagctg atattgttgt cggccaaccg   5580
cgccgaaaac gcagctgtca gacccacagc ctccaacgaa gaatgtatcg tcaaagtgat   5640
ccaagcacac tcatagttgg agtcgtactc caaaggcggc aatgacgagt cagacagata   5700
ctcgtcgact caggcgacga cggaattcct gcagcccatc tgcagaattc aggagagacc   5760
gggttggcgg cgtatttgtg tcccaaaaaa cagccccaat tgccccggag aagacggcca   5820
ggccgcctag atgacaaatt caacaactca cagctgactt tctgccattg ccactagggg   5880
ggggcctttt tatatggcca agccaagctc tccacgtcgg ttgggctgca cccaacaata   5940
aatgggtagg gttgcaccaa caaagggatg ggatgggggg tagaagatac gaggataacg   6000
gggctcaatg gcacaaataa gaacgaatac tgccattaag actcgtgatc cagcgactga   6060
caccattgca tcatctaagg gcctcaaaac tacctcggaa ctgctgcgct gatctggaca   6120
ccacagaggt tccgagcact ttaggttgca ccaaatgtcc caccaggtgc aggcagaaaa   6180
cgctggaaca gcgtgtacag tttgtcttaa caaaaagtga gggcgctgag gtcgagcagg   6240
gtggtgtgac ttgttatagc ctttagagct gcgaaagcgc gtatggattt ggctcatcag   6300
gccagattga gggtctgtgg acacatgtca tgttagtgta cttcaatcgc cccctggata   6360
tagccccgac aataggccgt ggcctcattt ttttgccttc cgcacatttc cattgctcgg   6420
tacccacacc ttgcttctcc tgcacttgcc aaccttaata ctggtttaca ttgaccaaca   6480
tcttacaagc ggggggcttg tctagggtat atataaacag tggctctccc aatcggttgc   6540
cagtctcttt tttcctttct ttccccacag attcgaaatc taaactacac atcacacaat   6600
gcctgttact gacgtcctta agcgaaagtc cggtgtcatc gtcggcgacg atgtccgagc   6660
cgtgagtatc cacgacaaga tcagtgtcga gacgacgcgt tttgtgtaat gacacaatcc   6720
gaaagtcgct agcaacacac actctctaca caaactaacc cagctctcca tggctgagga   6780
taagaccaag gtcgagttcc ctaccctgac tgagctgaag cactctatcc ctaacgcttg   6840
ctttgagtcc aacctcggac tctcgctcta ctacactgcc cgagcgatct tcaacgcatc   6900
tgcctctgct gctctgctct acgctgcccg atctactccc ttcattgccg ataacgttct   6960
gctccacgct ctggtttgcg ccacctacat ctacgtgcag ggtgtcatct tctggggttt   7020
ctttaccgtc ggtcacgact gtggtcactc tgccttctcc cgataccact ccgtcaactt   7080
catcattggc tgcatcatgc actctgccat tctgactccc ttcgagtcct ggcgagtgac   7140
ccaccgacac catcacaaga acactggcaa cattgataag gacgagatct tctaccctca   7200
tcggtccgtc aaggacctcc aggacgtgcg acaatgggtc tacaccctcg gaggtgcttg   7260
gtttgtctac ctgaaggtcg gatatgctcc tcgaaccatg tcccactttg acccctggga   7320
ccctctcctg cttcgacgag cctccgctgt catcgtgtcc ctcggagtct gggctgcctt   7380
```

cttcgctgcc tacgcctacc tcacatactc gctcggcttt gccgtcatgg gcctctacta 7440
ctatgctcct ctctttgtct ttgcttcgtt cctcgtcatt actaccttct tgcatcacaa 7500
cgacgaagct actccctggt acggtgactc ggagtggacc tacgtcaagg gcaacctgag 7560
ctccgtcgac cgatcgtacg gagctttcgt ggacaacctg tctcaccaca ttggcaccca 7620
ccaggtccat cacttgttcc ctatcattcc ccactacaag ctcaacgaag ccaccaagca 7680
ctttgctgcc gcttaccctc acctcgtgag acgtaacgac gagcccatca ttactgcctt 7740
cttcaagacc gctcacctct ttgtcaacta cggagctgtg cccgagactg ctcagatttt 7800
caccctcaaa gagtctgccg ctgcagccaa ggccaagagc gactaagcgg ccgcaagtgt 7860
ggatggggaa gtgagtgccc ggttctgtgt gcacaattgg caatccaaga tggatggatt 7920
caacacaggg atatagcgag ctacgtggtg gtgcgaggat atagcaacgg atatttatgt 7980
ttgacacttg agaatgtacg atacaagcac tgtccaagta caatactaaa catactgtac 8040
atactcatac tcgtacccgg gcaacggttt cacttgagtg cagtggctag tgctcttact 8100
cgtacagtgt gcaatactgc gtatcatagt ctttgatgta tatcgtattc attcatgtta 8160
gttgc 8165

<210> SEQ ID NO 23
<211> LENGTH: 8480
<212> TYPE: DNA
<213> ORGANISM: Artificial Sequence
<220> FEATURE:
<223> OTHER INFORMATION: Plasmid pDMW368

<400> SEQUENCE: 23
ggccgcaagt gtggatgggg aagtgagtgc ccggttctgt gtgcacaatt ggcaatccaa 60
gatggatgga ttcaacacag ggatatagcg agctacgtgg tggtgcgagg atatagcaac 120
ggatatttat gtttgacact tgagaatgta cgatacaagc actgtccaag tacaatacta 180
aacatactgt acatactcat actcgtaccc gggcaacggt ttcacttgag tgcagtggct 240
agtgctctta ctcgtacagt gtgcaatact gcgtatcata gtctttgatg tatatcgtat 300
tcattcatgt tagttgcgta cgagccggaa gcataaagtg taaagcctgg ggtgcctaat 360
gagtgagcta actcacatta attgcgttgc gctcactgcc cgctttccag tcgggaaacc 420
tgtcgtgcca gctgcattaa tgaatcggcc aacgcgcggg gagaggcggt ttgcgtattg 480
ggcgctcttc cgcttcctcg ctcactgact cgctgcgctc ggtcgttcgg ctgcggcgag 540
cggtatcagc tcactcaaag gcggtaatac ggttatccac agaatcaggg gataacgcag 600
gaaagaacat gtgagcaaaa ggccagcaaa aggccaggaa ccgtaaaaag gccgcgttgc 660
tggcgttttt ccataggctc cgcccccctg acgagcatca caaaaatcga cgctcaagtc 720
agaggtggcg aaacccgaca ggactataaa gataccaggc gtttccccct ggaagctccc 780
tcgtgcgctc tcctgttccg accctgccgc ttaccggata cctgtccgcc tttctccctt 840
cgggaagcgt ggcgctttct catagctcac gctgtaggta tctcagttcg gtgtaggtcg 900
ttcgctccaa gctgggctgt gtgcacgaac cccccgttca gcccgaccgc tgcgccttat 960
ccggtaacta tcgtcttgag tccaacccgg taagacacga cttatcgcca ctggcagcag 1020
ccactggtaa caggattagc agagcgaggt atgtaggcgg tgctacagag ttcttgaagt 1080
ggtggcctaa ctacggctac actagaagga cagtatttgg tatctgcgct ctgctgaagc 1140
cagttacctt cggaaaaaga gttggtagct cttgatccgg caaacaaacc accgctggta 1200
gcggtggttt ttttgtttgc aagcagcaga ttacgcgcag aaaaaaagga tctcaagaag 1260

```
atcctttgat cttttctacg gggtctgacg ctcagtggaa cgaaaactca cgttaaggga   1320
ttttggtcat gagattatca aaaaggatct tcacctagat ccttttaaat taaaaatgaa   1380
gttttaaatc aatctaaagt atatatgagt aaacttggtc tgacagttac caatgcttaa   1440
tcagtgaggc acctatctca gcgatctgtc tatttcgttc atccatagtt gcctgactcc   1500
ccgtcgtgta gataactacg atacgggagg gcttaccatc tggccccagt gctgcaatga   1560
taccgcgaga cccacgctca ccggctccag atttatcagc aataaaccag ccagccggaa   1620
gggccgagcg cagaagtggt cctgcaactt tatccgcctc catccagtct attaattgtt   1680
gccgggaagc tagagtaagt agttcgccag ttaatagttt gcgcaacgtt gttgccattg   1740
ctacaggcat cgtggtgtca cgctcgtcgt ttggtatggc ttcattcagc tccggttccc   1800
aacgatcaag gcgagttaca tgatccccca tgttgtgcaa aaaagcggtt agctccttcg   1860
gtcctccgat cgttgtcaga agtaagttgg ccgcagtgtt atcactcatg gttatggcag   1920
cactgcataa ttctcttact gtcatgccat ccgtaagatg cttttctgtg actggtgagt   1980
actcaaccaa gtcattctga gaatagtgta tgcggcgacc gagttgctct tgcccggcgt   2040
caatacggga taataccgcg ccacatagca gaactttaaa agtgctcatc attggaaaac   2100
gttcttcggg gcgaaaactc tcaaggatct taccgctgtt gagatccagt tcgatgtaac   2160
ccactcgtgc acccaactga tcttcagcat cttttacttt caccagcgtt tctgggtgag   2220
caaaaacagg aaggcaaaat gccgcaaaaa agggaataag ggcgacacgg aaatgttgaa   2280
tactcatact cttccttttt caatattatt gaagcattta tcagggttat tgtctcatga   2340
gcggatacat atttgaatgt atttagaaaa ataaacaaat aggggttccg cgcacatttc   2400
cccgaaaagt gccacctgac gcgccctgta gcggcgcatt aagcgcggcg ggtgtggtgg   2460
ttacgcgcag cgtgaccgct acacttgcca gcgccctagc gcccgctcct ttcgctttct   2520
tcccttcctt tctcgccacg ttcgccggct ttccccgtca agctctaaat cgggggctcc   2580
ctttagggtt ccgatttagt gctttacggc acctcgaccc caaaaaactt gattagggtg   2640
atggttcacg tagtgggcca tcgccctgat agacggtttt tcgccctttg acgttggagt   2700
ccacgttctt taatagtgga ctcttgttcc aaactggaac aacactcaac cctatctcgg   2760
tctattcttt tgatttataa gggattttgc cgatttcggc ctattggtta aaaaatgagc   2820
tgatttaaca aaaatttaac gcgaatttta acaaaatatt aacgcttaca atttccattc   2880
gccattcagg ctgcgcaact gttgggaagg gcgatcggtg cgggcctctt cgctattacg   2940
ccagctggcg aaagggggat gtgctgcaag gcgattaagt tgggtaacgc cagggttttc   3000
ccagtcacga cgttgtaaaa cgacggccag tgaattgtaa tacgactcac tatagggcga   3060
attgggtacc gggccccccc tcgaggtcga tggtgtcgat aagcttgata tcgaattcat   3120
gtcacacaaa ccgatcttcg cctcaaggaa acctaattct acatccgaga gactgccgag   3180
atccagtcta cactgattaa ttttcgggcc aataatttaa aaaaatcgtg ttatataata   3240
ttatatgtat tatatatata catcatgatg atactgacag tcatgtccca ttgctaaata   3300
gacagactcc atctgccgcc tccaactgat gttctcaata tttaaggggt catctcgcat   3360
tgtttaataa taaacagact ccatctaccg cctccaaatg atgttctcaa aatatattgt   3420
atgaacttat ttttattact tagtattatt agacaactta cttgctttat gaaaaacact   3480
tcctatttag gaaacaattt ataatggcag ttcgttcatt taacaattta tgtagaataa   3540
atgttataaa tgcgtatggg aaatcttaaa tatggatagc ataaatgata tctgcattgc   3600
ctaattcgaa atcaacagca acgaaaaaaa tcccttgtac aacataaata gtcatcgaga   3660
```

```
aatatcaact atcaaagaac agctattcac acgttactat tgagattatt attggacgag   3720
aatcacacac tcaactgtct ttctctcttc tagaaataca ggtacaagta tgtactattc   3780
tcattgttca tacttctagt catttcatcc cacatattcc ttggatttct ctccaatgaa   3840
tgacattcta tcttgcaaat tcaacaatta taataagata taccaaagta gcggtatagt   3900
ggcaatcaaa aagcttctct ggtgtgcttc tcgtatttat ttttattcta atgatccatt   3960
aaaggtatat atttatttct tgttatataa tccttttgtt tattacatgg gctggataca   4020
taaaggtatt ttgatttaat tttttgctta aattcaatcc cccctcgttc agtgtcaact   4080
gtaatggtag gaaattacca tacttttgaa gaagcaaaaa aaatgaaaga aaaaaaaaat   4140
cgtatttcca ggttagacgt tccgcagaat ctagaatgcg gtatgcggta cattgttctt   4200
cgaacgtaaa agttgcgctc cctgagatat tgtacatttt tgcttttaca agtacaagta   4260
catcgtacaa ctatgtacta ctgttgatgc atccacaaca gtttgttttg tttttttttg   4320
tttttttttt ttctaatgat tcattaccgc tatgtatacc tacttgtact tgtagtaagc   4380
cgggttattg gcgttcaatt aatcatagac ttatgaatct gcacggtgtg cgctgcgagt   4440
tacttttagc ttatgcatgc tacttgggtg taatattggg atctgttcgg aaatcaacgg   4500
atgctcaatc gatttcgaca gtaattaatt aagtcataca caagtcagct ttcttcgagc   4560
ctcatataag tataagtagt tcaacgtatt agcactgtac ccagcatctc cgtatcgaga   4620
aacacaacaa catgccccat tggacagatc atgcggatac acaggttgtg cagtatcata   4680
catactcgat cagacaggtc gtctgaccat catacaagct gaacaagcgc tccatacttg   4740
cacgctctct atatacacag ttaaattaca tatccatagt ctaacctcta acagttaatc   4800
ttctggtaag cctcccagcc agccttctgg tatcgcttgg cctcctcaat aggatctcgg   4860
ttctggccgt acagacctcg gccgacaatt atgatatccg ttccggtaga catgacatcc   4920
tcaacagttc ggtactgctg tccgagagcg tctcccttgt cgtcaagacc caccccgggg   4980
gtcagaataa gccagtcctc agagtcgccc ttaggtcggt tctgggcaat gaagccaacc   5040
acaaactcgg ggtcggatcg ggcaagctca atggtctgct tggagtactc gccagtggcc   5100
agagagccct tgcaagacag ctcggccagc atgagcagac ctctggccag cttctcgttg   5160
ggagagggga ctaggaactc cttgtactgg gagttctcgt agtcagagac gtcctccttc   5220
ttctgttcag agacagtttc ctcggcacca gctcgcaggc cagcaatgat tccggttccg   5280
ggtacaccgt gggcgttggt gatatcggac cactcggcga ttcggtgaca ccggtactgg   5340
tgcttgacag tgttgccaat atctgcgaac tttctgtcct cgaacaggaa gaaaccgtgc   5400
ttaagagcaa gttccttgag ggggagcaca gtgccggcgt aggtgaagtc gtcaatgatg   5460
tcgatatggg ttttgatcat gcacacataa ggtccgacct tatcggcaag ctcaatgagc   5520
tccttggtgg tggtaacatc cagagaagca cacaggttgg ttttcttggc tgccacgagc   5580
ttgagcactc gagcggcaaa ggcggacttg tggacgttag ctcgagcttc gtaggagggc   5640
attttggtgg tgaagaggag actgaaataa atttagtctg cagaactttt tatcggaacc   5700
ttatctgggg cagtgaagta tatgttatgg taatagttac gagttagttg aacttataga   5760
tagactggac tatacggcta tcggtccaaa ttagaaagaa cgtcaatggc tctctgggcg   5820
tcgcctttgc cgacaaaaat gtgatcatga tgaaagccag caatgacgtt gcagctgata   5880
ttgttgtcgg ccaaccgcgc cgaaaacgca gctgtcagac ccacagcctc caacgaagaa   5940
tgtatcgtca aagtgatcca agcacactca tagttggagt cgtactccaa aggcggcaat   6000
gacgagtcag acagatactc gtcgactcag gcgacgacgg aattcctgca gcccatctgc   6060
```

```
agaattcagg agagaccggg ttggcggcgt atttgtgtcc caaaaaacag ccccaattgc   6120
cccggagaag acggccaggc cgcctagatg acaaattcaa caactcacag ctgacttttct   6180
gccattgcca ctagggggggg gcctttttat atggccaagc caagctctcc acgtcggttg   6240
ggctgcaccc aacaataaat gggtagggtt gcaccaacaa agggatggga tggggggtag   6300
aagatacgag gataacgggg ctcaatggca caaataagaa cgaatactgc cattaagact   6360
cgtgatccag cgactgacac cattgcatca tctaagggcc tcaaaactac ctcggaactg   6420
ctgcgctgat ctggacacca cagaggttcc gagcacttta ggttgcacca aatgtcccac   6480
caggtgcagg cagaaaacgc tggaacagcg tgtacagttt gtcttaacaa aaagtgaggg   6540
cgctgaggtc gagcagggtg gtgtgacttg ttatagcctt tagagctgcg aaagcgcgta   6600
tggatttggc tcatcaggcc agattgaggg tctgtggaca catgtcatgt tagtgtactt   6660
caatcgcccc ctggatatag ccccgacaat aggccgtggc ctcatttttt tgccttccgc   6720
acatttccat tgctcggtac ccacaccttg cttctcctgc acttgccaac cttaatactg   6780
gtttacattg accaacatct tacaagcggg gggcttgtct agggtatata taaacagtgg   6840
ctctcccaat cggttgccag tctctttttt cctttcttc cccacagatt cgaaatctaa   6900
actacacatc acacaatgcc tgttactgac gtccttaagc gaaagtccgg tgtcatcgtc   6960
ggcgacgatg tccgagccgt gagtatccac gacaagatca gtgtcgagac gacgcgtttt   7020
gtgtaatgac acaatccgaa agtcgctagc aacacacact ctctacacaa actaacccag   7080
ctctccatgg ctccagatgc ggacaagttg agacagcgca aggcgcaatc gattcaagac   7140
acggctgatt cgcaagctac cgaactcaag attggcaccc tgaagggctt gcaggggaca   7200
gaaatcgtca ttgatggaga catttacgat ataaaagact ttgatcaccc cggtggtgaa   7260
tccatcatga cttttggggg aaacgatgtc accgccacgt acaagatgat ccacccctac   7320
cactctaagc accatttgga gaagatgaag aaagtgggac gagttccgga ctacacctcg   7380
gaatacaagt ttgatactcc ctttgagcgt gaaatcaagc aagaggtctt caagattgtg   7440
cgacgaggcc gcgagtttgg aacacctgga tacttcttcc gggctttctg ctacattgga   7500
cttttctttt acttgcagta tttgtgggtc acgactccca ctacctttgc cttggcgatc   7560
ttctatggtg tttcgcaagc tttcattggt ttgaacgtac aacatgatgc caaccacgga   7620
gctgcctcca agaagccttg gatcaataac ttgctaggat tgggggctga ctttatcgga   7680
ggttccaaat ggttgtggat gaaccagcac tggacgcacc acacatacac caaccaccat   7740
gagaaggatc ccgatgcctt gggcgctgaa ccaatgttgt tgttcaatga ttatcccttg   7800
ggtcacccaa agcgtacttt gattcaccac ttccaggcct tctattacct tttcgtcttg   7860
gccggatact gggtctcttc ggtcttcaac cctcaaattt tggacttgca acaccgcggt   7920
gctcaagcgg ttggaatgaa aatggagaac gattacattg ccaaaagccg aaagtatgcc   7980
atcttcttgc gtctcttgta tatttacacc aacattgtcg ctccgatcca aaaccaaggc   8040
ttctcgttga ccgtggtcgc ccacattttg accatgggcg tcgcttccag tttgactttg   8100
gcgactcttt ttgccttgtc gcacaatttt gaaaacgcgg atcgcgatcc cacttacgag   8160
gcccgcaagg gaggagagcc tgtttgttgg ttcaagtcgc aagtcgaaac ctcgtcaact   8220
tacggaggtt tcatctcggg ttgcttgacg ggcggactca acttccaagt ggaacaccac   8280
ttgttccctc gtatgagttc ggcctggtac ccctacattg cccctactgt tcgagaggtt   8340
tgcaaaaagc acggagtcaa gtacgcatac tatccctggg tctggcaaaa cttgatttca   8400
actgtcaagt atctgcatca aagcggaact ggatccaact ggaagaatgg cgccaacccc   8460
```

tactcgggaa aattgtaagc 8480

<210> SEQ ID NO 24
<211> LENGTH: 12649
<212> TYPE: DNA
<213> ORGANISM: Artificial Sequence
<220> FEATURE:
<223> OTHER INFORMATION: Plasmid pKUNF12T6E
<220> FEATURE:
<221> NAME/KEY: misc_feature
<222> LOCATION: (2507)..(2507)
<223> OTHER INFORMATION: n is a, c, g, or t
<220> FEATURE:
<221> NAME/KEY: misc_feature
<222> LOCATION: (2512)..(2515)
<223> OTHER INFORMATION: n is a, c, g, or t

<400> SEQUENCE: 24
taaccctcac taaagggaac aaaagctgga gctccaccgc ggacacaata tctggtcaaa 60
tttcagtttc gttacataaa tcgttatgtc aaaggagtgt gggaggttaa gagaattatc 120
accggcaaac tatctgttaa ttgctaggta cctctagacg tccacccggg tcgcttggcg 180
gccgaagagg ccggaatctc gggccgcggt ggcggccgct tagttggtct tggacttctt 240
gggcttcttc aggtaggact ggacaaagaa gttgccgaac agagcgagca gggtgatcat 300
gtacacgccg agcagctgga ccagagcctg agggtagtcg caggggaaga ggtagtcgta 360
cagggactgc accagcatag ccatgaactg ggtcatctgc agagtggtga tgtagggctt 420
gatgggcttg acgaagccga agccctgaga ggaaaagaag tagtaggcgt acatgacggt 480
gtggacgaag gagttgagga tgacggagaa gtaggcgtcg ccaccaggag cgtacttggc 540
aatagcccac cagatggcga agatggtggc atggtggtac acgtgcagga aggagacctg 600
gttgaacttc ttgcacagga tcatgatagc ggtgtccagg aactcgtagg ccttggagac 660
gtagaacacg tagacgattc gggacatgcc ctgagcgtgg gactcgttgc ccttctccat 720
gtcgttgccg aagaccttgt agccacccag gatagcctgt cggatggtct cgacgcacat 780
gtagagggac agtccgaaga ggaacaggtt gtggagcagc ttgatggtct tcagctcgaa 840
gggcttctcc atctgcttca tgatgggaat gccgaagagc agcatggcca tgtagccgac 900
ctcgaaggcg agcatggtgg agacgtccat catgggcaga ccgtcggtca gagcgtaggg 960
cttagctccg tccatccact ggtcgacacc ggtctcgact cgtccgacca cgtcgtccca 1020
gacagaggag ttggccatgg tgaatgattc ttatactcag aaggaaatgc ttaacgattt 1080
cgggtgtgag ttgacaagga gagagagaaa agaagaggaa aggtaattcg gggacggtgg 1140
tcttttatac ccttggctaa agtcccaacc acaaagcaaa aaaattttca gtagtctatt 1200
ttgcgtccgg catgggttac ccggatggcc agacaaagaa actagtacaa agtctgaaca 1260
agcgtagatt ccagactgca gtaccctacg cccttaacgg caagtgtggg aaccggggga 1320
ggtttgatat gtggggtgaa gggggctctc gccggggttg ggcccgctac tgggtcaatt 1380
tggggtcaat tggggcaatt ggggctgttt tttgggacac aaatacgccg ccaacccggt 1440
ctctcctgaa ttctgcatcg atcgaggaag aggacaagcg gctgcttctt aagtttgtga 1500
catcagtatc caaggcacca ttgcaaggat tcaaggcttt gaacccgtca tttgccattc 1560
gtaacgctgg tagacaggtt gatcggttcc ctacggcctc cacctgtgtc aatcttctca 1620
agctgcctga ctatcaggac attgatcaac ttcggaagaa acttttgtat gccattcgat 1680
cacatgctgg tttcgatttg tcttagagga acgcatatac agtaatcata gagaataaac 1740
gatattcatt tattaaagta gatagttgag gtagaagttg taaagagtga taaatagcgg 1800

-continued ccgcgcctac ttaagcaacg ggcttgataa cagcgggggg ggtgcccacg ttgttgcggt 1860
tgcggaagaa cagaacaccc ttaccagcac cctcggcacc agcgctgggc tcaacccact 1920
ggcacatacg cgcactgcgg tacatggcgc ggatgaagcc acgaggacca tcctggacat 1980
cagcccggta gtgcttgccc atgatgggct taatggcctc ggtggcctcg tccgcgttgt 2040
agaaggggat gctgctgacg tagtggtgga ggacatgagt ctcgatgatg ccgtggagaa 2100
ggtggcggcc gatgaagccc atctcacggt caatggtagc agcggcacca cggacgaagt 2160
tccactcgtc gttggtgtag tggggaaggg tagggtcggt gtgctggagg aaggtgatgg 2220
caacgagcca gtggttaacc cagaggtagg gaacaaagta ccagatggcc atgttgtaga 2280
aaccgaactt ctgaacgagg aagtacagag cagtggccat cagaccgata ccaatatcgc 2340
tgaggacgat gagcttagcg tcactgttct cgtacagagg gctgcgggga tcgaagtggt 2400
taacaccacc gccgaggccg ttatgcttgc ccttgccgcg accctcacgc tggcgctcgt 2460
ggtagttgtg gccggtaaca ttggtgatga ggtagttggg ccagccnacg annnnctcag 2520
taagatgagc gagctcgtgg gtcatctttc cgagacgagt agcctgctgc tcgcgggttc 2580
ggggaacgaa gaccatgtca cgctccatgt tgccagtggc cttgtggtgc tttcggtggg 2640
agatttgcca gctgaagtag gggacaagga gggaagagtg aagaacccag ccagtaatgt 2700
cgttgatgat gcgagaatcg gagaaagcac cgtgaccgca ctcatgggca ataacccaga 2760
gaccagtacc gaaaagaccc tgaagaacgg tgtacacggc ccacagacca gcgcgggcgg 2820
gggtggaggg gatatattcg gggtcacaa agttgtacca gatgctgaaa gtggtagtca 2880
ggaggacaat gtcgcggagg atataaccgt atcccttgag agcggagcgc ttgaagcagt 2940
gcttagggat ggcattgtag atgtccttga tggtaaagtc gggaacctcg aactggttgc 3000
cgtaggtgtc gagcatgaca ccatactcgg acttgggctt ggcgatatca acctcggaca 3060
tggacgagag cgatgtggaa gaggccgagt ggcggggaga gtctgaagga gagacggcgg 3120
cagactcaga atccgtcaca gtagttgagg tgacggtgcg tctaagcgca gggttctgct 3180
tgggcagagc cgaagtggac gccatggaga gctgggttag tttgtgtaga gagtgtgtgt 3240
tgctagcgac tttcggattg tgtcattaca caaaacgcgt cgtctcgaca ctgatcttgt 3300
cgtggatact cacggctcgg acatcgtcgc cgacgatgac accggacttt cgcttaagga 3360
cgtcagtaac aggcattgtg tgatgtgtag tttagatttc gaatctgtgg ggaaagaaag 3420
gaaaaaagag actggcaacc gattgggaga gccactgttt atatataccc tagacaagcc 3480
ccccgcttgt aagatgttgg tcaatgtaaa ccagtattaa ggttggcaag tgcaggagaa 3540
gcaaggtgtg ggtaccgagc aatggaaatg tgcggaaggc aaaaaaatga ggccacggcc 3600
tattgtcggg gctatatcca gggggcgatt gaagtacact aacatgacat gtgtccacag 3660
accctcaatc tggcctgatg agccaaatcc atacgcgctt tcgcagctct aaaggctata 3720
acaagtcaca ccaccctgct cgacctcagc gccctcactt tttgttaaga caaactgtac 3780
acgctgttcc agcgttttct gcctgcacct ggtgggacat ttggtgcaac ctaaagtgct 3840
cggaacctct gtggtgtcca gatcagcgca gcagttccga ggtagttttg aggcccttag 3900
atgatgcaat ggtgtcagtc gctggatcac gagtcttaat ggcagtattc gttcttattt 3960
gtgccattga gccccgttat cctcgtatct tctacccccc atcccatccc tttgttggtg 4020
caaccctacc catttattgt tgggtgcagc ccaaccgacg tggagagctt ggcttggcca 4080
tataaaaagg ccccccccta gtggcaatgg cagaaagtca gctgtgagtt gttgaatttg 4140
tcatctaggc ggcctggccg tcttctccgg ggcaattgtt cctctatagt actgcgtaca 4200

```
ctgtttaaac agtgtacgca gatctgcgac gacggaattc ctgcagccca tctgcagaat   4260
tcaggagaga ccgggttggc ggcgtatttg tgtcccaaaa aacagcccca attgccccaa   4320
ttgaccccaa attgacccag tagcgggccc aaccccggcg agagcccct tcaccccaca    4380
tatcaaacct cccccggttc ccacacttgc cgttaagggc gtagggtact gcagtctgga   4440
atctacgctt gttcagactt tgtactagtt tctttgtctg gccatccggg taacccatgc   4500
cggacgcaaa atagactact gaaaattttt ttgctttgtg gttgggactt tagccaaggg   4560
tataaaagac caccgtcccc gaattacctt tcctcttctt ttctctctct ccttgtcaac   4620
tcacacccga aatcgttaag catttccttc tgagtataag aatcattcac catggctgcc   4680
gctccctctg tgcgaacctt tacccgagcc gaggttctga acgctgaggc tctgaacgag   4740
ggcaagaagg acgctgaggc tcccttcctg atgatcatcg acaacaaggt gtacgacgtc   4800
cgagagttcg tccctgacca tcctggaggc tccgtgattc tcacccacgt tggcaaggac   4860
ggcaccgacg tctttgacac ctttcatccc gaggctgctt gggagactct cgccaacttc   4920
tacgttggag acattgacga gtccgaccga gacatcaaga acgatgactt tgccgctgag   4980
gtccgaaagc tgcgaaccct gttccagtct ctcggctact acgactcctc taaggcctac   5040
tacgccttca aggtctcctt caacctctgc atctggggac tgtccaccgt cattgtggcc   5100
aagtggggtc agacctccac cctcgccaac gtgctctctg ctgccctgct cggcctgttc   5160
tggcagcagt gcggatggct ggctcacgac tttctgcacc accaggtctt ccaggaccga   5220
ttctggggtg atctcttcgg agccttcctg ggaggtgtct gccagggctt ctcctcttcc   5280
tggtggaagg acaagcacaa cactcaccat gccgctccca acgtgcatgg cgaggatcct   5340
gacattgaca cccaccctct cctgacctgg tccgagcacg ctctggagat gttctccgac   5400
gtccccgatg aggagctgac ccgaatgtgg tctcgattca tggtcctgaa ccagacctgg   5460
ttctacttcc ccattctctc cttcgctcga ctgtcttggt gcctccagtc cattctcttt   5520
gtgctgccca acggtcaggc tcacaagccc tccggagctc gagtgcccat ctccctggtc   5580
gagcagctgt ccctcgccat gcactggacc tggtacctcg ctaccatgtt cctgttcatc   5640
aaggatcctg tcaacatgct cgtgtacttc ctggtgtctc aggctgtgtg cggaaacctg   5700
ctcgccatcg tgttctccct caaccacaac ggtatgcctg tgatctccaa ggaggaggct   5760
gtcgacatgg atttctttac caagcagatc atcactggtc gagatgtcca tcctggactg   5820
ttcgccaact ggttcaccgg tggcctgaac taccagatcg agcatcacct gttcccttcc   5880
atgcctcgac acaacttctc caagatccag cctgccgtcg agaccctgtg caagaagtac   5940
aacgtccgat accacaccac tggtatgatc gagggaactg ccgaggtctt ctcccgactg   6000
aacgaggtct ccaaggccac ctccaagatg ggcaaggctc agtaagcggc cgcatgagaa   6060
gataaatata taaatacatt gagatattaa atgcgctaga ttagagagcc tcatactgct   6120
cggagagaag ccaagacgag tactcaaagg ggattacacc atccatatcc acagacacaa   6180
gctggggaaa ggttctatat acactttccg gaataccgta gtttccgatg ttatcaatgg   6240
gggcagccag gatttcaggc acttcggtgt ctcggggtga aatggcgttc ttggcctcca   6300
tcaagtcgta ccatgtcttc atttgcctgt caaagtaaaa cagaagcaga tgaagaatga   6360
acttgaagtg aaggaattta aattgccccg gagaagacgg ccaggccgcc tagatgacaa   6420
attcaacaac tcacagctga ctttctgcca ttgccactag gggggggcct ttttatatgg   6480
ccaagccaag ctctccacgt cggttgggct gcacccaaca ataaatgggt agggttgcac   6540
caacaaaggg atgggatggg gggtagaaga tacgaggata acggggctca atggcacaaa   6600
```

```
taagaacgaa tactgccatt aagactcgtg atccagcgac tgacaccatt gcatcatcta   6660
agggcctcaa aactacctcg gaactgctgc gctgatctgg acaccacaga ggttccgagc   6720
actttaggtt gcaccaaatg tcccaccagg tgcaggcaga aaacgctgga acagcgtgta   6780
cagtttgtct taacaaaaag tgagggcgct gaggtcgagc agggtggtgt gacttgttat   6840
agcctttaga gctgcgaaag cgcgtatgga tttggctcat caggccagat tgagggtctg   6900
tggacacatg tcatgttagt gtacttcaat cgccccctgg atatagcccc gacaataggc   6960
cgtggcctca ttttttgcc ttccgcacat ttccattgct cggtacccac accttgcttc   7020
tcctgcactt gccaacctta atactggttt acattgacca acatcttaca agcgggggc    7080
ttgtctaggg tatatataaa cagtggctct cccaatcggt tgccagtctc tttttccctt   7140
tctttcccca cagattcgaa atctaaacta cacatcacac aatgcctgtt actgacgtcc   7200
ttaagcgaaa gtccggtgtc atcgtcggcg acgatgtccg agccgtgagt atccacgaca   7260
agatcagtgt cgagacgacg cgttttgtgt aatgacacaa tccgaaagtc gctagcaaca   7320
cacactctct acacaaacta acccagctct ccatggagtc cattgctccc ttcctgccct   7380
ccaagatgcc tcaggacctg ttcatggacc tcgccagcgc tatcggtgtc cgagctgctc   7440
cctacgtcga tcccctggag gctgccctgg ttgcccaggc cgagaagtac attcccacca   7500
ttgtccatca cactcgaggc ttcctggttg ccgtggagtc tcccctggct cgagagctgc   7560
ctctgatgaa cccctccac gtgctcctga tcgtgctcgc ctacctggtc accgtgtttg    7620
tgggtatgca gatcatgaag aactttgaac gattcgaggt caagaccttc tccctcctgc   7680
acaacttctg tctggtctcc atctccgcct acatgtgcgg tggcatcctg tacgaggctt   7740
atcaggccaa ctatggactg tttgagaacg ctgccgatca caccttcaag ggtctcccta   7800
tggctaagat gatctggctc ttctacttct ccaagatcat ggagtttgtc gacaccatga   7860
tcatggtcct caagaagaac aaccgacaga tttcctttct gcacgtgtac caccactctt   7920
ccatcttcac catctggtgg ctggtcacct tcgttgctcc caacggtgaa gcctacttct   7980
ctgctgccct gaactccttc atccacgtca tcatgtacgg ctactacttt ctgtctgccc   8040
tgggcttcaa gcaggtgtcg ttcatcaagt tctacatcac tcgatcccag atgacccagt   8100
tctgcatgat gtctgtccag tcttcctggg acatgtacgc catgaaggtc cttggccgac   8160
ctggataccc cttcttcatc accgctctgc tctggttcta catgtggacc atgctcggtc   8220
tcttctacaa cttttaccga aagaacgcca agctcgccaa gcaggccaag gctgacgctg   8280
ccaaggagaa ggccagaaag ctccagtaag cggccgcaag tgtggatggg gaagtgagtg   8340
cccggttctg tgtgcacaat tggcaatcca agatggatgg attcaacaca gggatatagc   8400
gagctacgtg gtggtgcgag gatatagcaa cggatattta tgtttgacac ttgagaatgt   8460
acgatacaag cactgtccaa gtacaatact aaacatactg tacatactca tactcgtacc   8520
cgggcaacgg tttcacttga gtgcagtggc tagtgctctt actcgtacag tgtgcaatac   8580
tgcgtatcat agtctttgat gtatatcgta ttcattcatg ttagttgcgt acgaagtcgt   8640
caatgatgtc gatatgggtt ttgatcatgc acacataagg tccgacctta tcggcaagct   8700
caatgagctc cttggtggtg gtaacatcca gagaagcaca caggttggtt ttcttggctg   8760
ccacgagctt gagcactcga gcggcaaagg cggacttgtg gacgttagct cgagcttcgt   8820
aggagggcat tttggtggtg aagaggagac tgaaataaat ttagtctgca gaacttttta   8880
tcggaacctt atctggggca gtgaagtata tgttatggta atagttacga gttagttgaa   8940
cttatagata gactggacta tacggctatc ggtccaaatt agaaagaacg tcaatggctc   9000
```

```
tctgggcgtc gcctttgccg acaaaaatgt gatcatgatg aaagccagca atgacgttgc   9060
agctgatatt gttgtcggcc aaccgcgccg aaaacgcagc tgtcagaccc acagcctcca   9120
acgaagaatg tatcgtcaaa gtgatccaag cacactcata gttggagtcg tactccaaag   9180
gcggcaatga cgagtcagac agatactcgt cgaccttttc cttgggaacc accaccgtca   9240
gcccttctga ctcacgtatt gtagccaccg acacaggcaa cagtccgtgg atagcagaat   9300
atgtcttgtc ggtccatttc tcaccaactt taggcgtcaa gtgaatgttg cagaagaagt   9360
atgtgccttc attgagaatc ggtgttgctg atttcaataa agtcttgaga tcagtttggc   9420
gcgccagctg cattaatgaa tcggccaacg cgcggggaga ggcggtttgc gtattgggcg   9480
ctcttccgct tcctcgctca ctgactcgct gcgctcggtc gttcggctgc ggcgagcggt   9540
atcagctcac tcaaaggcgg taatacggtt atccacagaa tcaggggata acgcaggaaa   9600
gaacatgtga gcaaaaggcc agcaaaaggc caggaaccgt aaaaaggccg cgttgctggc   9660
gtttttccat aggctccgcc cccctgacga gcatcacaaa aatcgacgct caagtcagag   9720
gtggcgaaac ccgacaggac tataaagata ccaggcgttt ccccctggaa gctccctcgt   9780
gcgctctcct gttccgaccc tgccgcttac cggatacctg tccgcctttc tcccttcggg   9840
aagcgtggcg ctttctcata gctcacgctg taggtatctc agttcggtgt aggtcgttcg   9900
ctccaagctg ggctgtgtgc acgaaccccc cgttcagccc gaccgctgcg ccttatccgg   9960
taactatcgt cttgagtcca acccggtaag acacgactta tcgccactgg cagcagccac  10020
tggtaacagg attagcagag cgaggtatgt aggcggtgct acagagttct tgaagtggtg  10080
gcctaactac ggctacacta gaagaacagt atttggtatc tgcgctctgc tgaagccagt  10140
taccttcgga aaaagagttg gtagctcttg atccggcaaa caaaccaccg ctggtagcgg  10200
tggttttttt gtttgcaagc agcagattac gcgcagaaaa aaaggatctc aagaagatcc  10260
tttgatcttt tctacggggt ctgacgctca gtggaacgaa aactcacgtt aagggatttt  10320
ggtcatgaga ttatcaaaaa ggatcttcac ctagatcctt ttaaattaaa aatgaagttt  10380
taaatcaatc taaagtatat atgagtaaac ttggtctgac agttaccaat gcttaatcag  10440
tgaggcacct atctcagcga tctgtctatt tcgttcatcc atagttgcct gactccccgt  10500
cgtgtagata actacgatac gggagggctt accatctggc cccagtgctg caatgatacc  10560
gcgagaccca cgctcaccgg ctccagattt atcagcaata aaccagccag ccggaagggc  10620
cgagcgcaga agtggtcctg caactttatc cgcctccatc cagtctatta attgttgccg  10680
ggaagctaga gtaagtagtt cgccagttaa tagtttgcgc aacgttgttg ccattgctac  10740
aggcatcgtg gtgtcacgct cgtcgtttgg tatggcttca ttcagctccg gttcccaacg  10800
atcaaggcga gttacatgat cccccatgtt gtgcaaaaaa gcggttagct ccttcggtcc  10860
tccgatcgtt gtcagaagta agttggccgc agtgttatca ctcatggtta tggcagcact  10920
gcataattct cttactgtca tgccatccgt aagatgcttt tctgtgactg gtgagtactc  10980
aaccaagtca ttctgagaat agtgtatgcg gcgaccgagt tgctcttgcc cggcgtcaat  11040
acgggataat accgcgccac atagcagaac tttaaaagtg ctcatcattg gaaaacgttc  11100
ttcggggcga aaactctcaa ggatcttacc gctgttgaga tccagttcga tgtaacccac  11160
tcgtgcaccc aactgatctt cagcatcttt tactttcacc agcgtttctg ggtgagcaaa  11220
aacaggaagg caaaatgccg caaaaaaggg aataagggcg acacggaaat gttgaatact  11280
catactcttc ctttttcaat attattgaag catttatcag ggttattgtc tcatgagcgg  11340
atacatattt gaatgtattt agaaaaataa acaaataggg gttccgcgca catttccccg  11400
```

```
aaaagtgcca cctgatgcgg tgtgaaatac cgcacagatg cgtaaggaga aaataccgca  11460

tcaggaaatt gtaagcgtta atattttgtt aaaattcgcg ttaaattttt gttaaatcag  11520

ctcatttttt aaccaatagg ccgaaatcgg caaaatccct tataaatcaa aagaatagac  11580

cgagataggg ttgagtgttg ttccagtttg gaacaagagt ccactattaa agaacgtgga  11640

ctccaacgtc aaagggcgaa aaaccgtcta tcagggcgat ggcccactac gtgaaccatc  11700

accctaatca agttttttgg ggtcgaggtg ccgtaaagca ctaaatcgga accctaaagg  11760

gagcccccga tttagagctt gacggggaaa gccggcgaac gtggcgagaa aggaagggaa  11820

gaaagcgaaa ggagcgggcg ctagggcgct ggcaagtgta gcggtcacgc tgcgcgtaac  11880

caccacaccc gccgcgctta atgcgccgct acagggcgcg tccattcgcc attcaggctg  11940

cgcaactgtt gggaagggcg atcggtgcgg gcctcttcgc tattacgcca gctggcgaaa  12000

gggggatgtg ctgcaaggcg attaagttgg gtaacgccag ggttttccca gtcacgacgt  12060

tgtaaaacga cggccagtga attgtaatac gactcactat agggcgaatt gggcccgacg  12120

tcgcatgcag tggtggtatt gtgactgggg atgtagttga gaataagtca tacacaagtc  12180

agctttcttc gagcctcata taagtataag tagttcaacg tattagcact gtacccagca  12240

tctccgtatc gagaaacaca acaacatgcc ccattggaca gatcatgcgg atacacaggt  12300

tgtgcagtat catacatact cgatcagaca ggtcgtctga ccatcataca agctgaacaa  12360

gcgctccata cttgcacgct ctctatatac acagttaaat tacatatcca tagtctaacc  12420

tctaacagtt aatcttctgg taagcctccc agccagcctt ctggtatcgc ttggcctcct  12480

caataggatc tcggttctgg ccgtacagac ctcggccgac aattatgata tccgttccgg  12540

tagacatgac atcctcaaca gttcggtact gctgtccgag agcgtctccc ttgtcgtcaa  12600

gacccacccc gggggtcaga ataagccagt cctcagagtc gcccttaat              12649
```

```
<210> SEQ ID NO 25
<211> LENGTH: 819
<212> TYPE: DNA
<213> ORGANISM: Thraustochytrium aureum
<220> FEATURE:
<221> NAME/KEY: misc_feature
<223> OTHER INFORMATION: synthetic elongase (codon-optimized) for
      Yarrowia lipolytica

<400> SEQUENCE: 25
```

```
atggccaact cctctgtctg ggacgacgtg gtcggacgag tcgagaccgg tgtcgaccag     60

tggatggacg gagctaagcc ctacgctctg accgacggtc tgcccatgat ggacgtctcc    120

accatgctcg ccttcgaggt cggctacatg gccatgctgc tcttcggcat tcccatcatg    180

aagcagatgg agaagccctt cgagctgaag accatcaagc tgctccacaa cctgttcctc    240

ttcggactgt ccctctacat gtgcgtcgag accatccgac aggctatcct gggtggctac    300

aaggtcttcg gcaacgacat ggagaagggc aacgagtccc acgctcaggg catgtcccga    360

atcgtctacg tgttctacgt ctccaaggcc tacgagttcc tggacaccgc tatcatgatc    420

ctgtgcaaga agttcaacca ggtctccttc ctgcacgtgt accaccatgc caccatcttc    480

gccatctggt gggctattgc caagtacgct cctggtggcg acgcctactt ctccgtcatc    540

ctcaactcct tcgtccacac cgtcatgtac gcctactact tcttttcctc tcagggcttc    600

ggcttcgtca agcccatcaa gccctacatc accactctgc agatgaccca gttcatggct    660

atgctggtgc agtccctgta cgactacctc ttcccctgcg actaccctca ggctctggtc    720

cagctgctcg gcgtgtacat gatcaccctg ctcgctctgt tcggcaactt ctttgtccag    780
```

tcctacctga agaagcccaa gaagtccaag accaactaa 819

<210> SEQ ID NO 26
<211> LENGTH: 272
<212> TYPE: PRT
<213> ORGANISM: Thraustochytrium aureum

<400> SEQUENCE: 26

```
Met Ala Asn Ser Ser Val Trp Asp Asp Val Val Gly Arg Val Glu Thr
1               5                   10                  15

Gly Val Asp Gln Trp Met Asp Gly Ala Lys Pro Tyr Ala Leu Thr Asp
            20                  25                  30

Gly Leu Pro Met Met Asp Val Ser Thr Met Leu Ala Phe Glu Val Gly
        35                  40                  45

Tyr Met Ala Met Leu Leu Phe Gly Ile Pro Ile Met Lys Gln Met Glu
    50                  55                  60

Lys Pro Phe Glu Leu Lys Thr Ile Lys Leu Leu His Asn Leu Phe Leu
65                  70                  75                  80

Phe Gly Leu Ser Leu Tyr Met Cys Val Glu Thr Ile Arg Gln Ala Ile
                85                  90                  95

Leu Gly Gly Tyr Lys Val Phe Gly Asn Asp Met Glu Lys Gly Asn Glu
            100                 105                 110

Ser His Ala Gln Gly Met Ser Arg Ile Val Tyr Val Phe Tyr Val Ser
        115                 120                 125

Lys Ala Tyr Glu Phe Leu Asp Thr Ala Ile Met Ile Leu Cys Lys Lys
    130                 135                 140

Phe Asn Gln Val Ser Phe Leu His Val Tyr His His Ala Thr Ile Phe
145                 150                 155                 160

Ala Ile Trp Trp Ala Ile Ala Lys Tyr Ala Pro Gly Gly Asp Ala Tyr
                165                 170                 175

Phe Ser Val Ile Leu Asn Ser Phe Val His Thr Val Met Tyr Ala Tyr
            180                 185                 190

Tyr Phe Phe Ser Ser Gln Gly Phe Gly Phe Val Lys Pro Ile Lys Pro
        195                 200                 205

Tyr Ile Thr Thr Leu Gln Met Thr Gln Phe Met Ala Met Leu Val Gln
    210                 215                 220

Ser Leu Tyr Asp Tyr Leu Phe Pro Cys Asp Tyr Pro Gln Ala Leu Val
225                 230                 235                 240

Gln Leu Leu Gly Val Tyr Met Ile Thr Leu Leu Ala Leu Phe Gly Asn
                245                 250                 255

Phe Phe Val Gln Ser Tyr Leu Lys Lys Pro Lys Lys Ser Lys Thr Asn
            260                 265                 270
```

<210> SEQ ID NO 27
<211> LENGTH: 37
<212> TYPE: DNA
<213> ORGANISM: Artificial Sequence
<220> FEATURE:
<223> OTHER INFORMATION: Primer AP

<400> SEQUENCE: 27
ggccacgcgt cgactagtac tttttttttt ttttttt 37

<210> SEQ ID NO 28
<211> LENGTH: 39
<212> TYPE: DNA
<213> ORGANISM: Artificial Sequence
<220> FEATURE:

```
<223> OTHER INFORMATION: Smart IV oligonucleotide primer

<400> SEQUENCE: 28

aagcagtggt atcaacgcag agtggccatt acggccggg                      39


<210> SEQ ID NO 29
<211> LENGTH: 23
<212> TYPE: DNA
<213> ORGANISM: Artificial Sequence
<220> FEATURE:
<223> OTHER INFORMATION: Primer CDSIII 5'

<400> SEQUENCE: 29

aagcagtggt atcaacgcag agt                                       23


<210> SEQ ID NO 30
<211> LENGTH: 20
<212> TYPE: DNA
<213> ORGANISM: Artificial Sequence
<220> FEATURE:
<223> OTHER INFORMATION: Degenerate primer 5-1A

<400> SEQUENCE: 30

gghcaycayr tbtayacaaa                                           20


<210> SEQ ID NO 31
<211> LENGTH: 20
<212> TYPE: DNA
<213> ORGANISM: Artificial Sequence
<220> FEATURE:
<223> OTHER INFORMATION: Degenerate primer 5-1B

<400> SEQUENCE: 31

gghcaycayr tbtayaccaa                                           20


<210> SEQ ID NO 32
<211> LENGTH: 20
<212> TYPE: DNA
<213> ORGANISM: Artificial Sequence
<220> FEATURE:
<223> OTHER INFORMATION: Degenerate primer 5-1C

<400> SEQUENCE: 32

gghcaycayr tbtayacgaa                                           20


<210> SEQ ID NO 33
<211> LENGTH: 20
<212> TYPE: DNA
<213> ORGANISM: Artificial Sequence
<220> FEATURE:
<223> OTHER INFORMATION: Degenerate primer 5-1D

<400> SEQUENCE: 33

gghcaycayr tbtayactaa                                           20


<210> SEQ ID NO 34
<211> LENGTH: 20
<212> TYPE: DNA
<213> ORGANISM: Artificial Sequence
<220> FEATURE:
<223> OTHER INFORMATION: Degenerate primer 5-4AR
<220> FEATURE:
<221> NAME/KEY: misc_feature
<222> LOCATION: (9)..(9)
<223> OTHER INFORMATION: n is a, c, g, or t

<400> SEQUENCE: 34
```

acrtgrytna cytgraagtt 20

<210> SEQ ID NO 35
<211> LENGTH: 20
<212> TYPE: DNA
<213> ORGANISM: Artificial Sequence
<220> FEATURE:
<223> OTHER INFORMATION: Degenerate primer 5-4BR
<220> FEATURE:
<221> NAME/KEY: misc_feature
<222> LOCATION: (9)..(9)
<223> OTHER INFORMATION: n is a, c, g, or t

<400> SEQUENCE: 35
acrtgrytna cytgraaatt 20

<210> SEQ ID NO 36
<211> LENGTH: 20
<212> TYPE: DNA
<213> ORGANISM: Artificial Sequence
<220> FEATURE:
<223> OTHER INFORMATION: Degenerate primer 5-4CR
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 36
acrtgngana cytgraagtt 20

<210> SEQ ID NO 37
<211> LENGTH: 20
<212> TYPE: DNA
<213> ORGANISM: Artificial Sequence
<220> FEATURE:
<223> OTHER INFORMATION: Degenerate primer 5-4DR
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 37
acrtgngana cytgraaatt 20

<210> SEQ ID NO 38
<211> LENGTH: 25
<212> TYPE: DNA
<213> ORGANISM: Artificial Sequence
<220> FEATURE:
<223> OTHER INFORMATION: Primer ODMW520

<400> SEQUENCE: 38
cgttctccat tttcattcca accgc 25

<210> SEQ ID NO 39
<211> LENGTH: 28
<212> TYPE: DNA
<213> ORGANISM: Artificial Sequence
<220> FEATURE:
<223> OTHER INFORMATION: Primer ODMW521

<400> SEQUENCE: 39
ggttgaagac cgaagagacc cagtatcc 28

<210> SEQ ID NO 40
<211> LENGTH: 22
<212> TYPE: DNA
<213> ORGANISM: Artificial Sequence
<220> FEATURE:
<223> OTHER INFORMATION: Primer DNR CDS 5'

<400> SEQUENCE: 40
caacgcagag tggccattac gg 22

<210> SEQ ID NO 41
<211> LENGTH: 28
<212> TYPE: DNA
<213> ORGANISM: Artificial Sequence
<220> FEATURE:
<223> OTHER INFORMATION: Primer ODMW541

<400> SEQUENCE: 41
ctcgcggcct cgtcgcacaa tcttgaag 28

<210> SEQ ID NO 42
<211> LENGTH: 29
<212> TYPE: DNA
<213> ORGANISM: Artificial Sequence
<220> FEATURE:
<223> OTHER INFORMATION: Primer ODMW542

<400> SEQUENCE: 42
gagtatcaaa cttgtattcc gaggtgtag 29

<210> SEQ ID NO 43
<211> LENGTH: 26
<212> TYPE: DNA
<213> ORGANISM: Artificial Sequence
<220> FEATURE:
<223> OTHER INFORMATION: Primer ODMW523

<400> SEQUENCE: 43
ggttcaagtc gcaagtcgaa acctcg 26

<210> SEQ ID NO 44
<211> LENGTH: 20
<212> TYPE: DNA
<213> ORGANISM: Artificial Sequence
<220> FEATURE:
<223> OTHER INFORMATION: Primer AUAP

<400> SEQUENCE: 44
ggccacgcgt cgactagtac 20

<210> SEQ ID NO 45
<211> LENGTH: 25
<212> TYPE: DNA
<213> ORGANISM: Artificial Sequence
<220> FEATURE:
<223> OTHER INFORMATION: Primer ODMW524

<400> SEQUENCE: 45
caacttacgg aggtttcatc tcggg 25

<210> SEQ ID NO 46
<211> LENGTH: 31
<212> TYPE: DNA
<213> ORGANISM: Artificial Sequence
<220> FEATURE:

<223> OTHER INFORMATION: Primer YL807

<400> SEQUENCE: 46
tttccatggc tccagatgcg gacaagttga g 31

<210> SEQ ID NO 47
<211> LENGTH: 29
<212> TYPE: DNA
<213> ORGANISM: Artificial Sequence
<220> FEATURE:
<223> OTHER INFORMATION: Primer YL810

<400> SEQUENCE: 47
caaggcatcg ggatccttct catggtggt 29

<210> SEQ ID NO 48
<211> LENGTH: 42
<212> TYPE: DNA
<213> ORGANISM: Artificial Sequence
<220> FEATURE:
<223> OTHER INFORMATION: Primer YL808

<400> SEQUENCE: 48
tttgcggccg cttacaattt tcccgagtag ggttggcgc ca 42

<210> SEQ ID NO 49
<211> LENGTH: 29
<212> TYPE: DNA
<213> ORGANISM: Artificial Sequence
<220> FEATURE:
<223> OTHER INFORMATION: Primer YL809

<400> SEQUENCE: 49
accaccatga gaaggatccc gatgccttg 29

<210> SEQ ID NO 50
<211> LENGTH: 4112
<212> TYPE: DNA
<213> ORGANISM: Artificial Sequence
<220> FEATURE:
<223> OTHER INFORMATION: Plasmid pRD5S

<400> SEQUENCE: 50
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcaggcgcc 240
attcgccatt caggctgcgc aactgttggg aagggcgatc ggtgcgggcc tcttcgctat 300
tacgccagct ggcgaaaggg ggatgtgctg caaggcgatt aagttgggta acgccagggt 360
tttcccagtc acgacgttgt aaaacgacgg ccagtgaatt cgagctcggt acctcgcgaa 420
tgcatctaga tccatggctc ccgacgccga caagctgcga cagcgaaagg ctcagtccat 480
ccaggacact gccgattctc aggctaccga gctcaagatt ggcaccctga agggtctcca 540
aggcaccgag atcgtcattg atggcgacat ctacgacatc aaagacttcg atcaccctgg 600
aggcgaatcc atcatgacct ttggtggcaa cgacgttact gccacctaca agatgattca 660
tccctaccac tcgaagcatc acctggagaa gatgaaaaag gtcggtcgag tgcccgacta 720
cacctccgag tacaagttcg atactccctt cgaacgagag atcaaacagg aggtcttcaa 780
gattgtgcga agaggtcgag agtttggaac acctggctac ttctttcgag ccttctgcta 840

-continued

```
catcggtctc ttcttttacc tgcagtatct ctgggttacc actcctacca ctttcgccct    900

tgctatcttc tacggtgtgt ctcaggcctt cattggcctg aacgtccagc acgacgccaa    960

ccacggagct gcctccaaaa agccctggat caacaatttg ctcggcctgg gtgccgactt   1020

tatcggaggc tccaagtggc tctggatgaa ccagcactgg acccatcaca cttacaccaa   1080

ccatcacgag aaggatcccg acgccctggg tgcagagcct atgctgctct tcaacgacta   1140

tcccttgggt caccccaagc gaaccctcat tcatcacttc caagccttct actatctgtt   1200

tgtccttgct ggctactggg tgtcttcggt gttcaaccct cagatcctgg acctccagca   1260

ccgaggtgcc caggctgtcg gcatgaagat ggagaacgac tacattgcca agtctcgaaa   1320

gtacgctatc ttcctgcgac tcctgtacat ctacaccaac attgtggctc ccatccagaa   1380

ccaaggcttt tcgctcaccg tcgttgctca cattcttact atgggtgtcg cctccagcct   1440

gaccctcgct actctgttcg ccctctccca caacttcgag aacgcagatc gggatcccac   1500

ctacgaggct cgaaagggag gcgagcctgt ctgttggttc aagtcgcagg tggaaacctc   1560

ctctacttac ggtggcttca tttccggttg ccttacaggc ggactcaact ttcaggtcga   1620

gcatcacctg tttcctcgaa tgtcctctgc ctggtacccc tacatcgctc ctaccgttcg   1680

agaggtctgc aaaaagcacg gcgtcaagta cgcctactat ccctgggtgt ggcagaacct   1740

catctcgacc gtcaagtacc tgcatcagtc cggaactggc tcgaactgga agaacggtgc   1800

caatccctac tctggcaagc tgtaagcggc cgcatcggat cccgggcccg tcgactgcag   1860

aggcctgcat gcaagcttgg cgtaatcatg gtcatagctg tttcctgtgt gaaattgtta   1920

tccgctcaca attccacaca acatacgagc cggaagcata aagtgtaaag cctggggtgc   1980

ctaatgagtg agctaactca cattaattgc gttgcgctca ctgcccgctt tccagtcggg   2040

aaacctgtcg tgccagctgc attaatgaat cggccaacgc gcggggagag gcggtttgcg   2100

tattgggcgc tcttccgctt cctcgctcac tgactcgctg cgctcggtcg ttcggctgcg   2160

gcgagcggta tcagctcact caaaggcggt aatacggtta tccacagaat caggggataa   2220

cgcaggaaag aacatgtgag caaaaggcca gcaaaaggcc aggaaccgta aaaaggccgc   2280

gttgctggcg tttttccata ggctccgccc ccctgacgag catcacaaaa atcgacgctc   2340

aagtcagagg tggcgaaacc cgacaggact ataaagatac caggcgtttc cccctggaag   2400

ctccctcgtg cgctctcctg ttccgaccct gccgcttacc ggatacctgt ccgcctttct   2460

cccttcggga agcgtggcgc tttctcatag ctcacgctgt aggtatctca gttcggtgta   2520

ggtcgttcgc tccaagctgg gctgtgtgca cgaacccccc gttcagcccg accgctgcgc   2580

cttatccggt aactatcgtc ttgagtccaa cccggtaaga cacgacttat cgccactggc   2640

agcagccact ggtaacagga ttagcagagc gaggtatgta ggcggtgcta cagagttctt   2700

gaagtggtgg cctaactacg gctacactag aagaacagta tttggtatct gcgctctgct   2760

gaagccagtt accttcggaa aaagagttgg tagctcttga tccggcaaac aaaccaccgc   2820

tggtagcggt ggtttttttg tttgcaagca gcagattacg cgcagaaaaa aaggatctca   2880

agaagatcct ttgatctttt ctacggggtc tgacgctcag tggaacgaaa actcacgtta   2940

agggattttg gtcatgagat tatcaaaaag gatcttcacc tagatccttt taaattaaaa   3000

atgaagtttt aaatcaatct aaagtatata tgagtaaact tggtctgaca gttaccaatg   3060

cttaatcagt gaggcaccta tctcagcgat ctgtctattt cgttcatcca tagttgcctg   3120

actccccgtc gtgtagataa ctacgatacg ggagggctta ccatctggcc ccagtgctgc   3180

aatgataccg cgagacccac gctcaccggc tccagattta tcagcaataa accagccagc   3240
```

```
cggaagggcc gagcgcagaa gtggtcctgc aactttatcc gcctccatcc agtctattaa   3300

ttgttgccgg gaagctagag taagtagttc gccagttaat agtttgcgca acgttgttgc   3360

cattgctaca ggcatcgtgg tgtcacgctc gtcgtttggt atggcttcat tcagctccgg   3420

ttcccaacga tcaaggcgag ttacatgatc ccccatgttg tgcaaaaaag cggttagctc   3480

cttcggtcct ccgatcgttg tcagaagtaa gttggccgca gtgttatcac tcatggttat   3540

ggcagcactg cataattctc ttactgtcat gccatccgta agatgctttt ctgtgactgg   3600

tgagtactca accaagtcat tctgagaata gtgtatgcgg cgaccgagtt gctcttgccc   3660

ggcgtcaata cgggataata ccgcgccaca tagcagaact ttaaaagtgc tcatcattgg   3720

aaaacgttct tcggggcgaa aactctcaag gatcttaccg ctgttgagat ccagttcgat   3780

gtaacccact cgtgcaccca actgatcttc agcatctttt actttcacca gcgtttctgg   3840

gtgagcaaaa acaggaaggc aaaatgccgc aaaaaaggga ataagggcga cacggaaatg   3900

ttgaatactc atactcttcc tttttcaata ttattgaagc atttatcagg gttattgtct   3960

catgagcgga tacatatttg aatgtattta gaaaaataaa caaatagggg ttccgcgcac   4020

atttccccga aaagtgccac ctgacgtcta agaaaccatt attatcatga cattaaccta   4080

taaaaatagg cgtatcacga ggccctttcg tc                                 4112
```

```
<210> SEQ ID NO 51
<211> LENGTH: 8480
<212> TYPE: DNA
<213> ORGANISM: Artificial Sequence
<220> FEATURE:
<223> OTHER INFORMATION: Plasmid pZURD5S

<400> SEQUENCE: 51

catggctccc gacgccgaca agctgcgaca gcgaaaggct cagtccatcc aggacactgc     60

cgattctcag gctaccgagc tcaagattgg caccctgaag ggtctccaag gcaccgagat    120

cgtcattgat ggcgacatct acgacatcaa agacttcgat caccctggag gcgaatccat    180

catgaccttt ggtggcaacg acgttactgc cacctacaag atgattcatc cctaccactc    240

gaagcatcac ctggagaaga tgaaaaaggt cggtcgagtg cccgactaca cctccgagta    300

caagttcgat actcccttcg aacgagagat caaacaggag gtcttcaaga ttgtgcgaag    360

aggtcgagag tttggaacac ctggctactt ctttcgagcc ttctgctaca tcggtctctt    420

cttttacctg cagtatctct gggttaccac tcctaccact ttcgcccttg ctatcttcta    480

cggtgtgtct caggccttca ttggcctgaa cgtccagcac gacgccaacc acggagctgc    540

ctccaaaaag ccctggatca acaatttgct cggcctgggt gccgacttta tcggaggctc    600

caagtggctc tggatgaacc agcactggac ccatcacact tacaccaacc atcacgagaa    660

ggatcccgac gccctgggtg cagagcctat gctgctcttc aacgactatc ccttgggtca    720

ccccaagcga accctcattc atcacttcca agccttctac tatctgtttg tccttgctgg    780

ctactgggtg tcttcggtgt tcaaccctca gatcctggac ctccagcacc gaggtgccca    840

ggctgtcggc atgaagatgg agaacgacta cattgccaag tctcgaaagt acgctatctt    900

cctgcgactc ctgtacatct acaccaacat tgtggctccc atccagaacc aaggcttttc    960

gctcaccgtc gttgctcaca ttcttactat gggtgtcgcc tccagcctga ccctcgctac   1020

tctgttcgcc ctctcccaca acttcgagaa cgcagatcgg gatcccacct acgaggctcg   1080

aaagggaggc gagcctgtct gttggttcaa gtcgcaggtg gaaacctcct ctacttacgg   1140

tggcttcatt tccggttgcc ttacaggcgg actcaacttt caggtcgagc atcacctgtt   1200
```

-continued

```
tcctcgaatg tcctctgcct ggtaccccta catcgctcct accgttcgag aggtctgcaa   1260

aaagcacggc gtcaagtacg cctactatcc ctgggtgtgg cagaacctca tctcgaccgt   1320

caagtacctg catcagtccg gaactggctc gaactggaag aacggtgcca atccctactc   1380

tggcaagctg taagcggccg caagtgtgga tggggaagtg agtgcccggt tctgtgtgca   1440

caattggcaa tccaagatgg atggattcaa cacagggata tagcgagcta cgtggtggtg   1500

cgaggatata gcaacggata tttatgtttg acacttgaga atgtacgata caagcactgt   1560

ccaagtacaa tactaaacat actgtacata ctcatactcg tacccgggca acggtttcac   1620

ttgagtgcag tggctagtgc tcttactcgt acagtgtgca atactgcgta tcatagtctt   1680

tgatgtatat cgtattcatt catgttagtt gcgtacgagc cggaagcata aagtgtaaag   1740

cctggggtgc ctaatgagtg agctaactca cattaattgc gttgcgctca ctgcccgctt   1800

tccagtcggg aaacctgtcg tgccagctgc attaatgaat cggccaacgc gcggggagag   1860

gcggtttgcg tattgggcgc tcttccgctt cctcgctcac tgactcgctg cgctcggtcg   1920

ttcggctgcg gcgagcggta tcagctcact caaaggcggt aatacggtta tccacagaat   1980

caggggataa cgcaggaaag aacatgtgag caaaaggcca gcaaaaggcc aggaaccgta   2040

aaaaggccgc gttgctggcg tttttccata ggctccgccc ccctgacgag catcacaaaa   2100

atcgacgctc aagtcagagg tggcgaaacc cgacaggact ataaagatac caggcgtttc   2160

cccctggaag ctccctcgtg cgctctcctg ttccgaccct gccgcttacc ggatacctgt   2220

ccgcctttct cccttcggga agcgtggcgc tttctcatag ctcacgctgt aggtatctca   2280

gttcggtgta ggtcgttcgc tccaagctgg gctgtgtgca cgaacccccc gttcagcccg   2340

accgctgcgc cttatccggt aactatcgtc ttgagtccaa cccggtaaga cacgacttat   2400

cgccactggc agcagccact ggtaacagga ttagcagagc gaggtatgta ggcggtgcta   2460

cagagttctt gaagtggtgg cctaactacg gctacactag aaggacagta tttggtatct   2520

gcgctctgct gaagccagtt accttcggaa aaagagttgg tagctcttga tccggcaaac   2580

aaaccaccgc tggtagcggt ggtttttttg tttgcaagca gcagattacg cgcagaaaaa   2640

aaggatctca agaagatcct ttgatctttt ctacggggtc tgacgctcag tggaacgaaa   2700

actcacgtta agggattttg gtcatgagat tatcaaaaag gatcttcacc tagatccttt   2760

taaattaaaa atgaagtttt aaatcaatct aaagtatata tgagtaaact tggtctgaca   2820

gttaccaatg cttaatcagt gaggcaccta tctcagcgat ctgtctattt cgttcatcca   2880

tagttgcctg actccccgtc gtgtagataa ctacgatacg ggagggctta ccatctggcc   2940

ccagtgctgc aatgataccg cgagacccac gctcaccggc tccagattta tcagcaataa   3000

accagccagc cggaagggcc gagcgcagaa gtggtcctgc aactttatcc gcctccatcc   3060

agtctattaa ttgttgccgg gaagctagag taagtagttc gccagttaat agtttgcgca   3120

acgttgttgc cattgctaca ggcatcgtgg tgtcacgctc gtcgtttggt atggcttcat   3180

tcagctccgg ttcccaacga tcaaggcgag ttacatgatc ccccatgttg tgcaaaaaag   3240

cggttagctc cttcggtcct ccgatcgttg tcagaagtaa gttggccgca gtgttatcac   3300

tcatggttat ggcagcactg cataattctc ttactgtcat gccatccgta agatgctttt   3360

ctgtgactgg tgagtactca accaagtcat tctgagaata gtgtatgcgg cgaccgagtt   3420

gctcttgccc ggcgtcaata cgggataata ccgcgccaca tagcagaact ttaaaagtgc   3480

tcatcattgg aaaacgttct tcggggcgaa aactctcaag gatcttaccg ctgttgagat   3540

ccagttcgat gtaacccact cgtgcaccca actgatcttc agcatctttt actttcacca   3600
```

-continued

```
gcgtttctgg gtgagcaaaa acaggaaggc aaaatgccgc aaaaaaggga ataagggcga   3660

cacggaaatg ttgaatactc atactcttcc tttttcaata ttattgaagc atttatcagg   3720

gttattgtct catgagcgga tacatatttg aatgtattta gaaaaataaa caaatagggg   3780

ttccgcgcac atttccccga aaagtgccac ctgacgcgcc ctgtagcggc gcattaagcg   3840

cggcgggtgt ggtggttacg cgcagcgtga ccgctacact tgccagcgcc ctagcgcccg   3900

ctcctttcgc tttcttccct tcctttctcg ccacgttcgc cggctttccc cgtcaagctc   3960

taaatcgggg gctcccttta gggttccgat ttagtgcttt acggcacctc gaccccaaaa   4020

aacttgatta gggtgatggt tcacgtagtg ggccatcgcc ctgatagacg gtttttcgcc   4080

ctttgacgtt ggagtccacg ttctttaata gtggactctt gttccaaact ggaacaacac   4140

tcaaccctat ctcggtctat tcttttgatt tataagggat tttgccgatt tcggcctatt   4200

ggttaaaaaa tgagctgatt taacaaaaat ttaacgcgaa ttttaacaaa atattaacgc   4260

ttacaatttc cattcgccat tcaggctgcg caactgttgg gaagggcgat cggtgcgggc   4320

ctcttcgcta ttacgccagc tggcgaaagg gggatgtgct gcaaggcgat taagttgggt   4380

aacgccaggg ttttcccagt cacgacgttg taaaacgacg gccagtgaat tgtaatacga   4440

ctcactatag ggcgaattgg gtaccgggcc ccccctcgag gtcgatggtg tcgataagct   4500

tgatatcgaa ttcatgtcac acaaaccgat cttcgcctca aggaaaccta attctacatc   4560

cgagagactg ccgagatcca gtctacactg attaattttc gggccaataa tttaaaaaaa   4620

tcgtgttata taatattata tgtattatat atatacatca tgatgatact gacagtcatg   4680

tcccattgct aaatagacag actccatctg ccgcctccaa ctgatgttct caatatttaa   4740

ggggtcatct cgcattgttt aataataaac agactccatc taccgcctcc aaatgatgtt   4800

ctcaaaatat attgtatgaa cttattttta ttacttagta ttattagaca acttacttgc   4860

tttatgaaaa acacttccta tttaggaaac aatttataat ggcagttcgt tcatttaaca   4920

atttatgtag aataaatgtt ataaatgcgt atgggaaatc ttaaatatgg atagcataaa   4980

tgatatctgc attgcctaat tcgaaatcaa cagcaacgaa aaaaatccct tgtacaacat   5040

aaatagtcat cgagaaatat caactatcaa agaacagcta ttcacacgtt actattgaga   5100

ttattattgg acgagaatca cacactcaac tgtctttctc tcttctagaa atacaggtac   5160

aagtatgtac tattctcatt gttcatactt ctagtcattt catcccacat attccttgga   5220

tttctctcca atgaatgaca ttctatcttg caaattcaac aattataata agatatacca   5280

aagtagcggt atagtggcaa tcaaaaagct tctctggtgt gcttctcgta tttattttta   5340

ttctaatgat ccattaaagg tatatattta tttcttgtta tataatcctt ttgtttatta   5400

catgggctgg atacataaag gtattttgat ttaatttttt gcttaaattc aatccccccct   5460

cgttcagtgt caactgtaat ggtaggaaat taccatactt ttgaagaagc aaaaaaaatg   5520

aaagaaaaaa aaaatcgtat ttccaggtta gacgttccgc agaatctaga atgcggtatg   5580

cggtacattg ttcttcgaac gtaaaagttg cgctccctga gatattgtac atttttgctt   5640

ttacaagtac aagtacatcg tacaactatg tactactgtt gatgcatcca caacagtttg   5700

ttttgttttt ttttgttttt tttttttcta atgattcatt accgctatgt atacctactt   5760

gtacttgtag taagccgggt tattggcgtt caattaatca tagacttatg aatctgcacg   5820

gtgtgcgctg cgagttactt ttagcttatg catgctactt gggtgtaata ttgggatctg   5880

ttcggaaatc aacggatgct caatcgattt cgacagtaat taattaagtc atacacaagt   5940

cagctttctt cgagcctcat ataagtataa gtagttcaac gtattagcac tgtacccagc   6000
```

-continued

```
atctccgtat cgagaaacac aacaacatgc cccattggac agatcatgcg gatacacagg   6060
ttgtgcagta tcatacatac tcgatcagac aggtcgtctg accatcatac aagctgaaca   6120
agcgctccat acttgcacgc tctctatata cacagttaaa ttacatatcc atagtctaac   6180
ctctaacagt taatcttctg gtaagcctcc cagccagcct tctggtatcg cttggcctcc   6240
tcaataggat ctcggttctg gccgtacaga cctcggccga caattatgat atccgttccg   6300
gtagacatga catcctcaac agttcggtac tgctgtccga gagcgtctcc cttgtcgtca   6360
agacccaccc cgggggtcag aataagccag tcctcagagt cgcccttagg tcggttctgg   6420
gcaatgaagc caaccacaaa ctcggggtcg gatcgggcaa gctcaatggt ctgcttggag   6480
tactcgccag tggccagaga gcccttgcaa gacagctcgg ccagcatgag cagacctctg   6540
gccagcttct cgttgggaga ggggactagg aactccttgt actgggagtt ctcgtagtca   6600
gagacgtcct ccttcttctg ttcagagaca gtttcctcgg caccagctcg caggccagca   6660
atgattccgg ttccgggtac accgtgggcg ttggtgatat cggaccactc ggcgattcgg   6720
tgacaccggt actggtgctt gacagtgttg ccaatatctg cgaactttct gtcctcgaac   6780
aggaagaaac cgtgcttaag agcaagttcc ttgagggggga gcacagtgcc ggcgtaggtg   6840
aagtcgtcaa tgatgtcgat atgggttttg atcatgcaca cataaggtcc gaccttatcg   6900
gcaagctcaa tgagctcctt ggtggtggta acatccagag aagcacacag gttggttttc   6960
ttggctgcca cgagcttgag cactcgagcg gcaaaggcgg acttgtggac gttagctcga   7020
gcttcgtagg agggcatttt ggtggtgaag aggagactga aataaattta gtctgcagaa   7080
ctttttatcg gaaccttatc tggggcagtg aagtatatgt tatggtaata gttacgagtt   7140
agttgaactt atagatagac tggactatac ggctatcggt ccaaattaga aagaacgtca   7200
atggctctct gggcgtcgcc tttgccgaca aaaatgtgat catgatgaaa gccagcaatg   7260
acgttgcagc tgatattgtt gtcggccaac cgcgccgaaa acgcagctgt cagacccaca   7320
gcctccaacg aagaatgtat cgtcaaagtg atccaagcac actcatagtt ggagtcgtac   7380
tccaaaggcg gcaatgacga gtcagacaga tactcgtcga ctcaggcgac gacggaattc   7440
ctgcagccca tctgcagaat tcaggagaga ccgggttggc ggcgtatttg tgtcccaaaa   7500
aacagcccca attgccccgg agaagacggc caggccgcct agatgacaaa ttcaacaact   7560
cacagctgac tttctgccat tgccactagg ggggggcctt tttatatggc caagccaagc   7620
tctccacgtc ggttgggctg cacccaacaa taaatgggta gggttgcacc aacaaaggga   7680
tgggatgggg ggtagaagat acgaggataa cggggctcaa tggcacaaat aagaacgaat   7740
actgccatta agactcgtga tccagcgact gacaccattg catcatctaa gggcctcaaa   7800
actacctcgg aactgctgcg ctgatctgga caccacagag gttccgagca ctttaggttg   7860
caccaaatgt cccaccaggt gcaggcagaa aacgctggaa cagcgtgtac agtttgtctt   7920
aacaaaaagt gagggcgctg aggtcgagca gggtggtgtg acttgttata gcctttagag   7980
ctgcgaaagc gcgtatggat ttggctcatc aggccagatt gagggtctgt ggacacatgt   8040
catgttagtg tacttcaatc gccccctgga tatagccccg acaataggcc gtggcctcat   8100
ttttttgcct tccgcacatt tccattgctc ggtacccaca ccttgcttct cctgcacttg   8160
ccaaccttaa tactggttta cattgaccaa catcttacaa gcggggggct tgtctagggt   8220
atatataaac agtggctctc ccaatcggtt gccagtctct tttttccttt ctttccccac   8280
agattcgaaa tctaaactac acatcacaca atgcctgtta ctgacgtcct taagcgaaag   8340
tccggtgtca tcgtcggcga cgatgtccga gccgtgagta tccacgacaa gatcagtgtc   8400
```

```
gagacgacgc gttttgtgta atgacacaat ccgaaagtcg ctagcaacac acactctcta   8460

cacaaactaa cccagctctc                                               8480


<210> SEQ ID NO 52
<211> LENGTH: 19
<212> TYPE: DNA
<213> ORGANISM: Artificial Sequence
<220> FEATURE:
<223> OTHER INFORMATION: Primer T7

<400> SEQUENCE: 52

ggaaacagct atgaccatg                                                  19


<210> SEQ ID NO 53
<211> LENGTH: 459
<212> TYPE: PRT
<213> ORGANISM: Rhizopus stolonifer (GenBank Accession No. AAX22052)

<400> SEQUENCE: 53

Met Ser Thr Leu Asp Arg Gln Ser Ile Phe Thr Ile Lys Glu Leu Glu
1               5                   10                  15

Ser Ile Ser Gln Arg Ile His Asp Gly Asp Glu Glu Ala Met Lys Phe
            20                  25                  30

Ile Ile Ile Asp Lys Lys Val Tyr Asp Val Thr Glu Phe Ile Glu Asp
        35                  40                  45

His Pro Gly Gly Ala Gln Val Leu Leu Thr His Val Gly Lys Asp Ala
    50                  55                  60

Ser Asp Val Phe His Ala Met His Pro Glu Ser Ala Tyr Glu Val Leu
65                  70                  75                  80

Asn Asn Tyr Phe Val Gly Asp Val Gln Glu Thr Val Val Thr Glu Lys
                85                  90                  95

Ser Ser Ser Ala Gln Phe Ala Val Glu Met Arg Gln Leu Arg Asp Gln
            100                 105                 110

Leu Lys Lys Glu Gly Tyr Phe His Ser Ser Lys Leu Phe Tyr Ala Tyr
        115                 120                 125

Lys Val Leu Ser Thr Leu Ala Ile Cys Ile Ala Gly Leu Ser Leu Leu
    130                 135                 140

Tyr Ala Tyr Gly Arg Thr Ser Thr Leu Ala Val Val Ala Ser Ala Ile
145                 150                 155                 160

Thr Val Gly Ile Phe Trp Gln Gln Cys Gly Trp Leu Ala His Asp Phe
                165                 170                 175

Gly His His Gln Cys Phe Glu Asp Arg Thr Trp Asn Asp Val Leu Val
            180                 185                 190

Val Phe Leu Gly Asn Phe Cys Gln Gly Phe Ser Leu Ser Trp Trp Lys
        195                 200                 205

Asn Lys His Asn Thr His His Ala Ser Thr Asn Val His Gly Gln Asp
    210                 215                 220

Pro Asp Ile Asp Thr Ala Pro Val Leu Leu Trp Asp Glu Tyr Ala Ser
225                 230                 235                 240

Ala Ala Tyr Tyr Ala Ser Leu Asp Gln Glu Pro Thr Met Val Ser Arg
                245                 250                 255

Phe Leu Ala Glu Gln Val Leu Pro His Gln Thr Arg Tyr Phe Phe Phe
            260                 265                 270

Ile Leu Ala Phe Ala Arg Leu Ser Trp Ala Leu Gln Ser Leu Ser Tyr
        275                 280                 285

Ser Phe Lys Lys Glu Ser Ile Asn Lys Ser Arg Gln Leu Asn Leu Phe
    290                 295                 300
```

```
Glu Arg Val Cys Ile Val Gly His Trp Ala Leu Phe Ala Phe Cys Ile
305                 310                 315                 320

Tyr Ser Trp Cys Ser Asn Val Tyr His Met Val Leu Phe Phe Leu Val
                325                 330                 335

Ser Gln Ala Thr Thr Gly Tyr Thr Leu Ala Leu Val Phe Ala Leu Asn
            340                 345                 350

His Asn Gly Met Pro Val Ile Thr Glu Glu Lys Ala Glu Ser Met Glu
        355                 360                 365

Phe Phe Glu Ile Gln Val Ile Thr Gly Arg Asp Val Thr Leu Ser Pro
    370                 375                 380

Leu Gly Asp Trp Phe Met Gly Gly Leu Asn Tyr Gln Ile Glu His His
385                 390                 395                 400

Val Phe Pro Asn Met Pro Arg His Asn Leu Pro Thr Val Lys Pro Met
                405                 410                 415

Val Lys Ser Leu Cys Gln Lys Tyr Asp Ile Asn Tyr His Asp Thr Gly
            420                 425                 430

Phe Leu Lys Gly Thr Leu Glu Val Leu Gln Thr Leu Asp Ile Thr Ser
        435                 440                 445

Lys Leu Ser Leu Gln Leu Ser Lys Lys Ser Phe
    450                 455

<210> SEQ ID NO 54
<211> LENGTH: 695
<212> TYPE: DNA
<213> ORGANISM: Pavlova lutheri

<400> SEQUENCE: 54

agggccaagg gtgccaacca ccttccacgt gagactacac accgtaggcc gatgggcaag      60

ggtggagacg gcggcgcgca ggcggtgagc gggaccgacg cgtctctcgc tgaggtgagc     120

tccgtcgata gcaagagcgt gcacgtcgtg ctctacggca agcgcgtgga tgtcacaaag     180

ttccagggct acgacgtggc ctggtggcgc gcgcgccata acacgcacca cgtgtgcacc     240

aacgaggatg gttcggaccc ggacatcaag acggcgcccc tgctcatcta cgtgcgagag     300

aacccgtcca ttgccaagcg gctcaacttc ttccagcgct ggcagcagta ctactatgtg     360

ccgaccatgg ccatcctcga cctctactgg cgcctggagt ccatcgcgta cgtggctgtg     420

cgcctgccta agatgtggat gcaggccgcc gctcttgccg ctcactacgc gctcctgtgc     480

tgggtcttcg cagcgcatct caacctcatc cctctcatga tggttgcacg cggcttcgcg     540

acgggcatcg ttgtctttgc aacccactat ggtgaggaca tcctcgaccg cgagcacgtc     600

gagggcatga cgctcgtcga gcagaccgcc aagacctccc gtaacatcac gggcggctgg     660

ctagtgaacg tgctcacggg cttcatctcc ctgca                                695

<210> SEQ ID NO 55
<211> LENGTH: 1106
<212> TYPE: DNA
<213> ORGANISM: Pavlova lutheri

<400> SEQUENCE: 55

agggccaagg gtgccaacca ccttccacgt gagactacac accgtaggcc gatgggcaag      60

ggtggagacg gcggcgcgca ggcggtgagc gggaccgacg cgtctctcgc tgaggtgagc     120

tccgtcgata gcaagagcgt gcacgtcgtg ctctacggca agcgcgtgga tgtcacaaag     180

ttccagggct acgacgtggc ctggtggcgc gcgcgccata acacgcacca cgtgtgcacc     240

aacgaggatg gttcggaccc ggacatcaag acggcgcccc tgctcatcta cgtgcgagag     300
```

```
aacccgtcca ttgccaagcg gctcaacttc ttccagcgct ggcagcagta ctactatgtg    360

ccgaccatgg ccatcctcga cctctactgg cgcctggagt ccatcgcgta cgtggctgtg    420

cgcctgccta agatgtggat gcaggccgcc gctcttgccg ctcactacgc gctcctgtgc    480

tgggtcttcg cagcgcatct caacctcatc cctctcatga tggttgcacg cggcttcgcg    540

acgggcatcg ttgtctttgc aacccactat ggtgaggaca tcctcgaccg cgagcacgtc    600

gagggcatga cgctcgtcga gcagaccgcc aagacctccc gtaacatcac gggcggctgg    660

ctagtgaacg tgctcacggg cttcatctcc ctgcagaccg agcatcacct cttccccatg    720

atgcccaccg gcaacctaat gactatccag cccgaggtac gcgacttctt caagaagcat    780

ggcctcgagt accgcgaggg caacctcttc cagtgcgtgc accagaacat caaggctctc    840

gccttcgagc acctcctcca ctgagcgtca ccactcaagc gtcctaagtg cacaggtact    900

gtcttctgac cgatggccgc gcggctccct cggctggcag tggggccaac gagtggcctc    960

gcgggatcgg gcacgatcgg gcctccatga aacttcagtg ttcagagaca agccgacaac   1020

ctccgcatcg tgagaaatct tttaaagcag tatgttccat cacgccgctt ttgcagtcaa   1080

taacattacc caaaaaaaaa aaaaaa                                        1106


<210> SEQ ID NO 56
<211> LENGTH: 287
<212> TYPE: PRT
<213> ORGANISM: Pavlova lutheri

<400> SEQUENCE: 56

Arg Ala Lys Gly Ala Asn His Leu Pro Arg Glu Thr Thr His Arg Arg
1               5                   10                  15

Pro Met Gly Lys Gly Gly Asp Gly Gly Ala Gln Ala Val Ser Gly Thr
            20                  25                  30

Asp Ala Ser Leu Ala Glu Val Ser Ser Val Asp Ser Lys Ser Val His
        35                  40                  45

Val Val Leu Tyr Gly Lys Arg Val Asp Val Thr Lys Phe Gln Gly Tyr
    50                  55                  60

Asp Val Ala Trp Trp Arg Ala Arg His Asn Thr His His Val Cys Thr
65                  70                  75                  80

Asn Glu Asp Gly Ser Asp Pro Asp Ile Lys Thr Ala Pro Leu Leu Ile
                85                  90                  95

Tyr Val Arg Glu Asn Pro Ser Ile Ala Lys Arg Leu Asn Phe Phe Gln
            100                 105                 110

Arg Trp Gln Gln Tyr Tyr Tyr Val Pro Thr Met Ala Ile Leu Asp Leu
        115                 120                 125

Tyr Trp Arg Leu Glu Ser Ile Ala Tyr Val Ala Val Arg Leu Pro Lys
    130                 135                 140

Met Trp Met Gln Ala Ala Ala Leu Ala Ala His Tyr Ala Leu Leu Cys
145                 150                 155                 160

Trp Val Phe Ala Ala His Leu Asn Leu Ile Pro Leu Met Met Val Ala
                165                 170                 175

Arg Gly Phe Ala Thr Gly Ile Val Val Phe Ala Thr His Tyr Gly Glu
            180                 185                 190

Asp Ile Leu Asp Arg Glu His Val Glu Gly Met Thr Leu Val Glu Gln
        195                 200                 205

Thr Ala Lys Thr Ser Arg Asn Ile Thr Gly Gly Trp Leu Val Asn Val
    210                 215                 220

Leu Thr Gly Phe Ile Ser Leu Gln Thr Glu His His Leu Phe Pro Met
```

```
225                 230                 235                 240

Met Pro Thr Gly Asn Leu Met Thr Ile Gln Pro Glu Val Arg Asp Phe
                245                 250                 255

Phe Lys Lys His Gly Leu Glu Tyr Arg Glu Gly Asn Leu Phe Gln Cys
            260                 265                 270

Val His Gln Asn Ile Lys Ala Leu Ala Phe Glu His Leu Leu His
        275                 280                 285


<210> SEQ ID NO 57
<211> LENGTH: 20
<212> TYPE: DNA
<213> ORGANISM: Artificial Sequence
<220> FEATURE:
<223> OTHER INFORMATION: Primer SeqE

<400> SEQUENCE: 57

cgacacactc caatctttcc                                                  20


<210> SEQ ID NO 58
<211> LENGTH: 20
<212> TYPE: DNA
<213> ORGANISM: Artificial Sequence
<220> FEATURE:
<223> OTHER INFORMATION: Primer SeqW

<400> SEQUENCE: 58

ggtggctgga gttagacatc                                                  20


<210> SEQ ID NO 59
<211> LENGTH: 22
<212> TYPE: DNA
<213> ORGANISM: Artificial Sequence
<220> FEATURE:
<223> OTHER INFORMATION: Primer AP1

<400> SEQUENCE: 59

gtaatacgac tcactatagg gc                                               22


<210> SEQ ID NO 60
<211> LENGTH: 20
<212> TYPE: DNA
<213> ORGANISM: Artificial Sequence
<220> FEATURE:
<223> OTHER INFORMATION: Primer GSP PvDES

<400> SEQUENCE: 60

ctgcgaagac ccagcacagg                                                  20


<210> SEQ ID NO 61
<211> LENGTH: 22
<212> TYPE: DNA
<213> ORGANISM: Artificial Sequence
<220> FEATURE:
<223> OTHER INFORMATION: Primer M13-28Rev

<400> SEQUENCE: 61

gtaatacgac tcactatagg gc                                               22


<210> SEQ ID NO 62
<211> LENGTH: 21
<212> TYPE: DNA
<213> ORGANISM: Artificial Sequence
<220> FEATURE:
<223> OTHER INFORMATION: Primer PavDes seq

<400> SEQUENCE: 62
```

ttgtggcgct caatcatctc c 21

<210> SEQ ID NO 63
<211> LENGTH: 1294
<212> TYPE: DNA
<213> ORGANISM: Pavlova lutheri

<400> SEQUENCE: 63
ctttgcgagc gcggcgcaga cgattgcggc ccgtagtgat cgcggtgcgc attgctgtgt 60
ttctagtttt gctgacgccc ggcccgataa tgacaccttc tcccgtttga aatactaata 120
agtaactata ttataatatt caaaggtggc gactatggat ctccttttct aaagttcagc 180
ggaattggga atcggagaaa tttcgagata tgtcataatc acgtgctcta tctcgaatga 240
accgcggccg gtgagcgatt actcgggaag ccaattccta ttaacgagtc aggggggatc 300
tttgaggtga gtcggccacg cagagagagc aaggaatcat cctcatccgc cgttctcgag 360
aaagagccaa gggtgccaac caccttccac gtgagactac acaccgtagg ccgatgggca 420
agggtggaga cggcggcgcg caggcggcga gcgggaccga cgcatctctc gctgaggtga 480
gctccgtcga tagcaagagc gtgcgcgtcg tgctctacgg caagcgcgtg gatgtcacaa 540
agttccagag ggcacacccg ggcgggagca aggtgttccg catcttccag gagcgcgacg 600
cgacggagca gttcgagtct taccactcgc ccaaggccat caagatgatg gagggcatgc 660
tcaagaagtc ggaggatgcg cccgcttccg tgcccctgcc ctcgcggtcc accatgggca 720
cggagttcaa ggagatgatt gagcgccaca agagggctgg tctctacgac ccttgcccgt 780
tggacgagct gttcaagctc accatcgtcc ttgcgcccat cttcgtgggc gcctatctcg 840
tgcggagcgg cgtctcgccc ctcgcgggcg cgctctccat gggctttggc ttctacctcg 900
acggctggct tgctcacrac tacctgcatc acgcagtctt caagggctcg gtcaacacgc 960
tcgtcaaggc gaacaacgcc atgggatacg ccctcggctt cctccagggc tacgacgtgg 1020
cctggtggcg cgcgcgccat aacacgcacc acgtgtgcac caacgaggat ggttcggacc 1080
cggacatcaa gacggcgccc ctgctcatct acgtgcgaga gaacccgtcc attgccaagc 1140
ggctcaactt cttccagcgc tggcagcagt actactatgt gccgaccatg gccatcctcg 1200
acctctactg gcgcctggag tccatcgcgt acgtggctgt gcgcctgcct aagatgtgga 1260
tgcaggccgc cgctcttgcc gctcactacg cgct 1294

<210> SEQ ID NO 64
<211> LENGTH: 1927
<212> TYPE: DNA
<213> ORGANISM: Pavlova lutheri

<400> SEQUENCE: 64
ctttgcgagc gcggcgcaga cgattgcggc ccgtagtgat cgcggtgcgc attgctgtgt 60
ttctagtttt gctgacgccc ggcccgataa tgacaccttc tcccgtttga aatactaata 120
agtaactata ttataatatt caaaggtggc gactatggat ctccttttct aaagttcagc 180
ggaattggga atcggagaaa tttcgagata tgtcataatc acgtgctcta tctcgaatga 240
accgcggccg gtgagcgatt actcgggaag ccaattccta ttaacgagtc aggggggatc 300
tttgaggtga gtcggccacg cagagagagc aaggaatcat cctcatccgc cgttctcgag 360
aaagagccaa gggtgccaac caccttccac gtgagactac acaccgtagg ccgatgggca 420
agggtggaga cggcggcgcg caggcggtga gcgggaccga cgcgtctctc gctgaggtga 480
gctccgtcga tagcaagagc gtgcacgtcg tgctctacgg caagcgcgtg gatgtcacaa 540

```
agttccagaa ggcacacccg ggcgggagca aggtgttccg catcttccag gagcgcgacg    600

cgacggagca gttcgagtct taccactcgc ccaaggccat caagatgatg gagggcatgc    660

tcaagaagtc ggaggatgcg cccgcttccg tgcccctgcc ctcgcggtcc accatgggca    720

cggagttcaa ggagatgatt gagcgccaca agagggctgg tctctacgac ccttgcccgt    780

tggacgagct gttcaagctc accatcgtcc ttgcgcccat cttcgtgggc gcctatctcg    840

tgcggagcgg cgtctcgccc ctcgcgggcg cgctctccat gggctttggc ttctacctcg    900

acggctggct tgctcacgac tacctgcatc acgcagtctt caagggctcg gtcaacacgc    960

tcgtcaaggc gaacaacgcc atgggatacg ccctcggctt cctccagggc tacgacgtgg   1020

cctggtggcg cgcgcgccat aacacgcacc acgtgtgcac caacgaggat ggttcggacc   1080

cggacatcaa gacggcgccc ctgctcatct acgtgcgaga gaacccgtcc attgccaagc   1140

ggctcaactt cttccagcgc tggcagcagt actactatgt gccgaccatg gccatcctcg   1200

acctctactg gcgcctggag tccatcgcgt acgtggctgt gcgcctgcct aagatgtgga   1260

tgcaggccgc cgctcttgcc gctcactacg cgctcctgtg ctgggtcttc gcagcgcatc   1320

tcaacctcat ccctctcatg atggttgcac gcggcttcgc gacgggcatc gttgtctttg   1380

caacccacta tggtgaggac atcctcgacc gcgagcacgt cgagggcatg acgctcgtcg   1440

agcagaccgc caagacctcc cgtaacatca cgggcggctg gctagtgaac gtgctcacgg   1500

gcttcatctc cctgcagacc gagcatcacc tcttccccat gatgcccacc ggcaacctaa   1560

tgactatcca gcccgaggta cgcgacttct tcaagaagca tggcctcgag taccgcgagg   1620

gcaacctctt ccagtgcgtg caccagaaca tcaaggctct cgccttcgag cacctcctcc   1680

actgagcgtc accactcaag cgtcctaagt gcacaggtac tgtcttctga ccgatggccg   1740

cgcggctccc tcggctggca gtggggccaa cgagtggcct cgcgggatcg ggcacgatcg   1800

ggcctccatg aaacttcagt gttcagagac aagccgacaa cctccgcatc gtgagaaatc   1860

ttttaaagca gtatgttcca tcacgccgct tttgcagtca ataacattac ccaaaaaaaa   1920

aaaaaaa                                                             1927
```

<210> SEQ ID NO 65
<211> LENGTH: 459
<212> TYPE: PRT
<213> ORGANISM: Rhizopus stolonifer (GenBank Accession No. ABB96724)

<400> SEQUENCE: 65

```
Met Ser Thr Leu Asp Arg Gln Ser Ile Phe Thr Ile Lys Glu Leu Glu
1               5                   10                  15

Ser Ile Ser Gln Arg Ile His Asp Gly Asp Glu Glu Ala Met Lys Phe
            20                  25                  30

Ile Ile Ile Asp Lys Lys Val Tyr Asp Val Thr Glu Phe Ile Glu Asp
        35                  40                  45

His Pro Gly Gly Ala Gln Val Leu Leu Thr His Val Gly Lys Asp Ala
    50                  55                  60

Ser Asp Val Phe His Ala Met His Pro Glu Ser Ala Tyr Glu Val Leu
65                  70                  75                  80

Asn Asn Tyr Phe Val Gly Asp Val Gln Glu Thr Val Val Thr Glu Lys
                85                  90                  95

Ser Ser Ser Ala Gln Phe Ala Val Glu Met Arg Gln Leu Arg Asp Gln
            100                 105                 110

Leu Lys Lys Glu Gly Tyr Phe His Ser Ser Lys Leu Phe Tyr Ala Tyr
        115                 120                 125
```

```
Lys Val Leu Ser Thr Leu Ala Ile Cys Ile Ala Gly Leu Ser Pro Leu
    130                 135                 140

Tyr Ala Tyr Gly Arg Thr Ser Thr Leu Ala Val Val Ala Ser Ala Ile
145                 150                 155                 160

Thr Val Gly Ile Phe Trp Gln Gln Cys Gly Trp Leu Ala His Asp Phe
                165                 170                 175

Gly His His Gln Cys Phe Glu Asp Arg Thr Trp Asn Asp Val Leu Val
            180                 185                 190

Val Phe Leu Gly Asn Phe Cys Gln Gly Phe Ser Leu Ser Trp Trp Lys
        195                 200                 205

Asn Lys His Asn Thr His His Ala Ser Thr Asn Val His Gly Gln Asp
    210                 215                 220

Pro Asp Ile Asp Thr Ala Pro Val Leu Leu Trp Asp Glu Tyr Ala Ser
225                 230                 235                 240

Ala Ala Tyr Tyr Ala Ser Leu Asp Gln Glu Pro Thr Met Val Ser Arg
                245                 250                 255

Phe Leu Ala Glu Gln Val Leu Pro His Gln Thr Arg Tyr Phe Phe Phe
            260                 265                 270

Ile Leu Ala Phe Ala Arg Leu Ser Trp Ala Leu Gln Ser Leu Ser Tyr
        275                 280                 285

Ser Phe Lys Lys Glu Ser Ile Asn Lys Ser Arg Gln Leu Asn Leu Phe
    290                 295                 300

Glu Arg Val Cys Ile Val Gly His Trp Ala Leu Ser Ala Phe Cys Ile
305                 310                 315                 320

Tyr Ser Trp Cys Ser Asn Val Tyr His Met Val Leu Phe Phe Leu Val
                325                 330                 335

Ser Gln Ala Thr Thr Gly Tyr Thr Leu Ala Leu Val Phe Ala Leu Asn
            340                 345                 350

His Asn Gly Met Pro Val Ile Thr Glu Glu Lys Ala Glu Ser Met Glu
        355                 360                 365

Phe Phe Glu Ile Gln Val Ile Thr Gly Arg Asp Val Thr Leu Ser Pro
    370                 375                 380

Leu Gly Asp Trp Phe Met Gly Gly Leu Asn Tyr Gln Ile Glu His His
385                 390                 395                 400

Val Phe Pro Asn Met Pro Arg His Asn Leu Pro Thr Val Lys Pro Met
                405                 410                 415

Val Lys Ser Leu Cys Gln Lys Tyr Asp Ile Asn Tyr His Asp Thr Gly
            420                 425                 430

Phe Leu Lys Gly Thr Leu Glu Val Leu Gln Thr Leu Asp Ile Thr Ser
        435                 440                 445

Lys Leu Ser Leu Gln Leu Ser Lys Lys Ser Phe
    450                 455


<210> SEQ ID NO 66
<211> LENGTH: 427
<212> TYPE: PRT
<213> ORGANISM: Pavlova salina
<300> PUBLICATION INFORMATION:
<302> TITLE: SYNTHESIS OF LONG-CHAIN POLYUNSATURATED FATTY ACIDS BY
      RECOMBINANT CELLS
<310> PATENT DOCUMENT NUMBER: WO 2005/103253
<311> PATENT FILING DATE: 2005-04-22
<312> PUBLICATION DATE: 2005-11-03
<313> RELEVANT RESIDUES IN SEQ ID NO: (1)..(427)

<400> SEQUENCE: 66

Met Gly Arg Gly Gly Asp Ser Ser Gly Gln Ala His Pro Ala Ala Glu
```

-continued

```
1               5                   10                  15

Leu Ala Val Pro Ser Asp Arg Ala Glu Val Ser Asn Ala Asp Ser Lys
            20                  25                  30

Ala Leu His Ile Val Leu Tyr Gly Lys Arg Val Asp Val Thr Lys Phe
        35                  40                  45

Gln Arg Thr His Pro Gly Gly Ser Lys Val Phe Arg Ile Phe Gln Asp
    50                  55                  60

Arg Asp Ala Thr Glu Gln Phe Glu Ser Tyr His Ser Lys Arg Ala Ile
65                  70                  75                  80

Lys Met Met Glu Gly Met Leu Lys Lys Ser Glu Asp Ala Pro Ala Asp
                85                  90                  95

Thr Pro Leu Pro Ser Gln Ser Pro Met Gly Lys Asp Phe Lys Ala Met
            100                 105                 110

Ile Glu Arg His Val Ala Ala Gly Tyr Tyr Asp Pro Cys Pro Leu Asp
        115                 120                 125

Glu Leu Phe Lys Leu Ser Leu Val Leu Leu Pro Thr Phe Ala Gly Met
    130                 135                 140

Tyr Met Leu Lys Ala Gly Val Gly Ser Pro Leu Cys Gly Ala Leu Met
145                 150                 155                 160

Val Ser Phe Gly Trp Tyr Leu Asp Gly Trp Leu Ala His Asp Tyr Leu
                165                 170                 175

His His Ser Val Phe Lys Gly Ser Val Ala Arg Thr Val Gly Trp Asn
            180                 185                 190

Asn Ala Ala Gly Tyr Phe Leu Gly Phe Val Gln Gly Tyr Ala Val Glu
        195                 200                 205

Trp Trp Arg Ala Arg His Asn Thr His His Val Cys Thr Asn Glu Asp
    210                 215                 220

Gly Ser Asp Pro Asp Ile Lys Thr Ala Pro Leu Leu Ile Tyr Val Arg
225                 230                 235                 240

Asn Lys Pro Ser Ile Ala Lys Arg Leu Asn Ala Phe Gln Arg Tyr Gln
                245                 250                 255

Gln Tyr Tyr Tyr Val Pro Val Met Ala Ile Leu Asp Leu Tyr Trp Arg
            260                 265                 270

Leu Glu Ser Ile Ala Tyr Val Ala Met Arg Leu Pro Lys Met Leu Pro
        275                 280                 285

Gln Ala Leu Ala Leu Val Ala His Tyr Ala Ile Val Ala Trp Val Phe
    290                 295                 300

Ala Gly Asn Tyr His Leu Leu Pro Leu Val Thr Val Leu Arg Gly Phe
305                 310                 315                 320

Gly Thr Gly Ile Thr Val Phe Ala Thr His Tyr Gly Glu Asp Ile Leu
                325                 330                 335

Asp Ala Asp Gln Val Arg His Met Thr Leu Val Glu Gln Thr Ala Leu
            340                 345                 350

Thr Ser Arg Asn Ile Ser Gly Gly Trp Leu Val Asn Val Leu Thr Gly
        355                 360                 365

Phe Ile Ser Leu Gln Thr Glu His His Leu Phe Pro Met Met Pro Thr
    370                 375                 380

Gly Asn Leu Met Thr Ile Gln Pro Glu Val Arg Ala Phe Phe Lys Lys
385                 390                 395                 400

His Gly Leu Glu Tyr Arg Glu Gly Asn Leu Ile Glu Cys Val Arg Gln
                405                 410                 415

Asn Ile Arg Ala Leu Ala Phe Glu His Leu Leu
            420                 425
```

<210> SEQ ID NO 67
<211> LENGTH: 1338
<212> TYPE: DNA
<213> ORGANISM: Mortierella alpina

<400> SEQUENCE: 67

```
atgggaacgg accaaggaaa aaccttcacc tgggaagagc tggcggccca taacaccaag     60
gacgacctac tcttggccat ccgcggcagg gtgtacgatg tcacaaagtt cttgagccgc    120
catcctggtg gagtggacac tctcctgctc ggagctggcc gagatgttac tccggtcttt    180
gagatgtatc acgcgtttgg ggctgcagat gccattatga agaagtacta tgtcggtaca    240
ctggtctcga atgagctgcc catcttcccg gagccaacgg tgttccacaa aaccatcaag    300
acgagagtcg agggctactt tacggatcgg aacattgatc ccaagaatag accagagatc    360
tggggacgat acgctcttat ctttggatcc ttgatcgctt cctactacgc gcagctcttt    420
gtgcctttcg ttgtcgaacg cacatggctt caggtggtgt ttgcaatcat catgggattt    480
gcgtgcgcac aagtcggact caaccctctt catgatgcgt ctcacttttc agtgacccac    540
aaccccactg tctggaagat tctgggagcc acgcacgact tttcaacgg agcatcgtac     600
ctggtgtgga tgtaccaaca tatgctcggc catcacccct acaccaacat tgctggagca    660
gatcccgacg tgtcgacgtc tgagcccgat gttcgtcgta tcaagcccaa ccaaaagtgg    720
tttgtcaacc acatcaacca gcacatgttt gttcctttcc tgtacggact gctggcgttc    780
aaggtgcgca ttcaggacat caacattttg tactttgtca agaccaatga cgctattcgt    840
gtcaatccca tctcgacatg gcacactgtg atgttctggg gcggcaaggc tttctttgtc    900
tggtatcgcc tgattgttcc cctgcagtat ctgcccctgg gcaaggtgct gctcttgttc    960
acggtcgcgg acatggtgtc gtcttactgg ctggcgctga ccttccaggc gaaccacgtt   1020
gttgaggaag ttcagtggcc gttgcctgac gagaacggga tcatccaaaa ggactgggca   1080
gctatgcagg tcgagactac gcaggattac gcacacgatt cgcacctctg gaccagcatc   1140
actggcagct tgaactacca ggctgtgcac catctgttcc ccaacgtgtc gcagcaccat   1200
tatcccgata ttctggccat catcaagaac acctgcagcg agtacaaggt tccatacctt   1260
gtcaaggata cgttttggca agcatttgct tcacatttgg agcacttgcg tgttcttgga   1320
ctccgtccca aggaagag                                                 1338
```

<210> SEQ ID NO 68
<211> LENGTH: 446
<212> TYPE: PRT
<213> ORGANISM: Mortierella alpina

<400> SEQUENCE: 68

```
Met Gly Thr Asp Gln Gly Lys Thr Phe Thr Trp Glu Glu Leu Ala Ala
1               5                   10                  15

His Asn Thr Lys Asp Asp Leu Leu Leu Ala Ile Arg Gly Arg Val Tyr
            20                  25                  30

Asp Val Thr Lys Phe Leu Ser Arg His Pro Gly Gly Val Asp Thr Leu
        35                  40                  45

Leu Leu Gly Ala Gly Arg Asp Val Thr Pro Val Phe Glu Met Tyr His
    50                  55                  60

Ala Phe Gly Ala Ala Asp Ala Ile Met Lys Lys Tyr Tyr Val Gly Thr
65                  70                  75                  80

Leu Val Ser Asn Glu Leu Pro Ile Phe Pro Glu Pro Thr Val Phe His
                85                  90                  95
```

```
Lys Thr Ile Lys Thr Arg Val Glu Gly Tyr Phe Thr Asp Arg Asn Ile
            100                 105                 110

Asp Pro Lys Asn Arg Pro Glu Ile Trp Gly Arg Tyr Ala Leu Ile Phe
        115                 120                 125

Gly Ser Leu Ile Ala Ser Tyr Tyr Ala Gln Leu Phe Val Pro Phe Val
    130                 135                 140

Val Glu Arg Thr Trp Leu Gln Val Val Phe Ala Ile Ile Met Gly Phe
145                 150                 155                 160

Ala Cys Ala Gln Val Gly Leu Asn Pro Leu His Asp Ala Ser His Phe
                165                 170                 175

Ser Val Thr His Asn Pro Thr Val Trp Lys Ile Leu Gly Ala Thr His
            180                 185                 190

Asp Phe Phe Asn Gly Ala Ser Tyr Leu Val Trp Met Tyr Gln His Met
        195                 200                 205

Leu Gly His His Pro Tyr Thr Asn Ile Ala Gly Ala Asp Pro Asp Val
    210                 215                 220

Ser Thr Ser Glu Pro Asp Val Arg Arg Ile Lys Pro Asn Gln Lys Trp
225                 230                 235                 240

Phe Val Asn His Ile Asn Gln His Met Phe Val Pro Phe Leu Tyr Gly
                245                 250                 255

Leu Leu Ala Phe Lys Val Arg Ile Gln Asp Ile Asn Ile Leu Tyr Phe
            260                 265                 270

Val Lys Thr Asn Asp Ala Ile Arg Val Asn Pro Ile Ser Thr Trp His
        275                 280                 285

Thr Val Met Phe Trp Gly Gly Lys Ala Phe Phe Val Trp Tyr Arg Leu
    290                 295                 300

Ile Val Pro Leu Gln Tyr Leu Pro Leu Gly Lys Val Leu Leu Leu Phe
305                 310                 315                 320

Thr Val Ala Asp Met Val Ser Ser Tyr Trp Leu Ala Leu Thr Phe Gln
                325                 330                 335

Ala Asn His Val Val Glu Glu Val Gln Trp Pro Leu Pro Asp Glu Asn
            340                 345                 350

Gly Ile Ile Gln Lys Asp Trp Ala Ala Met Gln Val Glu Thr Thr Gln
        355                 360                 365

Asp Tyr Ala His Asp Ser His Leu Trp Thr Ser Ile Thr Gly Ser Leu
    370                 375                 380

Asn Tyr Gln Ala Val His His Leu Phe Pro Asn Val Ser Gln His His
385                 390                 395                 400

Tyr Pro Asp Ile Leu Ala Ile Ile Lys Asn Thr Cys Ser Glu Tyr Lys
                405                 410                 415

Val Pro Tyr Leu Val Lys Asp Thr Phe Trp Gln Ala Phe Ala Ser His
            420                 425                 430

Leu Glu His Leu Arg Val Leu Gly Leu Arg Pro Lys Glu Glu
        435                 440                 445
```

```
<210> SEQ ID NO 69
<211> LENGTH: 6473
<212> TYPE: DNA
<213> ORGANISM: Artificial Sequence
<220> FEATURE:
<223> OTHER INFORMATION: Plasmid pY5-22

<400> SEQUENCE: 69

ggtggagctc cagcttttgt tccctttagt gagggttaat ttcgagcttg gcgtaatcat      60

ggtcatagct gtttcctgtg tgaaattgtt atccgctcac aattccacac aacgtacgag     120
```

-continued

```
ccggaagcat aaagtgtaaa gcctggggtg cctaatgagt gagctaactc acattaattg    180

cgttgcgctc actgcccgct ttccagtcgg gaaacctgtc gtgccagctg cattaatgaa    240

tcggccaacg cgcggggaga ggcggtttgc gtattgggcg ctcttccgct tcctcgctca    300

ctgactcgct gcgctcggtc gttcggctgc ggcgagcggt atcagctcac tcaaaggcgg    360

taatacggtt atccacagaa tcaggggata acgcaggaaa gaacatgtga gcaaaaggcc    420

agcaaaaggc caggaaccgt aaaaaggccg cgttgctggc gtttttccat aggctccgcc    480

cccctgacga gcatcacaaa aatcgacgct caagtcagag gtggcgaaac ccgacaggac    540

tataaagata ccaggcgttt ccccctggaa gctccctcgt gcgctctcct gttccgaccc    600

tgccgcttac cggatacctg tccgcctttc tcccttcggg aagcgtggcg ctttctcata    660

gctcacgctg taggtatctc agttcggtgt aggtcgttcg ctccaagctg ggctgtgtgc    720

acgaaccccc cgttcagccc gaccgctgcg ccttatccgg taactatcgt cttgagtcca    780

acccggtaag acacgactta tcgccactgg cagcagccac tggtaacagg attagcagag    840

cgaggtatgt aggcggtgct acagagttct tgaagtggtg gcctaactac ggctacacta    900

gaaggacagt atttggtatc tgcgctctgc tgaagccagt taccttcgga aaaagagttg    960

gtagctcttg atccggcaaa caaaccaccg ctggtagcgg tggttttttt gtttgcaagc   1020

agcagattac gcgcagaaaa aaaggatctc aagaagatcc tttgatcttt tctacggggt   1080

ctgacgctca gtggaacgaa aactcacgtt aagggatttt ggtcatgaga ttatcaaaaa   1140

ggatcttcac ctagatcctt ttaaattaaa aatgaagttt taaatcaatc taaagtatat   1200

atgagtaaac ttggtctgac agttaccaat gcttaatcag tgaggcacct atctcagcga   1260

tctgtctatt tcgttcatcc atagttgcct gactccccgt cgtgtagata actacgatac   1320

gggagggctt accatctggc cccagtgctg caatgatacc gcgagaccca cgctcaccgg   1380

ctccagattt atcagcaata aaccagccag ccggaagggc cgagcgcaga agtggtcctg   1440

caactttatc cgcctccatc cagtctatta attgttgccg ggaagctaga gtaagtagtt   1500

cgccagttaa tagtttgcgc aacgttgttg ccattgctac aggcatcgtg gtgtcacgct   1560

cgtcgtttgg tatggcttca ttcagctccg gttcccaacg atcaaggcga gttacatgat   1620

cccccatgtt gtgcaaaaaa gcggttagct ccttcggtcc tccgatcgtt gtcagaagta   1680

agttggccgc agtgttatca ctcatggtta tggcagcact gcataattct cttactgtca   1740

tgccatccgt aagatgcttt tctgtgactg gtgagtactc aaccaagtca ttctgagaat   1800

agtgtatgcg gcgaccgagt tgctcttgcc cggcgtcaat acgggataat accgcgccac   1860

atagcagaac tttaaaagtg ctcatcattg gaaaacgttc ttcggggcga aaactctcaa   1920

ggatcttacc gctgttgaga tccagttcga tgtaacccac tcgtgcaccc aactgatctt   1980

cagcatcttt tactttcacc agcgtttctg ggtgagcaaa aacaggaagg caaaatgccg   2040

caaaaaaggg aataagggcg acacggaaat gttgaatact catactcttc ctttttcaat   2100

attattgaag catttatcag ggttattgtc tcatgagcgg atacatattt gaatgtattt   2160

agaaaaataa acaaataggg gttccgcgca catttccccg aaaagtgcca cctgacgcgc   2220

cctgtagcgg cgcattaagc gcggcgggtg tggtggttac gcgcagcgtg accgctacac   2280

ttgccagcgc cctagcgccc gctcctttcg ctttcttccc ttcctttctc gccacgttcg   2340

ccggctttcc ccgtcaagct ctaaatcggg ggctcccttt agggttccga tttagtgctt   2400

tacggcacct cgaccccaaa aaacttgatt agggtgatgg ttcacgtagt gggccatcgc   2460

cctgatagac ggtttttcgc cctttgacgt tggagtccac gttctttaat agtggactct   2520
```

-continued

```
tgttccaaac tggaacaaca ctcaacccta tctcggtcta ttcttttgat ttataaggga   2580

ttttgccgat ttcggcctat tggttaaaaa atgagctgat ttaacaaaaa tttaacgcga   2640

attttaacaa aatattaacg cttacaattt ccattcgcca ttcaggctgc gcaactgttg   2700

ggaagggcga tcggtgcggg cctcttcgct attacgccag ctggcgaaag ggggatgtgc   2760

tgcaaggcga ttaagttggg taacgccagg gttttcccag tcacgacgtt gtaaaacgac   2820

ggccagtgaa ttgtaatacg actcactata gggcgaattg ggtaccgggc ccccccctcga   2880

ggtcgatggt gtcgataagc ttgatatcga attcatgtca cacaaaccga tcttcgcctc   2940

aaggaaacct aattctacat ccgagagact gccgagatcc agtctacact gattaatttt   3000

cgggccaata atttaaaaaa atcgtgttat ataatattat atgtattata tatatacatc   3060

atgatgatac tgacagtcat gtcccattgc taaatagaca gactccatct gccgcctcca   3120

actgatgttc tcaatattta aggggtcatc tcgcattgtt taataataaa cagactccat   3180

ctaccgcctc caaatgatgt tctcaaaata tattgtatga acttattttt attacttagt   3240

attattagac aacttacttg ctttatgaaa aacacttcct atttaggaaa caatttataa   3300

tggcagttcg ttcatttaac aatttatgta gaataaatgt tataaatgcg tatgggaaat   3360

cttaaatatg gatagcataa atgatatctg cattgcctaa ttcgaaatca acagcaacga   3420

aaaaaatccc ttgtacaaca taaatagtca tcgagaaata tcaactatca aagaacagct   3480

attcacacgt tactattgag attattattg gacgagaatc acacactcaa ctgtctttct   3540

ctcttctaga aatacaggta caagtatgta ctattctcat tgttcatact tctagtcatt   3600

tcatcccaca tattccttgg atttctctcc aatgaatgac attctatctt gcaaattcaa   3660

caattataat aagatatacc aaagtagcgg tatagtggca atcaaaaagc ttctctggtg   3720

tgcttctcgt atttattttt attctaatga tccattaaag gtatatattt atttcttgtt   3780

atataatcct tttgtttatt acatgggctg gatacataaa ggtattttga tttaattttt   3840

tgcttaaatt caatcccccc tcgttcagtg tcaactgtaa tggtaggaaa ttaccatact   3900

tttgaagaag caaaaaaaat gaaagaaaaa aaaaatcgta tttccaggtt agacgttccg   3960

cagaatctag aatgcggtat gcggtacatt gttcttcgaa cgtaaaagtt gcgctccctg   4020

agatattgta catttttgct tttacaagta caagtacatc gtacaactat gtactactgt   4080

tgatgcatcc acaacagttt gttttgtttt tttttgtttt tttttttttct aatgattcat   4140

taccgctatg tatacctact tgtacttgta gtaagccggg ttattggcgt tcaattaatc   4200

atagacttat gaatctgcac ggtgtgcgct gcgagttact tttagcttat gcatgctact   4260

tgggtgtaat attgggatct gttcggaaat caacggatgc tcaaccgatt tcgacagtaa   4320

ttaattaagt catacacaag tcagctttct tcgagcctca tataagtata agtagttcaa   4380

cgtattagca ctgtacccag catctccgta tcgagaaaca caacaacatg ccccattgga   4440

cagatcatgc ggatacacag gttgtgcagt atcatacata ctcgatcaga caggtcgtct   4500

gaccatcata caagctgaac aagcgctcca tacttgcacg ctctctatat acacagttaa   4560

attacatatc catagtctaa cctctaacag ttaatcttct ggtaagcctc ccagccagcc   4620

ttctggtatc gcttggcctc ctcaatagga tctcggttct ggccgtacag acctcggccg   4680

acaattatga tatccgttcc ggtagacatg acatcctcaa cagttcggta ctgctgtccg   4740

agagcgtctc ccttgtcgtc aagacccacc ccgggggtca gaataagcca gtcctcagag   4800

tcgcccttag gtcggttctg ggcaatgaag ccaaccacaa actcggggtc ggatcgggca   4860

agctcaatgg tctgcttgga gtactcgcca gtggccagag agcccttgca agacagctcg   4920
```

```
gccagcatga gcagacctct ggccagcttc tcgttgggag aggggactag gaactccttg   4980

tactgggagt tctcgtagtc agagacgtcc tccttcttct gttcagagac agtttcctcg   5040

gcaccagctc gcaggccagc aatgattccg gttccgggta caccgtgggc gttggtgata   5100

tcggaccact cggcgattcg gtgacaccgg tactggtgct tgacagtgtt gccaatatct   5160

gcgaactttc tgtcctcgaa caggaagaaa ccgtgcttaa gagcaagttc cttgaggggg   5220

agcacagtgc cggcgtaggt gaagtcgtca atgatgtcga tatgggtttt gatcatgcac   5280

acataaggtc cgaccttatc ggcaagctca atgagctcct tggtggtggt aacatccaga   5340

gaagcacaca ggttggtttt cttggctgcc acgagcttga gcactcgagc ggcaaaggcg   5400

gacttgtgga cgttagctcg agcttcgtag gagggcattt tggtggtgaa gaggagactg   5460

aaataaattt agtctgcaga actttttatc ggaaccttat ctggggcagt gaagtatatg   5520

ttatggtaat agttacgagt tagttgaact tatagataga ctggactata cggctatcgg   5580

tccaaattag aaagaacgtc aatggctctc tgggcgtcgc ctttgccgac aaaaatgtga   5640

tcatgatgaa agccagcaat gacgttgcag ctgatattgt tgtcggccaa ccgcgccgaa   5700

aacgcagctg tcagacccac agcctccaac gaagaatgta tcgtcaaagt gatccaagca   5760

cactcatagt tggagtcgta ctccaaaggc ggcaatgacg agtcagacag atactcgtcg   5820

actcaggcga cgacggaatt cctgcagccc atctgcagaa ttcaggagag accgggttgg   5880

cggcgtattt gtgtcccaaa aaacagcccc aattgcccca attgacccca aattgaccca   5940

gtagcgggcc caaccccggc gagagccccc ttcaccccac atatcaaacc tcccccggtt   6000

cccacacttg ccgttaaggg cgtagggtac tgcagtctgg aatctacgct tgttcagact   6060

ttgtactagt ttctttgtct ggccatccgg gtaacccatg ccggacgcaa aatagactac   6120

tgaaaatttt tttgctttgt ggttgggact ttagccaagg gtataaaaga ccaccgtccc   6180

cgaattacct ttcctcttct tttctctctc tccttgtcaa ctcacacccg aaatcgttaa   6240

gcatttcctt ctgagtataa gaatcattca ccatggatcc actagttcta gagcggccgc   6300

caccgcggcc cgagattccg gcctcttcgg ccgccaagcg acccgggtgg acgtctagag   6360

gtacctagca attaacagat agtttgccgg tgataattct cttaacctcc cacactcctt   6420

tgacataacg atttatgtaa cgaaactgaa atttgaccag atattgtgtc cgc          6473
```

<210> SEQ ID NO 70
<211> LENGTH: 6970
<212> TYPE: DNA
<213> ORGANISM: Artificial Sequence
<220> FEATURE:
<223> OTHER INFORMATION: Plasmid pY5-22GPD

<400> SEQUENCE: 70

```
tcgacgcagt aggatgtcct gcacgggtct tttgtggggg tgtggagaaa ggggtgcttg     60

gagatggaag ccggtagaac cgggctgctt gtgcttggag atggaagccg gtagaaccgg    120

gctgcttggg gggatttggg gccgctgggc tccaaagagg ggtaggcatt tcgttggggt    180

tacgtaattg cggcatttgg gtcctgcgcg catgtcccat tggtcagaat tagtccggat    240

aggagactta tcagccaatc acagcgccgg atccacctgt aggttgggtt gggtgggagc    300

acccctccac agagtagagt caaacagcag cagcaacatg atagttgggg gtgtgcgtgt    360

taaaggaaaa aaaagaagct tgggttatat tcccgctcta tttagaggtt gcgggataga    420

cgccgacgga gggcaatggc gccatggaac cttgcggata tcgatacgcc gcggcggact    480

gcgtccgaac cagctccagc agcgtttttt ccgggccatt gagccgactg cgaccccgcc    540
```

```
aacgtgtctt ggcccacgca ctcatgtcat gttggtgttg ggaggccact ttttaagtag    600

cacaaggcac ctagctcgca gcaaggtgtc cgaaccaaag aagcggctgc agtggtgcaa    660

acggggcgga aacggcggga aaaagccacg gggcacgaa ttgaggcacg ccctcgaatt     720

tgagacgagt cacggcccca ttcgcccgcg caatggctcg ccaacgcccg gtcttttgca    780

ccacatcagg ttaccccaag ccaaaccttt gtgttaaaaa gcttaacata ttataccgaa    840

cgtaggtttg ggcgggcttg ctccgtctgt ccaaggcaac atttatataa gggtctgcat    900

cgccggctca attgaatctt ttttcttctt ctcttctcta tattcattct tgaattaaac    960

acacatcaat ccgcggccgc caccgcggcc cgagattccg gcctcttcgg ccgccaagcg   1020

acccgggtgg acgtctagag gtacctagca attaacagat agtttgccgg tgataattct   1080

cttaacctcc cacactcctt tgacataacg atttatgtaa cgaaactgaa atttgaccag   1140

atattgtgtc cgcggtggag ctccagcttt tgttcccttt agtgagggtt aatttcgagc   1200

ttggcgtaat catggtcata gctgtttcct gtgtgaaatt gttatccgct cacaattcca   1260

cacaacgtac gagccggaag cataaagtgt aaagcctggg gtgcctaatg agtgagctaa   1320

ctcacattaa ttgcgttgcg ctcactgccc gctttccagt cgggaaacct gtcgtgccag   1380

ctgcattaat gaatcggcca acgcgcgggg agaggcggtt tgcgtattgg gcgctcttcc   1440

gcttcctcgc tcactgactc gctgcgctcg gtcgttcggc tgcggcgagc ggtatcagct   1500

cactcaaagg cggtaatacg gttatccaca gaatcagggg ataacgcagg aaagaacatg   1560

tgagcaaaag gccagcaaaa ggccaggaac cgtaaaaagg ccgcgttgct ggcgtttttc   1620

cataggctcc gcccccctga cgagcatcac aaaaatcgac gctcaagtca gaggtggcga   1680

aacccgacag gactataaag ataccaggcg tttccccctg gaagctccct cgtgcgctct   1740

cctgttccga ccctgccgct taccggatac ctgtccgcct ttctcccttc gggaagcgtg   1800

gcgctttctc atagctcacg ctgtaggtat ctcagttcgg tgtaggtcgt tcgctccaag   1860

ctgggctgtg tgcacgaacc ccccgttcag cccgaccgct gcgccttatc cggtaactat   1920

cgtcttgagt ccaacccggt aagacacgac ttatcgccac tggcagcagc cactggtaac   1980

aggattagca gagcgaggta tgtaggcggt gctacagagt tcttgaagtg gtggcctaac   2040

tacggctaca ctagaaggac agtatttggt atctgcgctc tgctgaagcc agttaccttc   2100

ggaaaaagag ttggtagctc ttgatccggc aaacaaacca ccgctggtag cggtggtttt   2160

tttgtttgca agcagcagat tacgcgcaga aaaaaaggat ctcaagaaga tcctttgatc   2220

ttttctacgg ggtctgacgc tcagtggaac gaaaactcac gttaagggat tttggtcatg   2280

agattatcaa aaaggatctt cacctagatc cttttaaatt aaaaatgaag ttttaaatca   2340

atctaaagta tatatgagta aacttggtct gacagttacc aatgcttaat cagtgaggca   2400

cctatctcag cgatctgtct atttcgttca tccatagttg cctgactccc cgtcgtgtag   2460

ataactacga tacgggaggg cttaccatct ggccccagtg ctgcaatgat accgcgagac   2520

ccacgctcac cggctccaga tttatcagca ataaaccagc cagccggaag ggccgagcgc   2580

agaagtggtc ctgcaacttt atccgcctcc atccagtcta ttaattgttg ccgggaagct   2640

agagtaagta gttcgccagt taatagtttg cgcaacgttg ttgccattgc tacaggcatc   2700

gtggtgtcac gctcgtcgtt tggtatggct tcattcagct ccggttccca acgatcaagg   2760

cgagttacat gatcccccat gttgtgcaaa aaagcggtta gctccttcgg tcctccgatc   2820

gttgtcagaa gtaagttggc cgcagtgtta tcactcatgg ttatggcagc actgcataat   2880

tctcttactg tcatgccatc cgtaagatgc ttttctgtga ctggtgagta ctcaaccaag   2940
```

-continued

```
tcattctgag aatagtgtat gcggcgaccg agttgctctt gcccggcgtc aatacgggat   3000
aataccgcgc cacatagcag aactttaaaa gtgctcatca ttggaaaacg ttcttcgggg   3060
cgaaaactct caaggatctt accgctgttg agatccagtt cgatgtaacc cactcgtgca   3120
cccaactgat cttcagcatc ttttactttc accagcgttt ctgggtgagc aaaaacagga   3180
aggcaaaatg ccgcaaaaaa gggaataagg gcgacacgga aatgttgaat actcatactc   3240
ttcctttttc aatattattg aagcatttat cagggttatt gtctcatgag cggatacata   3300
tttgaatgta tttagaaaaa taaacaaata ggggttccgc gcacatttcc ccgaaaagtg   3360
ccacctgacg cgccctgtag cggcgcatta agcgcggcgg gtgtggtggt tacgcgcagc   3420
gtgaccgcta cacttgccag cgccctagcg cccgctcctt tcgctttctt cccttccttt   3480
ctcgccacgt tcgccggctt tccccgtcaa gctctaaatc gggggctccc tttagggttc   3540
cgatttagtg ctttacggca cctcgacccc aaaaaacttg attagggtga tggttcacgt   3600
agtgggccat cgccctgata gacggttttt cgccctttga cgttggagtc cacgttcttt   3660
aatagtggac tcttgttcca aactggaaca acactcaacc ctatctcggt ctattctttt   3720
gatttataag ggattttgcc gatttcggcc tattggttaa aaaatgagct gatttaacaa   3780
aaatttaacg cgaattttaa caaaatatta acgcttacaa tttccattcg ccattcaggc   3840
tgcgcaactg ttgggaaggg cgatcggtgc gggcctcttc gctattacgc cagctggcga   3900
aagggggatg tgctgcaagg cgattaagtt gggtaacgcc agggttttcc cagtcacgac   3960
gttgtaaaac gacggccagt gaattgtaat acgactcact atagggcgaa ttgggtaccg   4020
ggcccccct cgaggtcgat ggtgtcgata agcttgatat cgaattcatg tcacacaaac   4080
cgatcttcgc ctcaaggaaa cctaattcta catccgagag actgccgaga tccagtctac   4140
actgattaat tttcgggcca ataatttaaa aaaatcgtgt tatataatat tatatgtatt   4200
atatatatac atcatgatga tactgacagt catgtcccat tgctaaatag acagactcca   4260
tctgccgcct ccaactgatg ttctcaatat ttaaggggtc atctcgcatt gtttaataat   4320
aaacagactc catctaccgc ctccaaatga tgttctcaaa atatattgta tgaacttatt   4380
tttattactt agtattatta gacaacttac ttgctttatg aaaaacactt cctatttagg   4440
aaacaattta taatggcagt tcgttcattt aacaatttat gtagaataaa tgttataaat   4500
gcgtatggga aatcttaaat atggatagca taaatgatat ctgcattgcc taattcgaaa   4560
tcaacagcaa cgaaaaaaat cccttgtaca acataaatag tcatcgagaa atatcaacta   4620
tcaaagaaca gctattcaca cgttactatt gagattatta ttggacgaga atcacacact   4680
caactgtctt tctctcttct agaaatacag gtacaagtat gtactattct cattgttcat   4740
acttctagtc atttcatccc acatattcct tggatttctc tccaatgaat gacattctat   4800
cttgcaaatt caacaattat aataagatat accaaagtag cggtatagtg gcaatcaaaa   4860
agcttctctg gtgtgcttct cgtatttatt tttattctaa tgatccatta aaggtatata   4920
tttatttctt gttatataat ccttttgttt attacatggg ctggatacat aaaggtattt   4980
tgatttaatt ttttgcttaa attcaatccc ccctcgttca gtgtcaactg taatggtagg   5040
aaattaccat acttttgaag aagcaaaaaa aatgaaagaa aaaaaaaatc gtatttccag   5100
gttagacgtt ccgcagaatc tagaatgcgg tatgcggtac attgttcttc gaacgtaaaa   5160
gttgcgctcc ctgagatatt gtacattttt gcttttacaa gtacaagtac atcgtacaac   5220
tatgtactac tgttgatgca tccacaacag tttgttttgt tttttttgt ttttttttt   5280
tctaatgatt cattaccgct atgtatacct acttgtactt gtagtaagcc gggttattgg   5340
```

```
cgttcaatta atcatagact tatgaatctg cacggtgtgc gctgcgagtt acttttagct   5400

tatgcatgct acttgggtgt aatattggga tctgttcgga aatcaacgga tgctcaaccg   5460

atttcgacag taattaatta agtcatacac aagtcagctt tcttcgagcc tcatataagt   5520

ataagtagtt caacgtatta gcactgtacc cagcatctcc gtatcgagaa acacaacaac   5580

atgccccatt ggacagatca tgcggataca caggttgtgc agtatcatac atactcgatc   5640

agacaggtcg tctgaccatc atacaagctg aacaagcgct ccatacttgc acgctctcta   5700

tatacacagt taaattacat atccatagtc taacctctaa cagttaatct tctggtaagc   5760

ctcccagcca gccttctggt atcgcttggc ctcctcaata ggatctcggt tctggccgta   5820

cagacctcgg ccgacaatta tgatatccgt tccggtagac atgacatcct caacagttcg   5880

gtactgctgt ccgagagcgt ctcccttgtc gtcaagaccc accccggggg tcagaataag   5940

ccagtcctca gagtcgccct taggtcggtt ctgggcaatg aagccaacca caaactcggg   6000

gtcggatcgg gcaagctcaa tggtctgctt ggagtactcg ccagtggcca gagagccctt   6060

gcaagacagc tcggccagca tgagcagacc tctggccagc ttctcgttgg gagaggggac   6120

taggaactcc ttgtactggg agttctcgta gtcagagacg tcctccttct tctgttcaga   6180

gacagtttcc tcggcaccag ctcgcaggcc agcaatgatt ccggttccgg gtacaccgtg   6240

ggcgttggtg atatcggacc actcggcgat tcggtgacac cggtactggt gcttgacagt   6300

gttgccaata tctgcgaact ttctgtcctc gaacaggaag aaaccgtgct taagagcaag   6360

ttccttgagg gggagcacag tgccggcgta ggtgaagtcg tcaatgatgt cgatatgggt   6420

tttgatcatg cacacataag gtccgacctt atcggcaagc tcaatgagct ccttggtggt   6480

ggtaacatcc agagaagcac acaggttggt tttcttggct gccacgagct tgagcactcg   6540

agcggcaaag gcggacttgt ggacgttagc tcgagcttcg taggagggca ttttggtggt   6600

gaagaggaga ctgaaataaa tttagtctgc agaacttttt atcggaacct tatctggggc   6660

agtgaagtat atgttatggt aatagttacg agttagttga acttatagat agactggact   6720

atacggctat cggtccaaat tagaaagaac gtcaatggct ctctgggcgt cgcctttgcc   6780

gacaaaaatg tgatcatgat gaaagccagc aatgacgttg cagctgatat tgttgtcggc   6840

caaccgcgcc gaaaacgcag ctgtcagacc cacagcctcc aacgaagaat gtatcgtcaa   6900

agtgatccaa gcacactcat agttggagtc gtactccaaa ggcggcaatg acgagtcaga   6960

cagatactcg                                                          6970
```

```
<210> SEQ ID NO 71
<211> LENGTH: 968
<212> TYPE: DNA
<213> ORGANISM: Yarrowia lipolytica
<300> PUBLICATION INFORMATION:
<302> TITLE: GLYCERALDEHYDE-3-PHOSPHATE DEHYDROGENASE AND
      PHOSPHOGLYCERATE MUTASE PROMOTERS FOR GENE EXPRESSION IN
      OLEAGINOUS YEAST
<310> PATENT DOCUMENT NUMBER: US-2005-0014270-A1
<311> PATENT FILING DATE: 2004-06-16
<312> PUBLICATION DATE: 2005-01-20
<313> RELEVANT RESIDUES IN SEQ ID NO: (1)..(968)

<400> SEQUENCE: 71

tcgacgcagt aggatgtcct gcacgggtct ttttgtgggg tgtggagaaa ggggtgcttg     60

gagatggaag ccggtagaac cgggctgctt gtgcttggag atggaagccg gtagaaccgg    120

gctgcttggg gggatttggg gccgctgggc tccaaagagg ggtaggcatt tcgttggggt    180

tacgtaattg cggcatttgg gtcctgcgcg catgtcccat tggtcagaat tagtccggat    240
```

```
aggagactta tcagccaatc acagcgccgg atccacctgt aggttgggtt gggtgggagc    300

acccctccac agagtagagt caaacagcag cagcaacatg atagttgggg gtgtgcgtgt    360

taaaggaaaa aaaagaagct tgggttatat tcccgctcta tttagaggtt gcgggataga    420

cgccgacgga gggcaatggc gccatggaac cttgcggata tcgatacgcc gcggcggact    480

gcgtccgaac cagctccagc agcgtttttt ccgggccatt gagccgactg cgaccccgcc    540

aacgtgtctt ggcccacgca ctcatgtcat gttggtgttg ggaggccact tttaagtag     600

cacaaggcac ctagctcgca gcaaggtgtc cgaaccaaag aagcggctgc agtggtgcaa    660

acggggcgga aacggcggga aaaagccacg gggcacgaa  ttgaggcacg ccctcgaatt    720

tgagacgagt cacggcccca ttcgcccgcg caatggctcg ccaacgcccg gtcttttgca    780

ccacatcagg ttaccccaag ccaaaccttt gtgttaaaaa gcttaacata ttataccgaa    840

cgtaggtttg ggcgggcttg ctccgtctgt ccaaggcaac atttatataa gggtctgcat    900

cgccggctca attgaatctt ttttcttctt ctcttctcta tattcattct tgaattaaac    960

acacatca                                                             968
```

<210> SEQ ID NO 72
<211> LENGTH: 8630
<212> TYPE: DNA
<213> ORGANISM: Artificial Sequence
<220> FEATURE:
<223> OTHER INFORMATION: Plasmid pYZDE2-S

<400> SEQUENCE: 72

```
ggtggagctc cagcttttgt tccctttagt gagggttaat ttcgagcttg gcgtaatcat     60

ggtcatagct gtttcctgtg tgaaattgtt atccgctcac aattccacac aacgtacgag    120

ccggaagcat aaagtgtaaa gcctggggtg cctaatgagt gagctaactc acattaattg    180

cgttgcgctc actgcccgct ttccagtcgg gaaacctgtc gtgccagctg cattaatgaa    240

tcggccaacg cgcggggaga ggcggtttgc gtattgggcg ctcttccgct tcctcgctca    300

ctgactcgct gcgctcggtc gttcggctgc ggcgagcggt atcagctcac tcaaaggcgg    360

taatacggtt atccacagaa tcaggggata acgcaggaaa gaacatgtga gcaaaaggcc    420

agcaaaaggc caggaaccgt aaaaaggccg cgttgctggc gtttttccat aggctccgcc    480

cccctgacga gcatcacaaa aatcgacgct caagtcagag gtggcgaaac ccgacaggac    540

tataaagata ccaggcgttt ccccctggaa gctccctcgt gcgctctcct gttccgaccc    600

tgccgcttac cggatacctg tccgcctttc tcccttcggg aagcgtggcg ctttctcata    660

gctcacgctg taggtatctc agttcggtgt aggtcgttcg ctccaagctg ggctgtgtgc    720

acgaaccccc cgttcagccc gaccgctgcg ccttatccgg taactatcgt cttgagtcca    780

acccggtaag acacgactta tcgccactgg cagcagccac tggtaacagg attagcagag    840

cgaggtatgt aggcggtgct acagagttct tgaagtggtg gcctaactac ggctacacta    900

gaaggacagt atttggtatc tgcgctctgc tgaagccagt taccttcgga aaaagagttg    960

gtagctcttg atccggcaaa caaaccaccg ctggtagcgg tggttttttt gtttgcaagc   1020

agcagattac gcgcagaaaa aaaggatctc aagaagatcc tttgatcttt tctacggggt   1080

ctgacgctca gtggaacgaa aactcacgtt aagggatttt ggtcatgaga ttatcaaaaa   1140

ggatcttcac ctagatcctt ttaaattaaa aatgaagttt taaatcaatc taaagtatat   1200

atgagtaaac ttggtctgac agttaccaat gcttaatcag tgaggcacct atctcagcga   1260

tctgtctatt tcgttcatcc atagttgcct gactccccgt cgtgtagata actacgatac   1320
```

```
gggagggctt accatctggc cccagtgctg caatgatacc gcgagaccca cgctcaccgg   1380
ctccagattt atcagcaata aaccagccag ccggaagggc cgagcgcaga agtggtcctg   1440
caactttatc cgcctccatc cagtctatta attgttgccg ggaagctaga gtaagtagtt   1500
cgccagttaa tagtttgcgc aacgttgttg ccattgctac aggcatcgtg gtgtcacgct   1560
cgtcgtttgg tatggcttca ttcagctccg gttcccaacg atcaaggcga gttacatgat   1620
cccccatgtt gtgcaaaaaa gcggttagct ccttcggtcc tccgatcgtt gtcagaagta   1680
agttggccgc agtgttatca ctcatggtta tggcagcact gcataattct cttactgtca   1740
tgccatccgt aagatgcttt tctgtgactg gtgagtactc aaccaagtca ttctgagaat   1800
agtgtatgcg gcgaccgagt tgctcttgcc cggcgtcaat acgggataat accgcgccac   1860
atagcagaac tttaaaagtg ctcatcattg gaaaacgttc ttcggggcga aaactctcaa   1920
ggatcttacc gctgttgaga tccagttcga tgtaacccac tcgtgcaccc aactgatctt   1980
cagcatcttt tactttcacc agcgtttctg ggtgagcaaa aacaggaagg caaaatgccg   2040
caaaaaaggg aataagggcg acacggaaat gttgaatact catactcttc ctttttcaat   2100
attattgaag catttatcag ggttattgtc tcatgagcgg atacatattt gaatgtattt   2160
agaaaaataa acaaataggg gttccgcgca catttccccg aaaagtgcca cctgacgcgc   2220
cctgtagcgg cgcattaagc gcggcgggtg tggtggttac gcgcagcgtg accgctacac   2280
ttgccagcgc cctagcgccc gctcctttcg ctttcttccc ttcctttctc gccacgttcg   2340
ccggctttcc ccgtcaagct ctaaatcggg ggctcccttt agggttccga tttagtgctt   2400
tacggcacct cgaccccaaa aaacttgatt agggtgatgg ttcacgtagt gggccatcgc   2460
cctgatagac ggtttttcgc cctttgacgt tggagtccac gttctttaat agtggactct   2520
tgttccaaac tggaacaaca ctcaacccta tctcggtcta ttcttttgat ttataaggga   2580
ttttgccgat ttcggcctat tggttaaaaa atgagctgat ttaacaaaaa tttaacgcga   2640
attttaacaa aatattaacg cttacaattt ccattcgcca ttcaggctgc gcaactgttg   2700
ggaagggcga tcggtgcggg cctcttcgct attacgccag ctggcgaaag ggggatgtgc   2760
tgcaaggcga ttaagttggg taacgccagg gttttcccag tcacgacgtt gtaaaacgac   2820
ggccagtgaa ttgtaatacg actcactata gggcgaattg ggtaccgggc ccccccctcga   2880
ggtcgatggt gtcgataagc ttgatatcga attcatgtca cacaaaccga tcttcgcctc   2940
aaggaaacct aattctacat ccgagagact gccgagatcc agtctacact gattaatttt   3000
cgggccaata atttaaaaaa atcgtgttat ataatattat atgtattata tatatacatc   3060
atgatgatac tgacagtcat gtcccattgc taaatagaca gactccatct gccgcctcca   3120
actgatgttc tcaatattta aggggtcatc tcgcattgtt taataataaa cagactccat   3180
ctaccgcctc caaatgatgt tctcaaaata tattgtatga acttattttt attacttagt   3240
attattagac aacttacttg ctttatgaaa aacacttcct atttaggaaa caatttataa   3300
tggcagttcg ttcatttaac aatttatgta gaataaatgt tataaatgcg tatgggaaat   3360
cttaaatatg gatagcataa atgatatctg cattgcctaa ttcgaaatca acagcaacga   3420
aaaaaatccc ttgtacaaca taaatagtca tcgagaaata tcaactatca aagaacagct   3480
attcacacgt tactattgag attattattg gacgagaatc acacactcaa ctgtctttct   3540
ctcttctaga aatacaggta caagtatgta ctattctcat tgttcatact tctagtcatt   3600
tcatcccaca tattccttgg atttctctcc aatgaatgac attctatctt gcaaattcaa   3660
caattataat aagatatacc aaagtagcgg tatagtggca atcaaaaagc ttctctggtg   3720
```

```
tgcttctcgt atttattttt attctaatga tccattaaag gtatatattt atttcttgtt   3780
atataatcct tttgtttatt acatgggctg gatacataaa ggtattttga tttaattttt   3840
tgcttaaatt caatcccccc tcgttcagtg tcaactgtaa tggtaggaaa ttaccatact   3900
tttgaagaag caaaaaaaat gaaagaaaaa aaaaatcgta tttccaggtt agacgttccg   3960
cagaatctag aatgcggtat gcggtacatt gttcttcgaa cgtaaaagtt gcgctccctg   4020
agatattgta catttttgct tttacaagta caagtacatc gtacaactat gtactactgt   4080
tgatgcatcc acaacagttt gttttgtttt tttttgtttt ttttttttct aatgattcat   4140
taccgctatg tatacctact tgtacttgta gtaagccggg ttattggcgt tcaattaatc   4200
atagacttat gaatctgcac ggtgtgcgct gcgagttact tttagcttat gcatgctact   4260
tgggtgtaat attgggatct gttcggaaat caacggatgc tcaaccgatt tcgacagtaa   4320
taatttgaat cgaatcggag cctaaaatga acccgagtat atctcataaa attctcggtg   4380
agaggtctgt gactgtcagt acaaggtgcc ttcattatgc cctcaacctt accatacctc   4440
actgaatgta gtgtacctct aaaaatgaaa tacagtgcca aaagccaagg cactgagctc   4500
gtctaacgga cttgatatac aaccaattaa aacaaatgaa aagaaataca gttctttgta   4560
tcatttgtaa caattaccct gtacaaacta aggtattgaa atcccacaat attcccaaag   4620
tccacccctt tccaaattgt catgcctaca actcatatac caagcactaa cctaccaaac   4680
accactaaaa ccccacaaaa tatatcttac cgaatataca gtaacaagct accaccacac   4740
tcgttgggtg cagtcgccag cttaaagata tctatccaca tcagccacaa ctcccttcct   4800
ttaataaacc gactacaccc ttggctattg aggttatgag tgaatatact gtagacaaga   4860
cactttcaag aagactgttt ccaaaacgta ccactgtcct ccactacaaa cacacccaat   4920
ctgcttcttc tagtcaaggt tgctacaccg gtaaattata aatcatcatt tcattagcag   4980
ggcagggccc tttttataga gtcttataca ctagcggacc ctgccggtag accaacccgc   5040
aggcgcgtca gtttgctcct tccatcaatg cgtcgtagaa acgacttact ccttcttgag   5100
cagctccttg accttgttgg caacaagtct ccgacctcgg aggtggagga agagcctccg   5160
atatcggcgg tagtgatacc agcctcgacg gactccttga cggcagcctc aacagcgtca   5220
ccggcgggct tcatgttaag agagaacttg agcatcatgg cggcagacag aatggtggca   5280
atggggttga ccttctgctt gccgagatcg gggcagatc cgtgacaggg ctcgtacaga   5340
ccgaacgcct cgttggtgtc gggcagagaa gccagagagg cggagggcag cagacccaga   5400
gaaccgggga tgacggaggc ctcgtcggag atgatatcgc caaacatgtt ggtggtgatg   5460
atgataccat tcatcttgga gggctgcttg atgaggatca tggcggccga gtcgatcagc   5520
tggtggttga gctcgagctg ggggaattcg tccttgagga ctcgagtgac agtctttcgc   5580
caaagtcgag aggaggccag cacgttggcc ttgtcaagag accacacggg aagagggggg   5640
ttgtgctgaa gggccaggaa ggcggccatt cgggcaattc gctcaacctc aggaacggag   5700
taggtctcgg tgtcggaagc gacgccagat ccgtcatcct cctttcgctc tccaaagtag   5760
atacctccga cgagctctcg gacaatgatg aagtcggtgc cctcaacgtt tcggatgggg   5820
gagagatcgg cgagcttggg cgacagcagc tggcagggtc gcaggttggc gtacaggttc   5880
aggtcctttc gcagcttgag gagaccctgc tcgggtcgca cgtcggttcg tccgtcggga   5940
gtggtccata cggtgttggc agcgcctccg acagcaccga gcataataga gtcagccttt   6000
cggcagatgt cgagagtagc gtcggtgatg ggctcgccct ccttctcaat ggcagctcct   6060
ccaatgagtc ggtcctcaaa cacaaactcg gtgccggagg cctcagcaac agacttgagc   6120
```

-continued

```
accttgacgg cctcggcaat cacctcgggg ccacagaagt cgccgccgag aagaacaatc   6180
ttcttggagt cagtcttggt cttcttagtt tcgggttcca ttgtggatgt gtgtggttgt   6240
atgtgtgatg tggtgtgtgg agtgaaaatc tgtggctggc aaacgctctt gtatatatac   6300
gcacttttgc ccgtgctatg tggaagacta aacctccgaa gattgtgact caggtagtgc   6360
ggtatcggct agggacccaa accttgtcga tgccgatagc gctatcgaac gtaccccagc   6420
cggccgggag tatgtcggag gggacatacg agatcgtcaa gggtttgtgg ccaactggta   6480
aatttaaatg atgtcgacgc agtaggatgt cctgcacggg tctttttgtg gggtgtggag   6540
aaaggggtgc ttggagatgg aagccggtag aaccgggctg cttgtgcttg gagatggaag   6600
ccggtagaac cgggctgctt ggggggattt ggggccgctg ggctccaaag aggggtaggc   6660
atttcgttgg ggttacgtaa ttgcggcatt tgggtcctgc gcgcatgtcc cattggtcag   6720
aattagtccg gataggagac ttatcagcca atcacagcgc cggatccacc tgtaggttgg   6780
gttgggtggg agcacccctc cacagagtag agtcaaacag cagcagcaac atgatagttg   6840
ggggtgtgcg tgttaaagga aaaaaaagaa gcttgggtta tattcccgct ctatttagag   6900
gttgcgggat agacgccgac ggagggcaat ggcgccatgg aaccttgcgg atatcgatac   6960
gccgcggcgg actgcgtccg aaccagctcc agcagcgttt tttccgggcc attgagccga   7020
ctgcgacccc gccaacgtgt cttggcccac gcactcatgt catgttggtg ttgggaggcc   7080
actttttaag tagcacaagg cacctagctc gcagcaaggt gtccgaacca aagaagcggc   7140
tgcagtggtg caaacggggc ggaaacggcg ggaaaaagcc acgggggcac gaattgaggc   7200
acgccctcga atttgagacg agtcacggcc ccattcgccc gcgcaatggc tcgccaacgc   7260
ccggtctttt gcaccacatc aggttacccc aagccaaacc tttgtgttaa aaagcttaac   7320
atattatacc gaacgtaggt ttgggcgggc ttgctccgtc tgtccaaggc aacatttata   7380
taagggtctg catcgccggc tcaattgaat cttttttctt cttctcttct ctatattcat   7440
tcttgaatta aacacacatc aatccatggc aaacagcagc gtgtgggatg atgtggtggg   7500
ccgcgtggag accggcgtgg accagtggat ggatggcgcc aagccgtacg cactcaccga   7560
tgggctcccg atgatggacg tgtccaccat gctggcattc gaggtgggat acatggccat   7620
gctgctcttc ggcatcccga tcatgaagca gatggagaag ccttttgagc tcaagaccat   7680
caagctcttg cacaacttgt ttctcttcgg actttccttg tacatgtgcg tggagaccat   7740
ccgccaggct atcctcggag gctacaaagt gtttggaaac gacatggaga agggcaacga   7800
gtctcatgct cagggcatgt ctcgcatcgt gtacgtgttc tacgtgtcca aggcatacga   7860
gttcttggat accgccatca tgatcctttg caagaagttc aaccaggttt ccttcttgca   7920
tgtgtaccac catgccactc atttttgcca tctggtgggc tatccgccaa gtacgctcca   7980
ggaggtgatg cgtacttttt cagtgatcct caactctttc gtgcacaccg tcatgtacgg   8040
catactactt cttctcctcc caagggttcg ggttcgtgaa gccaatcaag ccgtacatca   8100
ccacccttca gatgacccag ttcatggcaa tgcttgtgca gtccttgtac gactacctct   8160
tcccatgcga ctacccacag gctcttgtgc agctccttgg agtgtacatg atcaccttgc   8220
ttgccctctt cggcaacttt tttgtgcaga gctatcttaa aaagccaaaa aagagcaaga   8280
ccaactaaaa ctgcctgcat gatatgccgc tcgccggcgt tcgaattgac tcagaaagcg   8340
agttaaggcg acacgcaaac tctatatttt ttcaaacgtg ttgccgtcac tcattcgcca   8400
tctgtttact acgtgtctgt tcaatgagca tgttcttgaa tctaaagaat ctcgaatgtt   8460
ttttaaaaaa agaattcgat atcaagctta cgcgtcgacc cgggtggacg tctagaggta   8520
```

```
cctagcaatt aacagatagt ttgccggtga taattctctt aacctcccac actcctttga   8580

cataacgatt tatgtaacga aactgaaatt tgaccagata ttgtgtccgc             8630
```

<210> SEQ ID NO 73
<211> LENGTH: 18
<212> TYPE: DNA
<213> ORGANISM: Artificial Sequence
<220> FEATURE:
<223> OTHER INFORMATION: Primer GPDsense

<400> SEQUENCE: 73

```
atacgagatc gtcaaggg                                                  18
```

<210> SEQ ID NO 74
<211> LENGTH: 26
<212> TYPE: DNA
<213> ORGANISM: Artificial Sequence
<220> FEATURE:
<223> OTHER INFORMATION: Primer GPDantisense

<400> SEQUENCE: 74

```
gcggccgcgg attgatgtgt gtttaa                                         26
```

<210> SEQ ID NO 75
<211> LENGTH: 6339
<212> TYPE: DNA
<213> ORGANISM: Artificial Sequence
<220> FEATURE:
<223> OTHER INFORMATION: Plasmid pKR136
<220> FEATURE:
<221> NAME/KEY: misc_feature
<222> LOCATION: (4078)..(4078)
<223> OTHER INFORMATION: n is a, c, g, or t

<400> SEQUENCE: 75

```
ggccgcgaca caagtgtgag agtactaaat aaatgctttg gttgtacgaa atcattacac     60

taaataaaat aatcaaagct tatatatgcc ttccgctaag gccgaatgca aagaaattgg    120

ttctttctcg ttatcttttg ccacttttac tagtacgtat taattactac ttaatcatct    180

ttgtttacgg ctcattatat ccgtacgtcg agtcgacctg caggcatgca agcttggcgt    240

aatcatggtc atagctgttt cctgtgtgaa attgttatcc gctcacaatt ccacacaaca    300

tacgagccgg aagcataaag tgtaaagcct ggggtgccta atgagtgagc taactcacat    360

taattgcgtt gcgctcactg cccgctttcc agtcgggaaa cctgtcgtgc cagctgcatt    420

aatgaatcgg ccaacgcgcg gggagaggcg gtttgcgtat tgggcgctct tccgcttcct    480

cgctcactga ctcgctgcgc tcggtcgttc ggctgcggcg agcggtatca gctcactcaa    540

aggcggtaat acggttatcc acagaatcag gggataacgc aggaaagaac atgtgagcaa    600

aaggccagca aaaggccagg aaccgtaaaa aggccgcgtt gctggcgttt ttccataggc    660

tccgcccccc tgacgagcat cacaaaaatc gacgctcaag tcagaggtgg cgaaacccga    720

caggactata aagataccag gcgtttcccc ctggaagctc cctcgtgcgc tctcctgttc    780

cgaccctgcc gcttaccgga tacctgtccg cctttctccc ttcgggaagc gtggcgcttt    840

ctcatagctc acgctgtagg tatctcagtt cggtgtaggt cgttcgctcc aagctgggct    900

gtgtgcacga accccccgtt cagcccgacc gctgcgcctt atccggtaac tatcgtcttg    960

agtccaaccc ggtaagacac gacttatcgc cactggcagc agccactggt aacaggatta   1020

gcagagcgag gtatgtaggc ggtgctacag agttcttgaa gtggtggcct aactacggct   1080

acactagaag gacagtattt ggtatctgcg ctctgctgaa gccagttacc ttcggaaaaa   1140
```

```
gagttggtag ctcttgatcc ggcaaacaaa ccaccgctgg tagcggtggt ttttttgttt   1200
gcaagcagca gattacgcgc agaaaaaaag gatctcaaga agatcctttg atcttttcta   1260
cggggtctga cgctcagtgg aacgaaaact cacgttaagg gattttggtc atgagattat   1320
caaaaaggat cttcacctag atccttttaa attaaaaatg aagttttaaa tcaatctaaa   1380
gtatatatga gtaaacttgg tctgacagtt accaatgctt aatcagtgag gcacctatct   1440
cagcgatctg tctatttcgt tcatccatag ttgcctgact ccccgtcgtg tagataacta   1500
cgatacggga gggcttacca tctggcccca gtgctgcaat gataccgcga gacccacgct   1560
caccggctcc agatttatca gcaataaacc agccagccgg aagggccgag cgcagaagtg   1620
gtcctgcaac tttatccgcc tccatccagt ctattaattg ttgccgggaa gctagagtaa   1680
gtagttcgcc agttaatagt ttgcgcaacg ttgttgccat tgctacaggc atcgtggtgt   1740
cacgctcgtc gtttggtatg gcttcattca gctccggttc ccaacgatca aggcgagtta   1800
catgatcccc catgttgtgc aaaaaagcgg ttagctcctt cggtcctccg atcgttgtca   1860
gaagtaagtt ggccgcagtg ttatcactca tggttatggc agcactgcat aattctctta   1920
ctgtcatgcc atccgtaaga tgcttttctg tgactggtga gtactcaacc aagtcattct   1980
gagaatagtg tatgcggcga ccgagttgct cttgcccggc gtcaatacgg gataataccg   2040
cgccacatag cagaacttta aaagtgctca tcattggaaa acgttcttcg gggcgaaaac   2100
tctcaaggat cttaccgctg ttgagatcca gttcgatgta acccactcgt gcacccaact   2160
gatcttcagc atcttttact ttcaccagcg tttctgggtg agcaaaaaca ggaaggcaaa   2220
atgccgcaaa aaagggaata agggcgacac ggaaatgttg aatactcata ctcttccttt   2280
ttcaatatta ttgaagcatt tatcagggtt attgtctcat gagcggatac atatttgaat   2340
gtatttagaa aaataaacaa ataggggttc cgcgcacatt tccccgaaaa gtgccacctg   2400
acgtctaaga aaccattatt atcatgacat taacctataa aaataggcgt atcacgaggc   2460
cctttcgtct cgcgcgtttc ggtgatgacg gtgaaaacct ctgacacatg cagctcccgg   2520
agacggtcac agcttgtctg taagcggatg ccgggagcag acaagcccgt cagggcgcgt   2580
cagcgggtgt tggcgggtgt cggggctggc ttaactatgc ggcatcagag cagattgtac   2640
tgagagtgca ccatatgcgg tgtgaaatac cgcacagatg cgtaaggaga aaataccgca   2700
tcaggcgcca ttcgccattc aggctgcgca actgttggga agggcgatcg gtgcgggcct   2760
cttcgctatt acgccagctg gcgaaagggg gatgtgctgc aaggcgatta agttgggtaa   2820
cgccagggtt ttcccagtca cgacgttgta aaacgacggc cagtgaattc gagctcggta   2880
cccggggatc ctctagacgt acgtcctcga agagaagggt taataacaca tttttttaaca   2940
tttttaacac aaattttagt tatttaaaaa tttattaaaa aatttaaaat aagaagagga   3000
actctttaaa taaatctaac ttacaaaatt tatgattttt aataagtttt caccaataaa   3060
aaatgtcata aaaatatgtt aaaaagtata ttatcaatat tctctttatg ataaataaaa   3120
agaaaaaaaa aataaaagtt aagtgaaaat gagattgaag tgactttagg tgtgtataaa   3180
tatatcaacc ccgccaacaa tttatttaat ccaaatatat tgaagtatat tattccatag   3240
cctttattta tttatatatt tattatataa aagctttatt tgttctaggt tgttcatgaa   3300
atattttttt ggttttatct ccgttgtaag aaaatcatgt gctttgtgtc gccactcact   3360
attgcagctt tttcatgcat tggtcagatt gacggttgat tgtatttttg ttttttatgg   3420
ttttgtgtta tgacttaagt cttcatctct ttatctcttc atcaggtttg atggttacct   3480
aatatggtcc atgggtacat gcatggttaa attaggtggc caactttgtt gtgaacgata   3540
```

-continued

```
gaatttttt tatattaagt aaactatttt tatattatga aataataata aaaaaaatat   3600
tttatcatta ttaacaaaat catattagtt aatttgttaa ctctataata aaagaaatac   3660
tgtaacattc acattacatg gtaacatctt tccacccttt catttgtttt ttgtttgatg   3720
acttttttc ttgtttaaat ttatttccct tcttttaaat ttggaataca ttatcatcat   3780
atataaacta aaatactaaa aacaggatta cacaaatgat aaataataac acaaatattt   3840
ataaatctag ctgcaatata tttaaactag ctatatcgat attgtaaaat aaaactagct   3900
gcattgatac tgataaaaaa atatcatgtg ctttctggac tgatgatgca gtatactttt   3960
gacattgcct ttattttatt tttcagaaaa gctttcttag ttctgggttc ttcattattt   4020
gtttcccatc tccattgtga attgaatcat ttgcttcgtg tcacaaatac aatttagnta   4080
ggtacatgca ttggtcagat tcacggttta ttatgtcatg acttaagttc atggtagtac   4140
attacctgcc acgcatgcat tatattggtt agatttgata ggcaaatttg gttgtcaaca   4200
atataaatat aaataatgtt tttatattac gaaataacag tgatcaaaac aaacagtttt   4260
atctttatta acaagatttt gtttttgttt gatgacgttt tttaatgttt acgctttccc   4320
ccttcttttg aatttagaac actttatcat cataaaatca aatactaaaa aaattacata   4380
tttcataaat aataacacaa atatttttaa aaaatctgaa ataataatga acaatattac   4440
atattatcac gaaaattcat taataaaaat attatataaa taaaatgtaa tagtagttat   4500
atgtaggaaa aaagtactgc acgcataata tatacaaaaa gattaaaatg aactattata   4560
aataataaca ctaaattaat ggtgaatcat atcaaaataa tgaaaaagta aataaaattt   4620
gtaattaact tctatatgta ttacacacac aaataataaa taatagtaaa aaaaattatg   4680
ataaatattt accatctcat aagatattta aaataatgat aaaaatatag attatttttt   4740
atgcaactag ctagccaaaa agagaacacg ggtatatata aaaagagtac ctttaaattc   4800
tactgtactt cctttattcc tgacgttttt atatcaagtg gacatacgtg aagattttaa   4860
ttatcagtct aaatatttca ttagcactta atacttttct gttttattcc tatcctataa   4920
gtagtcccga ttctcccaac attgcttatt cacacaacta actaagaaag tcttccatag   4980
ccccccaagc ggccgcatgg gaacggacca aggaaaaacc ttcacctggg aagagctggc   5040
ggcccataac accaaggacg acctactctt ggccatccgc ggcagggtgt acgatgtcac   5100
aaagttcttg agccgccatc ctggtggagt ggacactctc ctgctcggag ctggccgaga   5160
tgttactccg gtctttgaga tgtatcacgc gtttggggct gcagatgcca ttatgaagaa   5220
gtactatgtc ggtacactgg tctcgaatga gctgcccatc ttcccggagc caacggtgtt   5280
ccacaaaacc atcaagacga gagtcgaggg ctactttacg gatcggaaca ttgatcccaa   5340
gaatagacca gagatctggg gacgatacgc tcttatcttt ggatccttga tcgcttccta   5400
ctacgcgcag ctctttgtgc ctttcgttgt cgaacgcaca tggcttcagg tggtgtttgc   5460
aatcatcatg ggatttgcgt gcgcacaagt cggactcaac cctcttcatg atgcgtctca   5520
cttttcagtg acccacaacc ccactgtctg gaagattctg ggagccacgc acgacttttt   5580
caacggagca tcgtacctgg tgtggatgta ccaacatatg ctcggccatc acccctacac   5640
caacattgct ggagcagatc ccgacgtgtc gacgtctgag cccgatgttc gtcgtatcaa   5700
gcccaaccaa aagtggtttg tcaaccacat caaccagcac atgtttgttc ctttcctgta   5760
cggactgctg gcgttcaagg tgcgcattca ggacatcaac attttgtact ttgtcaagac   5820
caatgacgct attcgtgtca atcccatctc gacatggcac actgtgatgt tctggggcgg   5880
caaggctttc tttgtctggt atcgcctgat tgttcccctg cagtatctgc cctgggcaa    5940
```

```
ggtgctgctc ttgttcacgg tcgcggacat ggtgtcgtct tactggctgg cgctgacctt   6000

ccaggcgaac cacgttgttg aggaagttca gtggccgttg cctgacgaga acgggatcat   6060

ccaaaaggac tgggcagcta tgcaggtcga gactacgcag gattacgcac acgattcgca   6120

cctctggacc agcatcactg gcagcttgaa ctaccaggct gtgcaccatc tgttccccaa   6180

cgtgtcgcag caccattatc ccgatattct ggccatcatc aagaacacct gcagcgagta   6240

caaggttcca taccttgtca aggatacgtt ttggcaagca tttgcttcac atttggagca   6300

cttgcgtgtt cttggactcc gtcccaagga agagtaggc                          6339
```

<210> SEQ ID NO 76
<211> LENGTH: 8319
<212> TYPE: DNA
<213> ORGANISM: Artificial Sequence
<220> FEATURE:
<223> OTHER INFORMATION: Plasmid pY98

<400> SEQUENCE: 76

```
ggccgccacc gcggcccgag attccggcct cttcggccgc caagcgaccc gggtggacgt     60

ctagaggtac ctagcaatta acagatagtt tgccggtgat aattctctta acctcccaca    120

ctcctttgac ataacgattt atgtaacgaa actgaaattt gaccagatat tgtgtccgcg    180

gtggagctcc agcttttgtt ccctttagtg agggttaatt tcgagcttgg cgtaatcatg    240

gtcatagctg tttcctgtgt gaaattgtta tccgctcaca attccacaca acgtacgagc    300

cggaagcata aagtgtaaag cctggggtgc ctaatgagtg agctaactca cattaattgc    360

gttgcgctca ctgcccgctt tccagtcggg aaacctgtcg tgccagctgc attaatgaat    420

cggccaacgc gcggggagag gcggtttgcg tattgggcgc tcttccgctt cctcgctcac    480

tgactcgctg cgctcggtcg ttcggctgcg gcgagcggta tcagctcact caaaggcggt    540

aatacggtta tccacagaat caggggataa cgcaggaaag aacatgtgag caaaaggcca    600

gcaaaaggcc aggaaccgta aaaaggccgc gttgctggcg tttttccata ggctccgccc    660

ccctgacgag catcacaaaa atcgacgctc aagtcagagg tggcgaaacc cgacaggact    720

ataaagatac caggcgtttc cccctggaag ctccctcgtg cgctctcctg ttccgaccct    780

gccgcttacc ggatacctgt ccgcctttct cccttcggga agcgtggcgc tttctcatag    840

ctcacgctgt aggtatctca gttcggtgta ggtcgttcgc tccaagctgg gctgtgtgca    900

cgaacccccc gttcagcccg accgctgcgc cttatccggt aactatcgtc ttgagtccaa    960

cccggtaaga cacgacttat cgccactggc agcagccact ggtaacagga ttagcagagc   1020

gaggtatgta ggcggtgcta cagagttctt gaagtggtgg cctaactacg gctacactag   1080

aaggacagta tttggtatct gcgctctgct gaagccagtt accttcggaa aaagagttgg   1140

tagctcttga tccggcaaac aaaccaccgc tggtagcggt ggtttttttg tttgcaagca   1200

gcagattacg cgcagaaaaa aaggatctca agaagatcct ttgatctttt ctacggggtc   1260

tgacgctcag tggaacgaaa actcacgtta agggattttg gtcatgagat tatcaaaaag   1320

gatcttcacc tagatccttt taaattaaaa atgaagtttt aaatcaatct aaagtatata   1380

tgagtaaact tggtctgaca gttaccaatg cttaatcagt gaggcaccta tctcagcgat   1440

ctgtctattt cgttcatcca tagttgcctg actccccgtc gtgtagataa ctacgatacg   1500

ggagggctta ccatctggcc ccagtgctgc aatgataccg cgagacccac gctcaccggc   1560

tccagattta tcagcaataa accagccagc cggaagggcc gagcgcagaa gtggtcctgc   1620

aactttatcc gcctccatcc agtctattaa ttgttgccgg gaagctagag taagtagttc   1680
```

```
gccagttaat agtttgcgca acgttgttgc cattgctaca ggcatcgtgg tgtcacgctc   1740
gtcgtttggt atggcttcat tcagctccgg ttcccaacga tcaaggcgag ttacatgatc   1800
ccccatgttg tgcaaaaaag cggttagctc cttcggtcct ccgatcgttg tcagaagtaa   1860
gttggccgca gtgttatcac tcatggttat ggcagcactg cataattctc ttactgtcat   1920
gccatccgta agatgctttt ctgtgactgg tgagtactca accaagtcat tctgagaata   1980
gtgtatgcgg cgaccgagtt gctcttgccc ggcgtcaata cgggataata ccgcgccaca   2040
tagcagaact ttaaaagtgc tcatcattgg aaaacgttct tcggggcgaa aactctcaag   2100
gatcttaccg ctgttgagat ccagttcgat gtaacccact cgtgcaccca actgatcttc   2160
agcatctttt actttcacca gcgtttctgg gtgagcaaaa acaggaaggc aaaatgccgc   2220
aaaaaaggga ataagggcga cacggaaatg ttgaatactc atactcttcc tttttcaata   2280
ttattgaagc atttatcagg gttattgtct catgagcgga tacatatttg aatgtattta   2340
gaaaaataaa caaatagggg ttccgcgcac atttccccga aaagtgccac ctgacgcgcc   2400
ctgtagcggc gcattaagcg cggcgggtgt ggtggttacg cgcagcgtga ccgctacact   2460
tgccagcgcc ctagcgcccg ctcctttcgc tttcttccct tcctttctcg ccacgttcgc   2520
cggctttccc cgtcaagctc taaatcgggg gctcccttta gggttccgat ttagtgcttt   2580
acggcacctc gaccccaaaa aacttgatta gggtgatggt tcacgtagtg ggccatcgcc   2640
ctgatagacg gtttttcgcc ctttgacgtt ggagtccacg ttctttaata gtggactctt   2700
gttccaaact ggaacaacac tcaaccctat ctcggtctat tcttttgatt tataagggat   2760
tttgccgatt tcggcctatt ggttaaaaaa tgagctgatt taacaaaaat ttaacgcgaa   2820
ttttaacaaa atattaacgc ttacaatttc cattcgccat tcaggctgcg caactgttgg   2880
gaagggcgat cggtgcgggc ctcttcgcta ttacgccagc tggcgaaagg gggatgtgct   2940
gcaaggcgat taagttgggt aacgccaggg ttttcccagt cacgacgttg taaaacgacg   3000
gccagtgaat tgtaatacga ctcactatag ggcgaattgg gtaccgggcc ccccctcgag   3060
gtcgatggtg tcgataagct tgatatcgaa ttcatgtcac acaaaccgat cttcgcctca   3120
aggaaaccta attctacatc cgagagactg ccgagatcca gtctacactg attaattttc   3180
gggccaataa tttaaaaaaa tcgtgttata taatattata tgtattatat atatacatca   3240
tgatgatact gacagtcatg tcccattgct aaatagacag actccatctg ccgcctccaa   3300
ctgatgttct caatatttaa ggggtcatct cgcattgttt aataataaac agactccatc   3360
taccgcctcc aaatgatgtt ctcaaaatat attgtatgaa cttattttta ttacttagta   3420
ttattagaca acttacttgc tttatgaaaa acacttccta tttaggaaac aatttataat   3480
ggcagttcgt tcatttaaca atttatgtag aataaatgtt ataaatgcgt atgggaaatc   3540
ttaaatatgg atagcataaa tgatatctgc attgcctaat tcgaaatcaa cagcaacgaa   3600
aaaaatccct tgtacaacat aaatagtcat cgagaaatat caactatcaa agaacagcta   3660
ttcacacgtt actattgaga ttattattgg acgagaatca cacactcaac tgtctttctc   3720
tcttctagaa atacaggtac aagtatgtac tattctcatt gttcatactt ctagtcattt   3780
catcccacat attccttgga tttctctcca atgaatgaca ttctatcttg caaattcaac   3840
aattataata agatatacca aagtagcggt atagtggcaa tcaaaaagct tctctggtgt   3900
gcttctcgta tttatttta ttctaatgat ccattaaagg tatatattta tttcttgtta    3960
tataatcctt ttgtttatta catgggctgg atacataaag gtattttgat ttaattttt    4020
gcttaaattc aatccccct cgttcagtgt caactgtaat ggtaggaaat taccatactt    4080
```

-continued

```
ttgaagaagc aaaaaaaatg aaagaaaaaa aaaatcgtat ttccaggtta gacgttccgc   4140

agaatctaga atgcggtatg cggtacattg ttcttcgaac gtaaaagttg cgctccctga   4200

gatattgtac atttttgctt ttacaagtac aagtacatcg tacaactatg tactactgtt   4260

gatgcatcca caacagtttg ttttgttttt ttttgttttt tttttttcta atgattcatt   4320

accgctatgt atacctactt gtacttgtag taagccgggt tattggcgtt caattaatca   4380

tagacttatg aatctgcacg gtgtgcgctg cgagttactt ttagcttatg catgctactt   4440

gggtgtaata ttgggatctg ttcggaaatc aacggatgct caaccgattt cgacagtaat   4500

taattaagtc atacacaagt cagctttctt cgagcctcat ataagtataa gtagttcaac   4560

gtattagcac tgtacccagc atctccgtat cgagaaacac aacaacatgc cccattggac   4620

agatcatgcg gatacacagg ttgtgcagta tcatacatac tcgatcagac aggtcgtctg   4680

accatcatac aagctgaaca agcgctccat acttgcacgc tctctatata cacagttaaa   4740

ttacatatcc atagtctaac ctctaacagt taatcttctg gtaagcctcc cagccagcct   4800

tctggtatcg cttggcctcc tcaataggat ctcggttctg gccgtacaga cctcggccga   4860

caattatgat atccgttccg gtagacatga catcctcaac agttcggtac tgctgtccga   4920

gagcgtctcc cttgtcgtca agacccaccc cgggggtcag aataagccag tcctcagagt   4980

cgcccttagg tcggttctgg gcaatgaagc caaccacaaa ctcggggtcg gatcgggcaa   5040

gctcaatggt ctgcttggag tactcgccag tggccagaga gcccttgcaa gacagctcgg   5100

ccagcatgag cagacctctg gccagcttct cgttgggaga ggggactagg aactccttgt   5160

actgggagtt ctcgtagtca gagacgtcct ccttcttctg ttcagagaca gtttcctcgg   5220

caccagctcg caggccagca atgattccgg ttccgggtac accgtgggcg ttggtgatat   5280

cggaccactc ggcgattcgg tgacaccggt actggtgctt gacagtgttg ccaatatctg   5340

cgaactttct gtcctcgaac aggaagaaac cgtgcttaag agcaagttcc ttgaggggga   5400

gcacagtgcc ggcgtaggtg aagtcgtcaa tgatgtcgat atgggttttg atcatgcaca   5460

cataaggtcc gaccttatcg gcaagctcaa tgagctcctt ggtggtggta acatccagag   5520

aagcacacag gttggttttc ttggctgcca cgagcttgag cactcgagcg gcaaaggcgg   5580

acttgtggac gttagctcga gcttcgtagg agggcatttt ggtggtgaag aggagactga   5640

aataaattta gtctgcagaa ctttttatcg gaaccttatc tggggcagtg aagtatatgt   5700

tatggtaata gttacgagtt agttgaactt atagatagac tggactatac ggctatcggt   5760

ccaaattaga aagaacgtca atggctctct gggcgtcgcc tttgccgaca aaaatgtgat   5820

catgatgaaa gccagcaatg acgttgcagc tgatattgtt gtcggccaac cgcgccgaaa   5880

acgcagctgt cagacccaca gcctccaacg aagaatgtat cgtcaaagtg atccaagcac   5940

actcatagtt ggagtcgtac tccaaaggcg gcaatgacga gtcagacaga tactcgtcga   6000

cgcagtagga tgtcctgcac gggtcttttt gtggggtgtg gagaaagggg tgcttggaga   6060

tggaagccgg tagaaccggg ctgcttgtgc ttggagatgg aagccggtag aaccgggctg   6120

cttgggggga tttggggccg ctgggctcca aagaggggta ggcatttcgt tggggttacg   6180

taattgcggc atttgggtcc tgcgcgcatg tcccattggt cagaattagt ccggatagga   6240

gacttatcag ccaatcacag cgccggatcc acctgtaggt tgggttgggt gggagcaccc   6300

ctccacagag tagagtcaaa cagcagcagc aacatgatag ttgggggtgt gcgtgttaaa   6360

ggaaaaaaaa gaagcttggg ttatattccc gctctattta gaggttgcgg gatagacgcc   6420

gacggagggc aatggcgcca tggaaccttg cggatatcga tacgccgcgg cggactgcgt   6480
```

-continued

```
ccgaaccagc tccagcagcg ttttttccgg gccattgagc cgactgcgac cccgccaacg   6540

tgtcttggcc cacgcactca tgtcatgttg gtgttgggag gccacttttt aagtagcaca   6600

aggcacctag ctcgcagcaa ggtgtccgaa ccaaagaagc ggctgcagtg gtgcaaacgg   6660

ggcggaaacg gcgggaaaaa gccacggggg cacgaattga ggcacgccct cgaatttgag   6720

acgagtcacg gccccattcg cccgcgcaat ggctcgccaa cgcccggtct tttgcaccac   6780

atcaggttac cccaagccaa acctttgtgt taaaaagctt aacatattat accgaacgta   6840

ggtttgggcg ggcttgctcc gtctgtccaa ggcaacattt atataagggt ctgcatcgcc   6900

ggctcaattg aatctttttt cttcttctct tctctatatt cattcttgaa ttaaacacac   6960

atcaatccgc ggccgcatgg gaacggacca aggaaaaacc ttcacctggg aagagctggc   7020

ggcccataac accaaggacg acctactctt ggccatccgc ggcagggtgt acgatgtcac   7080

aaagttcttg agccgccatc ctggtggagt ggacactctc ctgctcggag ctggccgaga   7140

tgttactccg gtctttgaga tgtatcacgc gtttggggct gcagatgcca ttatgaagaa   7200

gtactatgtc ggtacactgg tctcgaatga gctgcccatc ttcccggagc caacggtgtt   7260

ccacaaaacc atcaagacga gagtcgaggg ctactttacg gatcggaaca ttgatcccaa   7320

gaatagacca gagatctggg gacgatacgc tcttatcttt ggatccttga tcgcttccta   7380

ctacgcgcag ctctttgtgc ctttcgttgt cgaacgcaca tggcttcagg tggtgtttgc   7440

aatcatcatg ggatttgcgt gcgcacaagt cggactcaac cctcttcatg atgcgtctca   7500

cttttcagtg acccacaacc ccactgtctg gaagattctg ggagccacgc acgacttttt   7560

caacggagca tcgtacctgg tgtggatgta ccaacatatg ctcggccatc acccctacac   7620

caacattgct ggagcagatc ccgacgtgtc gacgtctgag cccgatgttc gtcgtatcaa   7680

gcccaaccaa aagtggtttg tcaaccacat caaccagcac atgtttgttc ctttcctgta   7740

cggactgctg gcgttcaagg tgcgcattca ggacatcaac attttgtact ttgtcaagac   7800

caatgacgct attcgtgtca atcccatctc gacatggcac actgtgatgt tctggggcgg   7860

caaggctttc tttgtctggt atcgcctgat tgttcccctg cagtatctgc cctgggcaa    7920

ggtgctgctc ttgttcacgg tcgcggacat ggtgtcgtct tactggctgg cgctgacctt   7980

ccaggcgaac cacgttgttg aggaagttca gtggccgttg cctgacgaga acgggatcat   8040

ccaaaaggac tgggcagcta tgcaggtcga gactacgcag gattacgcac acgattcgca   8100

cctctggacc agcatcactg gcagcttgaa ctaccaggct gtgcaccatc tgttccccaa   8160

cgtgtcgcag caccattatc ccgatattct ggccatcatc aagaacacct gcagcgagta   8220

caaggttcca taccttgtca aggatacgtt ttggcaagca tttgcttcac atttggagca   8280

cttgcgtgtt cttggactcc gtcccaagga agagtaggc                         8319
```

```
<210> SEQ ID NO 77
<211> LENGTH: 774
<212> TYPE: DNA
<213> ORGANISM: Euglena gracilis

<400> SEQUENCE: 77

atggaggtgg tgaatgaaat agtctcaatt gggcaggaag ttttacccaa agttgattat     60

gcccaactct ggagtgatgc cagtcactgt gaggtgcttt acttgtccat cgcatttgtc    120

atcttgaagt tcactcttgg cccccttggt ccaaaaggtc agtctcgtat gaagtttgtt    180

ttcaccaatt acaaccttct catgtccatt tattcgttgg gatcattcct ctcaatggca    240

tatgccatgt acaccatcgg tgttatgtct gacaactgcg agaaggcttt tgacaacaac    300
```

```
gtcttcagga tcaccacgca gttgttctat ttgagcaagt tcctggagta tattgactcc    360

ttctatttgc cactgatggg caagcctctg acctggttgc aattcttcca tcatttgggg    420

gcaccgatgg atatgtggct gttctataat taccgaaatg aagctgtttg gatttttgtg    480

ctgttgaatg gtttcatcca ctggatcatg tacggttatt attggaccag attgatcaag    540

ctgaagttcc ccatgccaaa atccctgatt acatcaatgc agatcattca attcaatgtt    600

ggtttctaca ttgtctggaa gtacaggaac attccctgtt atcgccaaga tgggatgagg    660

atgtttggct ggttcttcaa ttacttttat gttggcacag tcttgtgttt gttcttgaat    720

ttctatgtgc aaacgtatat cgtcaggaag cacaagggag ccaaaaagat tcag          774
```

<210> SEQ ID NO 78
<211> LENGTH: 1263
<212> TYPE: DNA
<213> ORGANISM: Euglena gracilis

<400> SEQUENCE: 78

```
atgaagtcaa agcgccaagc gcttcccctt acaattgatg gaacaacata tgatgtgtct     60

gcctgggtca atttccaccc tggtggtgcg gaaattatag agaattacca aggaagggat    120

gccactgatg ccttcatggt tatgcactct caagaagcct tcgacaagct caagcgcatg    180

cccaaaatca atcccagttc tgagttgcca ccccaggctg cagtgaatga agctcaagag    240

gatttccgga agctccgaga agagttgatc gcaactggca tgtttgatgc ctcccccctc    300

tggtactcat acaaaatcag caccacactg ggccttggag tgctgggtta tttcctgatg    360

gttcagtatc agatgtattt cattggggca gtgttgcttg ggatgcacta tcaacagatg    420

ggctggcttt ctcatgacat ttgccaccac cagactttca agaaccggaa ctggaacaac    480

ctcgtgggac tggtatttgg caatggtctg caaggttttt ccgtgacatg gtggaaggac    540

agacacaatg cacatcattc ggcaaccaat gttcaagggc acgaccctga tattgacaac    600

ctcccccctct tagcctggtc tgaggatgac gtcacacggg cgtcaccgat ttcccgcaag    660

ctcattcagt tccagcagta ctatttcttg gtcatctgta tcttgttgcg gttcatttgg    720

tgtttccaga gcgtgttgac cgtgcgcagt ttgaaggaca gagataacca attctatcgc    780

tctcagtata agaaggaggc cattggcctc gccctgcact ggaccttgaa gaccctgttc    840

cacttattct ttatgcccag catcctcaca tcgctgttgg tgtttttcgt ttcggagctg    900

gttggcggct tcggcattgc gatcgtggtg ttcatgaacc actacccact ggagaagatc    960

ggggactcag tctgggatgg ccatggattc tcggttggcc agatccatga gaccatgaac   1020

attcggcgag ggattatcac agattggttt ttcggaggct tgaattacca gattgagcac   1080

catttgtggc cgaccctccc tcgccacaac ctgacagcgg ttagctacca ggtggaacag   1140

ctgtgccaga agcacaacct gccgtatcgg aacccgctgc cccatgaagg gttggtcatc   1200

ctgctgcgct atctggcggt gttcgcccgg atggcggaga agcaacccgc ggggaaggct   1260

cta                                                                 1263
```

<210> SEQ ID NO 79
<211> LENGTH: 30
<212> TYPE: DNA
<213> ORGANISM: Artificial Sequence
<220> FEATURE:
<223> OTHER INFORMATION: Primer oEugEL1-1

<400> SEQUENCE: 79

```
agcggccgca ccatggaggt ggtgaatgaa                                      30
```

<210> SEQ ID NO 80
<211> LENGTH: 30
<212> TYPE: DNA
<213> ORGANISM: Artificial Sequence
<220> FEATURE:
<223> OTHER INFORMATION: Primer oEugEL1-2

<400> SEQUENCE: 80
tgcggccgct cactgaatct tttggctcc 30

<210> SEQ ID NO 81
<211> LENGTH: 4311
<212> TYPE: DNA
<213> ORGANISM: Artificial Sequence
<220> FEATURE:
<223> OTHER INFORMATION: Plasmid pKR906

<400> SEQUENCE: 81
agcggccgca ccatggaggt ggtgaatgaa atagtctcaa ttgggcagga agttttaccc 60
aaagttgatt atgcccaact ctggagtgat gccagtcact gtgaggtgct ttacttgtcc 120
atcgcatttg tcatcttgaa gttcactctt ggcccccttg gtccaaaagg tcagtctcgt 180
atgaagtttg ttttcaccaa ttacaacctt ctcatgtcca tttattcgtt gggatcattc 240
ctctcaatgg catatgccat gtacaccatc ggtgttatgt ctgacaactg cgagaaggct 300
tttgacaaca acgtcttcag gatcaccacg cagttgttct atttgagcaa gttcctggag 360
tatattgact ccttctattt gccactgatg ggcaagcctc tgacctggtt gcaattcttc 420
catcatttgg gggcaccgat ggatatgtgg ctgttctata attaccgaaa tgaagctgtt 480
tggatttttg tgctgttgaa tggtttcatc cactggatca tgtacggtta ttattggacc 540
agattgatca agctgaagtt ccccatgcca aaatccctga ttacatcaat gcagatcatt 600
caattcaatg ttggtttcta cattgtctgg aagtacagga acattccctg ttatcgccaa 660
gatgggatga ggatgtttgg ctggttcttc aattactttt atgttggcac agtcttgtgt 720
ttgttcttga atttctatgt gcaaacgtat atcgtcagga agcacaaggg agccaaaaag 780
attcagtgag cggccgcacc tgaattccag cacactggcg gccgttacta gtggatccga 840
gctcggtacc aagcttgatg catagcttga gtattctaac gcgtcaccta aatagcttgg 900
cgtaatcatg gtcatagctg tttcctgtgt gaaattgtta tccgctcaca attccacaca 960
acatacgagc cggaagcata aagtgtaaag cctggggtgc ctaatgagtg agctaactca 1020
cattaattgc gttgcgctca ctgcccgctt tccagtcggg aaacctgtcg tgccagctgc 1080
attaatgaat cggccaacgc gcggggagag gcggtttgcg tattgggcgc tcttccgctt 1140
cctcgctcac tgactcgctg cgctcggtcg ttcggctgcg gcgagcggta tcagctcact 1200
caaaggcggt aatacggtta tccacagaat caggggataa cgcaggaaag aacatgtgag 1260
caaaaggcca gcaaaagccc aggaaccgta aaaaggccgc gttgctggcg tttttccata 1320
ggctccgccc ccctgacgag catcacaaaa atcgacgctc aagtcagagg tggcgaaacc 1380
cgacaggact ataaagatac caggcgtttc cccctggaag ctccctcgtg cgctctcctg 1440
ttccgaccct gccgcttacc ggatacctgt ccgcctttct cccttcggga agcgtggcgc 1500
tttctcatag ctcacgctgt aggtatctca gttcggtgta ggtcgttcgc tccaagctgg 1560
gctgtgtgca cgaacccccc gttcagcccg accgctgcgc cttatccggt aactatcgtc 1620
ttgagtccaa cccggtaaga cacgacttat cgccactggc agcagccact ggtaacagga 1680
ttagcagagc gaggtatgta ggcggtgcta cagagttctt gaagtggtgg cctaactacg 1740

-continued

```
gctacactag aaggacagta tttggtatct gcgctctgct gaagccagtt accttcggaa   1800
aaagagttgg tagctcttga tccggcaaac aaaccaccgc tggtagcggt ggtttttttg   1860
tttgcaagca gcagattacg cgcagaaaaa aaggatctca agaagatcct ttgatctttt   1920
ctacggggtc tgacgctcag tggaacgaaa actcacgtta agggattttg gtcatgagat   1980
tatcaaaaag gatcttcacc tagatccttt taaattaaaa atgaagtttt agcacgtgtc   2040
agtcctgctc ctcggccacg aagtgcacgc agttgccggc cgggtcgcgc agggcgaact   2100
cccgccccca cggctgctcg ccgatctcgg tcatggccgg cccggaggcg tcccggaagt   2160
tcgtggacac gacctccgac cactcggcgt acagctcgtc caggccgcgc acccacaccc   2220
aggccagggt gttgtccggc accacctggt cctggaccgc gctgatgaac agggtcacgt   2280
cgtcccggac cacaccggcg aagtcgtcct ccacgaagtc ccgggagaac ccgagccggt   2340
cggtccagaa ctcgaccgct ccggcgacgt cgcgcgcggt gagcaccgga acggcactgg   2400
tcaacttggc catggtggcc ctcctcacgt gctattattg aagcatttat cagggttatt   2460
gtctcatgag cggatacata tttgaatgta tttagaaaaa taaacaaata ggggttccgc   2520
gcacatttcc ccgaaaagtg ccacctgtat gcggtgtgaa ataccgcaca gatgcgtaag   2580
gagaaaatac cgcatcagga aattgtaagc gttaataatt cagaagaact cgtcaagaag   2640
gcgatagaag gcgatgcgct gcgaatcggg agcggcgata ccgtaaagca cgaggaagcg   2700
gtcagcccat tcgccgccaa gctcttcagc aatatcacgg gtagccaacg ctatgtcctg   2760
atagcggtcc gccacaccca gccggccaca gtcgatgaat ccagaaaagc ggccattttc   2820
caccatgata ttcggcaagc aggcatcgcc atgggtcacg acgagatcct cgccgtcggg   2880
catgctcgcc ttgagcctgg cgaacagttc ggctggcgcg agcccctgat gctcttcgtc   2940
cagatcatcc tgatcgacaa gaccggcttc catccgagta cgtgctcgct cgatgcgatg   3000
tttcgcttgg tggtcgaatg ggcaggtagc cggatcaagc gtatgcagcc gccgcattgc   3060
atcagccatg atggatactt tctcggcagg agcaaggtga gatgacagga gatcctgccc   3120
cggcacttcg cccaatagca gccagtccct tcccgcttca gtgacaacgt cgagcacagc   3180
tgcgcaagga acgcccgtcg tggccagcca cgatagccgc gctgcctcgt cttgcagttc   3240
attcagggca ccggacaggt cggtcttgac aaaaagaacc gggcgcccct gcgctgacag   3300
ccggaacacg gcggcatcag agcagccgat tgtctgttgt gcccagtcat agccgaatag   3360
cctctccacc caagcggccg gagaacctgc gtgcaatcca tcttgttcaa tcatgcgaaa   3420
cgatcctcat cctgtctctt gatcagagct tgatcccctg cgccatcaga tccttggcgg   3480
cgagaaagcc atccagttta ctttgcaggg cttcccaacc ttaccagagg gcgccccagc   3540
tggcaattcc ggttcgcttg ctgtccataa aaccgcccag tctagctatc gccatgtaag   3600
cccactgcaa gctacctgct ttctctttgc gcttgcgttt tcccttgtcc agatagccca   3660
gtagctgaca ttcatccggg gtcagcaccg tttctgcgga ctggctttct acgtgaaaag   3720
gatctaggtg aagatccttt ttgataatct catgcctgac atttatattc cccagaacat   3780
caggttaatg gcgtttttga tgtcattttc gcggtggctg agatcagcca cttcttcccc   3840
gataacggag accggcacac tggccatatc ggtggtcatc atgcgccagc tttcatcccc   3900
gatatgcacc accgggtaaa gttcacggga gactttatct gacagcagac gtgcactggc   3960
caggggggatc accatccgtc gccccggcgt gtcaataata tcactctgta catccacaaa   4020
cagacgataa cggctctctc ttttataggt gtaaacctta aactgccgta cgtataggct   4080
gcgcaactgt tgggaagggc gatcggtgcg ggcctcttcg ctattacgcc agctggcgaa   4140
```

```
agggggatgt gctgcaaggc gattaagttg ggtaacgcca gggttttccc agtcacgacg   4200

ttgtaaaacg acggccagtg aattgtaata cgactcacta tagggcgaat tgggccctct   4260

agatgcatgc tcgagcggcc gccagtgtga tggatatctg cagaattcag g            4311


<210> SEQ ID NO 82
<211> LENGTH: 7085
<212> TYPE: DNA
<213> ORGANISM: Artificial Sequence
<220> FEATURE:
<223> OTHER INFORMATION: Plasmid pKR72

<400> SEQUENCE: 82

gtacggatcc gtcgacggcg cgcccgatca tccggatata gttcctcctt tcagcaaaaa     60

acccctcaag acccgtttag aggccccaag gggttatgct agttattgct cagcggtggc    120

agcagccaac tcagcttcct ttcgggcttt gttagcagcc ggatcgatcc aagctgtacc    180

tcactattcc tttgccctcg gacgagtgct ggggcgtcgg tttccactat cggcgagtac    240

ttctacacag ccatcggtcc agacggccgc gcttctgcgg gcgatttgtg tacgcccgac    300

agtcccggct ccggatcgga cgattgcgtc gcatcgaccc tgcgcccaag ctgcatcatc    360

gaaattgccg tcaaccaagc tctgatagag ttggtcaaga ccaatgcgga gcatatacgc    420

ccggagccgc ggcgatcctg caagctccgg atgcctccgc tcgaagtagc gcgtctgctg    480

ctccatacaa gccaaccacg gcctccagaa gaagatgttg gcgacctcgt attgggaatc    540

cccgaacatc gcctcgctcc agtcaatgac cgctgttatg cggccattgt ccgtcaggac    600

attgttggag ccgaaatccg cgtgcacgag gtgccggact tcggggcagt cctcggccca    660

aagcatcagc tcatcgagag cctgcgcgac ggacgcactg acggtgtcgt ccatcacagt    720

ttgccagtga tacacatggg gatcagcaat cgcgcatatg aaatcacgcc atgtagtgta    780

ttgaccgatt ccttgcggtc cgaatgggcc gaacccgctc gtctggctaa gatcggccgc    840

agcgatcgca tccatagcct ccgcgaccgg ctgcagaaca gcgggcagtt cggtttcagg    900

caggtcttgc aacgtgacac cctgtgcacg gcgggagatg caataggtca ggctctcgct    960

gaattcccca atgtcaagca cttccggaat cgggagcgcg gccgatgcaa agtgccgata   1020

aacataacga tctttgtaga aaccatcggc gcagctattt acccgcagga catatccacg   1080

ccctcctaca tcgaagctga aagcacgaga ttcttcgccc tccgagagct gcatcaggtc   1140

ggagacgctg tcgaactttt cgatcagaaa cttctcgaca gacgtcgcgg tgagttcagg   1200

cttttccatg ggtatatctc cttcttaaag ttaaacaaaa ttatttctag agggaaaccg   1260

ttgtggtctc cctatagtga gtcgtattaa tttcgcggga tcgagatcga tccaattcca   1320

atcccacaaa aatctgagct taacagcaca gttgctcctc tcagagcaga atcgggtatt   1380

caacaccctc atatcaacta ctacgttgtg tataacggtc cacatgccgg tatatacgat   1440

gactggggtt gtacaaaggc ggcaacaaac ggcgttcccg gagttgcaca caagaaattt   1500

gccactatta cagaggcaag agcagcagct gacgcgtaca caacaagtca gcaaacagac   1560

aggttgaact tcatccccaa aggagaagct caactcaagc ccaagagctt tgctaaggcc   1620

ctaacaagcc caccaaagca aaaagcccac tggctcacgc taggaaccaa aaggcccagc   1680

agtgatccag ccccaaaaga gatctccttt gccccggaga ttacaatgga cgatttcctc   1740

tatctttacg atctaggaag gaagttcgaa ggtgaaggtg acgacactat gttcaccact   1800

gataatgaga aggttagcct cttcaatttc agaaagaatg ctgacccaca gatggttaga   1860

gaggcctacg cagcaggtct catcaagacg atctacccga gtaacaatct ccaggagatc   1920
```

```
aaataccttc ccaagaaggt taaagatgca gtcaaaagat tcaggactaa ttgcatcaag   1980
aacacagaga aagacatatt tctcaagatc agaagtacta ttccagtatg gacgattcaa   2040
ggcttgcttc ataaaccaag gcaagtaata gagattggag tctctaaaaa ggtagttcct   2100
actgaatcta aggccatgca tggagtctaa gattcaaatc gaggatctaa cagaactcgc   2160
cgtgaagact ggcgaacagt tcatacagag tcttttacga ctcaatgaca agaagaaaat   2220
cttcgtcaac atggtggagc acgacactct ggtctactcc aaaaatgtca aagatacagt   2280
ctcagaagac caaagggcta ttgagacttt tcaacaaagg ataatttcgg gaaacctcct   2340
cggattccat tgcccagcta tctgtcactt catcgaaagg acagtagaaa aggaaggtgg   2400
ctcctacaaa tgccatcatt gcgataaagg aaaggctatc attcaagatg cctctgccga   2460
cagtggtccc aaagatggac ccccacccac gaggagcatc gtggaaaaag aagacgttcc   2520
aaccacgtct tcaaagcaag tggattgatg tgacatctcc actgacgtaa gggatgacgc   2580
acaatcccac tatccttcgc aagacccttc ctctatataa ggaagttcat ttcatttgga   2640
gaggacacgc tcgagctcat ttctctatta cttcagccat aacaaaagaa ctcttttctc   2700
ttcttattaa accatgaaaa agcctgaact caccgcgacg tctgtcgaga agtttctgat   2760
cgaaaagttc gacagcgtct ccgacctgat gcagctctcg gagggcgaag aatctcgtgc   2820
tttcagcttc gatgtaggag ggcgtggata tgtcctgcgg gtaaatagct gcgccgatgg   2880
tttctacaaa gatcgttatg tttatcggca ctttgcatcg gccgcgctcc cgattccgga   2940
agtgcttgac attggggaat tcagcgagag cctgacctat tgcatctccc gccgtgcaca   3000
gggtgtcacg ttgcaagacc tgcctgaaac cgaactgccc gctgttctgc agccggtcgc   3060
ggaggccatg gatgcgatcg ctgcggccga tcttagccag acgagcgggt tcggcccatt   3120
cggaccgcaa ggaatcggtc aatacactac atggcgtgat ttcatatgcg cgattgctga   3180
tccccatgtg tatcactggc aaactgtgat ggacgacacc gtcagtgcgt ccgtcgcgca   3240
ggctctcgat gagctgatgc tttgggccga ggactgcccc gaagtccggc acctcgtgca   3300
cgcggatttc ggctccaaca atgtcctgac ggacaatggc cgcataacag cggtcattga   3360
ctggagcgag gcgatgttcg gggattccca atacgaggtc gccaacatct tcttctggag   3420
gccgtggttg gcttgtatgg agcagcagac gcgctacttc gagcggaggc atccggagct   3480
tgcaggatcg ccgcggctcc gggcgtatat gctccgcatt ggtcttgacc aactctatca   3540
gagcttggtt gacggcaatt tcgatgatgc agcttgggcg cagggtcgat gcgacgcaat   3600
cgtccgatcc ggagccggga ctgtcgggcg tacacaaatc gcccgcagaa gcgcggccgt   3660
ctggaccgat ggctgtgtag aagtactcgc cgatagtgga aaccgacgcc ccagcactcg   3720
tccgagggca aaggaatagt gaggtaccta aagaaggagt gcgtcgaagc agatcgttca   3780
aacatttggc aataaagttt cttaagattg aatcctgttg ccggtcttgc gatgattatc   3840
atataatttc tgttgaatta cgttaagcat gtaataatta acatgtaatg catgacgtta   3900
tttatgagat gggtttttat gattagagtc ccgcaattat acatttaata cgcgatagaa   3960
aacaaaatat agcgcgcaaa ctaggataaa ttatcgcgcg cggtgtcatc tatgttacta   4020
gatcgatgtc gaatcgatca acctgcatta atgaatcggc caacgcgcgg ggagaggcgg   4080
tttgcgtatt gggcgctctt ccgcttcctc gctcactgac tcgctgcgct cggtcgttcg   4140
gctgcggcga gcggtatcag ctcactcaaa ggcggtaata cggttatcca cagaatcagg   4200
ggataacgca ggaaagaaca tgtgagcaaa aggccagcaa aaggccagga accgtaaaaa   4260
ggccgcgttg ctggcgtttt tccataggct ccgcccccct gacgagcatc acaaaaatcg   4320
```

```
acgctcaagt cagaggtggc gaaacccgac aggactataa agataccagg cgtttccccc   4380

tggaagctcc ctcgtgcgct ctcctgttcc gaccctgccg cttaccggat acctgtccgc   4440

ctttctccct tcgggaagcg tggcgctttc tcaatgctca cgctgtaggt atctcagttc   4500

ggtgtaggtc gttcgctcca agctgggctg tgtgcacgaa ccccccgttc agcccgaccg   4560

ctgcgcctta tccggtaact atcgtcttga gtccaacccg gtaagacacg acttatcgcc   4620

actggcagca gccactggta acaggattag cagagcgagg tatgtaggcg gtgctacaga   4680

gttcttgaag tggtggccta actacggcta cactagaagg acagtatttg gtatctgcgc   4740

tctgctgaag ccagttacct tcggaaaaag agttggtagc tcttgatccg gcaaacaaac   4800

caccgctggt agcggtggtt tttttgtttg caagcagcag attacgcgca gaaaaaaagg   4860

atctcaagaa gatcctttga tcttttctac ggggtctgac gctcagtgga acgaaaactc   4920

acgttaaggg attttggtca tgacattaac ctataaaaat aggcgtatca cgaggccctt   4980

tcgtctcgcg cgtttcggtg atgacggtga aaacctctga cacatgcagc tcccggagac   5040

ggtcacagct tgtctgtaag cggatgccgg gagcagacaa gcccgtcagg gcgcgtcagc   5100

gggtgttggc gggtgtcggg gctggcttaa ctatgcggca tcagagcaga ttgtactgag   5160

agtgcaccat atggacatat tgtcgttaga acgcggctac aattaataca taaccttatg   5220

tatcatacac atacgattta ggtgacacta tagaacggcg cgccaagctt gttgaaacat   5280

ccctgaagtg tctcatttta ttttatttat tctttgctga taaaaaaata aaataaaaga   5340

agctaagcac acggtcaacc attgctctac tgctaaaagg gttatgtgta gtgttttact   5400

gcataaatta tgcagcaaac aagacaactc aaattaaaaa atttcctttg cttgtttttt   5460

tgttgtctct gacttgactt tcttgtggaa gttggttgta taaggattgg gacaccattg   5520

tccttcttaa tttaatttta ttctttgctg ataaaaaaaa aaatttcata tagtgttaaa   5580

taataatttg ttaaataacc aaaaagtcaa atatgtttac tctcgtttaa ataattgaga   5640

ttcgtccagc aaggctaaac gattgtatag atttatgaca atatttactt ttttatagat   5700

aaatgttata ttataataaa tttatataca tatattatat gttatttatt attattttaa   5760

atccttcaat attttatcaa accaactcat aatttttttt ttatctgtaa gaagcaataa   5820

aattaaatag acccacttta aggatgatcc aacctttata cagagtaaga gagttcaaat   5880

agtacccttt catatacata tcaactaaaa tattagaaat atcatggatc aaaccttata   5940

aagacattaa ataagtggat aagtataata tataaatggg tagtatataa tatataaatg   6000

gatacaaact tctctcttta taattgttat gtctccttaa catcctaata taatacataa   6060

gtgggtaata tataatatat aaatggagac aaacttcttc cattataatt gttatgtctt   6120

cttaacactt atgtctcgtt cacaatgcta aggttagaat tgtttagaaa gtcttatagt   6180

acacatttgt ttttgtacta tttgaagcat tccataagcc gtcacgattc agatgattta   6240

taataataag aggaaattta tcatagaaca ataaggtgca tagatagagt gttaatatat   6300

cataacatcc tttgtttatt catagaagaa gtgagatgga gctcagttat tatactgtta   6360

catggtcgga tacaatattc catgctctcc atgagctctt acacctacat gcattttagt   6420

tcatacttgc ggccgcagta tatcttaaat tctttaatac ggtgtactag gatattgaac   6480

tggttcttga tgatgaaaac ctgggccgag attgcagcta tttatagtca taggtcttgt   6540

taacatgcat ggacatttgg ccacggggtg gcatgcagtt tgacgggtgt tgaaataaac   6600

aaaaatgagg tggcggaaga gaatacgagt ttgaggttgg gttagaaaca acaaatgtga   6660

gggctcatga tgggttgagt tggtgaatgt tttgggctgc tcgattgaca cctttgtgag   6720
```

```
tacgtgttgt tgtgcatggc ttttggggtc cagttttttt ttcttgacgc ggcgatcctg   6780

atcagctagt ggataagtga tgtccactgt gtgtgattgc gtttttgttt gaattttatg   6840

aacttagaca ttgctatgca aaggatactc tcattgtgtt ttgtcttctt ttgttccttg   6900

gctttttctt atgatccaag agactagtca gtgttgtggc attcgagact accaagatta   6960

attatgatgg gggaaggata agtaactgat tagtacggac tgttaccaaa ttaattaata   7020

agcggcaaat gaagggcatg gatcaaaagc ttggatctcc tgcaggatct ggccggccgg   7080

atctc                                                               7085


<210> SEQ ID NO 83
<211> LENGTH: 2540
<212> TYPE: DNA
<213> ORGANISM: Artificial Sequence
<220> FEATURE:
<223> OTHER INFORMATION: Plasmid pKS102

<400> SEQUENCE: 83

cgatcatccg gatatagttc ctcctttcag caaaaaaccc ctcaagaccc gtttagaggc     60

cccaaggggt tatgctagtt attgctcagc ggtggcagca gccaactcag cttcctttcg    120

ggctttgtta gcagccggat cgatccaagc tgtacctcac tattcctttg ccctcggacg    180

agtgctgggg cgtcggtttc cactatcggc gagtacttct acacagccat cggtccagac    240

ggccgcgctt ctgcgggcga tttgtgtacg cccgacagtc ccggctccgg atcggacgat    300

tgcgtcgcat cgaccctgcg cccaagctgc atcatcgaaa ttgccgtcaa ccaagctctg    360

atagagttgg tcaagaccaa tgcggagcat atacgcccgg agccgcggcg atcctgcaag    420

ctccggatgc ctccgctcga agtagcgcgt ctgctgctcc atacaagcca accacggcct    480

ccagaagaag atgttggcga cctcgtattg ggaatccccg aacatcgcct cgctccagtc    540

aatgaccgct gttatgcggc cattgtccgt caggacattg ttggagccga aatccgcgtg    600

cacgaggtgc cggacttcgg ggcagtcctc ggcccaaagc atcagctcat cgagagcctg    660

cgcgacggac gcactgacgg tgtcgtccat cacagtttgc cagtgataca catggggatc    720

agcaatcgcg catatgaaat cacgccatgt agtgtattga ccgattcctt gcggtccgaa    780

tgggccgaac ccgctcgtct ggctaagatc ggccgcagcg atcgcatcca tagcctccgc    840

gaccggctgc agaacagcgg gcagttcggt ttcaggcagg tcttgcaacg tgacaccctg    900

tgcacggcgg gagatgcaat aggtcaggct ctcgctgaat tccccaatgt caagcacttc    960

cggaatcggg agcgcggccg atgcaaagtg ccgataaaca taacgatctt tgtagaaacc   1020

atcggcgcag ctatttaccc gcaggacata tccacgccct cctacatcga agctgaaagc   1080

acgagattct tcgccctccg agagctgcat caggtcggag acgctgtcga acttttcgat   1140

cagaaacttc tcgacagacg tcgcggtgag ttcaggcttt tccatgggta tatctccttc   1200

ttaaagttaa acaaaattat ttctagaggg aaaccgttgt ggtctcccta tagtgagtcg   1260

tattaatttc gcgggatcga gatctgatca acctgcatta atgaatcggc caacgcgcgg   1320

ggagaggcgg tttgcgtatt gggcgctctt ccgcttcctc gctcactgac tcgctgcgct   1380

cggtcgttcg gctgcggcga gcggtatcag ctcactcaaa ggcggtaata cggttatcca   1440

cagaatcagg ggataacgca ggaaagaaca tgtgagcaaa aggccagcaa aaggccagga   1500

accgtaaaaa ggccgcgttg ctggcgtttt tccataggct ccgcccccct gacgagcatc   1560

acaaaaatcg acgctcaagt cagaggtggc gaaacccgac aggactataa agataccagg   1620

cgtttccccc tggaagctcc ctcgtgcgct ctcctgttcc gaccctgccg cttaccggat   1680
```

```
acctgtccgc ctttctccct tcgggaagcg tggcgctttc tcaatgctca cgctgtaggt   1740

atctcagttc ggtgtaggtc gttcgctcca agctgggctg tgtgcacgaa ccccccgttc   1800

agcccgaccg ctgcgcctta tccggtaact atcgtcttga gtccaacccg gtaagacacg   1860

acttatcgcc actggcagca gccactggta acaggattag cagagcgagg tatgtaggcg   1920

gtgctacaga gttcttgaag tggtggccta actacggcta cactagaagg acagtatttg   1980

gtatctgcgc tctgctgaag ccagttacct tcggaaaaag agttggtagc tcttgatccg   2040

gcaaacaaac caccgctggt agcggtggtt tttttgtttg caagcagcag attacgcgca   2100

gaaaaaaagg atctcaagaa gatcctttga tcttttctac ggggtctgac gctcagtgga   2160

acgaaaactc acgttaaggg attttggtca tgacattaac ctataaaaat aggcgtatca   2220

cgaggccctt tcgtctcgcg cgtttcggtg atgacggtga aaacctctga cacatgcagc   2280

tcccggagac ggtcacagct tgtctgtaag cggatgccgg gagcagacaa gcccgtcagg   2340

gcgcgtcagc gggtgttggc gggtgtcggg gctggcttaa ctatgcggca tcagagcaga   2400

ttgtactgag agtgcaccat atggacatat tgtcgttaga acgcggctac aattaataca   2460

taaccttatg tatcatacac atacgattta ggtgacacta tagaacggcg cgccaagctt   2520

ggatccgtcg acggcgcgcc                                               2540
```

<210> SEQ ID NO 84
<211> LENGTH: 4359
<212> TYPE: DNA
<213> ORGANISM: Artificial Sequence
<220> FEATURE:
<223> OTHER INFORMATION: Plasmid pKR197

<400> SEQUENCE: 84

```
cgcgcccgat catccggata tagttcctcc tttcagcaaa aaacccctca agacccgttt     60

agaggcccca aggggttatg ctagttattg ctcagcggtg gcagcagcca actcagcttc    120

ctttcgggct ttgttagcag ccggatcgat ccaagctgta cctcactatt cctttgccct    180

cggacgagtg ctggggcgtc ggtttccact atcggcgagt acttctacac agccatcggt    240

ccagacggcc gcgcttctgc gggcgatttg tgtacgcccg acagtcccgg ctccggatcg    300

gacgattgcg tcgcatcgac cctgcgccca agctgcatca tcgaaattgc cgtcaaccaa    360

gctctgatag agttggtcaa gaccaatgcg gagcatatac gcccggagcc gcggcgatcc    420

tgcaagctcc ggatgcctcc gctcgaagta gcgcgtctgc tgctccatac aagccaacca    480

cggcctccag aagaagatgt tggcgacctc gtattgggaa tccccgaaca tcgcctcgct    540

ccagtcaatg accgctgtta tgcggccatt gtccgtcagg acattgttgg agccgaaatc    600

cgcgtgcacg aggtgccgga cttcggggca gtcctcggcc caaagcatca gctcatcgag    660

agcctgcgcg acggacgcac tgacggtgtc gtccatcaca gtttgccagt gatacacatg    720

gggatcagca atcgcgcata tgaaatcacg ccatgtagtg tattgaccga ttccttgcgg    780

tccgaatggg ccgaacccgc tcgtctggct aagatcggcc gcagcgatcg catccatagc    840

ctccgcgacc ggctgcagaa cagcgggcag ttcggtttca ggcaggtctt gcaacgtgac    900

accctgtgca cggcgggaga tgcaataggt caggctctcg ctgaattccc caatgtcaag    960

cacttccgga atcgggagcg cggccgatgc aaagtgccga taaacataac gatctttgta   1020

gaaaccatcg gcgcagctat ttacccgcag gacatatcca cgccctccta catcgaagct   1080

gaaagcacga gattcttcgc cctccgagag ctgcatcagg tcggagacgc tgtcgaactt   1140

ttcgatcaga aacttctcga cagacgtcgc ggtgagttca ggcttttcca tgggtatatc   1200
```

-continued

```
tccttcttaa agttaaacaa aattatttct agagggaaac cgttgtggtc tccctatagt   1260
gagtcgtatt aatttcgcgg gatcgagatc tgatcaacct gcattaatga atcggccaac   1320
gcgcggggag aggcggtttg cgtattgggc gctcttccgc ttcctcgctc actgactcgc   1380
tgcgctcggt cgttcggctg cggcgagcgg tatcagctca ctcaaaggcg gtaatacggt   1440
tatccacaga atcaggggat aacgcaggaa agaacatgtg agcaaaaggc cagcaaaagg   1500
ccaggaaccg taaaaaggcc gcgttgctgg cgtttttcca taggctccgc ccccctgacg   1560
agcatcacaa aaatcgacgc tcaagtcaga ggtggcgaaa cccgacagga ctataaagat   1620
accaggcgtt tccccctgga agctccctcg tgcgctctcc tgttccgacc ctgccgctta   1680
ccggatacct gtccgccttt ctcccttcgg gaagcgtggc gctttctcaa tgctcacgct   1740
gtaggtatct cagttcggtg taggtcgttc gctccaagct gggctgtgtg cacgaacccc   1800
ccgttcagcc cgaccgctgc gccttatccg gtaactatcg tcttgagtcc aacccggtaa   1860
gacacgactt atcgccactg gcagcagcca ctggtaacag gattagcaga gcgaggtatg   1920
taggcggtgc tacagagttc ttgaagtggt ggcctaacta cggctacact agaaggacag   1980
tatttggtat ctgcgctctg ctgaagccag ttaccttcgg aaaaagagtt ggtagctctt   2040
gatccggcaa acaaaccacc gctggtagcg gtggtttttt tgtttgcaag cagcagatta   2100
cgcgcagaaa aaaaggatct caagaagatc ctttgatctt ttctacgggg tctgacgctc   2160
agtggaacga aaactcacgt taagggattt tggtcatgac attaacctat aaaaataggc   2220
gtatcacgag gccctttcgt ctcgcgcgtt tcggtgatga cggtgaaaac ctctgacaca   2280
tgcagctccc ggagacggtc acagcttgtc tgtaagcgga tgccgggagc agacaagccc   2340
gtcagggcgc gtcagcgggt gttggcgggt gtcggggctg gcttaactat gcggcatcag   2400
agcagattgt actgagagtg caccatatgg acatattgtc gttagaacgc ggctacaatt   2460
aatacataac cttatgtatc atacacatac gatttaggtg acactataga acggcgcgcc   2520
aagcttgttg aaacatccct gaagtgtctc attttatttt atttattctt tgctgataaa   2580
aaaataaaat aaaagaagct aagcacacgg tcaaccattg ctctactgct aaaagggtta   2640
tgtgtagtgt tttactgcat aaattatgca gcaaacaaga caactcaaat taaaaaattt   2700
cctttgcttg tttttttgtt gtctctgact tgactttctt gtggaagttg gttgtataag   2760
gattgggaca ccattgtcct tcttaattta attttattct ttgctgataa aaaaaaaaat   2820
ttcatatagt gttaaataat aatttgttaa ataaccaaaa agtcaaatat gtttactctc   2880
gtttaaataa ttgagattcg tccagcaagg ctaaacgatt gtatagattt atgacaatat   2940
ttactttttt atagataaat gttatattat aataaattta tatacatata ttatatgtta   3000
tttattatta ttttaaatcc ttcaatattt tatcaaacca actcataatt tttttttat   3060
ctgtaagaag caataaaatt aaatagaccc actttaagga tgatccaacc tttatacaga   3120
gtaagagagt tcaaatagta ccctttcata tacatatcaa ctaaaatatt agaaatatca   3180
tggatcaaac cttataaaga cattaaataa gtggataagt ataatatata aatgggtagt   3240
atataatata taaatggata caaacttctc tctttataat tgttatgtct ccttaacatc   3300
ctaatataat acataagtgg gtaatatata atatataaat ggagacaaac ttcttccatt   3360
ataattgtta tgtcttctta acacttatgt ctcgttcaca atgctaaggt tagaattgtt   3420
tagaaagtct tatagtacac atttgttttt gtactatttg aagcattcca taagccgtca   3480
cgattcagat gatttataat aataagagga aatttatcat agaacaataa ggtgcataga   3540
tagagtgtta atatatcata acatcctttg tttattcata gaagaagtga gatggagctc   3600
```

```
agttattata ctgttacatg gtcggataca atattccatg ctctccatga gctcttacac   3660

ctacatgcat tttagttcat acttgcggcc gcagtatatc ttaaattctt taatacggtg   3720

tactaggata ttgaactggt tcttgatgat gaaaacctgg gccgagattg cagctattta   3780

tagtcatagg tcttgttaac atgcatggac atttggccac ggggtggcat gcagtttgac   3840

gggtgttgaa ataaacaaaa atgaggtggc ggaagagaat acgagtttga ggttgggtta   3900

gaaacaacaa atgtgagggc tcatgatggg ttgagttggt gaatgttttg ggctgctcga   3960

ttgacacctt tgtgagtacg tgttgttgtg catggctttt ggggtccagt tttttttct   4020

tgacgcggcg atcctgatca gctagtggat aagtgatgtc cactgtgtgt gattgcgttt   4080

ttgtttgaat tttatgaact tagacattgc tatgcaaagg atactctcat tgtgttttgt   4140

cttcttttgt tccttggctt tttcttatga tccaagagac tagtcagtgt tgtggcattc   4200

gagactacca agattaatta tgatggggga aggataagta actgattagt acggactgtt   4260

accaaattaa ttaataagcg gcaaatgaag ggcatggatc aaaagcttgg atctcctgca   4320

ggatctggcc ggccggatct cgtacggatc cgtcgacgg                          4359
```

<210> SEQ ID NO 85
<211> LENGTH: 5147
<212> TYPE: DNA
<213> ORGANISM: Artificial Sequence
<220> FEATURE:
<223> OTHER INFORMATION: Plasmid pKR911

<400> SEQUENCE: 85

```
ggccgcaagt atgaactaaa atgcatgtag gtgtaagagc tcatggagag catggaatat     60

tgtatccgac catgtaacag tataataact gagctccatc tcacttcttc tatgaataaa    120

caaaggatgt tatgatatat taacactcta tctatgcacc ttattgttct atgataaatt    180

tcctcttatt attataaatc atctgaatcg tgacggctta tggaatgctt caaatagtac    240

aaaaacaaat gtgtactata agactttcta aacaattcta accttagcat tgtgaacgag    300

acataagtgt taagaagaca taacaattat aatggaagaa gtttgtctcc atttatatat    360

tatatattac ccacttatgt attatattag gatgttaagg agacataaca attataaaga    420

gagaagtttg tatccattta tatattatat actacccatt tatatattat acttatccac    480

ttatttaatg tctttataag gtttgatcca tgatatttct aatattttag ttgatatgta    540

tatgaaaggg tactatttga actctcttac tctgtataaa ggttggatca tccttaaagt    600

gggtctattt aattttattg cttcttacag ataaaaaaaa aattatgagt tggtttgata    660

aaatattgaa ggatttaaaa taataataaa taacatataa tatatgtata taaatttatt    720

ataatataac atttatctat aaaaaagtaa atattgtcat aaatctatac aatcgtttag    780

ccttgctgga cgaatctcaa ttatttaaac gagagtaaac atatttgact ttttggttat    840

ttaacaaatt attatttaac actatatgaa atttttttt ttatcagcaa agaataaaat     900

taaattaaga aggacaatgg tgtcccaatc cttatacaac caacttccac aagaaagtca    960

agtcagagac aacaaaaaaa caagcaaagg aaattttta atttgagttg tcttgtttgc    1020

tgcataattt atgcagtaaa acactacaca taaccctttt agcagtagag caatggttga   1080

ccgtgtgctt agcttctttt attttatttt tttatcagca aagaataaat aaaataaaat   1140

gagacacttc agggatgttt caacaagctt ggcgcgccgt tctatagtgt cacctaaatc   1200

gtatgtgtat gatacataag gttatgtatt aattgtagcc gcgttctaac gacaatatgt   1260

ccatatggtg cactctcagt acaatctgct ctgatgccgc atagttaagc cagccccgac   1320
```

```
acccgccaac acccgctgac gcgccctgac gggcttgtct gctcccggca tccgcttaca   1380
gacaagctgt gaccgtctcc gggagctgca tgtgtcagag gttttcaccg tcatcaccga   1440
aacgcgcgag acgaaagggc ctcgtgatac gcctattttt ataggttaat gtcatgacca   1500
aaatccctta acgtgagttt tcgttccact gagcgtcaga ccccgtagaa aagatcaaag   1560
gatcttcttg agatcctttt tttctgcgcg taatctgctg cttgcaaaca aaaaaaccac   1620
cgctaccagc ggtggtttgt ttgccggatc aagagctacc aactcttttt ccgaaggtaa   1680
ctggcttcag cagagcgcag ataccaaata ctgtccttct agtgtagccg tagttaggcc   1740
accacttcaa gaactctgta gcaccgccta catacctcgc tctgctaatc ctgttaccag   1800
tggctgctgc cagtggcgat aagtcgtgtc ttaccgggtt ggactcaaga cgatagttac   1860
cggataaggc gcagcggtcg ggctgaacgg ggggttcgtg cacacagccc agcttggagc   1920
gaacgaccta caccgaactg agatacctac agcgtgagca ttgagaaagc gccacgcttc   1980
ccgaagggag aaaggcggac aggtatccgg taagcggcag ggtcggaaca ggagagcgca   2040
cgagggagct tccaggggga aacgcctggt atctttatag tcctgtcggg tttcgccacc   2100
tctgacttga gcgtcgattt ttgtgatgct cgtcaggggg gcggagccta tggaaaaacg   2160
ccagcaacgc ggccttttta cggttcctgg ccttttgctg gccttttgct cacatgttct   2220
ttcctgcgtt atcccctgat tctgtggata accgtattac cgcctttgag tgagctgata   2280
ccgctcgccg cagccgaacg accgagcgca gcgagtcagt gagcgaggaa gcggaagagc   2340
gcccaatacg caaaccgcct ctccccgcgc gttggccgat tcattaatgc aggttgatca   2400
gatctcgatc ccgcgaaatt aatacgactc actataggga gaccacaacg gtttccctct   2460
agaaataatt ttgtttaact ttaagaagga gatataccca tggaaaagcc tgaactcacc   2520
gcgacgtctg tcgagaagtt tctgatcgaa aagttcgaca gcgtctccga cctgatgcag   2580
ctctcggagg gcgaagaatc tcgtgctttc agcttcgatg taggagggcg tggatatgtc   2640
ctgcgggtaa atagctgcgc cgatggtttc tacaaagatc gttatgttta tcggcacttt   2700
gcatcggccg cgctcccgat tccggaagtg cttgacattg gggaattcag cgagagcctg   2760
acctattgca tctcccgccg tgcacagggt gtcacgttgc aagacctgcc tgaaaccgaa   2820
ctgcccgctg ttctgcagcc ggtcgcggag gctatggatg cgatcgctgc ggccgatctt   2880
agccagacga gcgggttcgg cccattcgga ccgcaaggaa tcggtcaata cactacatgg   2940
cgtgatttca tatgcgcgat tgctgatccc catgtgtatc actggcaaac tgtgatggac   3000
gacaccgtca gtgcgtccgt cgcgcaggct ctcgatgagc tgatgctttg ggccgaggac   3060
tgccccgaag tccggcacct cgtgcacgcg gatttcggct ccaacaatgt cctgacggac   3120
aatggccgca taacagcggt cattgactgg agcgaggcga tgttcgggga ttcccaatac   3180
gaggtcgcca acatcttctt ctggaggccg tggttggctt gtatggagca gcagacgcgc   3240
tacttcgagc ggaggcatcc ggagcttgca ggatcgccgc ggctccgggc gtatatgctc   3300
cgcattggtc ttgaccaact ctatcagagc ttggttgacg gcaatttcga tgatgcagct   3360
tgggcgcagg gtcgatgcga cgcaatcgtc cgatccggag ccgggactgt cgggcgtaca   3420
caaatcgccc gcagaagcgc ggccgtctgg accgatggct gtgtagaagt actcgccgat   3480
agtggaaacc gacgccccag cactcgtccg agggcaaagg aatagtgagg tacagcttgg   3540
atcgatccgg ctgctaacaa agcccgaaag gaagctgagt tggctgctgc caccgctgag   3600
caataactag cataacccct tggggcctct aaacgggtct tgaggggttt tttgctgaaa   3660
ggaggaacta tatccggatg atcgggcgcg ccgtcgacgg atccgtacga gatccggccg   3720
```

```
gccagatcct gcaggagatc caagcttttg atccatgccc ttcatttgcc gcttattaat   3780

taatttggta acagtccgta ctaatcagtt acttatcctt cccccatcat aattaatctt   3840

ggtagtctcg aatgccacaa cactgactag tctcttggat cataagaaaa agccaaggaa   3900

caaaagaaga caaaacacaa tgagagtatc ctttgcatag caatgtctaa gttcataaaa   3960

ttcaaacaaa aacgcaatca cacacagtgg acatcactta tccactagct gatcaggatc   4020

gccgcgtcaa gaaaaaaaaa ctggaccccca aaagccatgc acaacaacac gtactcacaa   4080

aggtgtcaat cgagcagccc aaaacattca ccaactcaac ccatcatgag ccctcacatt   4140

tgttgtttct aacccaacct caaactcgta ttctcttccg ccacctcatt tttgtttatt   4200

tcaacacccg tcaaactgca tgccaccccg tggccaaatg tccatgcatg ttaacaagac   4260

ctatgactat aaatagctgc aatctcggcc caggttttca tcatcaagaa ccagttcaat   4320

atcctagtac accgtattaa agaatttaag atatactgcg gccgcaccat ggaggtggtg   4380

aatgaaatag tctcaattgg gcaggaagtt ttacccaaag ttgattatgc ccaactctgg   4440

agtgatgcca gtcactgtga ggtgctttac ttgtccatcg catttgtcat cttgaagttc   4500

actcttggcc cccttggtcc aaaaggtcag tctcgtatga agtttgtttt caccaattac   4560

aaccttctca tgtccattta ttcgttggga tcattcctct caatggcata tgccatgtac   4620

accatcggtg ttatgtctga caactgcgag aaggcttttg acaacaacgt cttcaggatc   4680

accacgcagt tgttctattt gagcaagttc ctggagtata ttgactcctt ctatttgcca   4740

ctgatgggca agcctctgac ctggttgcaa ttcttccatc atttgggggc accgatggat   4800

atgtggctgt tctataatta ccgaaatgaa gctgtttgga tttttgtgct gttgaatggt   4860

ttcatccact ggatcatgta cggttattat tggaccagat tgatcaagct gaagttcccc   4920

atgccaaaat ccctgattac atcaatgcag atcattcaat tcaatgttgg tttctacatt   4980

gtctggaagt acaggaacat tccctgttat cgccaagatg ggatgaggat gtttggctgg   5040

ttcttcaatt acttttatgt tggcacagtc ttgtgtttgt tcttgaattt ctatgtgcaa   5100

acgtatatcg tcaggaagca caagggagcc aaaaagattc agtgagc                 5147
```

```
<210> SEQ ID NO 86
<211> LENGTH: 6559
<212> TYPE: DNA
<213> ORGANISM: Artificial Sequence
<220> FEATURE:
<223> OTHER INFORMATION: Plasmid pKR680
<220> FEATURE:
<221> NAME/KEY: misc_feature
<222> LOCATION: (4340)..(4340)
<223> OTHER INFORMATION: n is a, c, g, or t

<400> SEQUENCE: 86
```

```
ggccgcgaca caagtgtgag agtactaaat aaatgctttg gttgtacgaa atcattacac     60

taaataaaat aatcaaagct tatatatgcc ttccgctaag gccgaatgca aagaaattgg    120

ttctttctcg ttatcttttg ccacttttac tagtacgtat taattactac ttaatcatct    180

ttgtttacgg ctcattatat ccggtctaga ggatccaagg ccgcgaagtt aaaagcaatg    240

ttgtcacttg tcgtactaac acatgatgtg atagtttatg ctagctagct ataacataag    300

ctgtctctga gtgtgttgta tattaataaa gatcatcact ggtgaatggt gatcgtgtac    360

gtaccctact tagtaggcaa tggaagcact tagagtgtgc tttgtgcatg gccttgcctc    420

tgttttgaga cttttgtaat gttttcgagt ttaaatcttt gcctttgcgt acgtgggcgg    480

atcccccggg ctgcaggaat tcactggccg tcgttttaca acgtcgtgac tgggaaaacc    540
```

```
ctggcgttac ccaacttaat cgccttgcag cacatccccc tttcgccagc tggcgtaata    600
gcgaagaggc ccgcaccgat cgcccttccc aacagttgcg cagcctgaat ggcgaatggc    660
gcctgatgcg gtattttctc cttacgcatc tgtgcggtat ttcacaccgc atatggtgca    720
ctctcagtac aatctgctct gatgccgcat agttaagcca gccccgacac ccgccaacac    780
ccgctgacgc gccctgacgg gcttgtctgc tcccggcatc cgcttacaga caagctgtga    840
ccgtctccgg gagctgcatg tgtcagaggt tttcaccgtc atcaccgaaa cgcgcgagac    900
gaaagggcct cgtgatacgc ctatttttat aggttaatgt catgataata atggtttctt    960
agacgtcagg tggcactttt cggggaaatg tgcgcggaac ccctatttgt ttatttttct   1020
aaatacattc aaatatgtat ccgctcatga gacaataacc ctgataaatg cttcaataat   1080
attgaaaaag gaagagtatg agtattcaac atttccgtgt cgcccttatt cccttttttg   1140
cggcattttg ccttcctgtt tttgctcacc cagaaacgct ggtgaaagta aaagatgctg   1200
aagatcagtt gggtgcacga gtgggttaca tcgaactgga tctcaacagc ggtaagatcc   1260
ttgagagttt tcgccccgaa gaacgttttc caatgatgag cacttttaaa gttctgctat   1320
gtggcgcggt attatcccgt attgacgccg ggcaagagca actcggtcgc cgcatacact   1380
attctcagaa tgacttggtt gagtactcac cagtcacaga aaagcatctt acggatggca   1440
tgacagtaag agaattatgc agtgctgcca taaccatgag tgataacact gcggccaact   1500
tacttctgac aacgatcgga ggaccgaagg agctaaccgc ttttttgcac aacatggggg   1560
atcatgtaac tcgccttgat cgttgggaac cggagctgaa tgaagccata ccaaacgacg   1620
agcgtgacac cacgatgcct gtagcaatgg caacaacgtt gcgcaaacta ttaactggcg   1680
aactacttac tctagcttcc cggcaacaat taatagactg gatggaggcg gataaagttg   1740
caggaccact tctgcgctcg gcccttccgg ctggctggtt tattgctgat aaatctggag   1800
ccggtgagcg tgggtctcgc ggtatcattg cagcactggg gccagatggt aagccctccc   1860
gtatcgtagt tatctacacg acggggagtc aggcaactat ggatgaacga aatagacaga   1920
tcgctgagat aggtgcctca ctgattaagc attggtaact gtcagaccaa gtttactcat   1980
atatacttta gattgattta aaacttcatt tttaatttaa aaggatctag gtgaagatcc   2040
tttttgataa tctcatgacc aaaatccctt aacgtgagtt ttcgttccac tgagcgtcag   2100
accccgtaga aaagatcaaa ggatcttctt gagatccttt ttttctgcgc gtaatctgct   2160
gcttgcaaac aaaaaaacca ccgctaccag cggtggtttg tttgccggat caagagctac   2220
caactctttt tccgaaggta actggcttca gcagagcgca gataccaaat actgtccttc   2280
tagtgtagcc gtagttaggc caccacttca agaactctgt agcaccgcct acatacctcg   2340
ctctgctaat cctgttacca gtggctgctg ccagtggcga taagtcgtgt cttaccgggt   2400
tggactcaag acgatagtta ccggataagg cgcagcggtc gggctgaacg gggggttcgt   2460
gcacacagcc cagcttggag cgaacgacct acaccgaact gagataccta cagcgtgagc   2520
tatgagaaag cgccacgctt cccgaaggga gaaaggcgga caggtatccg gtaagcggca   2580
gggtcggaac aggagagcgc acgagggagc ttccaggggg aaacgcctgg tatctttata   2640
gtcctgtcgg gtttcgccac ctctgacttg agcgtcgatt tttgtgatgc tcgtcagggg   2700
ggcggagcct atggaaaaac gccagcaacg cggccttttt acggttcctg gccttttgct   2760
ggccttttgc tcacatgttc tttcctgcgt tatcccctga ttctgtggat aaccgtatta   2820
ccgcctttga gtgagctgat accgctcgcc gcagccgaac gaccgagcgc agcgagtcag   2880
tgagcgagga agcggaagag cgcccaatac gcaaaccgcc tctccccgcg cgttggccga   2940
```

```
ttcattaatg cagctggcac gacaggtttc ccgactggaa agcgggcagt gagcgcaacg   3000

caattaatgt gagttagctc actcattagg caccccaggc tttacacttt atgcttccgg   3060

ctcgtatgtt gtgtggaatt gtgagcggat aacaatttca cacaggaaac agctatgacc   3120

atgattacgc caagcttgca tgcctgcagg tcgactcgac gtacgtcctc gaagagaagg   3180

gttaataaca catttttaa catttttaac acaaatttta gttatttaaa aatttattaa   3240

aaaatttaaa ataagaagag gaactcttta aataaatcta acttacaaaa tttatgattt   3300

ttaataagtt ttcaccaata aaaaatgtca taaaaatatg ttaaaaagta tattatcaat   3360

attctcttta tgataaataa aaagaaaaaa aaaataaaag ttaagtgaaa atgagattga   3420

agtgacttta ggtgtgtata aatatatcaa ccccgccaac aatttattta atccaaatat   3480

attgaagtat attattccat agcctttatt tatttatata tttattatat aaaagcttta   3540

tttgttctag gttgttcatg aaatattttt ttggttttat ctccgttgta agaaaatcat   3600

gtgctttgtg tcgccactca ctattgcagc tttttcatgc attggtcaga ttgacggttg   3660

attgtatttt tgttttttat ggttttgtgt tatgacttaa gtcttcatct ctttatctct   3720

tcatcaggtt tgatggttac ctaatatggt ccatgggtac atgcatggtt aaattaggtg   3780

gccaactttg ttgtgaacga tagaattttt tttatattaa gtaaactatt tttatattat   3840

gaaataataa taaaaaaaat attttatcat tattaacaaa atcatattag ttaatttgtt   3900

aactctataa taaaagaaat actgtaacat tcacattaca tggtaacatc tttccaccct   3960

ttcatttgtt ttttgtttga tgactttttt tcttgtttaa atttatttcc cttcttttaa   4020

atttggaata cattatcatc atatataaac taaaatacta aaaacaggat tacacaaatg   4080

ataaataata acacaaatat ttataaatct agctgcaata tatttaaact agctatatcg   4140

atattgtaaa ataaaactag ctgcattgat actgataaaa aaatatcatg tgctttctgg   4200

actgatgatg cagtatactt ttgacattgc ctttatttta tttttcagaa aagctttctt   4260

agttctgggt tcttcattat ttgtttccca tctccattgt gaattgaatc atttgcttcg   4320

tgtcacaaat acaatttagn taggtacatg cattggtcag attcacggtt tattatgtca   4380

tgacttaagt tcatggtagt acattacctg ccacgcatgc attatattgg ttagatttga   4440

taggcaaatt tggttgtcaa caatataaat ataaataatg tttttatatt acgaaataac   4500

agtgatcaaa acaaacagtt ttatctttat taacaagatt ttgtttttgt ttgatgacgt   4560

tttttaatgt ttacgctttc ccccttcttt tgaatttaga acactttatc atcataaaat   4620

caaatactaa aaaaattaca tatttcataa ataataacac aaatattttt aaaaaatctg   4680

aaataataat gaacaatatt acatattatc acgaaaattc attaataaaa atattatata   4740

aataaaatgt aatagtagtt atatgtagga aaaaagtact gcacgcataa tatatacaaa   4800

aagattaaaa tgaactatta taaataataa cactaaatta atggtgaatc atatcaaaat   4860

aatgaaaaag taaataaaat ttgtaattaa cttctatatg tattacacac acaaataata   4920

aataatagta aaaaaaatta tgataaatat ttaccatctc ataagatatt taaaataatg   4980

ataaaaatat agattatttt ttatgcaact agctagccaa aaagagaaca cgggtatata   5040

taaaaagagt acctttaaat tctactgtac ttcctttatt cctgacgttt ttatatcaag   5100

tggacatacg tgaagatttt aattatcagt ctaaatattt cattagcact taatactttt   5160

ctgttttatt cctatcctat aagtagtccc gattctccca acattgctta ttcacacaac   5220

taactaagaa agtcttccat agccccccaa gcggccgcgg gaattcgatt gaaatgaagt   5280

caaagcgcca agcgcttccc cttacaattg atggaacaac atatgatgtg tctgcctggg   5340
```

```
tcaatttcca ccctggtggt gcggaaatta tagagaatta ccaaggaagg gatgccactg   5400

atgccttcat ggttatgcac tctcaagaag ccttcgacaa gctcaagcgc atgcccaaaa   5460

tcaatcccag ttctgagttg ccaccccagg ctgcagtgaa tgaagctcaa gaggatttcc   5520

ggaagctccg agaagagttg atcgcaactg gcatgtttga tgcctccccc ctctggtact   5580

catacaaaat cagcaccaca ctgggccttg gagtgctggg ttatttcctg atggttcagt   5640

atcagatgta tttcattggg gcagtgttgc ttgggatgca ctatcaacag atgggctggc   5700

tttctcatga catttgccac caccagactt tcaagaaccg gaactggaac aacctcgtgg   5760

gactggtatt tggcaatggt ctgcaaggtt tttccgtgac atggtggaag gacagacaca   5820

atgcacatca ttcggcaacc aatgttcaag ggcacgaccc tgatattgac aacctccccc   5880

tcttagcctg gtctgaggat gacgtcacac gggcgtcacc gatttcccgc aagctcattc   5940

agttccagca gtactatttc ttggtcatct gtatcttgtt gcggttcatt tggtgtttcc   6000

agagcgtgtt gaccgtgcgc agtttgaagg acagagataa ccaattctat cgctctcagt   6060

ataagaagga ggccattggc ctcgccctgc actggacctt gaagaccctg ttccacttat   6120

tctttatgcc cagcatcctc acatcgctgt tggtgttttt cgtttcggag ctggttggcg   6180

gcttcggcat tgcgatcgtg gtgttcatga accactaccc actggagaag atcgggggact   6240

cagtctggga tggccatgga ttctcggttg gccagatcca tgagaccatg aacattcggc   6300

gagggattat cacagattgg tttttcggag gcttgaatta ccagattgag caccatttgt   6360

ggccgaccct ccctcgccac aacctgacag cggttagcta ccaggtggaa cagctgtgcc   6420

agaagcacaa cctgccgtat cggaacccgc tgccccatga agggttggtc atcctgctgc   6480

gctatctggc ggtgttcgcc cggatggcgg agaagcaacc cgcggggaag gctctataag   6540

gaatcactag tgaattcgc                                                 6559
```

<210> SEQ ID NO 87
<211> LENGTH: 9014
<212> TYPE: DNA
<213> ORGANISM: Artificial Sequence
<220> FEATURE:
<223> OTHER INFORMATION: Plasmid pKR913
<220> FEATURE:
<221> NAME/KEY: misc_feature
<222> LOCATION: (7839)..(7839)
<223> OTHER INFORMATION: n is a, c, g, or t

<400> SEQUENCE: 87

```
gtacgagatc cggccggcca gatcctgcag gagatccaag cttttgatcc atgcccttca     60

tttgccgctt attaattaat ttggtaacag tccgtactaa tcagttactt atccttcccc    120

catcataatt aatcttggta gtctcgaatg ccacaacact gactagtctc ttggatcata    180

agaaaaagcc aaggaacaaa agaagacaaa acacaatgag agtatccttt gcatagcaat    240

gtctaagttc ataaaattca aacaaaaacg caatcacaca cagtggacat cacttatcca    300

ctagctgatc aggatcgccg cgtcaagaaa aaaaaactgg accccaaaag ccatgcacaa    360

caacacgtac tcacaaaggt gtcaatcgag cagcccaaaa cattcaccaa ctcaacccat    420

catgagccct cacatttgtt gtttctaacc caacctcaaa ctcgtattct cttccgccac    480

ctcatttttg tttatttcaa cacccgtcaa actgcatgcc accccgtggc caaatgtcca    540

tgcatgttaa caagacctat gactataaat agctgcaatc tcggcccagg ttttcatcat    600

caagaaccag ttcaatatcc tagtacaccg tattaaagaa tttaagatat actgcggccg    660

caccatggag gtggtgaatg aaatagtctc aattgggcag gaagttttac ccaaagttga    720
```

-continued

```
ttatgcccaa ctctggagtg atgccagtca ctgtgaggtg ctttacttgt ccatcgcatt    780
tgtcatcttg aagttcactc ttggcccccct tggtccaaaa ggtcagtctc gtatgaagtt  840
tgttttcacc aattacaacc ttctcatgtc catttattcg ttgggatcat tcctctcaat    900
ggcatatgcc atgtacacca tcggtgttat gtctgacaac tgcgagaagg cttttgacaa    960
caacgtcttc aggatcacca cgcagttgtt ctatttgagc aagttcctgg agtatattga   1020
ctccttctat ttgccactga tgggcaagcc tctgacctgg ttgcaattct tccatcattt   1080
gggggcaccg atggatatgt ggctgttcta taattaccga aatgaagctg tttggatttt   1140
tgtgctgttg aatggtttca tccactggat catgtacggt tattattgga ccagattgat   1200
caagctgaag ttccccatgc caaaatccct gattacatca atgcagatca ttcaattcaa   1260
tgttggtttc tacattgtct ggaagtacag gaacattccc tgttatcgcc aagatgggat   1320
gaggatgttt ggctggttct tcaattactt ttatgttggc acagtcttgt gtttgttctt   1380
gaatttctat gtgcaaacgt atatcgtcag gaagcacaag ggagccaaaa agattcagtg   1440
agcggccgca agtatgaact aaaatgcatg taggtgtaag agctcatgga gagcatggaa   1500
tattgtatcc gaccatgtaa cagtataata actgagctcc atctcacttc ttctatgaat   1560
aaacaaagga tgttatgata tattaacact ctatctatgc accttattgt tctatgataa   1620
atttcctctt attattataa atcatctgaa tcgtgacggc ttatggaatg cttcaaatag   1680
tacaaaaaca aatgtgtact ataagacttt ctaaacaatt ctaaccttag cattgtgaac   1740
gagacataag tgttaagaag acataacaat tataatggaa gaagtttgtc tccatttata   1800
tattatatat tacccactta tgtattatat taggatgtta aggagacata acaattataa   1860
agagagaagt ttgtatccat ttatatatta tatactaccc atttatatat tatacttatc   1920
cacttattta atgtctttat aaggtttgat ccatgatatt tctaatattt tagttgatat   1980
gtatatgaaa gggtactatt tgaactctct tactctgtat aaaggttgga tcatccttaa   2040
agtgggtcta tttaatttta ttgcttctta cagataaaaa aaaaattatg agttggtttg   2100
ataaaatatt gaaggattta aaataataat aaataacata taatatatgt atataaattt   2160
attataatat aacatttatc tataaaaaag taaatattgt cataaatcta tacaatcgtt   2220
tagccttgct ggacgaatct caattattta aacgagagta aacatatttg actttttggt   2280
tatttaacaa attattattt aacactatat gaaatttttt tttttatcag caaagaataa   2340
aattaaatta agaaggacaa tggtgtccca atccttatac aaccaacttc cacaagaaag   2400
tcaagtcaga gacaacaaaa aaacaagcaa aggaaatttt ttaatttgag ttgtcttgtt   2460
tgctgcataa tttatgcagt aaaacactac acataaccct tttagcagta gagcaatggt   2520
tgaccgtgtg cttagcttct tttattttat ttttttatca gcaaagaata aataaaataa   2580
aatgagacac ttcagggatg tttcaacaag cttggcgcgc cgttctatag tgtcacctaa   2640
atcgtatgtg tatgatacat aaggttatgt attaattgta gccgcgttct aacgacaata   2700
tgtccatatg gtgcactctc agtacaatct gctctgatgc cgcatagtta agccagcccc   2760
gacacccgcc aacacccgct gacgcgccct gacgggcttg tctgctcccg gcatccgctt   2820
acagacaagc tgtgaccgtc tccgggagct gcatgtgtca gaggttttca ccgtcatcac   2880
cgaaacgcgc gagacgaaag ggcctcgtga tacgcctatt tttataggtt aatgtcatga   2940
ccaaaatccc ttaacgtgag ttttcgttcc actgagcgtc agaccccgta gaaaagatca   3000
aaggatcttc ttgagatcct ttttttctgc gcgtaatctg ctgcttgcaa acaaaaaaac   3060
caccgctacc agcggtggtt tgtttgccgg atcaagagct accaactctt tttccgaagg   3120
```

```
taactggctt cagcagagcg cagataccaa atactgtcct tctagtgtag ccgtagttag   3180

gccaccactt caagaactct gtagcaccgc ctacatacct cgctctgcta atcctgttac   3240

cagtggctgc tgccagtggc gataagtcgt gtcttaccgg gttggactca agacgatagt   3300

taccggataa ggcgcagcgg tcgggctgaa cggggggttc gtgcacacag cccagcttgg   3360

agcgaacgac ctacaccgaa ctgagatacc tacagcgtga gcattgagaa agcgccacgc   3420

ttcccgaagg gagaaaggcg gacaggtatc cggtaagcgg cagggtcgga acaggagagc   3480

gcacgaggga gcttccaggg ggaaacgcct ggtatcttta tagtcctgtc gggtttcgcc   3540

acctctgact tgagcgtcga tttttgtgat gctcgtcagg ggggcggagc ctatggaaaa   3600

acgccagcaa cgcggccttt ttacggttcc tggccttttg ctggcctttt gctcacatgt   3660

tctttcctgc gttatcccct gattctgtgg ataaccgtat taccgccttt gagtgagctg   3720

ataccgctcg ccgcagccga acgaccgagc gcagcgagtc agtgagcgag gaagcggaag   3780

agcgcccaat acgcaaaccg cctctccccg cgcgttggcc gattcattaa tgcaggttga   3840

tcagatctcg atcccgcgaa attaatacga ctcactatag ggagaccaca acggtttccc   3900

tctagaaata attttgttta actttaagaa ggagatatac ccatggaaaa gcctgaactc   3960

accgcgacgt ctgtcgagaa gtttctgatc gaaaagttcg acagcgtctc cgacctgatg   4020

cagctctcgg agggcgaaga atctcgtgct ttcagcttcg atgtaggagg gcgtggatat   4080

gtcctgcggg taaatagctg cgccgatggt ttctacaaag atcgttatgt ttatcggcac   4140

tttgcatcgg ccgcgctccc gattccggaa gtgcttgaca ttggggaatt cagcgagagc   4200

ctgacctatt gcatctcccg ccgtgcacag ggtgtcacgt tgcaagacct gcctgaaacc   4260

gaactgcccg ctgttctgca gccggtcgcg gaggctatgg atgcgatcgc tgcggccgat   4320

cttagccaga cgagcgggtt cggcccattc ggaccgcaag gaatcggtca atacactaca   4380

tggcgtgatt tcatatgcgc gattgctgat ccccatgtgt atcactggca aactgtgatg   4440

gacgacaccg tcagtgcgtc cgtcgcgcag gctctcgatg agctgatgct ttgggccgag   4500

gactgccccg aagtccggca cctcgtgcac gcggatttcg gctccaacaa tgtcctgacg   4560

gacaatggcc gcataacagc ggtcattgac tggagcgagg cgatgttcgg ggattcccaa   4620

tacgaggtcg ccaacatctt cttctggagg ccgtggttgg cttgtatgga gcagcagacg   4680

cgctacttcg agcggaggca tccggagctt gcaggatcgc cgcggctccg ggcgtatatg   4740

ctccgcattg gtcttgacca actctatcag agcttggttg acggcaattt cgatgatgca   4800

gcttgggcgc agggtcgatg cgacgcaatc gtccgatccg gagccgggac tgtcgggcgt   4860

acacaaatcg cccgcagaag cgcggccgtc tggaccgatg gctgtgtaga agtactcgcc   4920

gatagtggaa accgacgccc cagcactcgt ccgagggcaa aggaatagtg aggtacagct   4980

tggatcgatc cggctgctaa caaagcccga aaggaagctg agttggctgc tgccaccgct   5040

gagcaataac tagcataacc ccttggggcc tctaaacggg tcttgagggg ttttttgctg   5100

aaaggaggaa ctatatccgg atgatcgggc gcgccgtcga cggatccgta cgcaaaggca   5160

aagatttaaa ctcgaaaaca ttacaaaagt ctcaaaacag aggcaaggcc atgcacaaag   5220

cacactctaa gtgcttccat tgcctactaa gtagggtacg tacacgatca ccattcacca   5280

gtgatgatct ttattaatat acaacacact cagagacagc ttatgttata gctagctagc   5340

ataaactatc acatcatgtg ttagtacgac aagtgacaac attgctttta acttcgcggc   5400

cttggatcct ctagaccgga tataatgagc cgtaaacaaa gatgattaag tagtaattaa   5460

tacgtactag taaaagtggc aaaagataac gagaaagaac caatttcttt gcattcggcc   5520
```

-continued

```
ttagcggaag gcatatataa gctttgatta ttttatttag tgtaatgatt tcgtacaacc   5580
aaagcattta tttagtactc tcacacttgt gtcgcggccg cgaattcact agtgattcct   5640
tatagagcct tccccgcggg ttgcttctcc gccatccggg cgaacaccgc cagatagcgc   5700
agcaggatga ccaacccttc atggggcagc gggttccgat acggcaggtt gtgcttctgg   5760
cacagctgtt ccacctggta gctaaccgct gtcaggttgt ggcgagggag ggtcggccac   5820
aaatggtgct caatctggta attcaagcct ccgaaaaacc aatctgtgat aatccctcgc   5880
cgaatgttca tggtctcatg gatctggcca accgagaatc catggccatc ccagactgag   5940
tccccgatct tctccagtgg gtagtggttc atgaacacca cgatcgcaat gccgaagccg   6000
ccaaccagct ccgaaacgaa aaacaccaac agcgatgtga ggatgctggg cataaagaat   6060
aagtggaaca gggtcttcaa ggtccagtgc agggcgaggc caatggcctc cttcttatac   6120
tgagagcgat agaattggtt atctctgtcc ttcaaactgc gcacggtcaa cacgctctgg   6180
aaacaccaaa tgaaccgcaa caagatacag atgaccaaga aatagtactg ctggaactga   6240
atgagcttgc gggaaatcgg tgacgcccgt gtgacgtcat cctcagacca ggctaagagg   6300
gggaggttgt caatatcagg gtcgtgccct tgaacattgg ttgccgaatg atgtgcattg   6360
tgtctgtcct tccaccatgt cacggaaaaa ccttgcagac cattgccaaa taccagtccc   6420
acgaggttgt tccagttccg gttcttgaaa gtctggtggt ggcaaatgtc atgagaaagc   6480
cagcccatct gttgatagtg catcccaagc aacactgccc caatgaaata catctgatac   6540
tgaaccatca ggaaataacc cagcactcca aggcccagtg tggtgctgat tttgtatgag   6600
taccagaggg gggaggcatc aaacatgcca gttgcgatca actcttctcg gagcttccgg   6660
aaatcctctt gagcttcatt cactgcagcc tggggtggca actcagaact gggattgatt   6720
ttgggcatgc gcttgagctt gtcgaaggct tcttgagagt gcataaccat gaaggcatca   6780
gtggcatccc ttccttggta attctctata atttccgcac caccagggtg gaaattgacc   6840
caggcagaca catcatatgt tgttccatca attgtaaggg gaagcgcttg gcgctttgac   6900
ttcatttcaa tcgaattccc gcggccgctt ggggggctat ggaagacttt cttagttagt   6960
tgtgtgaata agcaatgttg ggagaatcgg gactacttat aggataggaa taaaacagaa   7020
aagtattaag tgctaatgaa atatttagac tgataattaa aatcttcacg tatgtccact   7080
tgatataaaa acgtcaggaa taaaggaagt acagtagaat ttaaaggtac tctttttata   7140
tatacccgtg ttctcttttt ggctagctag ttgcataaaa aataatctat atttttatca   7200
ttattttaaa tatcttatga gatggtaaat atttatcata attttttttta ctattattta   7260
ttatttgtgt gtgtaataca tatagaagtt aattacaaat tttatttact ttttcattat   7320
tttgatatga ttcaccatta atttagtgtt attatttata atagttcatt ttaatctttt   7380
tgtatatatt atgcgtgcag tactttttttc ctacatataa ctactattac attttattta   7440
tataatattt ttattaatga attttcgtga taatatgtaa tattgttcat tattatttca   7500
gattttttaa aaatatttgt gttattattt atgaaatatg taattttttt agtatttgat   7560
tttatgatga taaagtgttc taaattcaaa agaaggggga aagcgtaaac attaaaaaac   7620
gtcatcaaac aaaaacaaaa tcttgttaat aaagataaaa ctgtttgttt tgatcactgt   7680
tatttcgtaa tataaaaaca ttatttatat ttatattgtt gacaaccaaa tttgcctatc   7740
aaatctaacc aatataatgc atgcgtggca ggtaatgtac taccatgaac ttaagtcatg   7800
acataataaa ccgtgaatct gaccaatgca tgtacctanc taaattgtat ttgtgacacg   7860
aagcaaatga ttcaattcac aatggagatg ggaaacaaat aatgaagaac ccagaactaa   7920
```

```
gaaagctttt ctgaaaaata aaataaaggc aatgtcaaaa gtatactgca tcatcagtcc   7980

agaaagcaca tgatattttt ttatcagtat caatgcagct agttttattt tacaatatcg   8040

atatagctag tttaaatata ttgcagctag atttataaat atttgtgtta ttatttatca   8100

tttgtgtaat cctgttttta gtattttagt ttatatatga tgataatgta ttccaaattt   8160

aaaagaaggg aaataaattt aaacaagaaa aaaagtcatc aaacaaaaaa caaatgaaag   8220

ggtggaaaga tgttaccatg taatgtgaat gttacagtat ttctttttatt atagagttaa   8280

caaattaact aatatgattt tgttaataat gataaaatat ttttttttatt attatttcat   8340

aatataaaaa tagtttactt aatataaaaa aaattctatc gttcacaaca aagttggcca   8400

cctaatttaa ccatgcatgt acccatggac catattaggt aaccatcaaa cctgatgaag   8460

agataaagag atgaagactt aagtcataac acaaaaccat aaaaaacaaa aatacaatca   8520

accgtcaatc tgaccaatgc atgaaaaagc tgcaatagtg agtggcgaca caaagcacat   8580

gattttctta caacggagat aaaaccaaaa aaatatttca tgaacaacct agaacaaata   8640

aagcttttat ataataaata tataaataaa taaaggctat ggaataatat acttcaatat   8700

atttggatta aataaattgt tggcggggtt gatatattta tacacaccta aagtcacttc   8760

aatctcattt tcacttaact tttatttttt ttttcttttt atttatcata aagagaatat   8820

tgataatata ctttttaaca tatttttatg acatttttta ttggtgaaaa cttattaaaa   8880

atcataaatt ttgtaagtta gatttattta aagagttcct cttcttattt taaatttttt   8940

aataaatttt taaataacta aaatttgtgt taaaaatgtt aaaaaatgtg ttattaaccc   9000

ttctcttcga ggac                                                     9014
```

<210> SEQ ID NO 88
<211> LENGTH: 5561
<212> TYPE: DNA
<213> ORGANISM: Artificial Sequence
<220> FEATURE:
<223> OTHER INFORMATION: Plasmid pKR767

<400> SEQUENCE: 88

```
catggtcaat caatgagacg ccaacttctt aatctattga gacctgcagg tctagaaggg     60

cggatccccg ggtaccgagc tcgaattcac tggccgtcgt tttacaacgt cgtgactggg    120

aaaaccctgg cgttacccaa cttaatcgcc ttgcagcaca tccccctttc gccagctggc    180

gtaatagcga agaggcccgc accgatcgcc cttcccaaca gttgcgcagc ctgaatggcg    240

aatggcgcct gatgcggtat tttctcctta cgcatctgtg cggtatttca caccgcatat    300

ggtgcactct cagtacaatc tgctctgatg ccgcatagtt aagccagccc cgacacccgc    360

caacacccgc tgacgcgccc tgacgggctt gtctgctccc ggcatccgct tacagacaag    420

ctgtgaccgt ctccgggagc tgcatgtgtc agaggttttc accgtcatca ccgaaacgcg    480

cgagacgaaa gggcctcgtg atacgcctat ttttataggt taatgtcatg ataataatgg    540

tttcttagac gtcaggtggc acttttcggg gaaatgtgcg cggaacccct atttgtttat    600

tttctaaat acattcaaat atgtatccgc tcatgagaca ataaccctga taaatgcttc    660

aataatattg aaaaaggaag agtatgagta ttcaacattt ccgtgtcgcc cttattccct    720

tttttgcggc attttgcctt cctgtttttg ctcacccaga aacgctggtg aaagtaaaag    780

atgctgaaga tcagttgggt gcacgagtgg gttacatcga actggatctc aacagcggta    840

agatccttga gagttttcgc cccgaagaac gttttccaat gatgagcact tttaaagttc    900

tgctatgtgg cgcggtatta tcccgtattg acgccgggca agagcaactc ggtcgccgca    960
```

```
tacactattc tcagaatgac ttggttgagt actcaccagt cacagaaaag catcttacgg   1020

atggcatgac agtaagagaa ttatgcagtg ctgccataac catgagtgat aacactgcgg   1080

ccaacttact tctgacaacg atcggaggac cgaaggagct aaccgctttt ttgcacaaca   1140

tgggggatca tgtaactcgc cttgatcgtt gggaaccgga gctgaatgaa gccataccaa   1200

acgacgagcg tgacaccacg atgcctgtag caatggcaac aacgttgcgc aaactattaa   1260

ctggcgaact acttactcta gcttcccggc aacaattaat agactggatg gaggcggata   1320

aagttgcagg accacttctg cgctcggccc ttccggctgg ctggtttatt gctgataaat   1380

ctggagccgg tgagcgtggg tctcgcggta tcattgcagc actggggcca gatggtaagc   1440

cctcccgtat cgtagttatc tacacgacgg ggagtcaggc aactatggat gaacgaaata   1500

gacagatcgc tgagataggt gcctcactga ttaagcattg gtaactgtca gaccaagttt   1560

actcatatat actttagatt gatttaaaac ttcattttta atttaaaagg atctaggtga   1620

agatcctttt tgataatctc atgaccaaaa tcccttaacg tgagttttcg ttccactgag   1680

cgtcagaccc cgtagaaaag atcaaaggat cttcttgaga tccttttttt ctgcgcgtaa   1740

tctgctgctt gcaaacaaaa aaaccaccgc taccagcggt ggtttgtttg ccggatcaag   1800

agctaccaac tctttttccg aaggtaactg gcttcagcag agcgcagata ccaaatactg   1860

tccttctagt gtagccgtag ttaggccacc acttcaagaa ctctgtagca ccgcctacat   1920

acctcgctct gctaatcctg ttaccagtgg ctgctgccag tggcgataag tcgtgtctta   1980

ccgggttgga ctcaagacga tagttaccgg ataaggcgca gcggtcgggc tgaacggggg   2040

gttcgtgcac acagcccagc ttggagcgaa cgacctacac cgaactgaga tacctacagc   2100

gtgagctatg agaaagcgcc acgcttcccg aagggagaaa ggcggacagg tatccggtaa   2160

gcggcagggt cggaacagga gagcgcacga gggagcttcc agggggaaac gcctggtatc   2220

tttatagtcc tgtcgggttt cgccacctct gacttgagcg tcgatttttg tgatgctcgt   2280

caggggggcg gagcctatgg aaaaacgcca gcaacgcggc ctttttacgg ttcctggcct   2340

tttgctggcc ttttgctcac atgttctttc ctgcgttatc ccctgattct gtggataacc   2400

gtattaccgc ctttgagtga gctgataccg ctcgccgcag ccgaacgacc gagcgcagcg   2460

agtcagtgag cgaggaagcg gaagagcgcc caatacgcaa accgcctctc cccgcgcgtt   2520

ggccgattca ttaatgcagc tggcacgaca ggtttcccga ctggaaagcg ggcagtgagc   2580

gcaacgcaat taatgtgagt tagctcactc attaggcacc ccaggcttta cactttatgc   2640

ttccggctcg tatgttgtgt ggaattgtga gcggataaca atttcacaca ggaaacagct   2700

atgaccatga ttacgccaag cttgcatgcc tgcaggctag cctaagtacg tactcaaaat   2760

gccaacaaat aaaaaaaaag ttgctttaat aatgccaaaa caaattaata aaacacttac   2820

aacaccggat tttttttaat taaaatgtgc catttaggat aaatagttaa tatttttaat   2880

aattatttaa aaagccgtat ctactaaaat gatttttatt tggttgaaaa tattaatatg   2940

tttaaatcaa cacaatctat caaaattaaa ctaaaaaaaa aataagtgta cgtggttaac   3000

attagtacag taatataaga ggaaaatgag aaattaagaa attgaaagcg agtctaattt   3060

ttaaattatg aacctgcata tataaaagga aagaaagaat ccaggaagaa aagaaatgaa   3120

accatgcatg gtcccctcgt catcacgagt ttctgccatt tgcaatagaa acactgaaac   3180

acctttctct ttgtcactta attgagatgc cgaagccacc tcacaccatg aacttcatga   3240

ggtgtagcac ccaaggcttc catagccatg catactgaag aatgtctcaa gctcagcacc   3300

ctacttctgt gacgtgtccc tcattcacct tcctctcttc cctataaata accacgcctc   3360
```

```
aggttctccg cttcacaact caaacattct ctccattggt ccttaaacac tcatcagtca   3420

tcaccgcggc cgcatgggaa cggaccaagg aaaaaccttc acctgggaag agctggcggc   3480

ccataacacc aaggacgacc tactcttggc catccgcggc agggtgtacg atgtcacaaa   3540

gttcttgagc cgccatcctg gtggagtgga cactctcctg ctcggagctg gccgagatgt   3600

tactccggtc tttgagatgt atcacgcgtt tggggctgca gatgccatta tgaagaagta   3660

ctatgtcggt acactggtct cgaatgagct gcccatcttc ccggagccaa cggtgttcca   3720

caaaaccatc aagacgagag tcgagggcta ctttacggat cggaacattg atcccaagaa   3780

tagaccagag atctggggac gatacgctct tatctttgga tccttgatcg cttcctacta   3840

cgcgcagctc tttgtgcctt tcgttgtcga acgcacatgg cttcaggtgg tgtttgcaat   3900

catcatggga tttgcgtgcg cacaagtcgg actcaaccct cttcatgatg cgtctcactt   3960

ttcagtgacc cacaacccca ctgtctggaa gattctggga gccacgcacg actttttcaa   4020

cggagcatcg tacctggtgt ggatgtacca acatatgctc ggccatcacc cctacaccaa   4080

cattgctgga gcagatcccg acgtgtcgac gtctgagccc gatgttcgtc gtatcaagcc   4140

caaccaaaag tggtttgtca accacatcaa ccagcacatg tttgttcctt tcctgtacgg   4200

actgctggcg ttcaaggtgc gcattcagga catcaacatt ttgtactttg tcaagaccaa   4260

tgacgctatt cgtgtcaatc ccatctcgac atggcacact gtgatgttct ggggcggcaa   4320

ggctttcttt gtctggtatc gcctgattgt tcccctgcag tatctgcccc tgggcaaggt   4380

gctgctcttg ttcacggtcg cggacatggt gtcgtcttac tggctggcgc tgaccttcca   4440

ggcgaaccac gttgttgagg aagttcagtg gccgttgcct gacgagaacg ggatcatcca   4500

aaaggactgg gcagctatgc aggtcgagac tacgcaggat tacgcacacg attcgcacct   4560

ctggaccagc atcactggca gcttgaacta ccaggctgtg caccatctgt tccccaacgt   4620

gtcgcagcac cattatcccg atattctggc catcatcaag aacacctgca gcgagtacaa   4680

ggttccatac cttgtcaagg atacgttttg gcaagcattt gcttcacatt tggagcactt   4740

gcgtgttctt ggactccgtc ccaaggaaga gtaggcggcc gcatttcgca ccaaatcaat   4800

gaaagtaata atgaaaagtc tgaataagaa tacttaggct tagatgcctt tgttacttgt   4860

gtaaaataac ttgagtcatg tacctttggc ggaaacagaa taaataaaag gtgaaattcc   4920

aatgctctat gtataagtta gtaatactta atgtgttcta cggttgtttc aatatcatca   4980

aactctaatt gaaactttag aaccacaaat ctcaatcttt tcttaatgaa atgaaaaatc   5040

ttaattgtac catgtttatg ttaaacacct tacaattggt tggagaggag gaccaaccga   5100

tgggacaaca ttgggagaaa gagattcaat ggagatttgg ataggagaac aacattcttt   5160

ttcacttcaa tacaagatga gtgcaacact aaggatatgt atgagacttt cagaagctac   5220

gacaacatag atgagtgagg tggtgattcc tagcaagaaa gacattagag gaagccaaaa   5280

tcgaacaagg aagacatcaa gggcaagaga caggaccatc catctcagga aaaggagctt   5340

tgggatagtc cgagaagttg tacaagaaat tttttggagg gtgagtgatg cattgctggt   5400

gactttaact caatcaaaat tgagaaagaa agaaaaggga gggggctcac atgtgaatag   5460

aagggaaacg ggagaatttt acagttttga tctaatgggc atcccagcta gtggtaacat   5520

attcaccatg tttaaccttc acgtacgtct agaggatccc c                        5561
```

<210> SEQ ID NO 89
<211> LENGTH: 11889
<212> TYPE: DNA
<213> ORGANISM: Artificial Sequence
<220> FEATURE:

<223> OTHER INFORMATION: Plasmid pKR916
<220> FEATURE:
<221> NAME/KEY: misc_feature
<222> LOCATION: (7810)..(7810)
<223> OTHER INFORMATION: n is a, c, g, or t

<400> SEQUENCE: 89

```
ggagatccaa gcttttgatc catgcccttc atttgccgct tattaattaa tttggtaaca      60

gtccgtacta atcagttact tatccttccc ccatcataat taatcttggt agtctcgaat     120

gccacaacac tgactagtct cttggatcat aagaaaaagc caaggaacaa aagaagacaa     180

aacacaatga gagtatcctt tgcatagcaa tgtctaagtt cataaaattc aaacaaaaac     240

gcaatcacac acagtggaca tcacttatcc actagctgat caggatcgcc gcgtcaagaa     300

aaaaaaactg gaccccaaaa gccatgcaca acaacacgta ctcacaaagg tgtcaatcga     360

gcagcccaaa acattcacca actcaaccca tcatgagccc tcacatttgt tgtttctaac     420

ccaacctcaa actcgtattc tcttccgcca cctcattttt gtttatttca acacccgtca     480

aactgcatgc caccccgtgg ccaaatgtcc atgcatgtta acaagaccta tgactataaa     540

tagctgcaat ctcggcccag gttttcatca tcaagaacca gttcaatatc ctagtacacc     600

gtattaaaga atttaagata tactgcggcc gcaccatgga ggtggtgaat gaaatagtct     660

caattgggca ggaagtttta cccaaagttg attatgccca actctggagt gatgccagtc     720

actgtgaggt gctttacttg tccatcgcat ttgtcatctt gaagttcact cttggccccc     780

ttggtccaaa aggtcagtct cgtatgaagt ttgttttcac caattacaac cttctcatgt     840

ccatttattc gttgggatca ttcctctcaa tggcatatgc catgtacacc atcggtgtta     900

tgtctgacaa ctgcgagaag gcttttgaca acaacgtctt caggatcacc acgcagttgt     960

tctatttgag caagttcctg gagtatattg actccttcta tttgccactg atgggcaagc    1020

ctctgacctg gttgcaattc ttccatcatt tgggggcacc gatggatatg tggctgttct    1080

ataattaccg aaatgaagct gtttggattt ttgtgctgtt gaatggtttc atccactgga    1140

tcatgtacgg ttattattgg accagattga tcaagctgaa gttccccatg ccaaaatccc    1200

tgattacatc aatgcagatc attcaattca atgttggttt ctacattgtc tggaagtaca    1260

ggaacattcc ctgttatcgc caagatggga tgaggatgtt tggctggttc ttcaattact    1320

tttatgttgg cacagtcttg tgtttgttct tgaatttcta tgtgcaaacg tatatcgtca    1380

ggaagcacaa gggagccaaa aagattcagt gagcggccgc aagtatgaac taaaatgcat    1440

gtaggtgtaa gagctcatgg agagcatgga atattgtatc cgaccatgta acagtataat    1500

aactgagctc catctcactt cttctatgaa taaacaaagg atgttatgat atattaacac    1560

tctatctatg caccttattg ttctatgata aatttcctct tattattata aatcatctga    1620

atcgtgacgg cttatggaat gcttcaaata gtacaaaaac aaatgtgtac tataagactt    1680

tctaaacaat tctaacctta gcattgtgaa cgagacataa gtgttaagaa gacataacaa    1740

ttataatgga agaagtttgt ctccatttat atattatata ttacccactt atgtattata    1800

ttaggatgtt aaggagacat aacaattata aagagagaag tttgtatcca tttatatatt    1860

atatactacc catttatata ttatacttat ccacttattt aatgtcttta taaggtttga    1920

tccatgatat ttctaatatt ttagttgata tgtatatgaa agggtactat ttgaactctc    1980

ttactctgta taaaggttgg atcatcctta aagtgggtct atttaatttt attgcttctt    2040

acagataaaa aaaaaattat gagttggttt gataaaatat tgaaggattt aaaataataa    2100

taaataacat ataatatatg tatataaatt tattataata taacatttat ctataaaaaa    2160
```

```
gtaaatattg tcataaatct atacaatcgt ttagccttgc tggacgaatc tcaattattt   2220

aaacgagagt aaacatattt gactttttgg ttatttaaca aattattatt taacactata   2280

tgaaattttt tttttatca gcaaagaata aaattaaatt aagaaggaca atggtgtccc   2340

aatccttata caaccaactt ccacaagaaa gtcaagtcag agacaacaaa aaaacaagca   2400

aaggaaattt tttaatttga gttgtcttgt ttgctgcata atttatgcag taaaacacta   2460

cacataaccc ttttagcagt agagcaatgg ttgaccgtgt gcttagcttc ttttatttta   2520

ttttttatc agcaaagaat aaataaaata aaatgagaca cttcagggat gtttcaacaa   2580

gcttggcgcg ccgttctata gtgtcaccta aatcgtatgt gtatgataca taaggttatg   2640

tattaattgt agccgcgttc taacgacaat atgtccatat ggtgcactct cagtacaatc   2700

tgctctgatg ccgcatagtt aagccagccc cgacacccgc caacacccgc tgacgcgccc   2760

tgacgggctt gtctgctccc ggcatccgct tacagacaag ctgtgaccgt ctccgggagc   2820

tgcatgtgtc agaggttttc accgtcatca ccgaaacgcg cgagacgaaa gggcctcgtg   2880

atacgcctat ttttataggt taatgtcatg accaaaatcc cttaacgtga gttttcgttc   2940

cactgagcgt cagaccccgt agaaaagatc aaaggatctt cttgagatcc tttttttctg   3000

cgcgtaatct gctgcttgca aacaaaaaaa ccaccgctac cagcggtggt ttgtttgccg   3060

gatcaagagc taccaactct ttttccgaag gtaactggct tcagcagagc gcagatacca   3120

aatactgtcc ttctagtgta gccgtagtta ggccaccact tcaagaactc tgtagcaccg   3180

cctacatacc tcgctctgct aatcctgtta ccagtggctg ctgccagtgg cgataagtcg   3240

tgtcttaccg ggttggactc aagacgatag ttaccggata aggcgcagcg gtcgggctga   3300

acggggggtt cgtgcacaca gcccagcttg gagcgaacga cctacaccga actgagatac   3360

ctacagcgtg agcattgaga aagcgccacg cttcccgaag ggagaaaggc ggacaggtat   3420

ccggtaagcg gcagggtcgg aacaggagag cgcacgaggg agcttccagg gggaaacgcc   3480

tggtatcttt atagtcctgt cgggtttcgc cacctctgac ttgagcgtcg atttttgtga   3540

tgctcgtcag gggggcggag cctatggaaa aacgccagca acgcggcctt tttacggttc   3600

ctggcctttt gctggccttt tgctcacatg ttctttcctg cgttatcccc tgattctgtg   3660

gataaccgta ttaccgcctt tgagtgagct gataccgctc gccgcagccg aacgaccgag   3720

cgcagcgagt cagtgagcga ggaagcggaa gagcgcccaa tacgcaaacc gcctctcccc   3780

gcgcgttggc cgattcatta atgcaggttg atcagatctc gatcccgcga aattaatacg   3840

actcactata gggagaccac aacggtttcc ctctagaaat aattttgttt aactttaaga   3900

aggagatata cccatggaaa agcctgaact caccgcgacg tctgtcgaga agtttctgat   3960

cgaaaagttc gacagcgtct ccgacctgat gcagctctcg gagggcgaag aatctcgtgc   4020

tttcagcttc gatgtaggag ggcgtggata tgtcctgcgg gtaaatagct gcgccgatgg   4080

tttctacaaa gatcgttatg tttatcggca ctttgcatcg gccgcgctcc cgattccgga   4140

agtgcttgac attggggaat tcagcgagag cctgacctat tgcatctccc gccgtgcaca   4200

gggtgtcacg ttgcaagacc tgcctgaaac cgaactgccc gctgttctgc agccggtcgc   4260

ggaggctatg gatgcgatcg ctgcggccga tcttagccag acgagcgggt tcggcccatt   4320

cggaccgcaa ggaatcggtc aatacactac atggcgtgat ttcatatgcg cgattgctga   4380

tccccatgtg tatcactggc aaactgtgat ggacgacacc gtcagtgcgt ccgtcgcgca   4440

ggctctcgat gagctgatgc tttgggccga ggactgcccc gaagtccggc acctcgtgca   4500

cgcggatttc ggctccaaca atgtcctgac ggacaatggc cgcataacag cggtcattga   4560
```

```
ctggagcgag gcgatgttcg gggattccca atacgaggtc gccaacatct tcttctggag   4620
gccgtggttg gcttgtatgg agcagcagac gcgctacttc gagcggaggc atccggagct   4680
tgcaggatcg ccgcggctcc gggcgtatat gctccgcatt ggtcttgacc aactctatca   4740
gagcttggtt gacggcaatt tcgatgatgc agcttgggcg cagggtcgat gcgacgcaat   4800
cgtccgatcc ggagccggga ctgtcgggcg tacacaaatc gcccgcagaa gcgcggccgt   4860
ctggaccgat ggctgtgtag aagtactcgc cgatagtgga aaccgacgcc ccagcactcg   4920
tccgagggca aaggaatagt gaggtacagc ttggatcgat ccggctgcta acaaagcccg   4980
aaaggaagct gagttggctg ctgccaccgc tgagcaataa ctagcataac cccttggggc   5040
ctctaaacgg gtcttgaggg gttttttgct gaaaggagga actatatccg gatgatcggg   5100
cgcgccgtcg acggatccgt acgcaaaggc aaagatttaa actcgaaaac attacaaaag   5160
tctcaaaaca gaggcaaggc catgcacaaa gcacactcta agtgcttcca ttgcctacta   5220
agtagggtac gtacacgatc accattcacc agtgatgatc tttattaata tacaacacac   5280
tcagagacag cttatgttat agctagctag cataaactat cacatcatgt gttagtacga   5340
caagtgacaa cattgctttt aacttcgcgg ccttggatcc tctagaccgg atataatgag   5400
ccgtaaacaa agatgattaa gtagtaatta atacgtacta gtaaaagtgg caaaagataa   5460
cgagaaagaa ccaatttctt tgcattcggc cttagcggaa ggcatatata agctttgatt   5520
attttattta gtgtaatgat ttcgtacaac caaagcattt atttagtact ctcacacttg   5580
tgtcgcggcc gcgaattcac tagtgattcc ttatagagcc ttccccgcgg gttgcttctc   5640
cgccatccgg gcgaacaccg ccagatagcg cagcaggatg accaaccctt catggggcag   5700
cgggttccga tacggcaggt tgtgcttctg gcacagctgt tccacctggt agctaaccgc   5760
tgtcaggttg tggcgaggga gggtcggcca caaatggtgc tcaatctggt aattcaagcc   5820
tccgaaaaac caatctgtga taatccctcg ccgaatgttc atggtctcat ggatctggcc   5880
aaccgagaat ccatggccat cccagactga gtccccgatc ttctccagtg ggtagtggtt   5940
catgaacacc acgatcgcaa tgccgaagcc gccaaccagc tccgaaacga aaaacaccaa   6000
cagcgatgtg aggatgctgg gcataaagaa taagtggaac agggtcttca aggtccagtg   6060
cagggcgagg ccaatggcct ccttcttata ctgagagcga tagaattggt tatctctgtc   6120
cttcaaactg cgcacggtca acacgctctg gaaacaccaa atgaaccgca acaagataca   6180
gatgaccaag aaatagtact gctggaactg aatgagcttg cgggaaatcg gtgacgcccg   6240
tgtgacgtca tcctcagacc aggctaagag ggggaggttg tcaatatcag ggtcgtgccc   6300
ttgaacattg gttgccgaat gatgtgcatt gtgtctgtcc ttccaccatg tcacggaaaa   6360
accttgcaga ccattgccaa ataccagtcc cacgaggttg ttccagttcc ggttcttgaa   6420
agtctggtgg tggcaaatgt catgagaaag ccagcccatc tgttgatagt gcatcccaag   6480
caacactgcc ccaatgaaat acatctgata ctgaaccatc aggaaataac ccagcactcc   6540
aaggcccagt gtggtgctga ttttgtatga gtaccagagg ggggaggcat caaacatgcc   6600
agttgcgatc aactcttctc ggagcttccg gaaatcctct tgagcttcat tcactgcagc   6660
ctggggtggc aactcagaac tgggattgat tttgggcatg cgcttgagct tgtcgaaggc   6720
ttcttgagag tgcataacca tgaaggcatc agtggcatcc cttccttggt aattctctat   6780
aatttccgca ccaccagggt ggaaattgac ccaggcagac acatcatatg ttgttccatc   6840
aattgtaagg ggaagcgctt ggcgctttga cttcatttca atcgaattcc cgcggccgct   6900
tggggggcta tggaagactt tcttagttag ttgtgtgaat aagcaatgtt gggagaatcg   6960
```

```
ggactactta taggatagga ataaaacaga aaagtattaa gtgctaatga aatatttaga   7020
ctgataatta aaatcttcac gtatgtccac ttgatataaa aacgtcagga ataaaggaag   7080
tacagtagaa tttaaaggta ctctttttat atatacccgt gttctctttt tggctagcta   7140
gttgcataaa aaataatcta tatttttatc attattttaa atatcttatg agatggtaaa   7200
tatttatcat aatttttttt actattattt attatttgtg tgtgtaatac atatagaagt   7260
taattacaaa ttttatttac tttttcatta ttttgatatg attcaccatt aatttagtgt   7320
tattatttat aatagttcat tttaatcttt ttgtatatat tatgcgtgca gtactttttt   7380
cctacatata actactatta cattttattt atataatatt tttattaatg aattttcgtg   7440
ataatatgta atattgttca ttattatttc agatttttta aaaatatttg tgttattatt   7500
tatgaaatat gtaatttttt tagtatttga ttttatgatg ataaagtgtt ctaaattcaa   7560
aagaaggggg aaagcgtaaa cattaaaaaa cgtcatcaaa caaaaacaaa atcttgttaa   7620
taaagataaa actgtttgtt ttgatcactg ttatttcgta atataaaaac attatttata   7680
tttatattgt tgacaaccaa atttgcctat caaatctaac caatataatg catgcgtggc   7740
aggtaatgta ctaccatgaa cttaagtcat gacataataa accgtgaatc tgaccaatgc   7800
atgtacctan ctaaattgta tttgtgacac gaagcaaatg attcaattca caatggagat   7860
gggaaacaaa taatgaagaa cccagaacta agaaagcttt tctgaaaaat aaaataaagg   7920
caatgtcaaa agtatactgc atcatcagtc cagaaagcac atgatatttt tttatcagta   7980
tcaatgcagc tagttttatt ttacaatatc gatatagcta gtttaaatat attgcagcta   8040
gatttataaa tatttgtgtt attatttatc atttgtgtaa tcctgttttt agtattttag   8100
tttatatatg atgataatgt attccaaatt taaaagaagg gaaataaatt taaacaagaa   8160
aaaaagtcat caaacaaaaa acaaatgaaa gggtggaaag atgttaccat gtaatgtgaa   8220
tgttacagta tttcttttat tatagagtta acaaattaac taatatgatt ttgttaataa   8280
tgataaaata ttttttttat tattatttca taatataaaa atagtttact taatataaaa   8340
aaaattctat cgttcacaac aaagttggcc acctaattta accatgcatg tacccatgga   8400
ccatattagg taaccatcaa acctgatgaa gagataaaga gatgaagact taagtcataa   8460
cacaaaacca taaaaaacaa aaatacaatc aaccgtcaat ctgaccaatg catgaaaaag   8520
ctgcaatagt gagtggcgac acaaagcaca tgattttctt acaacggaga taaaaccaaa   8580
aaaatatttc atgaacaacc tagaacaaat aaagctttta tataataaat atataaataa   8640
ataaaggcta tggaataata tacttcaata tatttggatt aaataaattg ttggcggggt   8700
tgatatattt atacacacct aaagtcactt caatctcatt ttcacttaac ttttattttt   8760
tttttctttt tatttatcat aaagagaata ttgataatat actttttaac atatttttat   8820
gacatttttt attggtgaaa acttattaaa aatcataaat tttgtaagtt agatttattt   8880
aaagagttcc tcttcttatt ttaaattttt taataaattt ttaaataact aaaatttgtg   8940
ttaaaaatgt taaaaaatgt gttattaacc cttctcttcg aggacgtacg agatccggcc   9000
ggccagatcc tgcaggtctc aatagattaa gaagttggcg tctcattgat tgaccatggg   9060
ggatcctcta gacgtacgtg aaggttaaac atggtgaata tgttaccact agctgggatg   9120
cccattagat caaaactgta aaattctccc gtttcccttc tattcacatg tgagcccccct   9180
ccctttttctt tctttctcaa ttttgattga gttaaagtca ccagcaatgc atcactcacc   9240
ctccaaaaaa tttcttgtac aacttctcgg actatcccaa agctcctttt cctgagatgg   9300
atggtcctgt ctcttgccct tgatgtcttc cttgttcgat tttggcttcc tctaatgtct   9360
```

```
ttcttgctag gaatcaccac ctcactcatc tatgttgtcg tagcttctga aagtctcata   9420
catatcctta gtgttgcact catcttgtat tgaagtgaaa aagaatgttg ttctcctatc   9480
caaatctcca ttgaatctct ttctcccaat gttgtcccat cggttggtcc tcctctccaa   9540
ccaattgtaa ggtgtttaac ataaacatgg tacaattaag atttttcatt tcattaagaa   9600
aagattgaga tttgtggttc taaagtttca attagagttt gatgatattg aaacaaccgt   9660
agaacacatt aagtattact aacttataca tagagcattg gaatttcacc ttttatttat   9720
tctgtttccg ccaaaggtac atgactcaag ttattttaca caagtaacaa aggcatctaa   9780
gcctaagtat tcttattcag acttttcatt attactttca ttgatttggt gcgaaatgcg   9840
gccgcctact cttccttggg acggagtcca agaacacgca agtgctccaa atgtgaagca   9900
aatgcttgcc aaaacgtatc cttgacaagg tatggaacct tgtactcgct gcaggtgttc   9960
ttgatgatgg ccagaatatc gggataatgg tgctgcgaca cgttggggaa cagatggtgc  10020
acagcctggt agttcaagct gccagtgatg ctggtccaga ggtgcgaatc gtgtgcgtaa  10080
tcctgcgtag tctcgacctg catagctgcc cagtcctttt ggatgatccc gttctcgtca  10140
ggcaacggcc actgaacttc ctcaacaacg tggttcgcct ggaaggtcag cgccagccag  10200
taagacgaca ccatgtccgc gaccgtgaac aagagcagca ccttgcccag ggcagatac   10260
tgcaggggaa caatcaggcg ataccagaca aagaaagcct tgccgcccca gaacatcaca  10320
gtgtgccatg tcgagatggg attgacacga atagcgtcat tggtcttgac aaagtacaaa  10380
atgttgatgt cctgaatgcg caccttgaac gccagcagtc cgtacaggaa aggaacaaac  10440
atgtgctggt tgatgtggtt gacaaaccac ttttggttgg gcttgatacg acgaacatcg  10500
ggctcagacg tcgacacgtc gggatctgct ccagcaatgt tggtgtaggg gtgatggccg  10560
agcatatgtt ggtacatcca caccaggtac gatgctccgt tgaaaaagtc gtgcgtggct  10620
cccagaatct tccagacagt ggggttgtgg gtcactgaaa agtgagacgc atcatgaaga  10680
gggttgagtc cgacttgtgc gcacgcaaat cccatgatga ttgcaaacac cacctgaagc  10740
catgtgcgtt cgacaacgaa aggcacaaag agctgcgcgt agtaggaagc gatcaaggat  10800
ccaaagataa gagcgtatcg tccccagatc tctggtctat tcttgggatc aatgttccga  10860
tccgtaaagt agccctcgac tctcgtcttg atggttttgt ggaacaccgt tggctccggg  10920
aagatgggca gctcattcga gaccagtgta ccgacatagt acttcttcat aatggcatct  10980
gcagccccaa acgcgtgata catctcaaag accggagtaa catctcggcc agctccgagc  11040
aggagagtgt ccactccacc aggatggcgg ctcaagaact ttgtgacatc gtacaccctg  11100
ccgcggatgg ccaagagtag gtcgtccttg gtgttatggg ccgccagctc ttcccaggtg  11160
aaggtttttc cttggtccgt tcccatgcgg ccgcggtgat gactgatgag tgtttaagga  11220
ccaatggaga gaatgtttga gttgtgaagc ggagaacctg aggcgtggtt atttataggg  11280
aagagaggaa ggtgaatgag ggacacgtca cagaagtagg gtgctgagct tgagacattc  11340
ttcagtatgc atggctatgg aagccttggg tgctacacct catgaagttc atggtgtgag  11400
gtggcttcgg catctcaatt aagtgacaaa gagaaaggtg tttcagtgtt tctattgcaa  11460
atggcagaaa ctcgtgatga cgaggggacc atgcatggtt tcatttcttt tcttcctgga  11520
ttctttcttt ccttttatat atgcaggttc ataatttaaa aattagactc gctttcaatt  11580
tcttaatttc tcattttcct cttatattac tgtactaatg ttaaccacgt acacttattt  11640
tttttttagt ttaattttga tagattgtgt tgatttaaac atattaatat tttcaaccaa  11700
ataaaaatca ttttagtaga tacggctttt taaataatta ttaaaaatat taactattta  11760
```

```
tcctaaatgg cacattttaa ttaaaaaaaa tccggtgttg taagtgtttt attaatttgt  11820

tttggcatta ttaaagcaac ttttttttta tttgttggca ttttgagtac gtacttaggc  11880

tagcctgca                                                          11889
```

<210> SEQ ID NO 90
<211> LENGTH: 5661
<212> TYPE: DNA
<213> ORGANISM: Artificial Sequence
<220> FEATURE:
<223> OTHER INFORMATION: Plasmid pKR974

<400> SEQUENCE: 90

```
gtacgtctag aggatccccc atggtcaatc aatgagacgc caacttctta atctattgag     60

acctgcaggt ctagaagggc ggatccccgg gtaccgagct cgaattcact ggccgtcgtt    120

ttacaacgtc gtgactggga aaaccctggc gttacccaac ttaatcgcct tgcagcacat    180

ccccctttcg ccagctggcg taatagcgaa gaggcccgca ccgatcgccc ttcccaacag    240

ttgcgcagcc tgaatggcga atggcgcctg atgcggtatt ttctccttac gcatctgtgc    300

ggtatttcac accgcatatg gtgcactctc agtacaatct gctctgatgc cgcatagtta    360

agccagcccc gacacccgcc aacacccgct gacgcgccct gacgggcttg tctgctcccg    420

gcatccgctt acagacaagc tgtgaccgtc tccgggagct gcatgtgtca gaggttttca    480

ccgtcatcac cgaaacgcgc gagacgaaag ggcctcgtga tacgcctatt tttataggtt    540

aatgtcatga taataatggt ttcttagacg tcaggtggca cttttcgggg aaatgtgcgc    600

ggaaccccta tttgtttatt tttctaaata cattcaaata tgtatccgct catgagacaa    660

taaccctgat aaatgcttca ataatattga aaaaggaaga gtatgagtat tcaacatttc    720

cgtgtcgccc ttattccctt ttttgcggca ttttgccttc ctgtttttgc tcacccagaa    780

acgctggtga aagtaaaaga tgctgaagat cagttgggtg cacgagtggg ttacatcgaa    840

ctggatctca acagcggtaa gatccttgag agttttcgcc ccgaagaacg ttttccaatg    900

atgagcactt ttaaagttct gctatgtggc gcggtattat cccgtattga cgccgggcaa    960

gagcaactcg gtcgccgcat acactattct cagaatgact tggttgagta ctcaccagtc   1020

acagaaaagc atcttacgga tggcatgaca gtaagagaat tatgcagtgc tgccataacc   1080

atgagtgata acactgcggc caacttactt ctgacaacga tcggaggacc gaaggagcta   1140

accgcttttt tgcacaacat gggggatcat gtaactcgcc ttgatcgttg ggaaccggag   1200

ctgaatgaag ccataccaaa cgacgagcgt gacaccacga tgcctgtagc aatggcaaca   1260

acgttgcgca aactattaac tggcgaacta cttactctag cttcccggca acaattaata   1320

gactggatgg aggcggataa agttgcagga ccacttctgc gctcggccct tccggctggc   1380

tggtttattg ctgataaatc tggagccggt gagcgtgggt ctcgcggtat cattgcagca   1440

ctggggccag atggtaagcc ctcccgtatc gtagttatct acacgacggg gagtcaggca   1500

actatggatg aacgaaatag acagatcgct gagataggtg cctcactgat taagcattgg   1560

taactgtcag accaagttta ctcatatata ctttagattg atttaaaact tcatttttaa   1620

tttaaaagga tctaggtgaa gatccttttt gataatctca tgaccaaaat cccttaacgt   1680

gagttttcgt tccactgagc gtcagacccc gtagaaaaga tcaaaggatc ttcttgagat   1740

cctttttttc tgcgcgtaat ctgctgcttg caaacaaaaa aaccaccgct accagcggtg   1800

gtttgtttgc cggatcaaga gctaccaact ctttttccga aggtaactgg cttcagcaga   1860

gcgcagatac caaatactgt ccttctagtg tagccgtagt taggccacca cttcaagaac   1920
```

```
tctgtagcac cgcctacata cctcgctctg ctaatcctgt taccagtggc tgctgccagt   1980
ggcgataagt cgtgtcttac cgggttggac tcaagacgat agttaccgga taaggcgcag   2040
cggtcgggct gaacgggggg ttcgtgcaca cagcccagct tggagcgaac gacctacacc   2100
gaactgagat acctacagcg tgagctatga gaaagcgcca cgcttcccga agggagaaag   2160
gcggacaggt atccggtaag cggcagggtc ggaacaggag agcgcacgag ggagcttcca   2220
gggggaaacg cctggtatct ttatagtcct gtcgggtttc gccacctctg acttgagcgt   2280
cgatttttgt gatgctcgtc aggggggcgg agcctatgga aaaacgccag caacgcggcc   2340
tttttacggt tcctggcctt ttgctggcct tttgctcaca tgttctttcc tgcgttatcc   2400
cctgattctg tggataaccg tattaccgcc tttgagtgag ctgataccgc tcgccgcagc   2460
cgaacgaccg agcgcagcga gtcagtgagc gaggaagcgg aagagcgccc aatacgcaaa   2520
ccgcctctcc ccgcgcgttg gccgattcat taatgcagct ggcacgacag gtttcccgac   2580
tggaaagcgg gcagtgagcg caacgcaatt aatgtgagtt agctcactca ttaggcaccc   2640
caggctttac actttatgct tccggctcgt atgttgtgtg gaattgtgag cggataacaa   2700
tttcacacag gaaacagcta tgaccatgat tacgccaagc ttgcatgcct gcaggctagc   2760
ctaagtacgt actcaaaatg ccaacaaata aaaaaaaagt tgctttaata atgccaaaac   2820
aaattaataa aacacttaca acaccggatt ttttttaatt aaaatgtgcc atttaggata   2880
aatagttaat atttttaata attatttaaa aagccgtatc tactaaaatg atttttattt   2940
ggttgaaaat attaatatgt ttaaatcaac acaatctatc aaaattaaac taaaaaaaaa   3000
ataagtgtac gtggttaaca ttagtacagt aatataagag gaaaatgaga aattaagaaa   3060
ttgaaagcga gtctaatttt taaattatga acctgcatat ataaaaggaa agaaagaatc   3120
caggaagaaa agaaatgaaa ccatgcatgg tcccctcgtc atcacgagtt tctgccattt   3180
gcaatagaaa cactgaaaca cctttctctt tgtcacttaa ttgagatgcc gaagccacct   3240
cacaccatga acttcatgag gtgtagcacc caaggcttcc atagccatgc atactgaaga   3300
atgtctcaag ctcagcaccc tacttctgtg acgtgtccct cattcacctt cctctcttcc   3360
ctataaataa ccacgcctca ggttctccgc ttcacaactc aaacattctc tccattggtc   3420
cttaaacact catcagtcat caccgcggcc gccaattcat ggccccgcag acggagctcc   3480
gccagcgcca cgccgccgtc gccgagacgc cggtggccgg caagaaggcc tttacatggc   3540
aggaggtcgc gcagcacaac acggcggcct cggcctggat cattatccgc ggcaaggtct   3600
acgacgtgac cgagtgggcc aacaagcacc ccggcggccg cgagatggtg ctgctgcacg   3660
ccggtcgcga ggccaccgac acgttcgact cgtaccaccc gttcagcgac aaggccgagt   3720
cgatcttgaa caagtatgag attggcacgt tcacgggccc gtccgagttt ccgaccttca   3780
agccggacac gggcttctac aaggagtgcc gcaagcgcgt tggcgagtac ttcaagaaga   3840
acaacctcca tccgcaggac ggcttcccgg gcctctggcg catgatggtc gtgtttgcgg   3900
tcgccggcct cgccttgtac ggcatgcact tttcgactat ctttgcgctg cagctcgcgg   3960
ccgcggcgct ctttggcgtc tgccaggcgc tgccgctgct ccacgtcatg cacgactcgt   4020
cgcacgcgtc gtacaccaac atgccgttct tccattacgt cgtcggccgc tttgccatgg   4080
actggtttgc cggcggctcg atggtgtcat ggctcaacca gcacgtcgtg ggccaccaca   4140
tctacacgaa cgtcgcgggc tcggacccgg atcttccggt caacatggac ggcgacatcc   4200
gccgcatcgt gaaccgccag gtgttccagc ccatgtacgc attccagcac atctaccttc   4260
cgccgctcta tggcgtgctt ggcctcaagt tccgcatcca ggacttcacc gacacgttcg   4320
```

```
gctcgcacac gaacggcccg atccgcgtca acccgcacgc gctctcgacg tggatggcca   4380

tgatcagctc caagtcgttc tgggccttct accgcgtgta ccttccgctt gccgtgctcc   4440

agatgcccat caagacgtac cttgcgatct tcttcctcgc cgagtttgtc acgggctggt   4500

acctcgcgtt caacttccaa gtaagccatg tctcgaccga gtgcggctac ccatgcggcg   4560

acgaggccaa gatggcgctc caggacgagt gggcagtctc gcaggtcaag acgtcggtcg   4620

actacgccca tggctcgtgg atgacgacgt tccttgccgg cgcgctcaac taccaggtcg   4680

tgcaccactt gttccccagc gtgtcgcagt accactaccc ggcgatcgcg cccatcatcg   4740

tcgacgtctg caaggagtac aacatcaagt acgccatctt gccggacttt acggcggcgt   4800

tcgttgccca cttgaagcac ctccgcaaca tgggccagca gggcatcgcc gccacgatcc   4860

acatgggcta actcgagctc agctagatcg cggccgcatt tcgcaccaaa tcaatgaaag   4920

taataatgaa aagtctgaat aagaatactt aggcttagat gcctttgtta cttgtgtaaa   4980

ataacttgag tcatgtacct ttggcggaaa cagaataaat aaaaggtgaa attccaatgc   5040

tctatgtata agttagtaat acttaatgtg ttctacggtt gtttcaatat catcaaactc   5100

taattgaaac tttagaacca caaatctcaa tcttttctta atgaaatgaa aaatcttaat   5160

tgtaccatgt ttatgttaaa caccttacaa ttaattggtt ggagaggagg accaaccgat   5220

gggacaacat tgggagaaag agattcaatg gagatttgga taggagaaca acattctttt   5280

tcacttcaat acaagatgag tgcaacacta aggatatgta tgagactttc agaagctacg   5340

acaacataga tgagtgaggt ggtgattcct agcaagaaag acattagagg aagccaaaat   5400

cgaacaagga agacatcaag ggcaagagac aggaccatcc atctcaggaa aaggagcttt   5460

gggatagtcc gagaagttgt acaagaaatt ttttggaggg tgagtgatgc attgctggtg   5520

actttaactc aatcaaaatt gagaaagaaa gaaaagggag ggggctcaca tgtgaataga   5580

agggaaacgg gagaatttta cagttttgat ctaatgggca tcccagctag tggtaacata   5640

ttcaccatgt ttaaccttca c                                              5661
```

<210> SEQ ID NO 91
<211> LENGTH: 1413
<212> TYPE: DNA
<213> ORGANISM: Saprolegnia diclina

<400> SEQUENCE: 91

```
atggccccgc agacggagct ccgccagcgc cacgccgccg tcgccgagac gccggtggcc     60

ggcaagaagg cctttacatg gcaggaggtc gcgcagcaca acacggcggc ctcggcctgg    120

atcattatcc gcggcaaggt ctacgacgtg accgagtggg ccaacaagca ccccggcggc    180

cgcgagatgg tgctgctgca cgccggtcgc gaggccaccg acacgttcga ctcgtaccac    240

ccgttcagcg acaaggccga gtcgatcttg aacaagtatg agattggcac gttcacgggc    300

ccgtccgagt ttccgacctt caagccggac acgggcttct acaaggagtg ccgcaagcgc    360

gttggcgagt acttcaagaa gaacaacctc catccgcagg acggcttccc gggcctctgg    420

cgcatgatgg tcgtgtttgc ggtcgccggc ctcgccttgt acggcatgca cttttcgact    480

atctttgcgc tgcagctcgc ggccgcggcg ctctttggcg tctgccaggc gctgccgctg    540

ctccacgtca tgcacgactc gtcgcacgcg tcgtacacca acatgccgtt cttccattac    600

gtcgtcggcc gctttgccat ggactggttt gccggcggct cgatggtgtc atggctcaac    660

cagcacgtcg tgggccacca catctacacg aacgtcgcgg gctcggaccc ggatcttccg    720

gtcaacatgg acggcgacat ccgccgcatc gtgaaccgcc aggtgttcca gcccatgtac    780
```

```
gcattccagc acatctacct tccgccgctc tatggcgtgc ttggcctcaa gttccgcatc     840

caggacttca ccgacacgtt cggctcgcac acgaacggcc cgatccgcgt caacccgcac     900

gcgctctcga cgtggatggc catgatcagc tccaagtcgt tctgggcctt ctaccgcgtg     960

taccttccgc ttgccgtgct ccagatgccc atcaagacgt accttgcgat cttcttcctc    1020

gccgagtttg tcacgggctg gtacctcgcg ttcaacttcc aagtaagcca tgtctcgacc    1080

gagtgcggct acccatgcgg cgacgaggcc aagatggcgc tccaggacga gtgggcagtc    1140

tcgcaggtca agacgtcggt cgactacgcc catggctcgt ggatgacgac gttccttgcc    1200

ggcgcgctca actaccaggt cgtgcaccac ttgttcccca gcgtgtcgca gtaccactac    1260

ccggcgatcg cgcccatcat cgtcgacgtc tgcaaggagt acaacatcaa gtacgccatc    1320

ttgccggact ttacggcggc gttcgttgcc cacttgaagc acctccgcaa catgggccag    1380

cagggcatcg ccgccacgat ccacatgggc taa                                  1413
```

<210> SEQ ID NO 92
<211> LENGTH: 5621
<212> TYPE: DNA
<213> ORGANISM: Artificial Sequence
<220> FEATURE:
<223> OTHER INFORMATION: Plasmid pKR1033

<400> SEQUENCE: 92

```
ggccgcattt cgcaccaaat caatgaaagt aataatgaaa agtctgaata agaatactta      60

ggcttagatg cctttgttac ttgtgtaaaa taacttgagt catgtacctt tggcggaaac     120

agaataaata aaaggtgaaa ttccaatgct ctatgtataa gttagtaata cttaatgtgt     180

tctacggttg tttcaatatc atcaaactct aattgaaact ttagaaccac aaatctcaat     240

cttttcttaa tgaaatgaaa aatcttaatt gtaccatgtt tatgttaaac accttacaat     300

taattggttg gagaggagga ccaaccgatg ggacaacatt gggagaaaga gattcaatgg     360

agatttggat aggagaacaa cattcttttt cacttcaata caagatgagt gcaacactaa     420

ggatatgtat gagactttca gaagctacga caacatagat gagtgaggtg gtgattccta     480

gcaagaaaga cattagagga agccaaaatc gaacaaggaa gacatcaagg gcaagagaca     540

ggaccatcca tctcaggaaa aggagctttg ggatagtccg agaagttgta caagaaattt     600

tttggagggt gagtgatgca ttgctggtga ctttaactca atcaaaattg agaaagaaag     660

aaaagggagg gggctcacat gtgaatagaa gggaaacggg agaattttac agttttgatc     720

taatgggcat cccagctagt ggtaacatat tcaccatgtt taaccttcac gtacgtctag     780

aggatccccc atggtcaatc aatgagacgc caacttctta atctattgag acctgcaggt     840

ctagaagggc ggatccccgg gtaccgagct cgaattcact ggccgtcgtt ttacaacgtc     900

gtgactggga aaaccctggc gttacccaac ttaatcgcct tgcagcacat ccccctttcg     960

ccagctggcg taatagcgaa gaggcccgca ccgatcgccc ttcccaacag ttgcgcagcc    1020

tgaatggcga atggcgcctg atgcggtatt ttctccttac gcatctgtgc ggtatttcac    1080

accgcatatg gtgcactctc agtacaatct gctctgatgc cgcatagtta agccagcccc    1140

gacacccgcc aacacccgct gacgcgccct gacgggcttg tctgctcccg gcatccgctt    1200

acagacaagc tgtgaccgtc tccgggagct gcatgtgtca gaggttttca ccgtcatcac    1260

cgaaacgcgc gagacgaaag ggcctcgtga tacgcctatt tttataggtt aatgtcatga    1320

taataatggt ttcttagacg tcaggtggca cttttcgggg aaatgtgcgc ggaaccccta    1380

tttgtttatt tttctaaata cattcaaata tgtatccgct catgagacaa taaccctgat    1440
```

-continued

```
aaatgcttca ataatattga aaaaggaaga gtatgagtat tcaacatttc cgtgtcgccc   1500

ttattccctt ttttgcggca ttttgccttc ctgtttttgc tcacccagaa acgctggtga   1560

aagtaaaaga tgctgaagat cagttgggtg cacgagtggg ttacatcgaa ctggatctca   1620

acagcggtaa gatccttgag agttttcgcc ccgaagaacg ttttccaatg atgagcactt   1680

ttaaagttct gctatgtggc gcggtattat cccgtattga cgccgggcaa gagcaactcg   1740

gtcgccgcat acactattct cagaatgact tggttgagta ctcaccagtc acagaaaagc   1800

atcttacgga tggcatgaca gtaagagaat tatgcagtgc tgccataacc atgagtgata   1860

acactgcggc caacttactt ctgacaacga tcggaggacc gaaggagcta accgcttttt   1920

tgcacaacat gggggatcat gtaactcgcc ttgatcgttg ggaaccggag ctgaatgaag   1980

ccataccaaa cgacgagcgt gacaccacga tgcctgtagc aatggcaaca acgttgcgca   2040

aactattaac tggcgaacta cttactctag cttcccggca acaattaata gactggatgg   2100

aggcggataa agttgcagga ccacttctgc gctcggccct tccggctggc tggtttattg   2160

ctgataaatc tggagccggt gagcgtgggt ctcgcggtat cattgcagca ctggggccag   2220

atggtaagcc ctcccgtatc gtagttatct acacgacggg gagtcaggca actatggatg   2280

aacgaaatag acagatcgct gagataggtg cctcactgat taagcattgg taactgtcag   2340

accaagttta ctcatatata ctttagattg atttaaaact tcatttttaa tttaaaagga   2400

tctaggtgaa gatccttttt gataatctca tgaccaaaat cccttaacgt gagttttcgt   2460

tccactgagc gtcagacccc gtagaaaaga tcaaaggatc ttcttgagat cctttttttc   2520

tgcgcgtaat ctgctgcttg caaacaaaaa aaccaccgct accagcggtg gtttgtttgc   2580

cggatcaaga gctaccaact ctttttccga aggtaactgg cttcagcaga gcgcagatac   2640

caaatactgt ccttctagtg tagccgtagt taggccacca cttcaagaac tctgtagcac   2700

cgcctacata cctcgctctg ctaatcctgt taccagtggc tgctgccagt ggcgataagt   2760

cgtgtcttac cgggttggac tcaagacgat agttaccgga taaggcgcag cggtcgggct   2820

gaacgggggg ttcgtgcaca cagcccagct tggagcgaac gacctacacc gaactgagat   2880

acctacagcg tgagctatga gaaagcgcca cgcttcccga agggagaaag gcggacaggt   2940

atccggtaag cggcagggtc ggaacaggag agcgcacgag ggagcttcca gggggaaacg   3000

cctggtatct ttatagtcct gtcgggtttc gccacctctg acttgagcgt cgatttttgt   3060

gatgctcgtc aggggggcgg agcctatgga aaaacgccag caacgcggcc tttttacggt   3120

tcctggcctt ttgctggcct tttgctcaca tgttctttcc tgcgttatcc cctgattctg   3180

tggataaccg tattaccgcc tttgagtgag ctgataccgc tcgccgcagc cgaacgaccg   3240

agcgcagcga gtcagtgagc gaggaagcgg aagagcgccc aatacgcaaa ccgcctctcc   3300

ccgcgcgttg gccgattcat taatgcagct ggcacgacag gtttcccgac tggaaagcgg   3360

gcagtgagcg caacgcaatt aatgtgagtt agctcactca ttaggcaccc caggctttac   3420

actttatgct tccggctcgt atgttgtgtg gaattgtgag cggataacaa tttcacacag   3480

gaaacagcta tgaccatgat tacgccaagc ttgcatgcct gcaggctagc ctaagtacgt   3540

actcaaaatg ccaacaaata aaaaaaaagt tgctttaata atgccaaaac aaattaataa   3600

aacacttaca acaccggatt ttttttaatt aaaatgtgcc atttaggata aatagttaat   3660

atttttaata attatttaaa aagccgtatc tactaaaatg atttttattt ggttgaaaat   3720

attaatatgt ttaaatcaac acaatctatc aaaattaaac taaaaaaaaa ataagtgtac   3780

gtggttaaca ttagtacagt aatataagag gaaaatgaga aattaagaaa ttgaaagcga   3840
```

```
gtctaatttt taaattatga acctgcatat ataaaaggaa agaaagaatc caggaagaaa   3900

agaaatgaaa ccatgcatgg tcccctcgtc atcacgagtt tctgccattt gcaatagaaa   3960

cactgaaaca cctttctctt tgtcacttaa ttgagatgcc gaagccacct cacaccatga   4020

acttcatgag gtgtagcacc caaggcttcc atagccatgc atactgaaga atgtctcaag   4080

ctcagcaccc tacttctgtg acgtgtccct cattcacctt cctctcttcc ctataaataa   4140

ccacgcctca ggttctccgc ttcacaactc aaacattctc tccattggtc cttaaacact   4200

catcagtcat caccgcggcc gcaaaccatg gctccagatg cggacaagtt gagacagcgc   4260

aaggcgcaat cgattcaaga cacggctgat tcgcaagcta ccgaactcaa gattggcacc   4320

ctgaagggct tgcaggggac agaaatcgtc attgatggag acatttacga tataaaagac   4380

tttgatcacc ccggtggtga atccatcatg acttttgggg gaaacgatgt caccgccacg   4440

tacaagatga tccaccccta ccactctaag caccatttgg agaagatgaa gaaagtggga   4500

cgagttccgg actacacctc ggaatacaag tttgatactc cctttgagcg tgaaatcaag   4560

caagaggtct tcaagattgt gcgacgaggc cgcgagtttg gaacacctgg atacttcttc   4620

cgggctttct gctacattgg acttttcttt tacttgcagt atttgtgggt cacgactccc   4680

actacctttg ccttggcgat cttctatggt gtttcgcaag ctttcattgg tttgaacgta   4740

caacatgatg ccaaccacgg agctgcctcc aagaagcctt ggatcaataa cttgctagga   4800

ttgggggctg actttatcgg aggttccaaa tggttgtgga tgaaccagca ctggacgcac   4860

cacacataca ccaaccacca tgagaaggat cccgatgcct tgggcgctga accaatgttg   4920

ttgttcaatg attatccctt gggtcaccca aagcgtactt tgattcacca cttccaggcc   4980

ttctattacc ttttcgtctt ggccggatac tgggtctctt cggtcttcaa ccctcaaatt   5040

ttggacttgc aacaccgcgg tgctcaagcg gttggaatga aaatggagaa cgattacatt   5100

gccaaaagcc gaaagtatgc catcttcttg cgtctcttgt atatttacac caacattgtc   5160

gctccgatcc aaaaccaagg cttctcgttg accgtggtcg cccacatttt gaccatgggc   5220

gtcgcttcca gtttgacttt ggcgactctt tttgccttgt cgcacaattt tgaaaacgcg   5280

gatcgcgatc ccacttacga ggcccgcaag ggaggagagc ctgtttgttg gttcaagtcg   5340

caagtcgaaa cctcgtcaac ttacggaggt ttcatctcgg gttgcttgac gggcggactc   5400

aacttccaag tggaacacca cttgttccct cgtatgagtt cggcctggta cccctacatt   5460

gcccctactg ttcgagaggt ttgcaaaaag cacggagtca agtacgcata ctatccctgg   5520

gtctggcaaa acttgatttc aactgtcaag tatctgcatc aaagcggaac tggatccaac   5580

tggaagaatg gcgccaaccc ctactcggga aaattgtaag c                        5621
```

```
<210> SEQ ID NO 93
<211> LENGTH: 11949
<212> TYPE: DNA
<213> ORGANISM: Artificial Sequence
<220> FEATURE:
<223> OTHER INFORMATION: Plasmid pKR1038
<220> FEATURE:
<221> NAME/KEY: misc_feature
<222> LOCATION: (7810)..(7810)
<223> OTHER INFORMATION: n is a, c, g, or t

<400> SEQUENCE: 93

ggagatccaa gcttttgatc catgcccttc atttgccgct tattaattaa tttggtaaca     60

gtccgtacta atcagttact tatccttccc ccatcataat taatcttggt agtctcgaat    120

gccacaacac tgactagtct cttggatcat aagaaaaagc caaggaacaa aagaagacaa    180
```

```
aacacaatga gagtatcctt tgcatagcaa tgtctaagtt cataaaattc aaacaaaaac    240
gcaatcacac acagtggaca tcacttatcc actagctgat caggatcgcc gcgtcaagaa    300
aaaaaaactg gaccccaaaa gccatgcaca acaacacgta ctcacaaagg tgtcaatcga    360
gcagcccaaa acattcacca actcaaccca tcatgagccc tcacatttgt tgtttctaac    420
ccaacctcaa actcgtattc tcttccgcca cctcattttt gtttatttca acacccgtca    480
aactgcatgc caccccgtgg ccaaatgtcc atgcatgtta acaagaccta tgactataaa    540
tagctgcaat ctcggcccag gttttcatca tcaagaacca gttcaatatc ctagtacacc    600
gtattaaaga atttaagata tactgcggcc gcaccatgga ggtggtgaat gaaatagtct    660
caattgggca ggaagtttta cccaaagttg attatgccca actctggagt gatgccagtc    720
actgtgaggt gctttacttg tccatcgcat ttgtcatctt gaagttcact cttggccccc    780
ttggtccaaa aggtcagtct cgtatgaagt ttgttttcac caattacaac cttctcatgt    840
ccatttattc gttgggatca ttcctctcaa tggcatatgc catgtacacc atcggtgtta    900
tgtctgacaa ctgcgagaag gcttttgaca acaacgtctt caggatcacc acgcagttgt    960
tctatttgag caagttcctg gagtatattg actccttcta tttgccactg atgggcaagc   1020
ctctgacctg gttgcaattc ttccatcatt tgggggcacc gatggatatg tggctgttct   1080
ataattaccg aaatgaagct gtttggattt ttgtgctgtt gaatggtttc atccactgga   1140
tcatgtacgg ttattattgg accagattga tcaagctgaa gttccccatg ccaaaatccc   1200
tgattacatc aatgcagatc attcaattca atgttggttt ctacattgtc tggaagtaca   1260
ggaacattcc ctgttatcgc caagatggga tgaggatgtt tggctggttc ttcaattact   1320
tttatgttgg cacagtcttg tgtttgttct tgaatttcta tgtgcaaacg tatatcgtca   1380
ggaagcacaa gggagccaaa aagattcagt gagcggccgc aagtatgaac taaaatgcat   1440
gtaggtgtaa gagctcatgg agagcatgga atattgtatc cgaccatgta acagtataat   1500
aactgagctc catctcactt cttctatgaa taaacaaagg atgttatgat atattaacac   1560
tctatctatg caccttattg ttctatgata aatttcctct tattattata aatcatctga   1620
atcgtgacgg cttatggaat gcttcaaata gtacaaaaac aaatgtgtac tataagactt   1680
tctaaacaat tctaacctta gcattgtgaa cgagacataa gtgttaagaa gacataacaa   1740
ttataatgga agaagtttgt ctccatttat atattatata ttacccactt atgtattata   1800
ttaggatgtt aaggagacat aacaattata aagagagaag tttgtatcca tttatatatt   1860
atatactacc catttatata ttatacttat ccacttattt aatgtcttta taaggtttga   1920
tccatgatat ttctaatatt ttagttgata tgtatatgaa agggtactat ttgaactctc   1980
ttactctgta taaaggttgg atcatcctta aagtgggtct atttaatttt attgcttctt   2040
acagataaaa aaaaaattat gagttggttt gataaaatat tgaaggattt aaaataataa   2100
taaataacat ataatatatg tatataaatt tattataata taacatttat ctataaaaaa   2160
gtaaatattg tcataaatct atacaatcgt ttagccttgc tggacgaatc tcaattattt   2220
aaacgagagt aaacatattt gactttttgg ttatttaaca aattattatt taacactata   2280
tgaaattttt ttttttatca gcaaagaata aaattaaatt aagaaggaca atggtgtccc   2340
aatccttata caaccaactt ccacaagaaa gtcaagtcag agacaacaaa aaaacaagca   2400
aaggaaattt tttaatttga gttgtcttgt ttgctgcata atttatgcag taaaacacta   2460
cacataaccc ttttagcagt agagcaatgg ttgaccgtgt gcttagcttc ttttatttta   2520
ttttttttatc agcaaagaat aaataaaata aaatgagaca cttcagggat gtttcaacaa   2580
```

```
gcttggcgcg ccgttctata gtgtcaccta aatcgtatgt gtatgataca taaggttatg   2640
tattaattgt agccgcgttc taacgacaat atgtccatat ggtgcactct cagtacaatc   2700
tgctctgatg ccgcatagtt aagccagccc cgacacccgc caacacccgc tgacgcgccc   2760
tgacgggctt gtctgctccc ggcatccgct tacagacaag ctgtgaccgt ctccgggagc   2820
tgcatgtgtc agaggttttc accgtcatca ccgaaacgcg cgagacgaaa gggcctcgtg   2880
atacgcctat ttttataggt taatgtcatg accaaaatcc cttaacgtga gttttcgttc   2940
cactgagcgt cagaccccgt agaaaagatc aaaggatctt cttgagatcc tttttttctg   3000
cgcgtaatct gctgcttgca aacaaaaaaa ccaccgctac cagcggtggt ttgtttgccg   3060
gatcaagagc taccaactct ttttccgaag gtaactggct tcagcagagc gcagatacca   3120
aatactgtcc ttctagtgta gccgtagtta ggccaccact tcaagaactc tgtagcaccg   3180
cctacatacc tcgctctgct aatcctgtta ccagtggctg ctgccagtgg cgataagtcg   3240
tgtcttaccg ggttggactc aagacgatag ttaccggata aggcgcagcg gtcgggctga   3300
acggggggtt cgtgcacaca gcccagcttg gagcgaacga cctacaccga actgagatac   3360
ctacagcgtg agcattgaga aagcgccacg cttcccgaag ggagaaaggc ggacaggtat   3420
ccggtaagcg gcagggtcgg aacaggagag cgcacgaggg agcttccagg gggaaacgcc   3480
tggtatcttt atagtcctgt cgggtttcgc cacctctgac ttgagcgtcg atttttgtga   3540
tgctcgtcag gggggcggag cctatggaaa aacgccagca acgcggcctt tttacggttc   3600
ctggcctttt gctggccttt tgctcacatg ttctttcctg cgttatcccc tgattctgtg   3660
gataaccgta ttaccgcctt tgagtgagct gataccgctc gccgcagccg aacgaccgag   3720
cgcagcgagt cagtgagcga ggaagcggaa gagcgcccaa tacgcaaacc gcctctcccc   3780
gcgcgttggc cgattcatta atgcaggttg atcagatctc gatcccgcga aattaatacg   3840
actcactata gggagaccac aacggtttcc ctctagaaat aattttgttt aactttaaga   3900
aggagatata cccatggaaa agcctgaact caccgcgacg tctgtcgaga agtttctgat   3960
cgaaaagttc gacagcgtct ccgacctgat gcagctctcg gagggcgaag aatctcgtgc   4020
tttcagcttc gatgtaggag ggcgtggata tgtcctgcgg gtaaatagct gcgccgatgg   4080
tttctacaaa gatcgttatg tttatcggca ctttgcatcg gccgcgctcc cgattccgga   4140
agtgcttgac attggggaat tcagcgagag cctgacctat tgcatctccc gccgtgcaca   4200
gggtgtcacg ttgcaagacc tgcctgaaac cgaactgccc gctgttctgc agccggtcgc   4260
ggaggctatg gatgcgatcg ctgcggccga tcttagccag acgagcgggt tcggcccatt   4320
cggaccgcaa ggaatcggtc aatacactac atggcgtgat ttcatatgcg cgattgctga   4380
tccccatgtg tatcactggc aaactgtgat ggacgacacc gtcagtgcgt ccgtcgcgca   4440
ggctctcgat gagctgatgc tttgggccga ggactgcccc gaagtccggc acctcgtgca   4500
cgcggatttc ggctccaaca atgtcctgac ggacaatggc cgcataacag cggtcattga   4560
ctggagcgag gcgatgttcg gggattccca atacgaggtc gccaacatct tcttctggag   4620
gccgtggttg gcttgtatgg agcagcagac gcgctacttc gagcggaggc atccggagct   4680
tgcaggatcg ccgcggctcc gggcgtatat gctccgcatt ggtcttgacc aactctatca   4740
gagcttggtt gacggcaatt tcgatgatgc agcttgggcg cagggtcgat gcgacgcaat   4800
cgtccgatcc ggagccggga ctgtcgggcg tacacaaatc gcccgcagaa gcgcggccgt   4860
ctggaccgat ggctgtgtag aagtactcgc cgatagtgga aaccgacgcc ccagcactcg   4920
tccgagggca aaggaatagt gaggtacagc ttggatcgat ccggctgcta acaaagcccg   4980
```

```
aaaggaagct gagttggctg ctgccaccgc tgagcaataa ctagcataac cccttggggc   5040
ctctaaacgg gtcttgaggg gtttttttgct gaaaggagga actatatccg gatgatcggg   5100
cgcgccgtcg acggatccgt acgcaaaggc aaagatttaa actcgaaaac attacaaaag   5160
tctcaaaaca gaggcaaggc catgcacaaa gcacactcta agtgcttcca ttgcctacta   5220
agtagggtac gtacacgatc accattcacc agtgatgatc tttattaata tacaacacac   5280
tcagagacag cttatgttat agctagctag cataaactat cacatcatgt gttagtacga   5340
caagtgacaa cattgctttt aacttcgcgg ccttggatcc tctagaccgg atataatgag   5400
ccgtaaacaa agatgattaa gtagtaatta atacgtacta gtaaaagtgg caaaagataa   5460
cgagaaagaa ccaatttctt tgcattcggc cttagcggaa ggcatatata agctttgatt   5520
attttattta gtgtaatgat ttcgtacaac caaagcattt atttagtact ctcacacttg   5580
tgtcgcggcc gcgaattcac tagtgattcc ttatagagcc ttccccgcgg gttgcttctc   5640
cgccatccgg gcgaacaccg ccagatagcg cagcaggatg accaaccctt catggggcag   5700
cgggttccga tacggcaggt tgtgcttctg gcacagctgt tccacctggt agctaaccgc   5760
tgtcaggttg tggcgaggga gggtcggcca caaatggtgc tcaatctggt aattcaagcc   5820
tccgaaaaac caatctgtga taatccctcg ccgaatgttc atggtctcat ggatctggcc   5880
aaccgagaat ccatggccat cccagactga gtccccgatc ttctccagtg ggtagtggtt   5940
catgaacacc acgatcgcaa tgccgaagcc gccaaccagc tccgaaacga aaaacaccaa   6000
cagcgatgtg aggatgctgg gcataaagaa taagtggaac agggtcttca aggtccagtg   6060
cagggcgagg ccaatggcct ccttcttata ctgagagcga tagaattggt tatctctgtc   6120
cttcaaactg cgcacggtca acacgctctg gaaacaccaa atgaaccgca acaagataca   6180
gatgaccaag aaatagtact gctggaactg aatgagcttg cgggaaatcg gtgacgcccg   6240
tgtgacgtca tcctcagacc aggctaagag gggggaggttg tcaatatcag ggtcgtgccc   6300
ttgaacattg gttgccgaat gatgtgcatt gtgtctgtcc ttccaccatg tcacggaaaa   6360
accttgcaga ccattgccaa ataccagtcc cacgaggttg ttccagttcc ggttcttgaa   6420
agtctggtgg tggcaaatgt catgagaaag ccagcccatc tgttgatagt gcatcccaag   6480
caacactgcc ccaatgaaat acatctgata ctgaaccatc aggaaataac ccagcactcc   6540
aaggcccagt gtggtgctga ttttgtatga gtaccagagg ggggaggcat caaacatgcc   6600
agttgcgatc aactcttctc ggagcttccg gaaatcctct tgagcttcat tcactgcagc   6660
ctggggtggc aactcagaac tgggattgat tttgggcatg cgcttgagct tgtcgaaggc   6720
ttcttgagag tgcataacca tgaaggcatc agtggcatcc cttccttggt aattctctat   6780
aatttccgca ccaccagggt ggaaattgac ccaggcagac acatcatatg ttgttccatc   6840
aattgtaagg ggaagcgctt ggcgctttga cttcatttca atcgaattcc cgcggccgct   6900
tggggggcta tggaagactt tcttagttag ttgtgtgaat aagcaatgtt gggagaatcg   6960
ggactactta taggatagga ataaaacaga aaagtattaa gtgctaatga aatatttaga   7020
ctgataatta aaatcttcac gtatgtccac ttgatataaa aacgtcagga ataaaggaag   7080
tacagtagaa tttaaaggta ctctttttat atatacccgt gttctctttt tggctagcta   7140
gttgcataaa aaataatcta tatttttatc attattttaa atatcttatg agatggtaaa   7200
tatttatcat aatttttttt actattattt attatttgtg tgtgtaatac atatagaagt   7260
taattacaaa ttttatttac tttttcatta ttttgatatg attcaccatt aatttagtgt   7320
tattatttat aatagttcat tttaatcttt ttgtatatat tatgcgtgca gtactttttt   7380
```

-continued

```
cctacatata actactatta cattttattt atataatatt tttattaatg aattttcgtg   7440

ataatatgta atattgttca ttattatttc agatttttta aaaatatttg tgttattatt   7500

tatgaaatat gtaatttttt tagtatttga ttttatgatg ataaagtgtt ctaaattcaa   7560

aagaaggggg aaagcgtaaa cattaaaaaa cgtcatcaaa caaaaacaaa atcttgttaa   7620

taaagataaa actgtttgtt ttgatcactg ttatttcgta atataaaaac attatttata   7680

tttatattgt tgacaaccaa atttgcctat caaatctaac caatataatg catgcgtggc   7740

aggtaatgta ctaccatgaa cttaagtcat gacataataa accgtgaatc tgaccaatgc   7800

atgtacctan ctaaattgta tttgtgacac gaagcaaatg attcaattca caatggagat   7860

gggaaacaaa taatgaagaa cccagaacta agaaagcttt tctgaaaaat aaaataaagg   7920

caatgtcaaa agtatactgc atcatcagtc cagaaagcac atgatatttt tttatcagta   7980

tcaatgcagc tagttttatt ttacaatatc gatatagcta gtttaaatat attgcagcta   8040

gatttataaa tatttgtgtt attatttatc atttgtgtaa tcctgttttt agtattttag   8100

tttatatatg atgataatgt attccaaatt taaaagaagg gaaataaatt taaacaagaa   8160

aaaaagtcat caaacaaaaa acaaatgaaa gggtggaaag atgttaccat gtaatgtgaa   8220

tgttacagta tttcttttat tatagagtta acaaattaac taatatgatt ttgttaataa   8280

tgataaaata ttttttttat tattatttca taatataaaa atagtttact taatataaaa   8340

aaaattctat cgttcacaac aaagttggcc acctaattta accatgcatg tacccatgga   8400

ccatattagg taaccatcaa acctgatgaa gagataaaga gatgaagact taagtcataa   8460

cacaaaacca taaaaaacaa aaatacaatc aaccgtcaat ctgaccaatg catgaaaaag   8520

ctgcaatagt gagtggcgac acaaagcaca tgattttctt acaacggaga taaaaccaaa   8580

aaaatatttc atgaacaacc tagaacaaat aaagctttta tataataaat atataaataa   8640

ataaaggcta tggaataata tacttcaata tatttggatt aaataaattg ttggcggggt   8700

tgatatattt atacacacct aaagtcactt caatctcatt ttcacttaac ttttattttt   8760

tttttctttt tatttatcat aaagagaata ttgataaatat actttttaac atatttttat   8820

gacatttttt attggtgaaa acttattaaa aatcataaat tttgtaagtt agatttattt   8880

aaagagttcc tcttcttatt ttaaattttt taataaattt ttaaataact aaaatttgtg   8940

ttaaaaatgt taaaaaatgt gttattaacc cttctcttcg aggacgtacg agatccggcc   9000

ggccagatcc tgcaggtctc aatagattaa gaagttggcg tctcattgat tgaccatggg   9060

ggatcctcta gacgtacgtg aaggttaaac atggtgaata tgttaccact agctgggatg   9120

cccattagat caaaactgta aaattctccc gtttcccttc tattcacatg tgagcccccct   9180

cccttttctt tctttctcaa ttttgattga gttaaagtca ccagcaatgc atcactcacc   9240

ctccaaaaaa tttcttgtac aacttctcgg actatcccaa agctcctttt cctgagatgg   9300

atggtcctgt ctcttgccct tgatgtcttc cttgttcgat tttggcttcc tctaatgtct   9360

ttcttgctag gaatcaccac ctcactcatc tatgttgtcg tagcttctga aagtctcata   9420

catatcctta gtgttgcact catcttgtat tgaagtgaaa aagaatgttg ttctcctatc   9480

caaatctcca ttgaatctct ttctcccaat gttgtcccat cggttggtcc tcctctccaa   9540

ccaattaatt gtaaggtgtt taacataaac atggtacaat taagattttt catttcatta   9600

agaaaagatt gagatttgtg gttctaaagt ttcaattaga gtttgatgat attgaaacaa   9660

ccgtagaaca cattaagtat tactaactta tacatagagc attggaattt caccttttat   9720

ttattctgtt tccgccaaag gtacatgact caagttattt tacacaagta acaaaggcat   9780
```

```
ctaagcctaa gtattcttat tcagactttt cattattact ttcattgatt tggtgcgaaa   9840

tgcggccgct tacaattttc ccgagtaggg gttggcgcca ttcttccagt tggatccagt   9900

tccgctttga tgcagatact tgacagttga aatcaagttt tgccagaccc agggatagta   9960

tgcgtacttg actccgtgct tttgcaaac ctctcgaaca gtaggggcaa tgtaggggta  10020

ccaggccgaa ctcatacgag ggaacaagtg gtgttccact tggaagttga gtccgcccgt  10080

caagcaaccc gagatgaaac ctccgtaagt tgacgaggtt tcgacttgcg acttgaacca  10140

acaaacaggc tctcctccct tgcgggcctc gtaagtggga tcgcgatccg cgttttcaaa  10200

attgtgcgac aaggcaaaaa gagtcgccaa agtcaaactg gaagcgacgc ccatggtcaa  10260

aatgtgggcg accacggtca acgagaagcc ttggttttgg atcggagcga caatgttggt  10320

gtaaatatac aagagacgca agaagatggc atactttcgg cttttggcaa tgtaatcgtt  10380

ctccattttc attccaaccg cttgagcacc gcggtgttgc aagtccaaaa tttgagggtt  10440

gaagaccgaa gagacccagt atccggccaa gacgaaaagg taatagaagg cctggaagtg  10500

gtgaatcaaa gtacgctttg ggtgacccaa gggataatca ttgaacaaca acattggttc  10560

agcgcccaag gcatcgggat ccttctcatg gtggttggtg tatgtgtggt gcgtccagtg  10620

ctggttcatc cacaaccatt tggaacctcc gataaagtca gcccccaatc ctagcaagtt  10680

attgatccaa ggcttcttgg aggcagctcc gtggttggca tcatgttgta cgttcaaacc  10740

aatgaaagct tgcgaaacac catagaagat cgccaaggca aaggtagtgg gagtcgtgac  10800

ccacaaatac tgcaagtaaa agaaaagtcc aatgtagcag aaagcccgga agaagtatcc  10860

aggtgttcca aactcgcggc ctcgtcgcac aatcttgaag acctcttgct tgatttcacg  10920

ctcaaaggga gtatcaaact tgtattccga ggtgtagtcc ggaactcgtc ccactttctt  10980

catcttctcc aaatggtgct tagagtggta ggggtggatc atcttgtacg tggcggtgac  11040

atcgtttccc ccaaaagtca tgatggattc accaccgggg tgatcaaagt cttttatatc  11100

gtaaatgtct ccatcaatga cgatttctgt cccctgcaag cccttcaggg tgccaatctt  11160

gagttcggta gcttgcgaat cagccgtgtc ttgaatcgat tgcgccttgc gctgtctcaa  11220

cttgtccgca tctggagcca tggtttgcgg ccgcggtgat gactgatgag tgtttaagga  11280

ccaatggaga gaatgtttga gttgtgaagc ggagaacctg aggcgtggtt atttataggg  11340

aagagaggaa ggtgaatgag ggacacgtca cagaagtagg gtgctgagct tgagacattc  11400

ttcagtatgc atggctatgg aagccttggg tgctacacct catgaagttc atggtgtgag  11460

gtggcttcgg catctcaatt aagtgacaaa gagaaaggtg tttcagtgtt tctattgcaa  11520

atggcagaaa ctcgtgatga cgaggggacc atgcatggtt tcatttcttt tcttcctgga  11580

ttctttcttt ccttttatat atgcaggttc ataatttaaa aattagactc gctttcaatt  11640

tcttaatttc tcattttcct cttatattac tgtactaatg ttaaccacgt acacttattt  11700

tttttttagt ttaattttga tagattgtgt tgatttaaac atattaatat tttcaaccaa  11760

ataaaaatca ttttagtaga tacggctttt taaataatta ttaaaaatat taactattta  11820

tcctaaatgg cacattttaa ttaaaaaaaa tccggtgttg taagtgtttt attaatttgt  11880

tttggcatta ttaaagcaac ttttttttta tttgttggca ttttgagtac gtacttaggc  11940

tagcctgca                                                          11949
```

```
<210> SEQ ID NO 94
<211> LENGTH: 8671
<212> TYPE: DNA
<213> ORGANISM: Artificial Sequence
<220> FEATURE:
```

<223> OTHER INFORMATION: Plasmid pKR328

<400> SEQUENCE: 94

```
ggatctggcc ggccggatct cgtacggatc cgtcgacggc gcgcccgatc atccggatat     60
agttcctcct ttcagcaaaa aacccctcaa gacccgttta gaggccccaa ggggttatgc    120
tagttattgc tcagcggtgg cagcagccaa ctcagcttcc tttcgggctt tgttagcagc    180
cggatcgatc caagctgtac ctcactattc ctttgccctc ggacgagtgc tggggcgtcg    240
gtttccacta tcggcgagta cttctacaca gccatcggtc cagacggccg cgcttctgcg    300
ggcgatttgt gtacgcccga cagtcccggc tccggatcgg acgattgcgt cgcatcgacc    360
ctgcgcccaa gctgcatcat cgaaattgcc gtcaaccaag ctctgataga gttggtcaag    420
accaatgcgg agcatatacg cccggagccg cggcgatcct gcaagctccg gatgcctccg    480
ctcgaagtag cgcgtctgct gctccataca agccaaccac ggcctccaga agaagatgtt    540
ggcgacctcg tattgggaat ccccgaacat cgcctcgctc cagtcaatga ccgctgttat    600
gcggccattg tccgtcagga cattgttgga gccgaaatcc gcgtgcacga ggtgccggac    660
ttcggggcag tcctcggccc aaagcatcag ctcatcgaga gcctgcgcga cggacgcact    720
gacggtgtcg tccatcacag tttgccagtg atacacatgg ggatcagcaa tcgcgcatat    780
gaaatcacgc catgtagtgt attgaccgat tccttgcggt ccgaatgggc cgaacccgct    840
cgtctggcta agatcggccg cagcgatcgc atccatagcc tccgcgaccg gctgcagaac    900
agcgggcagt tcggtttcag gcaggtcttg caacgtgaca ccctgtgcac ggcgggagat    960
gcaataggtc aggctctcgc tgaattcccc aatgtcaagc acttccggaa tcgggagcgc   1020
ggccgatgca aagtgccgat aaacataacg atctttgtag aaaccatcgg cgcagctatt   1080
tacccgcagg acatatccac gccctcctac atcgaagctg aaagcacgag attcttcgcc   1140
ctccgagagc tgcatcaggt cggagacgct gtcgaacttt tcgatcagaa acttctcgac   1200
agacgtcgcg gtgagttcag gcttttccat gggtatatct ccttcttaaa gttaaacaaa   1260
attatttcta gagggaaacc gttgtggtct ccctatagtg agtcgtatta atttcgcggg   1320
atcgagatcg atccaattcc aatcccacaa aaatctgagc ttaacagcac agttgctcct   1380
ctcagagcag aatcgggtat tcaacaccct catatcaact actacgttgt gtataacggt   1440
ccacatgccg gtatatacga tgactggggt tgtacaaagg cggcaacaaa cggcgttccc   1500
ggagttgcac acaagaaatt tgccactatt acagaggcaa gagcagcagc tgacgcgtac   1560
acaacaagtc agcaaacaga caggttgaac ttcatcccca aaggagaagc tcaactcaag   1620
cccaagagct ttgctaaggc cctaacaagc ccaccaaagc aaaaagccca ctggctcacg   1680
ctaggaacca aaaggcccag cagtgatcca gccccaaaag agatctcctt tgccccggag   1740
attacaatgg acgatttcct ctatctttac gatctaggaa ggaagttcga aggtgaaggt   1800
gacgacacta tgttcaccac tgataatgag aaggttagcc tcttcaattt cagaaagaat   1860
gctgacccac agatggttag agaggcctac gcagcaggtc tcatcaagac gatctacccg   1920
agtaacaatc tccaggagat caaatacctt cccaagaagg ttaaagatgc agtcaaaaga   1980
ttcaggacta attgcatcaa gaacacagag aaagacatat ttctcaagat cagaagtact   2040
attccagtat ggacgattca aggcttgctt cataaaccaa ggcaagtaat agagattgga   2100
gtctctaaaa aggtagttcc tactgaatct aaggccatgc atggagtcta agattcaaat   2160
cgaggatcta acagaactcg ccgtgaagac tggcgaacag ttcatacaga gtcttttacg   2220
actcaatgac aagaagaaaa tcttcgtcaa catggtggag cacgacactc tggtctactc   2280
```

```
caaaaatgtc aaagatacag tctcagaaga ccaaagggct attgagactt ttcaacaaag   2340
gataatttcg ggaaacctcc tcggattcca ttgcccagct atctgtcact tcatcgaaag   2400
gacagtagaa aaggaaggtg gctcctacaa atgccatcat tgcgataaag gaaaggctat   2460
cattcaagat gcctctgccg acagtggtcc caaagatgga cccccaccca cgaggagcat   2520
cgtggaaaaa gaagacgttc caaccacgtc ttcaaagcaa gtggattgat gtgacatctc   2580
cactgacgta agggatgacg cacaatccca ctatccttcg caagaccctt cctctatata   2640
aggaagttca tttcatttgg agaggacacg ctcgagctca tttctctatt acttcagcca   2700
taacaaaaga actcttttct cttcttatta aaccatgaaa aagcctgaac tcaccgcgac   2760
gtctgtcgag aagtttctga tcgaaaagtt cgacagcgtc tccgacctga tgcagctctc   2820
ggagggcgaa gaatctcgtg ctttcagctt cgatgtagga gggcgtggat atgtcctgcg   2880
ggtaaatagc tgcgccgatg gtttctacaa agatcgttat gtttatcggc actttgcatc   2940
ggccgcgctc ccgattccgg aagtgcttga cattggggaa ttcagcgaga gcctgaccta   3000
ttgcatctcc cgccgtgcac agggtgtcac gttgcaagac ctgcctgaaa ccgaactgcc   3060
cgctgttctg cagccggtcg cggaggccat ggatgcgatc gctgcggccg atcttagcca   3120
gacgagcggg ttcggcccat tcggaccgca aggaatcggt caatacacta catggcgtga   3180
tttcatatgc gcgattgctg atccccatgt gtatcactgg caaactgtga tggacgacac   3240
cgtcagtgcg tccgtcgcgc aggctctcga tgagctgatg ctttgggccg aggactgccc   3300
cgaagtccgg cacctcgtgc acgcggattt cggctccaac aatgtcctga cggacaatgg   3360
ccgcataaca gcggtcattg actggagcga ggcgatgttc ggggattccc aatacgaggt   3420
cgccaacatc ttcttctgga ggccgtggtt ggcttgtatg gagcagcaga cgcgctactt   3480
cgagcggagg catccggagc ttgcaggatc gccgcggctc cgggcgtata tgctccgcat   3540
tggtcttgac caactctatc agagcttggt tgacggcaat ttcgatgatg cagcttgggc   3600
gcagggtcga tgcgacgcaa tcgtccgatc cggagccggg actgtcgggc gtacacaaat   3660
cgcccgcaga agcgcggccg tctggaccga tggctgtgta gaagtactcg ccgatagtgg   3720
aaaccgacgc cccagcactc gtccgagggc aaaggaatag tgaggtacct aaagaaggag   3780
tgcgtcgaag cagatcgttc aaacatttgg caataaagtt tcttaagatt gaatcctgtt   3840
gccggtcttg cgatgattat catataattt ctgttgaatt acgttaagca tgtaataatt   3900
aacatgtaat gcatgacgtt atttatgaga tgggttttta tgattagagt cccgcaatta   3960
tacatttaat acgcgataga aaacaaaata tagcgcgcaa actaggataa attatcgcgc   4020
gcggtgtcat ctatgttact agatcgatgt cgaatcgatc aacctgcatt aatgaatcgg   4080
ccaacgcgcg gggagaggcg gtttgcgtat tgggcgctct tccgcttcct cgctcactga   4140
ctcgctgcgc tcggtcgttc ggctgcggcg agcggtatca gctcactcaa aggcggtaat   4200
acggttatcc acagaatcag gggataacgc aggaaagaac atgtgagcaa aaggccagca   4260
aaaggccagg aaccgtaaaa aggccgcgtt gctggcgttt ttccataggc tccgcccccc   4320
tgacgagcat cacaaaaatc gacgctcaag tcagaggtgg cgaaacccga caggactata   4380
aagataccag gcgtttcccc ctggaagctc cctcgtgcgc tctcctgttc cgaccctgcc   4440
gcttaccgga tacctgtccg cctttctccc ttcgggaagc gtggcgcttt ctcaatgctc   4500
acgctgtagg tatctcagtt cggtgtaggt cgttcgctcc aagctgggct gtgtgcacga   4560
accccccgtt cagcccgacc gctgcgcctt atccggtaac tatcgtcttg agtccaaccc   4620
ggtaagacac gacttatcgc cactggcagc agccactggt aacaggatta gcagagcgag   4680
```

```
gtatgtaggc ggtgctacag agttcttgaa gtggtggcct aactacggct acactagaag   4740
gacagtattt ggtatctgcg ctctgctgaa gccagttacc ttcggaaaaa gagttggtag   4800
ctcttgatcc ggcaaacaaa ccaccgctgg tagcggtggt ttttttgttt gcaagcagca   4860
gattacgcgc agaaaaaaag gatctcaaga agatcctttg atcttttcta cggggtctga   4920
cgctcagtgg aacgaaaact cacgttaagg gattttggtc atgacattaa cctataaaaa   4980
taggcgtatc acgaggccct ttcgtctcgc gcgtttcggt gatgacggtg aaaacctctg   5040
acacatgcag ctcccggaga cggtcacagc ttgtctgtaa gcggatgccg ggagcagaca   5100
agcccgtcag ggcgcgtcag cgggtgttgg cgggtgtcgg ggctggctta actatgcggc   5160
atcagagcag attgtactga gagtgcacca tatggacata ttgtcgttag aacgcggcta   5220
caattaatac ataaccttat gtatcataca catacgattt aggtgacact atagaacggc   5280
gcgccaagct tggatctcct gcagcccggg ggatccgccc acgtacggta ccatctgcta   5340
atattttaaa tcacatgcaa gagaggaggc atggttccat ttctaccttc cacattattt   5400
gagaaaaacg aacttgttct gtgttttatt tttgcccttc acattagtac aacgtggaag   5460
actcatggtt acacagaatc atacataagt acaatgcttg tccctaagaa aacaagcact   5520
cgttgtattg aacctttacg gctcatgcgg ccgcgaattc actagtgatt gaattcgcgg   5580
ccgcttagtc cgacttggcc ttggcggccg cggccgactc tttgagcgtg aagatctgcg   5640
ccgtctcggg cacagcgccg tagttgacaa agaggtgcgc ggtcttgaag aaggccgtga   5700
tgatgggctc gtcgttcctg cgcacgaggt gcgggtacgc ggccgcaaag tgcttggtgg   5760
cttcgttgag cttgtagtgc ggaatgatcg ggaacaagtg gtggacctgg tgcgtgccaa   5820
tgtggtggct caggttgtcc acgaacgcgc cgtacgagcg gtcgacgctc gagaggttgc   5880
ccttgacgta cgtccactcc gagtcgccgt accacggcgt cgcttcgtcg ttgtggtgca   5940
agaaggtcgt aatgacgagg aacgaagcaa agacaaagag cggcgcatag tagtagaggc   6000
ccatgacggc aaagccgagc gagtatgtga ggtacgcgta cgcggcgaag aaggcggccc   6060
agacgccgag cgacacgatg acggccgacg cgcggcgaag gaggagcggg tcccacgggt   6120
caaagtggct catcgtgcgc ggggcatacc cgaccttcaa gtagacaaac cacgcaccgc   6180
cgagcgtgta gacccattgg cgcacgtcct ggaggtcctt gaccgaccgg tgcgggtaaa   6240
agatctcgtc cttatcaatg ttgcccgtgt tcttgtggtg gtggcggtgc gtcacgcgcc   6300
agctctcgaa cggcgtcaaa atcgcagagt gcatgatgca gccgatgata aagttgacgc   6360
tgtggtagcg cgagaaggcc gagtggccgc agtcgtggcc gaccgtgaag aagccccaga   6420
agatgacgcc ctgcacgtag atgtaggtgg cgcaaacgag cgcgtggagc agaacgttat   6480
cggcaatgaa cggcgtcgag cgcgccgcgt agagcagcgc cgccgaggcc gacgcgttga   6540
agatcgcgcg ggccgtgtag tagagcgaga ggccgaggtt cgactcaaag cacgcgttcg   6600
ggatcgagtg cttgagctcc gtgagcgtcg ggaactcgac cttcgtctta tcctcagtca   6660
tgcggccgct gaagtattgc ttcttagtta acctttcctt tctctctcag ctatgtgaat   6720
tcattttgct ttcgtcacaa tttatatagt gaaattggat ctttggagtt aacgccttca   6780
caggattatc gtgttagaac aatgcttttt catgttctaa ttagtagtac attacaaatg   6840
tgcactctat tcaataagca tcttttggca cgttaataaa tcatgtgaaa aaaaaatact   6900
actatttcaa agaaagtgtt gtaaaaagaa acggaaagag agctggcttc agttgttgag   6960
acttgtttgc tagtaaaaat ggtgtgaaga gtgattcatg gtgaggtggt ttttcgtccc   7020
tttctgtttg catgaaaaac aaatggcaag agatgacgta ggattccttc ccttaacgat   7080
```

-continued

```
tatctgtttt taatttcaaa tatacatata ggaatttatg aattactaag gttgtaaaat   7140

atgctggtca tttatttatg gctaaaatat tttttttct cgtaaatata aaaatattta   7200

aaatttattt ttatcatatt ttttatcctt ataaaattat gtgtacaacc tatataaaaa   7260

aatatcatat ttaatattga ttatatgttt aatcaatata aaaaatcatt atcatatatt   7320

tagatttatt cgaatataca tctaaacaaa aaataacata ttttaatttt atgaagaaaa   7380

aaaaatattt tatcctttat ttatttaaga ttaattaata gttatgtatt gtggaaagac   7440

ttttacacat gcaatagata tactgaatca attagatgcc aatgctgagt tggaaatcac   7500

ttgaggaggg gaggagactt gccaatgctt ttcagtttca tttaaatgat ttagtggagg   7560

agatagagta gtgataaagg catgccccaa ttttggagtg tatatatgag tggaaataag   7620

agagggatag agagaaaaaa taaagagagt aaaaataatt aatgtgaaat gatatgataa   7680

aaaaataaag aaagagataa agagaaaaat gaaatgagag atagatgaaa tagagagtag   7740

atacatgttt gtttaggttt tttttaggaa ataacacatt tttttctcat cacttattac   7800

tcactgtcaa tttcctctct ttcaatcata atgatatgat ttgtttaaca aaaatgtgaa   7860

aaaacatata aagtaaaata tttttataaa ttgataaata aaaatttaca aaatttattt   7920

cttattaaat tgaatagaaa atgaaagaaa agaaaagaaa aagtatatat aaaatgatat   7980

agctttaaaa agaataaatt tttcatatca gtcttttttt aataatttag aaatatttaa   8040

gtatatagca aaaatataat gtactttaca tatgcataaa taataatttg aaaatagaac   8100

taatagaata gagaaaaaag taatataata attaactata tgaaaattta gaagggacaa   8160

tatttttaat taagaatata aacaatattt cttttcatgt aatgagggac ggatgtacgg   8220

ggccagtgtt ggagtcaaag ccaaaatagt cacggggaaa ttaatgcact gcatgactat   8280

tcgaaaaaat tcactagcct tacttagatg ttagattaat agctaggggg tgcagataat   8340

tttgaaaggc atgaaaaaca ttaatttgta cattgcaagc ttttgatgac aagctttgca   8400

attgttcaca ctaccttatg ccatttataa atagagtgat tggcatatga aggaaatcat   8460

gagagtcgaa gcgaaaaaca aagcttgaga gtgtaggaaa aatacagttt ttttggtaaa   8520

aatacagtat ttgaatagga gcgaaaaata tcctttcaaa atgatccttt tctttttttt   8580

ttttttctt gttgttcttg gtcagttatt caaaggaaaa gggattgaaa taaaaacttg   8640

catgtgggat cgtacgtcga gtcgacctgc a                                  8671
```

DELTA-5 DESATURASE AND ITS USE IN MAKING POLYUNSATURATED FATTY ACIDS

This application claims the benefit of U.S. Provisional Patent Application 60/801,119, filed May 17, 2006, the entire contents of which are herein incorporated by reference.

FIELD OF THE INVENTION

This invention is in the field of biotechnology. More specifically, this invention pertains to the identification of nucleic acid fragments encoding a delta-5 fatty acid desaturase enzyme and the use of this desaturase in making long chain polyunsaturated fatty acids (PUFAs).

BACKGROUND OF THE INVENTION

The importance of PUFAs is undisputed. For example, certain PUFAs are important biological components of healthy cells and are recognized as: "essential" fatty acids that cannot be synthesized de novo in mammals and instead must be obtained either in the diet or derived by further desaturation and elongation of linoleic acid (LA; 18:2 omega-6) or α-linolenic acid (ALA; 18:3 omega-3); constituents of plasma membranes of cells, where they may be found in such forms as phospholipids or triacylglycerols; necessary for proper development (particularly in the developing infant brain) and for tissue formation and repair; and, precursors to several biologically active eicosanoids of importance in mammals (e.g., prostacyclins, eicosanoids, leukotrienes, prostaglandins). Additionally, a high intake of long-chain omega-3 PUFAs produces cardiovascular protective effects (Dyerberg, J. et al., *Amer. J. Clin. Nutr.,* 28:958-966 (1975); Dyerberg, J. et al., *Lancet,* 2(8081):117-119 (Jul. 15, 1978); Shimokawa, H., *World Rev. Nutr. Diet,* 88:100-108 (2001); von Schacky, C. and Dyerberg, J., *World Rev. Nutr. Diet,* 88:90-99 (2001)). And, numerous other studies document wide-ranging health benefits conferred by administration of omega-3 and/or omega-6 PUFAs against a variety of symptoms and diseases (e.g., asthma, psoriasis, eczema, diabetes, cancer).

A variety of different hosts including plants, algae, fungi and yeast are being investigated as means for commercial PUFA production. Genetic engineering has demonstrated that the natural abilities of some hosts (even those natively limited to LA and ALA fatty acid production) can be substantially altered to result in high-level production of various long-chain omega-3/omega-6 PUFAs. Whether this is the result of natural abilities or recombinant technology, production of arachidonic acid (ARA; 20:4 omega-6), eicosapentaenoic acid (EPA; 20:5 omega-3) and docosahexaenoic acid (DHA; 22:6 omega-3) may all require expression of a delta-5 desaturase.

Most delta-5 desaturase enzymes identified so far have the primary ability to convert dihomo-gamma-linolenic acid (DGLA; 20:3 omega-6) to ARA, with secondary activity in converting eicosatetraenoic acid (ETA; 20:4 omega-3) to EPA (where DHA is subsequently synthesized from EPA following reaction with an additional $C_{20/22}$ elongase and a delta-4 desaturase). The delta-5 desaturase has a role in both the delta-6 desaturase/delta-6 elongase pathway (which is predominantly found in algae, mosses, fungi, nematodes and humans and which is characterized by the production of gamma-linolenic acid (GLA; 18:3 omega-6) omega and/or stearidonic acid (STA; 18:4 omega-3))omega and the delta-9 elongase/delta-8 desaturase pathway (which operates in some organisms, such as euglenoid species and which is characterized by the production of eicosadienoic acid (EDA; 20:2 omega-6)omega and/or eicosatrienoic acid (ETrA; 20:3 omega-3)) omega (FIG. 1).

Based on the role delta-5 desaturase enzymes play in the synthesis of e.g., ARA, EPA and DHA, there has been considerable effort to identify and characterize these enzymes from various sources. As such, numerous delta-5 desaturases have been disclosed in both the open literature (e.g., GenBank Accession No. AF199596, No. AF226273, No. AF320509, No. AB072976, No. AF489588, No. AJ510244, No. AF419297, No. AF07879, No. AF067654 and No. AB022097) and the patent literature (e.g., U.S. Pat. Nos. 5,972,664 and 6,075,183). Also, commonly owned, co-pending application having Provisional Application No. 60/801,172 (filed May 17, 2006) discloses amino acid and nucleic acid sequences for a delta-5 desaturase enzyme from *Euglena gracilis*, while commonly owned, co-pending application having Provisional Application No. 60/915,733 (filed May 3, 2007) discloses amino acid and nucleic acid sequences for a delta-5 desaturase enzyme from *Euglena anabaena.*

The instant invention concerns the identification and isolation of additional genes encoding delta-5 desaturases from *Peridinium* sp. CCMP626 that would be suitable for heterologous expression in a variety of host organisms for use in the production of omega-3/omega-6 fatty acids.

SUMMARY OF THE INVENTION

The present invention concerns an isolated polynucleotide comprising:

(a) a nucleotide sequence encoding a polypeptide having delta-5 desaturase activity, wherein the polypeptide has at least 70%, 75%, 80%, 85%, 90%, 95%, or 100% amino acid identity, based on the Clustal W method of alignment, when compared to an amino acid sequence as set forth in SEQ ID NO:2;

(b) a nucleotide sequence encoding a polypeptide having delta-5 desaturase activity, wherein the nucleotide sequence has at least 70%, 75%, 80%, 85%, 90%, 95%, or 100% sequence identity, based on the BLASTN method of alignment, when compared to a nucleotide sequence as set forth in SEQ ID NO:1 or SEQ ID NO:3;

(c) a nucleotide sequence encoding a polypeptide having delta-5 desaturase activity, wherein the nucleotide sequence hybridizes under stringent conditions to a nucleotide sequence as set forth in SEQ ID NO:1 or SEQ ID NO:3; or (d) a complement of the nucleotide sequence of (a), (b) or (c), wherein the complement and the nucleotide sequence consist of the same number of nucleotides and are 100% complementary.

In a second embodiment, the invention concerns a recombinant DNA construct comprising any of the isolated polynucleotides of the invention operably linked to at least one regulatory sequence.

In a third embodiment, the invention concerns a cell comprising in its genome the recombinant DNA construct of the invention. Such cells can be plant cells or yeast cells.

In a fourth embodiment, the invention concerns a method for transforming a cell, comprising transforming a cell with a recombinant construct of the invention or an isolated polynucleotide of the invention and selecting those cells transformed with the recombinant construct or the isolated polynucleotide.

In a fifth embodiment, the invention concerns transgenic seed comprising in its genome the recombinant construct of the invention or a transgenic seed obtained from a plant made by a method of the invention. Also of interest is oil or by-products obtained from such transgenic seeds.

In a sixth embodiment, the invention concerns a method for making long-chain polyunsaturated fatty acids in a plant cell comprising:

(a) transforming a cell with the recombinant construct of the invention; and
(b) selecting those transformed cells that make long-chain polyunsaturated fatty acids.

In a seventh embodiment, the invention concerns a method for producing at least one polyunsaturated fatty acid in an oilseed plant cell comprising:

(a) transforming an oilseed plant cell with a first recombinant DNA construct comprising an isolated polynucleotide encoding at least one delta-5 desaturase polypeptide, operably linked to at least one regulatory sequence and at least one additional recombinant DNA construct comprising an isolated polynucleotide, operably linked to at least one regulatory sequence, encoding a polypeptide selected from the group consisting of a delta-4 desaturase, a delta-5 desaturase, a delta-6 desaturase, a delta-8 desaturase, a delta-12 desaturase, a delta-15 desaturase, a delta-17 desaturase, a delta-9 desaturase, a delta-9 elongase, a $C_{14/16}$ elongase, a $C_{16/18}$ elongase, a $C_{18/20}$ elongase and a $C_{20/22}$ elongase;
(b) regenerating an oilseed plant from the transformed cell of step (a); and
(c) selecting those seeds obtained from the plants of step (b) having an altered level of polyunsaturated fatty acids when compared to the level in seeds obtained from a nontransformed oilseed plant.

In an eighth embodiment, the invention concerns an oilseed plant comprising in its genome the recombinant construct of the invention. Suitable oilseed plants include, but are not limited to, soybean, *Brassica* species, sunflower, maize, cotton, flax and safflower.

In a ninth embodiment, the invention concerns an oilseed plant comprising:

(a) a first recombinant DNA construct comprising an isolated polynucleotide encoding at least one delta-5 desaturase polypeptide, operably linked to at least one regulatory sequence; and
(b) at least one additional recombinant DNA construct comprising an isolated polynucleotide, operably linked to at least one regulatory sequence, encoding a polypeptide selected from the group consisting of a delta-4 desaturase, a delta-5 desaturase, a delta-6 desaturase, a delta-8 desaturase, a delta-12 desaturase, a delta-15 desaturase, a delta-17 desaturase, a delta-9 desaturase, a delta-9 elongase, a $C_{14/16}$ elongase, a $C_{16/18}$ elongase, a $C_{18/20}$ elongase and a $C_{20/22}$ elongase.

Also of interest are transgenic seeds obtained from such oilseed plants as well as oil or by-products obtained from these transgenic seeds. A preferred by-product is lecithin.

In a tenth embodiment, the invention concerns food or feed incorporating an oil or seed of the invention or food or feed comprising an ingredient derived from the processing of the seeds.

In an eleventh embodiment, the invention concerns progeny plants obtained from obtained from a plant made by the method of the invention or an oilseed plant of the invention.

BRIEF DESCRIPTION OF THE DRAWINGS AND SEQUENCE LISTINGS

FIG. 3 shows a portion of an alignment between and among delta-5 desaturase proteins and delta-8 desaturase proteins using a Clustal W analysis (MegAlign™ program of DNASTAR software).

Figure 4:
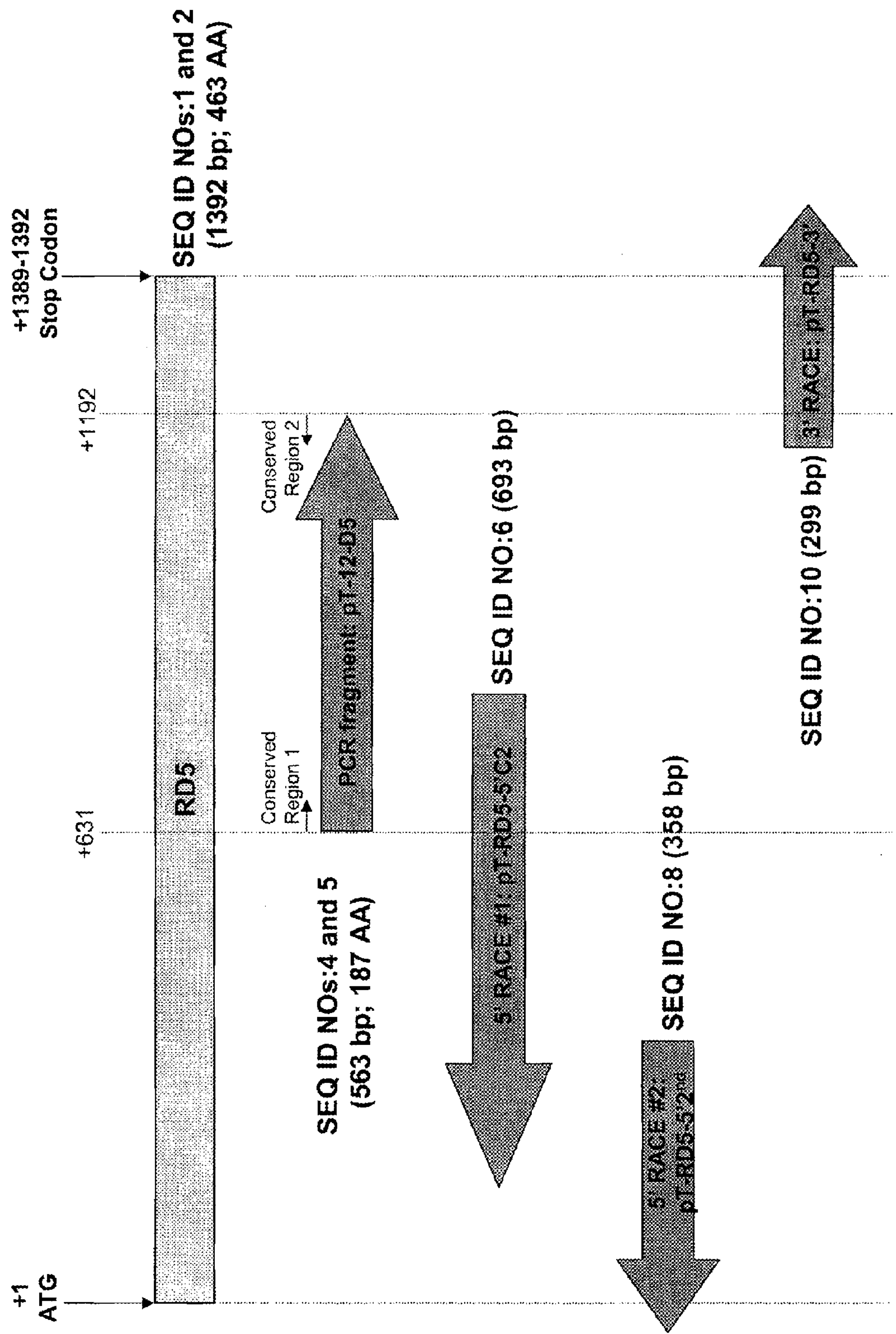

FIG. 4 graphically represents the relationship between SEQ ID NOs:1, 2, 4, 5, 6, 8 and 10, each of which relates to the *Peridinium* sp. CCMP626 delta-5 desaturase.

Figure 5:
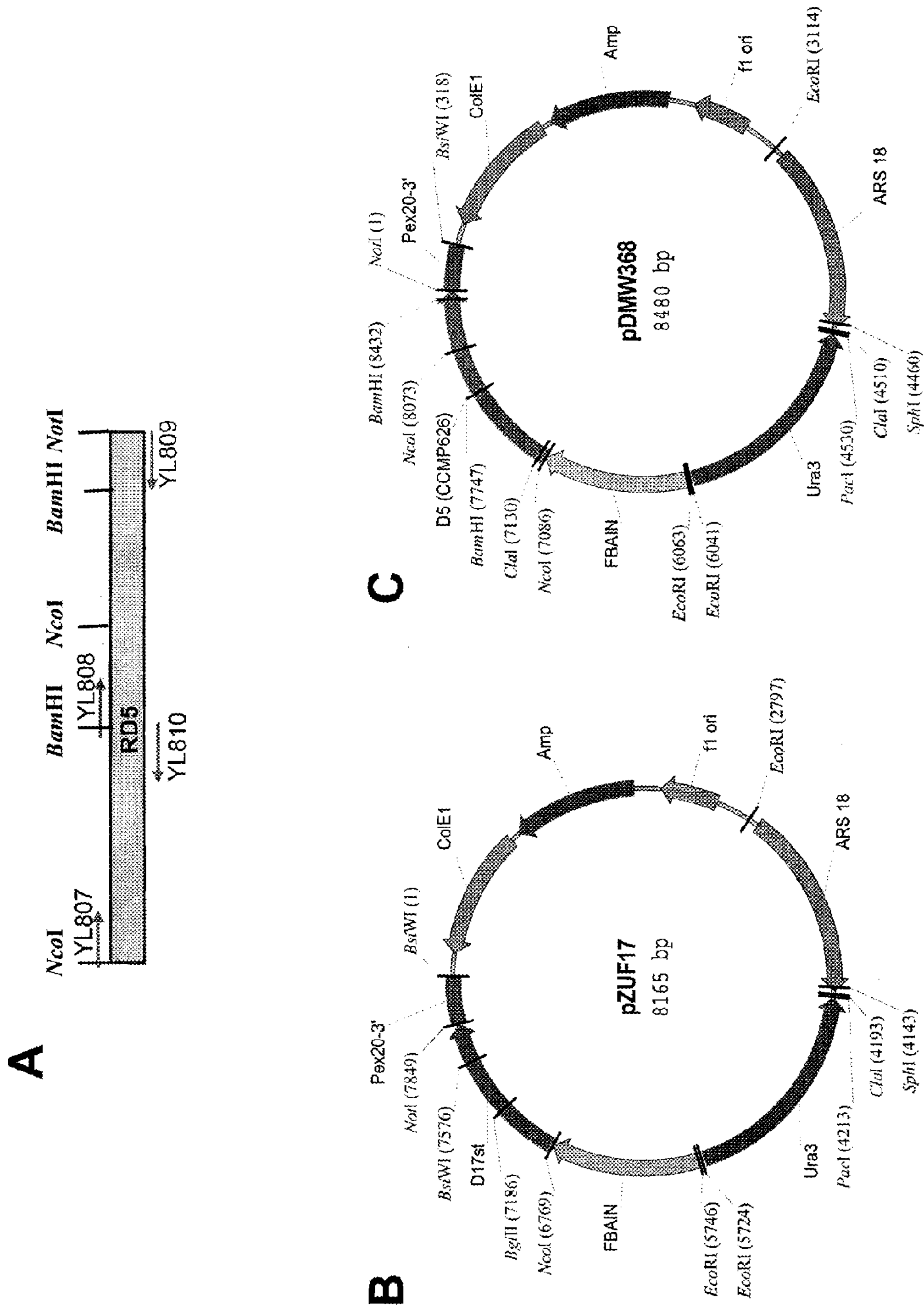

FIG. 5A illustrates the cloning strategy utilized for amplification of the *Peridinium* sp. CCMP626 delta-5 desaturase gene (RD5). FIG. 5B is a plasmid map of pZUF17, while FIG. 5C is a plasmid map of pDMW368.

Figure 6:
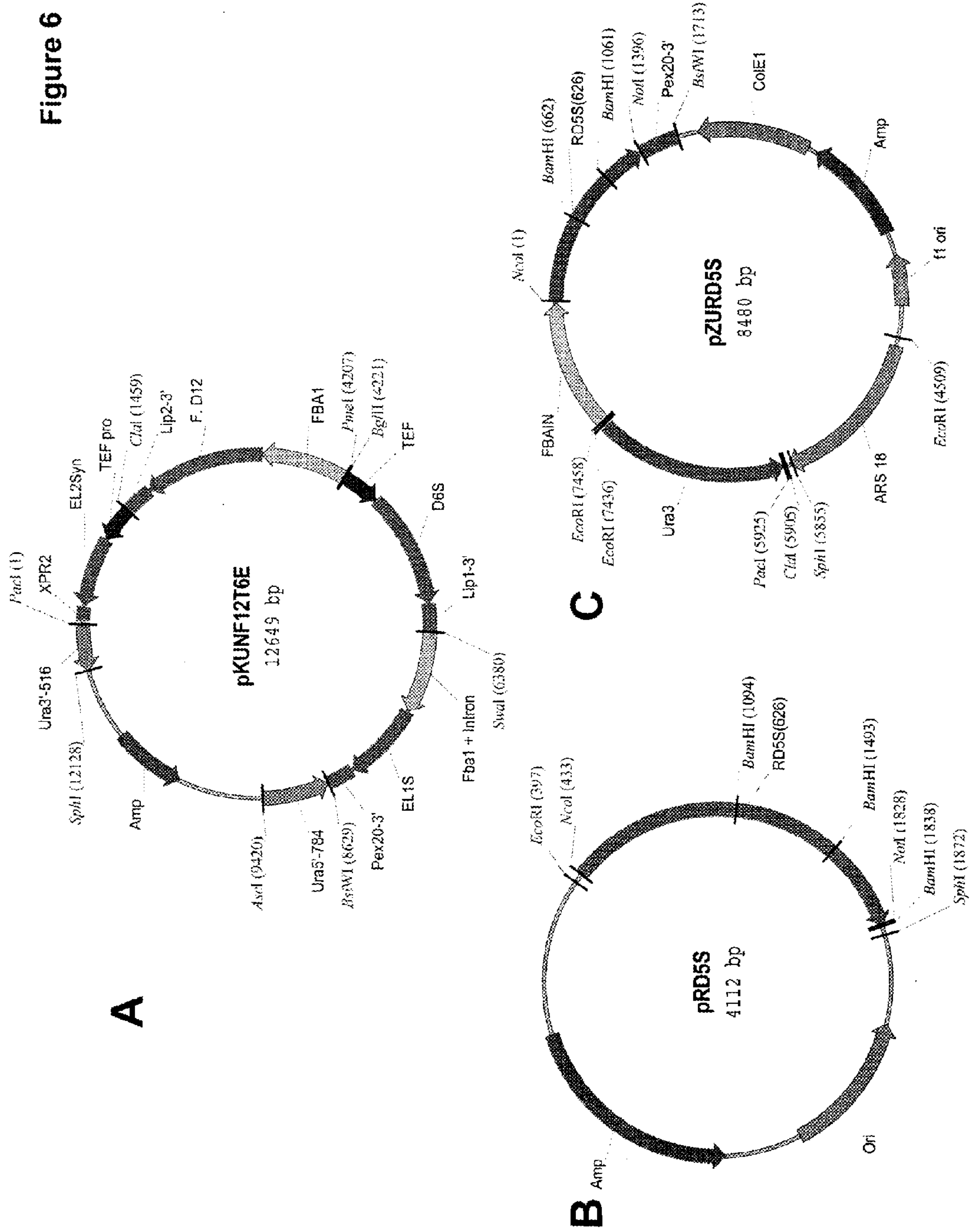

FIG. 6 provides plasmid maps for the following: (A) pKUNF12T6E; (B) pRD5S; and, (C) pZURD5S.

FIGS. 7A and 7B show a comparison of the DNA sequence of the *Peridinium* sp. CCMP626 delta-5 desaturase gene (designated as "RD5"; SEQ ID NO:1) and the synthetic gene (designated as "RD5S"; SEQ ID NO:3) codon-optimized for expression in *Yarrowia lipolytica.*

FIGS. 8A and 8B show a Clustal V alignment (with default parameters) of a *Pavlova lutheri* delta-8 desaturase (SEQ ID NO:18), a *Pavlova salina* delta-8 desaturase (SEQ ID NO:66), a *Euglena gracilis* delta-8 desaturase (SEQ ID NO:16) and two different *Rhizopus stolonifer* delta-6 fatty acid desaturases (SEQ ID NOs:53 and 65).

Figure 9:
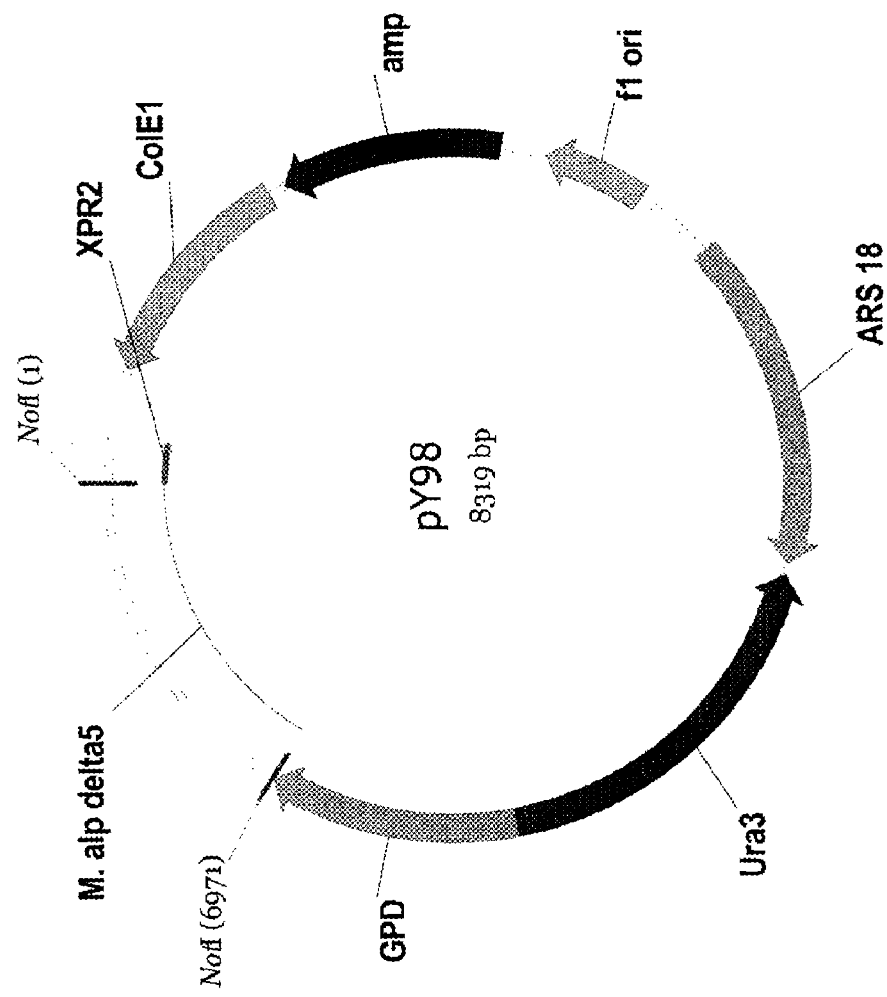

FIG. 9 provides a plasmid map for pY98.

FIG. 10A provides the fatty acid profiles for *Yarrowia lipolytica* expressing pY98 (SEQ ID NO:76; comprising a *Mortierella alpina* delta-5 desaturase gene designated as "MaD5") or pDMW368 (SEQ ID NO:23; comprising the *Peridinium* sp. CCMP626 delta-5 desaturase gene designated as "RD5") and fed various substrates. FIG. 10B provides a comparison of the omega-3 and omega-6 substrate specificity of MaD5 versus RD5.

FIG. 11 provides plasmid maps for the following: (A) pKR916; (B) pKR1038; and, (C) pKR328.

FIG. 12A provides the average fatty acid profiles for ten events having the highest delta-5 desaturase activity when the *Mortierella alpina* enzyme (MaD5) is transformed into soybean embryos. FIG. 12B provides the average fatty acid profiles for ten events having the highest delta-5 desaturase activity when the *Peridinium* sp. CCMP626 enzyme (RD5) is transformed into soybean embryos. Fatty acids are identified as 16:0 (palmitate), 18:0 (stearic acid), 18:1 (oleic acid), LA, ALA, EDA, SCI, DGLA, ARA, ERA, JUP, ETA and EPA. Fatty acids listed as "others" include: 18:2 (5,9), GLA, STA, 20:0, 20:1(11), 20:2 (7,11) or 20:2 (8,11) and DPA. Each of these "other" fatty acids is present at a relative abundance of less than 3.0% of the total fatty acids. Fatty acid compositions for an individual embryo were expressed as the weight percent (wt. %) of total fatty acids and the average fatty acid composition is an average of six individual embryos for each event.

Figure 13:
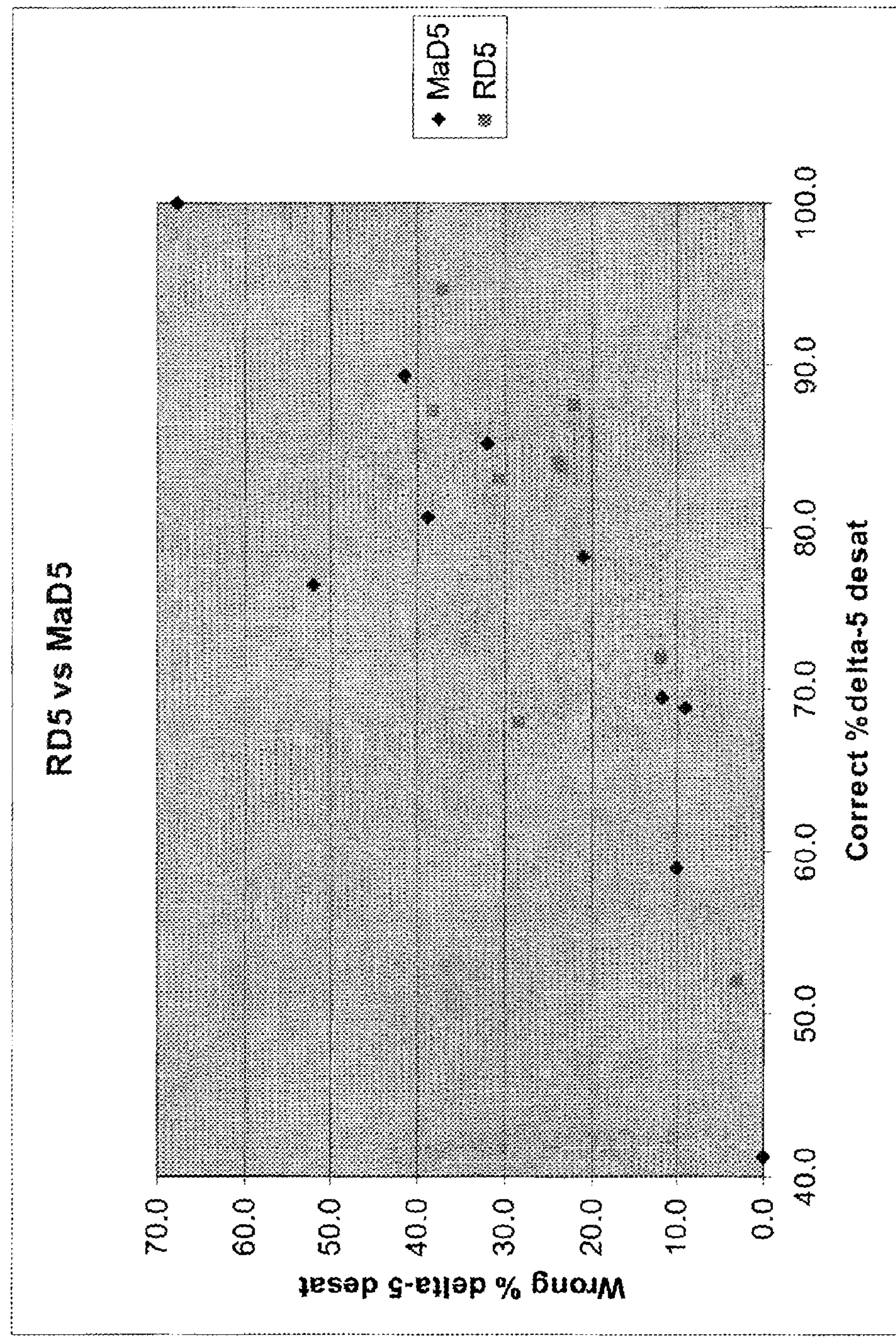

FIG. 13 provides the activity of the delta-5 desaturase for the "correct" substrates (i.e., DGLA and ETA) versus the "wrong" substrates (i.e., EDA and ERA). The activity of the delta-5 desaturase for the "correct" substrates ("Correct % delta-5 desat") is plotted on the x-axis and the activity of the delta-5 desaturase for the "wrong" substrates ("Wrong % delta-5 desat") is plotted on the y-axis for MaD5 (see FIG. 12A) or RD5 (see FIG. 12B).

The invention can be more fully understood from the following detailed description and the accompanying sequence descriptions, which form a part of this application.

The following sequences comply with 37 C.F.R. §1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs:1-26, 50, 51, 53-56, 63-72 and 75-76 are ORFs encoding genes or proteins (or portions thereof), or plasmids, as identified in Table 1.

TABLE 1

Summary Of Nucleic Acid And Protein SEQ ID Numbers

| Description and Abbreviation | Nucleic acid SEQ ID NO. | Protein SEQ ID NO. |
|---|---|---|
| *Peridinium* sp. CCMP626 delta-5 desaturase ("RD5") | 1 (1392 bp) | 2 (463 AA) |
| Synthetic delta-5 desaturase, derived from *Peridinium* sp. CCMP626, codon-optimized for expression in *Yarrowia lipolytica* ("RD5S") | 3 (1392 bp) | 2 (463 AA) |
| *Peridinium* sp. CCMP626-fragment of pT-12-D5 | 4 (563 bp) | 5 (187 AA) |
| *Peridinium* sp. CCMP626--fragment of pT-RD5-5'C2 | 6 (693 bp) | — |
| *Peridinium* sp. CCMP626--5' sequence relative to SEQ ID NO: 4 | 7 (511 bp) | — |
| *Peridinium* sp. CCMP626--fragment of pT-RD5-5'$2^{nd}$ | 8 (358 bp) | — |
| *Peridinium* sp. CCMP626--5' sequence relative to SEQ ID NO: 6 | 9 (161 bp) | — |
| *Peridinium* sp. CCMP626--fragment of pT-RD5-3' | 10 (299 bp) | — |
| *Peridinium* sp. CCMP626-3' sequence relative to SEQ ID NO: 4 | 11 (247 bp) | — |
| *Pythium irregulare* delta-5 desaturase (GenBank Accession No. AAL13311) | — | 12 (456 AA) |
| *Phytophthora megasperma* delta-5 desaturase (GenBank Accession No. CAD53323) | — | 13 (477 AA) |
| *Phaeodactylum tricornutum* delta-5 desaturase (GenBank Accession No. AAL92562) | — | 14 (469 AA) |
| *Dictyostelium discoideum* delta-5 desaturase (GenBank Accession No. XP_640331) | — | 15 (467 AA) |
| *Euglena gracilis* delta-8 desaturase (PCT Publications No. WO 2006/012325 and No. WO 2006/012326) | — | 16 (421 AA) |
| *Pavlova lutheri* (CCMP459) delta-8 desaturase | 17 (1269 bp) | 18 (423 AA) |
| Conserved Region 1 | — | 19 (7 AA) |
| Conserved Region 2 | — | 20 (7 AA) |
| *Thalassiosira pseudonana* delta-8 sphingolipid desaturase (GenBank Accession No. AAX14502) | — | 21 (476 AA) |
| Plasmid pZUF17 | 22 (8165 bp) | — |
| Plasmid pDMW368 | 23 (8480 bp) | — |
| Plasmid pKUNF12T6E | 24 (12,649 bp) | — |
| Synthetic $C_{18/20}$ elongase gene derived from *Thraustochytrium aureum* (U.S. Pat. No. 6,677,145), codon-optimized for expression in *Yarrowia lipolytica* ("EL2S") | 25 (819 bp) | 26 (272 AA) |
| Plasmid pRD5S | 50 (4112 bp) | — |

TABLE 1-continued

Summary Of Nucleic Acid And Protein SEQ ID Numbers

| Description and Abbreviation | Nucleic acid SEQ ID NO. | Protein SEQ ID NO. |
|---|---|---|
| Plasmid pZURD5S | 51 (8480 bp) | — |
| *Rhizopus stolonifer* delta-6 fatty acid desaturase (NCBI Accession No. AAX22052) | — | 53 (459 AA) |
| *Pavlova lutheri* delta-8 desaturase--portion of cDNA insert from clone eps1c.pk002.f22 (5' end of cDNA insert) | 54 (695 bp) | — |
| *Pavlova lutheri* delta-8 desaturase--fully sequenced EST eps1c.pk002.f22:fis (full insert sequence) | 55 (1106 bp) | — |
| *Pavlova lutheri* delta-8 desaturase-translation of nucleotides 1-864 of fully sequenced EST eps1c.pk002.f22:fis (full insert sequence; SEQ ID NO: 55) | — | 56 (287 AA) |
| *Pavlova lutheri* delta-8 desaturase--full 5' end sequence from genome walking | 63 (1294 bp) | — |
| *Pavlova lutheri* delta-8 desaturase-assembled sequence | 64 (1927 bp) | — |
| *Rhizopus stolonifer* delta-6 fatty acid desaturase (NCBI Accession No. ABB96724) | — | 65 (459 AA) |
| *Pavlova salina* delta-8 desaturase | — | 66 (427 AA) |
| *Mortierella alpina* delta-5 desaturase | 67 (1338 bp) | 68 (446 AA) |
| Plasmid pY5-22 | 69 (6473 bp) | — |
| Plasmid pY5-22GPD | 70 (6970 bp) | — |
| *Yarrowia lipolytica* glyceraldehyde-3-phosphate dehydrogenase promoter (GPD) | 71 (968 bp) | — |
| Plasmid pYZDE2-S | 72 (8630 bp) | — |
| Plasmid pKR136 | 75 (6339 bp) | — |
| Plasmid pY98 | 76 (8319 bp) | — |
| *Euglena gracilis* delta-9 elongase ("EgD9e") | 77 (774 bp) | — |
| *Euglena gracilis* delta-8 desaturase ("EgD8") | 78 (1263 bp) | — |
| Plasmid pKR906 | 81 (4311 bp) | — |
| Plasmid pKR72 | 82 (7085 bp) | — |
| Plasmid pKS102 | 83 (2540 bp) | — |
| Plasmid pKR197 | 84 (4359 bp) | — |
| Plasmid pKR911 | 85 (5147 bp) | — |
| Plasmid pKR680 | 86 (6559 bp) | — |
| Plasmid pKR913 | 87 (9014 bp) | — |
| Plasmid pKR767 | 88 (5561 bp) | — |
| Plasmid pKR916 | 89 (11,889 bp) | — |
| Plasmid pKR974 | 90 (5661 bp) | — |
| *Saprolegnia diclina* delta-5 desaturase ("SdD5") | 91 (1413 bp) | — |
| Plasmid pKR1033 | 92 (5621 bp) | — |
| Plasmid pKR1038 | 93 (11,949 bp) | — |
| Plasmid pKR328 | 94 (8671 bp) | — |

SEQ ID NOs:27-29 correspond to AP primer, Smart IV oligonucleotide primer and CDSIII 5' primer, respectively, used for *Peridinium* sp. CCMP626 cDNA synthesis.

SEQ ID NOs:30-33 correspond to degenerate oligonucleotide primers 5-1A, 5-1B, 5-1C and 5-1D, respectively, that encode Conserved Region 1.

SEQ ID NOs:34-37 correspond to degenerate oligonucleotide primers 5-4AR, 5-4BR, 5-4CR and 5-4DR, respectively, that encode Conserved Region 2.

SEQ ID NOs:38-42 correspond to primers ODMW520, ODMW521, DNR CDS 5', ODMW541 and ODMW542, respectively, used for 5' RACE.

SEQ ID NOs:43-45 correspond to primers ODMW523, AUAP and ODMW524, respectively, used for 3' RACE.

SEQ ID NOs:46-49 correspond to primers YL807, YL810, YL808 and YL809, respectively, used for amplification of the full length cDNA of RD5.

SEQ ID NO:52 corresponds to primer T7, used for sequencing the *Pavlova lutheri* (CCMP459) cDNA library.

SEQ ID NOs:57 and 58 correspond to primers SeqE and SeqW, respectively, used for sequencing *Pavlova lutheri* (CCMP459) clones.

SEQ ID NOs:59 and 60 correspond to the universal primer AP1 and primer GSP PvDES, respectively, used for amplification of genomic *Pavlova lutheri* (CCMP459) DNA.

SEQ ID NOs:61 and 62 correspond to primers M13-28Rev and PavDES seq, respectively, used for sequencing *Pavlova lutheri* (CCMP459) genomic inserts.

SEQ ID NOs:73 and 74 are primers GPDsense and GPDantisense, respectively, used for amplifying the GPD promoter.

SEQ ID NOs:79 and 80 correspond to primers oEugEL1-1 and oEugEL1-2, respectively, used to amplify a *Euglena gracilis* delta-9 elongase (EgD9e).

DETAILED DESCRIPTION OF THE INVENTION

All patents, patent applications, and publications cited herein are incorporated by reference in their entirety. This specifically includes the following Applicants' Assignee's co-pending applications: U.S. Pat. Nos. 7,125,672, 7,189,559, 7,192,762, 7,198,937, 7,202,356, U.S. patent application Ser. Nos. 10/840,579 and 10/840,325 (filed May 6, 2004), U.S. patent application Ser. No. 10/869,630 (filed Jun. 16, 2004), U.S. patent application Ser. No. 10/882,760 (filed Jul. 1, 2004), U.S. patent application Ser. No. 10/985,254 and No. 10/985,691 (filed Nov. 10, 2004), U.S. patent application Ser. No. 11/024,544 (filed Dec. 29, 2004), U.S. patent application Ser. No. 11/166,993 (filed Jun. 24, 2005), U.S. patent application Ser. No. 11/183,664 (filed Jul. 18, 2005), U.S. patent application Ser. No. 11/185,301 (filed Jul. 20, 2005), U.S. patent application Ser. No. 11/190,750 (filed Jul. 27, 2005), U.S. patent application Ser. No. 11/198,975 (filed Aug. 8, 2005), U.S. patent application Ser. No. 11/225,354 (filed Sep. 13, 2005), U.S. patent application Ser. No. 11/253,882 (filed Oct. 19, 2005), U.S. patent application Ser. Nos. 11/264,784 and 11/264,737 (filed Nov. 1, 2005), U.S. patent application Ser. No. 11/265,761 (filed Nov. 2, 2005), U.S. patent application Ser. No. 11/737,772 (filed Apr. 20, 2007), U.S. patent application Ser. No. 11/787,772 (filed Apr. 17, 2007), U.S. patent application Ser. No. 11/740,298 (filed Apr. 26, 2007), U.S. Patent Applications No. 60/801,172 and No. 60/801,119 (filed May 17, 2006), U.S. Patent Application No. 60/853,563 (filed Oct. 23, 2006), U.S. Patent Application No. 60/855,177 (filed Oct. 30, 2006), U.S. patent application Ser. Nos. 11/601,563 and 11/601,564 (filed Nov. 16, 2006), U.S. patent application Ser. No. 11/635,258 (filed Dec. 7, 2006), U.S. patent application Ser. No. 11/613,420 (filed Dec. 20, 2006), U.S. Patent Application No. 60/909,790 (filed Apr. 3, 2007), U.S. Patent Application No. 60/911,925 (filed Apr. 16, 2007), U.S. Patent Application No. 60/910,831 (filed Apr. 10, 2007) and U.S. Patent Application No. 60/915,733 (filed May 3, 2007). This additionally includes the following Applicants' Assignee's co-pending applications: PCT Publication No. US 2004/0172682, concerning the production of PUFAs in plants; and, U.S. Pat. No. 7,129,089, concerning annexin promoters and their use in expression of transgenes in plants.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

In accordance with the subject invention, Applicants identify a novel *Peridinium* sp. CCMP626 delta-5 desaturase enzyme and gene encoding the same that may be used for the manipulation of biochemical pathways for the production of healthful PUFAs. Thus, the subject invention finds many applications.

PUFAs, or derivatives thereof, made by the methodology disclosed herein can be used as dietary substitutes, or supplements, particularly infant formulas, for patients undergoing intravenous feeding or for preventing or treating malnutrition. Alternatively, the purified PUFAs (or derivatives thereof) may be incorporated into cooking oils, fats or margarines formulated so that in normal use the recipient would receive the desired amount for dietary supplementation. The PUFAs may also be incorporated into infant formulas, nutritional supplements or other food products and may find use as anti-inflammatory or cholesterol lowering agents. Optionally, the compositions may be used for pharmaceutical use (human or veterinary).

Supplementation of humans or animals with PUFAs produced by recombinant means can result in increased levels of the added PUFAs, as well as their metabolic progeny. For example, treatment with EPA can result not only in increased levels of EPA, but also downstream products of EPA such as eicosanoids (i.e., prostaglandins, leukotrienes, thromboxanes). Complex regulatory mechanisms can make it desirable to combine various PUFAs, or add different conjugates of PUFAs, in order to prevent, control or overcome such mechanisms to achieve the desired levels of specific PUFAs in an individual.

Definitions

In this disclosure, a number of terms and abbreviations are used. The following definitions are provided.

"Open reading frame" is abbreviated ORF.

"Polymerase chain reaction" is abbreviated PCR.

"American Type Culture Collection" is abbreviated ATCC.

"Polyunsaturated fatty acid(s)" is abbreviated PUFA(s).

"Triacylglycerols" are abbreviated TAGs.

The term "invention" or "present invention" as used herein is not meant to be limiting to any one specific embodiment of the invention but applies generally to any and all embodiments of the invention as described in the claims and specification.

The term "fatty acids" refers to long chain aliphatic acids (alkanoic acids) of varying chain lengths, from about $C_{12}$ to $C_{22}$ (although both longer and shorter chain-length acids are known). The predominant chain lengths are between $C_{16}$ and $C_{22}$. The structure of a fatty acid is represented by a simple notation system of "X:Y", where X is the total number of carbon (C) atoms in the particular fatty acid and Y is the number of double bonds. Additional details concerning the differentiation between "saturated fatty acids" versus "unsaturated fatty acids", "monounsaturated fatty acids" versus "polyunsaturated fatty acids" (or "PUFAs"), and "omega-6 fatty acids" (omega-6 or n-6) versus "omega-3 fatty acids" (omega-3 or n-3) are provided in U.S. Patent Publication No. 2005/0136519.

Fatty acids are described herein by a simple notation system of "X:Y", wherein X is number of carbon (C) atoms in the particular fatty acid and Y is the number of double bonds. The number following the fatty acid designation indicates the position of the double bond from the carboxyl end of the fatty acid with the "c" affix for the cis-configuration of the double bond (e.g., palmitic acid (16:0), stearic acid (18:0), oleic acid (18:1, 9c), petroselinic acid (18:1, 6c), LA (18:2, 9c,12c), GLA (18:3, 6c,9c,12c) and ALA (18:3, 9c,12c,15c)). Unless otherwise specified, 18:1, 18:2 and 18:3 refer to oleic, LA and ALA fatty acids, respectively. If not specifically written as otherwise, double bonds are assumed to be of the cis configuration. For instance, the double bonds in 18:2 (9,12) would be assumed to be in the cis configuration.

Nomenclature used to describe PUFAs in the present disclosure is shown below in Table 2. In the column titled "Shorthand Notation", the omega-reference system is used to indicate the number of carbons, the number of double bonds and the position of the double bond closest to the omega carbon, counting from the omega carbon (which is numbered 1 for this purpose). The remainder of the Table summarizes the common names of omega-3 and omega-6 fatty acids and their precursors, the abbreviations that will be used throughout the specification and each compounds' chemical name.

TABLE 2

Nomenclature of Polyunsaturated Fatty Acids And Precursors

| Common Name | Abbreviation | Chemical Name | Shorthand Notation |
|---|---|---|---|
| Myristic | — | tetradecanoic | 14:0 |
| Palmitic | Palmitate | hexadecanoic | 16:0 |
| Palmitoleic | — | 9-hexadecenoic | 16:1 |
| Stearic | — | octadecanoic | 18:0 |
| Oleic | — | cis-9-octadecenoic | 18:1 |
| Linoleic | LA | cis-9,12-octadecadienoic | 18:2 omega-6 |
| γ-Linoleic | GLA | cis-6,9,12-octadecatrienoic | 18:3 omega-6 |
| Eicosadienoic | EDA | cis-11,14-eicosadienoic | 20:2 omega-6 |
| Dihomo-γ-Linoleic | DGLA | cis-8,11,14-eicosatrienoic | 20:3 omega-6 |
| Arachidonic | ARA | cis-5,8,11,14-eicosatetraenoic | 20:4 omega-6 |
| α-Linolenic | ALA | cis-9,12,15-octadecatrienoic | 18:3 omega-3 |
| Stearidonic | STA | cis-6,9,12,15-octadecatetraenoic | 18:4 omega-3 |
| Eicosatrienoic | ETrA or ERA | cis-11,14,17-eicosatrienoic | 20:3 omega-3 |
| Sciadonic | SCI | cis-5,11,14-eicosatrienoic | 20:3b omega-6 |
| Juniperonic | JUP | cis-5,11,14,17-eicosatetraenoic | 20:4b omega-3 |
| Eicosa-tetraenoic | ETA | cis-8,11,14,17-eicosatetraenoic | 20:4 omega-3 |
| Eicosa-pentaenoic | EPA | cis-5,8,11,14,17-eicosapentaenoic | 20:5 omega-3 |
| Docosa-pentaenoic | DPA | cis-7,10,13,16,19-docosapentaenoic | 22:5 omega-3 |
| Docosa-hexaenoic | DHA | cis-4,7,10,13,16,19-docosahexaenoic | 22:6 omega-3 |

The terms "triacylglycerol", "oil" and "TAGs" refer to neutral lipids composed of three fatty acyl residues esterified to a glycerol molecule (and such terms will be used interchangeably throughout the present disclosure herein). Such oils can contain long chain PUFAs, as well as shorter saturated and unsaturated fatty acids and longer chain saturated fatty acids. Thus, "oil biosynthesis" generically refers to the synthesis of TAGs in the cell.

"Percent (%) PUFAs in the total lipid and oil fractions" refers to the percent of PUFAs relative to the total fatty acids in those fractions. The term "total lipid fraction" or "lipid fraction" both refer to the sum of all lipids (i.e., neutral and polar) within an oleaginous organism, thus including those lipids that are located in the phosphatidylcholine (PC) fraction, phosphatidyletanolamine (PE) fraction and triacylglycerol (TAG or oil) fraction. However, the terms "lipid" and "oil" will be used interchangeably throughout the specification.

A metabolic pathway, or biosynthetic pathway, in a biochemical sense, can be regarded as a series of chemical reactions occurring within a cell, catalyzed by enzymes, to achieve either the formation of a metabolic product to be used or stored by the cell, or the initiation of another metabolic pathway (then called a flux generating step). Many of these pathways are elaborate, and involve a step by step modification of the initial substance to shape it into a product having the exact chemical structure desired.

The term "PUFA biosynthetic pathway" refers to a metabolic process that converts oleic acid to LA, EDA, GLA, DGLA, ARA, ALA, STA, ETrA, ETA, EPA, DPA and DHA. This process is well described in the literature (e.g., see PCT Publication No. WO 2006/052870). Briefly, this process involves elongation of the carbon chain through the addition of carbon atoms and desaturation of the molecule through the addition of double bonds, via a series of special desaturation and elongation enzymes (i.e., "PUFA biosynthetic pathway enzymes") present in the endoplasmic reticulim membrane. More specifically, "PUFA biosynthetic pathway enzymes" refer to any of the following enzymes (and genes which encode said enzymes) associated with the biosynthesis of a PUFA, including: a delta-4 desaturase, a delta-5 desaturase, a delta-6 desaturase, a delta-12 desaturase, a delta-15 desaturase, a delta-17 desaturase, a delta-9 desaturase, a delta-8 desaturase, a delta-9 elongase, a $C_{14/16}$ elongase, a $C_{16/18}$ elongase, a $C_{18/20}$ elongase and/or a $C_{20/22}$ elongase.

Figure 1:
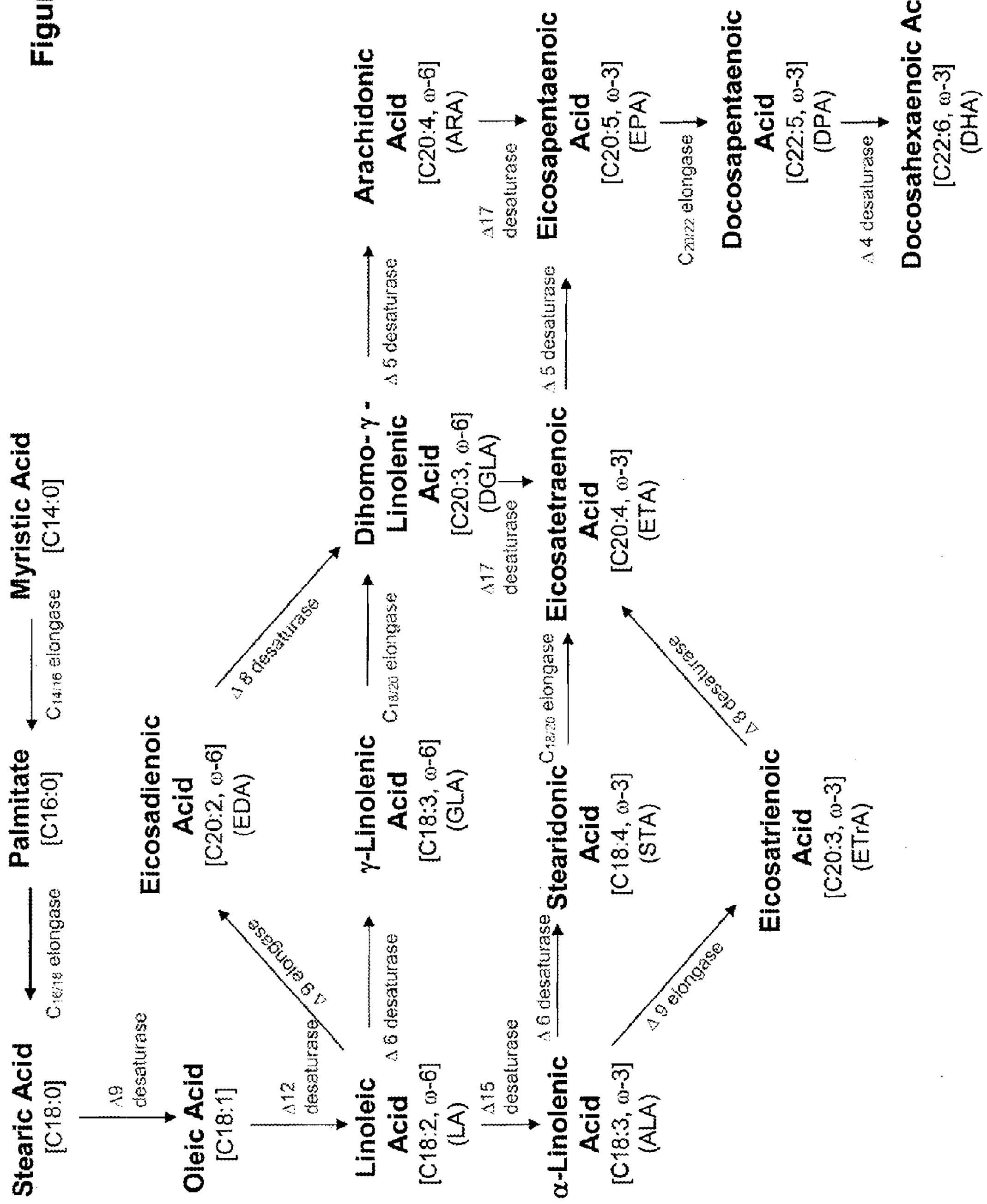
FIG. 1 illustrates the omega-3/omega-6 fatty acid biosynthetic pathway.

The term "omega-3/omega-6 fatty acid biosynthetic pathway" refers to a set of genes which, when expressed under the appropriate conditions encode enzymes that catalyze the production of either or both omega-3 and omega-6 fatty acids. Typically the genes involved in the omega-3/omega-6 fatty acid biosynthetic pathway encode PUFA biosynthetic pathway enzymes. A representative pathway is illustrated in FIG. 1, providing for the conversion of myristic acid through various intermediates to DHA, which demonstrates how both omega-3 and omega-6 fatty acids may be produced from a common source. The pathway is naturally divided into two portions where one portion will generate omega-3 fatty acids and the other portion, only omega-6 fatty acids. That portion that only generates omega-3 fatty acids will be referred to herein as the omega-3 fatty acid biosynthetic pathway, whereas that portion that generates only omega-6 fatty acids will be referred to herein as the omega-6 fatty acid biosynthetic pathway.

The term "functional" as used herein in context with the omega-3/omega-6 fatty acid biosynthetic pathway means that some (or all) of the genes in the pathway express active enzymes, resulting in in vivo catalysis or substrate conversion. It should be understood that "omega-3/omega-6 fatty acid biosynthetic pathway" or "functional omega-3/omega-6 fatty acid biosynthetic pathway" does not imply that all the genes listed in the above paragraph are required, as a number of fatty acid products will only require the expression of a subset of the genes of this pathway.

The term "delta-6 desaturase/delta-6 elongase pathway" will refer to a PUFA biosynthetic pathway that minimally includes at least one delta-6 desaturase and at least one $C_{18/20}$ elongase, thereby enabling biosynthesis of DGLA and/or ETA from LA and ALA, respectively, with GLA and/or STA as intermediate fatty acids. With expression of other desaturases and elongases, ARA, EPA, DPA and DHA may also be synthesized.

The term "delta-9 elongase/delta-8 desaturase pathway" will refer to a PUFA biosynthetic pathway that minimally includes at least one delta-9 elongase and at least one delta-8 desaturase, thereby enabling biosynthesis of DGLA and/or ETA from LA and ALA, respectively, with EDA and/or ETrA as intermediate fatty acids. With expression of other desaturases and elongases, ARA, EPA, DPA and DHA may also be synthesized.

The term "intermediate fatty acid" refers to any fatty acid produced in a fatty acid metabolic pathway that can be further converted to an intended product fatty acid in this pathway by the action of other metabolic pathway enzymes. For instance, when EPA is produced using the delta-9 elongase/delta-8 desaturase pathway, EDA, ETrA, DGLA, ETA and ARA can be produced and are considered "intermediate fatty acids" since these fatty acids can be further converted to EPA via action of other metabolic pathway enzymes.

The term "by-product fatty acid" refers to any fatty acid produced in a fatty acid metabolic pathway that is not the intended fatty acid product of the pathway nor an "intermediate fatty acid" of the pathway. For instance, when EPA is produced using the delta-9 elongase/delta-8 desaturase pathway, sciadonic acid (SCI) and juniperonic acid (JUP) also can be produced by the action of a delta-5 desaturase on either EDA or ETrA, respectively. They are considered to be "by-product fatty acids" since neither can be further converted to EPA by the action of other metabolic pathway enzymes.

The term "desaturase" refers to a polypeptide that can desaturate, i.e., introduce a double bond, in one or more fatty acids to produce a fatty acid or precursor of interest. Despite use of the omega-reference system throughout the specification to refer to specific fatty acids, it is more convenient to indicate the activity of a desaturase by counting from the carboxyl end of the substrate using the delta-system. Of particular interest herein are delta-5 desaturases that catalyze the conversion of DGLA to ARA and/or ETA to EPA. Other desaturases include: 1.) delta-17 desaturases that desaturate a fatty acid between the $17^{th}$ and $18^{th}$ carbon atom numbered from the carboxyl-terminal end of the molecule and which, for example, catalyze the conversion of ARA to EPA and/or DGLA to ETA; 2.) delta-6 desaturases that catalyze the conversion of LA to GLA and/or ALA to STA; 3.) delta-12 desaturases that catalyze the conversion of oleic acid to LA; 4.) delta-15 desaturases that catalyze the conversion of LA to ALA and/or GLA to STA; 5.) delta-4 desaturases that catalyze the conversion of DPA to DHA; 6.) delta-8 desaturases that catalyze the conversion of EDA to DGLA and/or ETrA to ETA; and, 7.) delta-9 desaturases that catalyze the conversion of palmitate to palmitoleic acid (16:1) and/or stearate to oleic acid. In the art, delta-15 and delta-17 desaturases are also occasionally referred to as "omega-3 desaturases", "w-3 desaturases", and/or "omega-3 desaturases", based on their ability to convert omega-6 fatty acids into their omega-3 counterparts (e.g., conversion of LA into ALA and ARA into EPA, respectively). In some embodiments, it is most desirable to empirically determine the specificity of a particular fatty acid desaturase by transforming a suitable host with the gene for the fatty acid desaturase and determining its effect on the fatty acid profile of the host.

The term "delta-5 desaturase" refers to an enzyme that desaturates a fatty acid between the fifth and sixth carbon atom numbered from the carboxyl-terminal end of the molecule. Preferably, a delta-5 desaturase converts dihomo-gamma-linolenic acid [20:3, DGLA] to arachidonic acid [20:4, ARA] or converts eicosatetraenoic acid [20:4, ETA] to eicosapentaenoic acid [20:5, EPA].

For the purposes herein, the term "RD5" refers to a delta-5 desaturase enzyme (SEQ ID NO:2) isolated from *Peridinium* sp. CCMP626, encoded by SEQ ID NO:1 herein. Similarly, the term "RD5S" refers to a synthetic delta-5 desaturase derived from *Peridinium* sp. CCMP626 that is codon-optimized for expression in *Yarrowia lipolytica* (i.e., SEQ ID NOs:3 and 2).

The terms "conversion efficiency" and "percent substrate conversion" refer to the efficiency by which a particular enzyme (e.g., a desaturase) can convert substrate to product. The conversion efficiency is measured according to the following formula: ([product]/[substrate+product])*100, where 'product' includes the immediate product and all products in the pathway derived from it.

The term "elongase" refers to a polypeptide that can elongate a fatty acid carbon chain to produce an acid that is 2 carbons longer than the fatty acid substrate that the elongase acts upon. This process of elongation occurs in a multi-step mechanism in association with fatty acid synthase, as described in U.S. Patent Publication No. 2005/0132442 and PCT Publication No. WO 2005/047480. Examples of reactions catalyzed by elongase systems are the conversion of GLA to DGLA, STA to ETA and EPA to DPA. In general, the substrate selectivity of elongases is somewhat broad but segregated by both chain length and the degree and type of unsaturation. For example, a $C_{14/16}$ elongase will utilize a $C_{14}$ substrate (e.g., myristic acid), a $C_{16/18}$ elongase will utilize a $C_{16}$ substrate (e.g., palmitate), a $C_{18/20}$ elongase (also known as a delta-6 elongase as the terms can be used interchangeably) will utilize a $C_{18}$ substrate (e.g., GLA, STA) and a $C_{20/22}$ elongase will utilize a $C_{20}$ substrate (e.g., EPA). In like manner, a delta-9 elongase is able to catalyze the conversion of LA and ALA to EDA and ETrA, respectively. It is important to note that some elongases have broad specificity and thus a single enzyme may be capable of catalyzing several elongase reactions (e.g., thereby acting as both a $C_{16/18}$ elongase and a $C_{18/20}$ elongase).

The term "oleaginous" refers to those organisms that tend to store their energy source in the form of lipid (Weete, In: Fungal Lipid Biochemistry, $2^{nd}$ Ed., Plenum, 1980). The term "oleaginous yeast" refers to those microorganisms classified as yeasts that can make oil. Generally, the cellular oil or TAG content of oleaginous microorganisms follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.,* 57:419-25 (1991)). It is not uncommon for oleaginous microorganisms to accumulate in excess of about 25% of their dry cell weight as oil. Examples of oleaginous yeast include, but are no means limited to, the following genera: *Yarrowia, Candida, Rhodotorula, Rhodosporidium, Cryptococcus, Trichosporon* and *Lipomyces.*

The term "conservative amino acid substitution" refers to a substitution of an amino acid residue in a given protein with another amino acid, without altering the chemical or functional nature of that protein. For example, it is well known in the art that alterations in a gene that result in the production of a chemically equivalent amino acid at a given site (but that do not affect the structural and functional properties of the encoded, folded protein) are common. For the purposes of the present invention, "conservative amino acid substitutions" are defined as exchanges within one of the following five groups:

1. small aliphatic, nonpolar or slightly polar residues: Ala [A], Ser [S], Thr [T] (Pro [P], Gly [G]);
2. polar, negatively charged residues and their amides: Asp [D], Asn [N], Glu [E], Gln [Q];
3. polar, positively charged residues: His [H], Arg [R], Lys [K];
4. large aliphatic, nonpolar residues: Met [M], Leu [L], Ile [I], Val [V] (Cys [C]); and,
5. large aromatic residues: Phe [F], Tyr [Y], Trp [W].

Conservative amino acid substitutions generally maintain: 1) the structure of the polypeptide backbone in the area of the substitution; 2) the charge or hydrophobicity of the molecule at the target site; or 3) the bulk of the side chain. Additionally, in many cases, alterations of the N-terminal and C-terminal portions of the protein molecule would also not be expected to alter the activity of the protein.

As used herein, "nucleic acid" means a polynucleotide and includes single or double-stranded polymer of deoxyribonucleotide or ribonucleotide bases. Nucleic acids may also include fragments and modified nucleotides. Thus, the terms "polynucleotide", "nucleic acid sequence", "nucleotide sequence" or "nucleic acid fragment" are used interchangeably and is a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deosycytidylate, "G" for guanylate or deoxyguanylate, "U" for uridlate, "T" for deosythymidylate, "R" for purines (A or G), "Y" for pyrimidiens (C or T), "K" for G or T, "H" for A or C or T, "I" for inosine, and "N" for any nucleotide.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of chimeric genes to produce the desired phenotype in a transformed plant. Chimeric genes can be designed for use in suppression by linking a nucleic acid fragment or subfragment thereof, whether or not it encodes an active enzyme, in the sense or antisense orientation relative to a plant promoter sequence.

The term "conserved domain" or "motif" means a set of amino acids conserved at specific positions along an aligned sequence of evolutionarily related proteins. While amino acids at other positions can vary between homologous proteins, amino acids that are highly conserved at specific positions indicate amino acids that are essential in the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family.

The terms "homology", "homologous", "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that substantially similar nucleic acid sequences encompassed by this invention are also defined by their ability to hybridize (under moderately stringent conditions, e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, or 90% sequence identity, up to and including 100% sequence identity (i.e., fully complementary) with each other.

The term "stringent conditions" or "stringent hybridization conditions" includes reference to conditions under which a probe will selectively hybridize to its target sequence. Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth et al., *Anal. Biochem.* 138:267-284 (1984): $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistryand Molecular Biology—Hybridization with Nucleic Acid Probes*, Part I, Chapter 2 "Overview of principles of hybridization and the strategy of nucleic acid probe assays", Elsevier, New York (1993); and *Current Protocols in Molecular Biology*, Chapter 2, Ausubel et al., Eds., Greene Publishing and Wiley-Interscience, New York (1995). Hybridization and/or wash conditions can be applied for at least 10, 30, 60, 90, 120, or 240 minutes.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.*, 215: 403-410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches the complete amino acid and nucleotide sequence encoding encoding particular algal proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable of hybridizing to one another. For example, with respect to DNA, adenosine is complementary to thymine and cytosine is complementary to guanine. Accordingly, the invention herein also includes isolated nucleic acid fragments that are complementary to the complete sequences as reported in the accompanying Sequence Listing, as well as those substantially similar nucleic acid sequences.

The terms "homology" and "homologous" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the present invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that homologous nucleic acid sequences encompassed by this invention are also defined by their ability to hybridize, under moderately stringent conditions (e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein.

"Codon degeneracy" refers to the nature in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the instant algal polypeptide as set forth in SEQ ID NO:2. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Chemically synthesized", as related to a sequence of DNA, means that the component nucleotides were assembled in vitro. Manual chemical synthesis of DNA may be accomplished using well-established procedures or, automated chemical synthesis can be performed using one of a number of commercially available machines. "Synthetic genes" can be assembled from oligonucleotide building blocks that are chemically synthesized using procedures known to those skilled in the art. These building blocks are ligated and annealed to form gene segments that are then enzymatically assembled to construct the entire gene. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell, where sequence information is available.

"Gene" refers to a nucleic acid fragment that expresses a specific protein, and that may refer to the coding region alone or may include regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene that is introduced into the host organism by gene transfer. Foreign genes can comprise native genes inserted into a non-native organism, native genes introduced into a new location within the native host, or chimeric genes. A "transgene" is a gene that has been introduced into the genome by a transformation procedure. A "codon-optimized gene" is a gene having its frequency of codon usage designed to mimic the frequency of preferred codon usage of the host cell.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing sites, effector binding sites and stem-loop structures.

The term "allele" refers to one of several alternative forms of a gene occupying a given locus on a chromosome. When all the alleles present at a given locus on a chromosome are the same, then that plant is homozygous at that locus. If the alleles present at a given locus on a chromosome differ, then that plant is heterozygous at that locus.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

A promoter sequence may consist of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue-specificity of a promoter. New promoters of various types useful in plant cells are constantly being discovered; numerous examples may be found in the compilation by Okamuro, J. K., and Goldberg, R. B., *Biochemistry of Plants,* 15:1-82 (1989).

"Translation leader sequence" refers to a polynucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D., *Mol. Biotechnol.,* 3:225-236 (1995)).

The terms "3' non-coding sequences" and "transcription terminator" refer to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" or "mRNA" refers to the RNA that is without introns and that can be translated into protein by the cell. "cDNA" refers to a double-stranded DNA that is complementary to, and derived from, mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; PCT Publication No. WO 99/28508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated and yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragments of the invention. Expression may also refer to translation of mRNA into a polypeptide.

"Mature" protein refers to a post-translationally processed polypeptide, i.e., one from which any pre- or propeptides present in the primary translation product have been removed. "Precursor" protein refers to the primary product of translation of mRNA, i.e., with pre- and propeptides still present. Pre- and propeptides may be (but are not limited to) intracellular localization signals.

"Transformation" refers to the transfer of a nucleic acid molecule into a host organism, resulting in genetically stable inheritance. The nucleic acid molecule may be a plasmid that replicates autonomously, for example, or, it may integrate into the genome of the host organism. Host organisms containing the transformed nucleic acid fragments are referred to as "transgenic" or "recombinant" or "transformed" organisms.

The terms "plasmid", "vector" and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Expression cassette" refers to a specific vector containing a foreign gene and having elements in addition to the foreign gene that allow for enhanced expression of that gene in a foreign host.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and, 5.) *Sequence Analysis Primer* (Gribskov, M. and Devereux, J., Eds.) Stockton: NY (1991).

Preferred methods to determine identity are designed to give the best match between the sequences tested. Methods to determine identity and similarity are codified in publicly available computer programs. Sequence alignments and percent identity calculations may be performed using the MegAlign™ program of the LASERGENE bioinformatics computing suite (DNASTAR Inc., Madison, Wis.). Multiple alignment of the sequences is performed using the "Clustal method of alignment" which encompasses several varieties of the algorithm including the "Clustal V method of alignment" corresponding to the alignment method labeled Clustal V (described by Higgins and Sharp, *CABIOS,* 5:151-153 (1989); Higgins, D. G. et al., *Comput. Appl. Biosci.,* 8:189-191 (1992)) and found in the MegAlign™ program of the LASERGENE bioinformatics computing suite (DNASTAR Inc.). For multiple alignments, the default values correspond to GAP PENALTY=10 and GAP LENGTH PENALTY=10. Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program. Additionally the "Clustal W method of alignment" is available and corresponds to the alignment method labeled Clustal W (described by Higgins and Sharp, *CABIOS,* 5:151-153 (1989); Higgins, D. G. et al., *Comput. Appl. Biosci.,* 8:189-191 (1992)) and found in the MegAlign™ v6.1 program of the LASERGENE bioinformatics computing suite (DNASTAR Inc.). Default parameters for multiple alignment correspond to GAP PENALTY=10, GAP LENGTH PENALTY=0.2, Delay Divergen Seqs(%)=30, DNA Transition Weight=0.5, Protein Weight Matrix=Gonnet Series, DNA Weight Matrix=IUB. After alignment of the sequences using the Clustal W program, it is possible to obtain a "percent identity" by viewing the "sequence distances" table in the same program.

"BLASTN method of alignment" is an algorithm provided by the National Center for Biotechnology Information (NCBI) to compare nucleotide sequences using default parameters.

It is well understood by one skilled in the art that many levels of sequence identity are useful in identifying polypeptides, from other species, wherein such polypeptides have the same or similar function or activity. Suitable nucleic acid fragments (isolated polynucleotides of the present invention) encode polypeptides that are at least about 70% identical, preferably at least about 75% identical, and more preferably at least about 80% identical to the amino acid sequences reported herein. Preferred nucleic acid fragments encode amino acid sequences that are at least about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Although preferred ranges are described above, any integer amino acid identity from 67% to 100% may be useful in describing the present invention, such as 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%.

Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

The term "conserved domain" or "motif" means a set of amino acids conserved at specific positions along an aligned sequence of evolutionarily related proteins. While amino acids at other positions can vary between homologous proteins, amino acids that are highly conserved at specific positions indicate amino acids that are essential in the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.,* 215:403-410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, *Comput. Methods Genome Res*., [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized. With regard to the BLASTP algorithm used herein default parameters will include the Robinson and Robinson amino acid frequencies (Robinson A. B., Robinson L. R., *Proc. Natl Acad. Sci. U.S.A.,* 88:8880-8884 (1991)), the BLOSUM62 scoring matrix and the gap cost Δ(g)=11+g.

The term "plant parts" includes differentiated and undifferentiated tissues including, but not limited to the following: roots, stems, shoots, leaves, pollen, seeds, tumor tissue and various forms of cells and culture (e.g., single cells, protoplasts, embryos and callus tissue). The plant tissue may be in plant or in a plant organ, tissue or cell culture.

The term "plant organ" refers to plant tissue or group of tissues that constitute a morphologically and functionally distinct part of a plant.

The term "genome" refers to the following: (1) the entire complement of genetic material (genes and non-coding sequences) present in each cell of an organism, or virus or organelle; (2) a complete set of chromosomes inherited as a (haploid) unit from one parent.

Standard recombinant DNA and molecular cloning techniques used herein are well known in the art and are described by Sambrook, J., Fritsch, E. F. and Maniatis, T., *Molecular Cloning: A Laboratory Manual,* $2^{nd}$ ed., Cold Spring Harbor Laboratory: Cold Spring Harbor, N.Y. (1989) (hereinafter "Maniatis"); by Silhavy, T. J., Bennan, M. L. and Enquist, L. W., *Experiments with Gene Fusions*, Cold Spring Harbor Laboratory Cold Spring Harbor, N.Y. (1984); and by Ausubel, F. M. et al., *Current Protocols in Molecular Biology*, published by Greene Publishing Assoc. and Wiley-Interscience, Hoboken, N.J. (1987).

The terms "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., *EMBO J.* 4:2411-2418 (1985); De Almeida et al., *Mol. Gen. Genetics* 218:78-86 (1989)), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others.

The term "expression", as used herein, refers to the production of a functional end-product (e.g., a mRNA or a protein [either precursor or mature]).

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

"Mature" protein refers to a post-translationally processed polypeptide (i.e., one from which any pre- or propeptides present in the primary translation product have been removed). "Precursor" protein refers to the primary product of translation of mRNA (i.e., with pre- and propeptides still present). Pre- and propeptides may be but are not limited to intracellular localization signals.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms.

As used herein, "transgenic" refers to a plant or a cell which comprises within its genome a heterologous polynucleotide. Preferably, the heterologous polynucleotide is stably integrated within the genome such that the polynucleotide is passed on to successive generations. The heterologous polynucleotide may be integrated into the genome alone or as part of an expression construct. Transgenic is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Antisense inhibition" refers to the production of antisense RNA transcripts capable of suppressing the expression of the target protein. "Co-suppression" refers to the production of sense RNA transcripts capable of suppressing the expression of identical or substantially similar foreign or endogenous genes (U.S. Pat. No. 5,231,020). Co-suppression constructs in plants previously have been designed by focusing on overexpression of a nucleic acid sequence having homology to an endogenous mRNA, in the sense orientation, which results in the reduction of all RNA having homology to the overexpressed sequence (Vaucheret et al., *Plant J.* 16:651-659 (1998); Gura, *Nature* 404:804-808 (2000)). The overall efficiency of this phenomenon is low, and the extent of the RNA reduction is widely variable. More recent work has described the use of "hairpin" structures that incorporate all, or part, of an mRNA encoding sequence in a complementary orientation that results in a potential "stem-loop" structure for the expressed RNA (PCT Publication No. WO 99/53050, published Oct. 21, 1999; PCT Publication No. WO 02/00904, published Jan. 3, 2002). This increases the frequency of co-suppression in the recovered transgenic plants. Another variation describes the use of plant viral sequences to direct the suppression, or "silencing", of proximal mRNA encoding sequences (PCT Publication No. WO 98/36083, published Aug. 20, 1998). Both of these co-suppressing phenomena have not been elucidated mechanistically, although genetic evidence has begun to unravel this complex situation (Elmayan et al., *Plant Cell* 10:1747-1757 (1998)).

An Overview Microbial Biosynthesis of Fatty Acids and Triacylglycerols

In general, lipid accumulation in oleaginous microorganisms is triggered in response to the overall carbon to nitrogen ratio present in the growth medium. This process, leading to the de novo synthesis of free palmitate (16:0) in oleaginous microorganisms, is described in detail in PCT Publication No. WO 2004/101757. Palmitate is the precursor of longer-chain saturated and unsaturated fatty acid derivates, which are formed through the action of elongases and desaturases (FIG. 1).

TAGs (the primary storage unit for fatty acids) are formed by a series of reactions that involve: 1.) the esterification of one molecule of acyl-CoA to glycerol-3-phosphate via an acyltransferase to produce lysophosphatidic acid; 2.) the esterification of a second molecule of acyl-CoA via an acyltransferase to yield 1,2-diacylglycerol phosphate (commonly identified as phosphatidic acid); 3.) removal of a phosphate by phosphatidic acid phosphatase to yield 1,2-diacylglycerol (DAG); and, 4.) the addition of a third fatty acid by the action of an acyltransferase to form TAG. A wide spectrum of fatty acids can be incorporated into TAGs, including saturated and unsaturated fatty acids and short-chain and long-chain fatty acids.

Biosynthesis of Omega Fatty Acids

The metabolic process wherein oleic acid is converted to omega-3/omega-6 fatty acids involves elongation of the carbon chain through the addition of carbon atoms and desaturation of the molecule through the addition of double bonds. This requires a series of special desaturation and elongation enzymes present in the endoplasmic reticulim membrane. However, as seen in FIG. 1 and as described below, there are often multiple alternate pathways for production of a specific omega-3/omega-6 fatty acid.

Specifically, all pathways require the initial conversion of oleic acid to LA, the first of the omega-6 fatty acids, by a delta-12 desaturase. Then, using the "delta-6 desaturase/delta-6 elongase pathway", omega-6 fatty acids are formed as follows: (1) LA is converted to GLA by a delta-6 desaturase; (2) GLA is converted to DGLA by a $C_{18/20}$ elongase; and, (3) DGLA is converted to ARA by a delta-5 desaturase. Alternatively, the "delta-6 desaturase/delta-6 elongase pathway" can be utilized for formation of omega-3 fatty acids as follows: (1) LA is converted to ALA, the first of the omega-3 fatty acids, by a delta-15 desaturase; (2) ALA is converted to STA by a delta-6 desaturase; (3) STA is converted to ETA by a $C_{18/20}$ elongase; (4) ETA is converted to EPA by a delta-5 desaturase; (5) EPA is converted to DPA by a $C_{20/22}$ elongase; and, (6) DPA is converted to DHA by a delta-4 desaturase. Optionally, omega-6 fatty acids may be converted to omega-3 fatty acids; for example, ETA and EPA are produced from DGLA and ARA, respectively, by delta-17 desaturase activity.

Alternate pathways for the biosynthesis of omega-3/omega-6 fatty acids utilize a delta-9 elongase and delta-8 desaturase. More specifically, LA and ALA may be converted to EDA and ETrA, respectively, by a delta-9 elongase; then, a delta-8 desaturase converts EDA to DGLA and/or ETrA to ETA.

It is contemplated that the particular functionalities required to be expressed in a specific host organism for production of omega-3/omega-6 fatty acids will depend on the host cell (and its native PUFA profile and/or desaturase/elongase profile), the availability of substrate, and the desired end product(s). One skilled in the art will be able to identify various candidate genes encoding each of the enzymes desired for omega-3/omega-6 fatty acid biosynthesis. Useful desaturase and elongase sequences may be derived from any source, e.g., isolated from a natural source (from bacteria, algae, fungi, plants, animals, etc.), produced via a semi-synthetic route or synthesized de novo. Although the particular source of the desaturase and elongase genes introduced into the host is not critical, considerations for choosing a specific polypeptide having desaturase or elongase activity include: 1.) the substrate specificity of the polypeptide; 2.) whether the polypeptide or a component thereof is a rate-limiting enzyme; 3.) whether the desaturase or elongase is essential for synthesis of a desired PUFA; and/or, 4.) co-factors required by the polypeptide. The expressed polypeptide preferably has parameters compatible with the biochemical environment of its location in the host cell (see PCT Publication No. WO 2004/101757 for additional details).

In additional embodiments, it will also be useful to consider the conversion efficiency of each particular desaturase and/or elongase. More specifically, since each enzyme rarely functions with 100% efficiency to convert substrate to product, the final lipid profile of un-purified oils produced in a host cell will typically be a mixture of various PUFAs consisting of the desired omega-3/omega-6 fatty acid, as well as various upstream intermediary PUFAs. Thus, each enzyme's conversion efficiency is also a variable to consider, when optimizing biosynthesis of a desired fatty acid.

With each of the considerations above in mind, candidate genes having the appropriate desaturase and elongase activities (e.g., delta-6 desaturases, $C_{18/20}$ elongases, delta-5 desaturases, delta-17 desaturases, delta-15 desaturases, delta-9 desaturases, delta-12 desaturases, $C_{14/16}$ elongases, $C_{16/18}$ elongases, delta-9 elongases, delta-8 desaturases, delta-4 desaturases and $C_{20/22}$ elongases) can be identified according to publicly available literature (e.g., GenBank), the patent literature, and experimental analysis of organisms having the ability to produce PUFAs. These genes will be suitable for introduction into a specific host organism, to enable or enhance the organism's synthesis of PUFAs.

Sequence Identification of a Novel *Peridinium* sp. CCMP626 Delta-5 Desaturase

In the present invention, a nucleotide sequence (SEQ ID NO:1) has been isolated from *Peridinium* sp. CCMP626 encoding a delta-5 desaturase (SEQ ID NO:2), designated herein as "RD5".

Comparison of the RD5 nucleotide base and deduced amino acid sequences to public databases reveals that the most similar known sequences are about 67% identical to the amino acid sequence of RD5 reported herein over a length of 463 amino acids using a Clustal W alignment method. More preferred amino acid fragments are at least about 70%-80% identical to the sequences herein, where those sequences that are at least about 80%-90% identical are particularly suitable and those sequences that are at least about 90%-95% identical are most preferred. Similarly, preferred RD5 encoding nucleic acid sequences corresponding to the instant ORF are those encoding active proteins and which are at least about 70%-80% identical to the nucleic acid sequences of RD5 reported herein, where those sequences that are at least about 80%-90% identical are particularly suitable and those sequences that are at least about 90%-95% identical are most preferred.

In alternate embodiments, the instant RD5 desaturase sequence can be codon-optimized for expression in a particular host organism. As is well known in the art, this can be a useful means to further optimize the expression of the enzyme in the alternate host, since use of host-preferred codons can substantially enhance the expression of the foreign gene encoding the polypeptide. In general, host-preferred codons can be determined within a particular host species of interest by examining codon usage in proteins (preferably those expressed in the largest amount) and determining which codons are used with highest frequency. Then, the coding sequence for a polypeptide of interest having e.g., desaturase activity can be synthesized in whole or in part using the codons preferred in the host species.

In one preferred embodiment of the invention herein, RD5 was codon-optimized for expression in *Yarrowia lipolytica*. This was possible by first determining the *Y. lipolytica* codon usage profile (see PCT Publication No. WO 04/101757 and U.S. Pat. No. 7,125,672) and identifying those codons that were preferred. Then, for further optimization of gene expression in *Y. lipolytica*, the consensus sequence around the 'ATG' initiation codon was determined. This optimization resulted in modification of 247 bp of the 1392 bp coding region (17.7%) and optimization of 229 codons of the total 463 codons (49.4%). None of the modifications in the codon-optimized gene ("RD5S"; SEQ ID NO:3) changed the amino acid sequence of the encoded protein (SEQ ID NO:2). As described in Example 11, the codon-optimized gene was 8.9% more efficient desaturating DGLA to ARA than the wildtype gene, when expressed in *Y. lipolytica.*

One skilled in the art would be able to use the teachings herein to create various other codon-optimized delta-5 desaturase proteins suitable for optimal expression in alternate hosts (i.e., other than *Yarrowia lipolytica*), based on the wildtype RD5 sequence. Accordingly, the instant invention relates to any codon-optimized delta-5 desaturase protein that is derived from the wildtype RD5 (i.e., encoded by SEQ ID NO:2). This includes, but is not limited to, the nucleotide sequence set forth in SEQ ID NO:3, which encodes a synthetic delta-5 desaturase protein (i.e., RD5S) that was codon-optimized for expression in *Yarrowia lipolytica.*

Identification and Isolation of Homologs

Any of the instant desaturase sequences (i.e., RD5, RD5S) or portions thereof may be used to search for delta-5 desaturase homologs in the same or other bacterial, algal, fungal, or plant species using sequence analysis software. In general, such computer software matches similar sequences by assigning degrees of homology to various substitutions, deletions, and other modifications.

Alternatively, any of the instant desaturase sequences or portions thereof may also be employed as hybridization reagents for the identification of delta-5 homologs. The basic components of a nucleic acid hybridization test include a probe, a sample suspected of containing the gene or gene fragment of interest and a specific hybridization method. Probes of the present invention are typically single-stranded nucleic acid sequences that are complementary to the nucleic acid sequences to be detected. Probes are "hybridizable" to the nucleic acid sequence to be detected. Although the probe length can vary from 5 bases to tens of thousands of bases, typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added (e.g., guanidinium chloride, guanidinium thiocyanate, sodium thiocyanate, lithium tetrachloroacetate, sodium perchlorate, rubidium tetrachloroacetate, potassium iodide, cesium trifluoroacetate). If desired, one can add formamide to the hybridization mixture, typically 30-50% (v/v).

Various hybridization solutions can be employed. Typically, these comprise from about 20 to 60% volume, preferably 30%, of a polar organic solvent. A common hybridization solution employs about 30-50% v/v formamide, about 0.15 to 1 M sodium chloride, about 0.05 to 0.1 M buffers (e.g., sodium citrate, Tris-HCl, PIPES or HEPES (pH range about 6-9)), about 0.05 to 0.2% detergent (e.g., sodium dodecylsulfate), or between 0.5-20 mM EDTA, FICOLL (Pharmacia Inc.) (about 300-500 kdal), polyvinylpyrrolidone (about 250-500 kdal), and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate) and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

In additional embodiments, any of the delta-5 desaturase nucleic acid fragments described herein (or any homologs identified thereof) may be used to isolate genes encoding homologous proteins from the same or other bacterial, algal, fungal, or plant species. Isolation of homologous genes using sequence-dependent protocols is well known in the art. Examples of sequence-dependent protocols include, but are not limited to: 1.) methods of nucleic acid hybridization; 2.) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor, S. et al., *Proc. Natl. Acad. Sci. U.S.A.,* 82:1074 (1985); or strand displacement amplification (SDA), Walker, et al., *Proc. Natl. Acad. Sci. U.S.A.,* 89:392 (1992)]; and 3.) methods of library construction and screening by complementation.

For example, genes encoding similar proteins or polypeptides to the delta-5 desaturases described herein could be isolated directly by using all or a portion of the instant nucleic acid fragments as DNA hybridization probes to screen libraries from e.g., any desired yeast or fungus using methodology well known to those skilled in the art (wherein those organisms producing ARA [or derivatives thereof] would be preferred). Specific oligonucleotide probes based upon the instant nucleic acid sequences can be designed and synthesized by methods known in the art (Maniatis, supra). Moreover, the entire sequences can be used directly to synthesize DNA probes by methods known to the skilled artisan (e.g., random primers DNA labeling, nick translation or end-labeling techniques), or RNA probes using available in vitro transcription systems. In addition, specific primers can be designed and used to amplify a part of (or full-length of) the instant sequences. The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotides as specific hybridization probes in the Diagnosis of Genetic Disorders", in *Human Genetic Diseases: A Practical Approach*, K. E. Davis Ed., (1986) pp 33-50, IRL: Herndon, Va.; and Rychlik, W., In *Methods in Molecular Biology*, White, B. A. Ed., (1993) Vol. 15, pp 31-39, PCR Protocols: Current Methods and Applications. Humania: Totowa, N.J.).

Generally two short segments of the instant sequences may be used in PCR protocols to amplify longer nucleic acid fragments encoding homologous genes from DNA or RNA. PCR may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding eukaryotic genes.

Alternatively, the second primer sequence may be based upon sequences derived from the cloning vector. For example, the skilled artisan can follow the RACE protocol (Frohman et al., *Proc. Natl. Acad. Sci. U.S.A.,* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (Gibco/BRL, Gaithersburg, Md.), specific 3' or 5' cDNA fragments can be isolated (Ohara et al., *Proc. Natl. Acad. Sci. U.S.A.,* 86:5673 (1989); Loh et al., *Science,* 243:217 (1989)).

In other embodiments, any of the delta-5 desaturase nucleic acid fragments described herein (or any homologs identified thereof) may be used for creation of new and improved fatty acid desaturases. As is well known in the art, in vitro mutagenesis and selection, chemical mutagenesis, "gene shuffling" methods or other means can be employed to obtain mutations of naturally occurring desaturase genes. Alternatively, improved fatty acids may be synthesized by domain swapping, wherein a functional domain from any of the delta-5 desaturase nucleic acid fragments described herein are exchanged with a functional domain in an alternate desaturase gene to thereby result in a novel protein.

Methods for Production of Various Omega-3 and/or Omega-6 Fatty Acids

It is expected that introduction of chimeric genes encoding the delta-5 desaturases described herein (i.e., RD5, RD5S or other mutant enzymes, codon-optimized enzymes or homologs thereof), under the control of the appropriate promoters will result in increased production of ARA and/or EPA in the transformed host organism, respectively. As such, the present invention encompasses a method for the direct production of PUFAs comprising exposing a fatty acid substrate (i.e., DGLA or ETA) to the desaturase enzymes described herein (e.g., RD5, RD5S), such that the substrate is converted to the desired fatty acid product (i.e., ARA or EPA, respectively).

More specifically, it is an object of the present invention to provide a method for the production of ARA in a host cell (e.g., oleaginous yeast, soybean), wherein the host cell comprises:

(i) an isolated nucleotide molecule encoding a delta-5 desaturase polypeptide having at least 67% identity when compared to a polypeptide having an amino acid sequence as set forth in SEQ ID NO:2, based on BLASTP algorithms or Clustal W alignment methods; and, (ii) a source of dihomo-γ-linoleic acid;

wherein the host cell is grown under conditions such that the delta-5 desaturase is expressed and the DGLA is converted to ARA, and wherein the ARA is optionally recovered.

The person of skill in the art will recognize that the broad substrate range of the delta-5 desaturase may additionally allow for the use of the enzyme for the conversion of ETA to EPA. Accordingly the invention provides a method for the production of EPA, wherein the host cell comprises:

(i) an isolated nucleotide molecule encoding a delta-5 desaturase polypeptide having at least 67% identity when compared to a polypeptide having an amino acid sequence as set forth in SEQ ID NO:2, based on BLASTP algorithms or Clustal W alignment methods; and, (ii) a source of ETA;

wherein the host cell is grown under conditions such that the delta-5 desaturase is expressed and the ETA is converted to EPA, and wherein the EPA is optionally recovered.

Alternatively, each delta-5 desaturase gene and its corresponding enzyme product described herein can be used indirectly for the production of omega-3 fatty acids (see U.S. Patent Publication No. 2005/0136519). Indirect production of omega-3/omega-6 PUFAs occurs wherein the fatty acid substrate is converted indirectly into the desired fatty acid product, via means of an intermediate step(s) or pathway intermediate(s). Thus, it is contemplated that the delta-5 desaturases described herein (e.g., RD5, RD5S or other mutant enzymes, codon-optimized enzymes or homologs thereof) may be expressed in conjunction with additional genes encoding enzymes of the PUFA biosynthetic pathway (e.g., delta-6 desaturases, $C_{18/20}$ elongases, delta-17 desaturases, delta-15 desaturases, delta-9 desaturases, delta-12 desaturases, $C_{14/16}$ elongases, $C_{16/18}$ elongases, delta-9 elongases, delta-8 desaturases, delta-4 desaturases, $C_{20/22}$ elongases) to result in higher levels of production of longer-chain omega-3 fatty acids (e.g., EPA, DPA and DHA). The particular genes included within a particular expression cassette will depend on the host cell (and its PUFA profile and/or desaturase/elongase profile), the availability of substrate and the desired end product(s).

In alternative embodiments, it may be useful to disrupt a host organism's native delta-5 desaturase, based on the complete sequences described herein, the complement of those complete sequences, substantial portions of those sequences, codon-optimized desaturases derived therefrom and those sequences that are substantially homologous thereto.

Plant Expression Systems, Cassettes and Vectors, and Transformation

In one embodiment, this invention concerns a recombinant construct comprising any one of the delta-5 desaturase polynucleotides of the invention operably linked to at least one regulatory sequence suitable for expression in a plant. A promoter is a DNA sequence that directs cellular machinery of a plant to produce RNA from the contiguous coding sequence downstream (3') of the promoter. The promoter region influences the rate, developmental stage, and cell type in which the RNA transcript of the gene is made. The RNA transcript is processed to produce mRNA which serves as a template for translation of the RNA sequence into the amino acid sequence of the encoded polypeptide. The 5' non-translated leader sequence is a region of the mRNA upstream of the protein coding region that may play a role in initiation and translation of the mRNA. The 3' transcription termination/polyadenylation signal is a non-translated region downstream of the protein coding region that functions in the plant cell to cause termination of the RNA transcript and the addition of polyadenylate nucleotides to the 3' end of the RNA.

The origin of the promoter chosen to drive expression of the delta-5 desaturase coding sequence is not important as long as it has sufficient transcriptional activity to accomplish the invention by expressing translatable mRNA for the desired nucleic acid fragments in the desired host tissue at the right time. Either heterologous or non-heterologous (i.e., endogenous) promoters can be used to practice the invention. For example, suitable promoters include, but are not limited to: the alpha prime subunit of beta conglycinin promoter, the Kunitz trypsin inhibitor 3 promoter, the annexin promoter, the glycinin Gy1 promoter, the beta subunit of beta conglycinin promoter, the P34/Gly Bd m 30K promoter, the albumin promoter, the Leg A1 promoter and the Leg A2 promoter.

The annexin, or P34, promoter is described in PCT Publication No. WO 2004/071178 (published Aug. 26, 2004). The level of activity of the annexin promoter is comparable to that of many known strong promoters, such as: (1) the CaMV 35S promoter (Atanassova et al., *Plant Mol. Biol.* 37:275-285 (1998); Battraw and Hall, *Plant Mol. Biol.* 15:527-538 (1990); Holtorf et al., *Plant Mol. Biol.* 29:637-646 (1995); Jefferson et al., *EMBO J.* 6:3901-3907 (1987); Wilmink et al., *Plant Mol. Biol.* 28:949-955 (1995)); (2) the *Arabidopsis* oleosin promoters (Plant et al., *Plant Mol. Biol.* 25:193-205 (1994); Li, Texas A&M University Ph.D. dissertation, pp. 107-128 (1997)); (3) the *Arabidopsis* ubiquitin extension protein promoters (Callis et al., *J Biol. Chem.* 265(21):12486-93 (1990)); (4) a tomato ubiquitin gene promoter (Rollfinke et al., *Gene.* 211(2):267-76 (1998)); (5) a soybean heat shock protein promoter (Schoffl et al., *Mol Gen Genet.* 217(2-3): 246-53 (1989)); and, (6) a maize H3 histone gene promoter (Atanassova et al., *Plant Mol Biol.* 37(2):275-85 (1989)).

Another useful feature of the annexin promoter is its expression profile in developing seeds. The annexin promoter is most active in developing seeds at early stages (before 10 days after pollination) and is largely quiescent in later stages. The expression profile of the annexin promoter is different from that of many seed-specific promoters, e.g., seed storage protein promoters, which often provide highest activity in later stages of development (Chen et al., *Dev. Genet.* 10:112-122 (1989); Ellerstrom et al., *Plant Mol. Biol.* 32:1019-1027 (1996); Keddie et al., *Plant Mol. Biol.* 24:327-340 (1994); Plant et al., (supra); Li, (supra)). The annexin promoter has a more conventional expression profile but remains distinct from other known seed specific promoters. Thus, the annexin promoter will be a very attractive candidate when overexpression, or suppression, of a gene in embryos is desired at an early developing stage. For example, it may be desirable to overexpress a gene regulating early embryo development or a gene involved in the metabolism prior to seed maturation.

Following identification of an appropriate promoter suitable for expression of a specific delta-5 desaturase coding sequence, the promoter is then operably linked in a sense orientation using conventional means well known to those skilled in the art.

Standard recombinant DNA and molecular cloning techniques used herein are well known in the art and are described more fully in Sambrook, J. et al., In *Molecular Cloning: A Laboratory Manual;* 2nd ed.; Cold Spring Harbor Laboratory Press: Cold Spring Harbor, N.Y., 1989 (hereinafter "Sambrook et al., 1989") or Ausubel, F. M., Brent, R., Kingston, R. E., Moore, D. D., Seidman, J. G., Smith, J. A. and Struhl, K., Eds.; In *Current Protocols in Molecular Biology*; John Wiley and Sons: New York, 1990 (hereinafter "Ausubel et al., 1990").

Once the recombinant construct has been made, it may then be introduced into a plant cell of choice by methods well known to those of ordinary skill in the art (e.g., transfection, transformation and electroporation). Oilseed plant cells are the preferred plant cells. The transformed plant cell is then cultured and regenerated under suitable conditions permitting expression of the long-chain PUFA which is then optionally recovered and purified.

The recombinant constructs of the invention may be introduced into one plant cell; or, alternatively, each construct may be introduced into separate plant cells.

Expression in a plant cell may be accomplished in a transient or stable fashion as is described above.

The desired long-chain PUFAs can be expressed in seed. Also within the scope of this invention are seeds or plant parts obtained from such transformed plants.

Plant parts include differentiated and undifferentiated tissues including, but not limited to the following: roots, stems, shoots, leaves, pollen, seeds, tumor tissue and various forms of cells and culture (e.g., single cells, protoplasts, embryos and callus tissue). The plant tissue may be in plant or in a plant organ, tissue or cell culture.

The term "plant organ" refers to plant tissue or a group of tissues that constitute a morphologically and functionally distinct part of a plant. The term "genome" refers to the following: (1) the entire complement of genetic material (genes and non-coding sequences) that is present in each cell of an organism, or virus or organelle; and/or (2) a complete set of chromosomes inherited as a (haploid) unit from one parent.

Thus, this invention also concerns a method for transforming a cell, comprising transforming a cell with the recombinant construct of the invention and selecting those cells transformed with the recombinant construct of the invention.

Also of interest is a method for producing a transformed plant comprising transforming a plant cell with the delta-5 desaturase polynucleotides of the instant invention and regenerating a plant from the transformed plant cell.

Methods for transforming dicots (primarily by use of *Agrobacterium tumefaciens*) and obtaining transgenic plants have been published, among others, for: cotton (U.S. Pat. No. 5,004,863; U.S. Pat. No. 5,159,135); soybean (U.S. Pat. No. 5,569,834; U.S. Pat. No. 5,416,011); *Brassica* (U.S. Pat. No. 5,463,174); peanut (Cheng et al. *Plant Cell Rep.* 15:653-657 (1996); McKently et al. *Plant Cell Rep.* 14:699-703 (1995)); papaya (Ling, K. et al. *Bio/technology* 9:752-758 (1991)); and pea (Grant et al. *Plant Cell Rep.* 15:254-258 (1995)). For a review of other commonly used methods of plant transformation see Newell, C. A. (*Mol. Biotechnol.* 16:53-65 (2000)). One of these methods of transformation uses *Agrobacterium rhizogenes* (Tepfler, M. and Casse-Delbart, F. *Microbiol. Sci.* 4:24-28 (1987)). Transformation of soybeans using direct delivery of DNA has been published using PEG fusion (PCT Publication No. WO 92/17598), electroporation (Chowrira, G. M. et al., *Mol. Biotechnol.* 3:17-23 (1995); Christou, P. et al., *Proc. Natl. Acad. Sci*. U.S.A. 84:3962-3966 (1987)), microinjection and particle bombardement (McCabe, D. E. et. al., *Bio/Technology* 6:923 (1988); Christou et al., *Plant Physiol.* 87:671-674 (1988)).

There are a variety of methods for the regeneration of plants from plant tissue. The particular method of regeneration will depend on the starting plant tissue and the particular plant species to be regenerated. The regeneration, development and cultivation of plants from single plant protoplast transformants or from various transformed explants is well known in the art (Weissbach and Weissbach, In: Methods for Plant Molecular Biology, (Eds.), Academic: San Diego, Calif. (1988)). This regeneration and growth process typically includes the steps of selection of transformed cells and culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

In addition to the above discussed procedures, practitioners are familiar with the standard resource materials which describe specific conditions and procedures for: the construction, manipulation and isolation of macromolecules (e.g., DNA molecules, plasmids, etc.); the generation of recombinant DNA fragments and recombinant expression constructs; and, the screening and isolating of clones. See, for example: Sambrook et al., Molecular Cloning: A Laboratory Manual, Cold Spring Harbor: NY (1989); Maliga et al., Methods in Plant Molecular Biology, Cold Spring Harbor: NY (1995); Birren et al., Genome Analysis: Detecting Genes, Vol. 1, Cold Spring Harbor: NY (1998); Birren et al., Genome Analysis: Analyzing DNA, Vol. 2, Cold Spring Harbor: NY (1998); Plant Molecular Biology: A Laboratory Manual, eds. Clark, Springer: NY (1997).

Examples of oilseed plants include, but are not limited to: soybean, *Brassica* species, sunflower, maize, cotton, flax and safflower.

Examples of PUFAs having at least twenty carbon atoms and four or more carbon-carbon double bonds include, but are not limited to, omega-3 fatty acids such as EPA, DPA and DHA and the omega-6 fatty acid ARA. Seeds obtained from such plants are also within the scope of this invention as well as oil obtained from such seeds.

Thus, in one embodiment this invention concerns an oilseed plant comprising:

(a) a first recombinant DNA construct comprising an isolated polynucleotide encoding a delta-5 desaturase polypeptide, operably linked to at least one regulatory sequence; and, (b) at least one additional recombinant DNA construct comprising an isolated polynucleotide, operably linked to at least one regulatory sequence, encoding a polypeptide selected from the group consisting of a delta-4 desaturase, a delta-5 desaturase, a delta-6 desaturase, a delta-8 desaturase, a delta-9 desaturase, a delta-9 elongase, a delta-12 desaturase, a delta-15 desaturase, a delta-17 desaturase, a $C_{14/16}$ elongase, a $C_{16/18}$ elongase, a $C_{18/20}$ elongase and a $C_{20/22}$ elongase.

Additional desaturases are discussed, for example, in U.S. Pat. Nos. 6,075,183, 5,968,809, 6,136,574, 5,972,664, 6,051,754, 6,410,288 and PCT Publication Nos. WO 98/46763, WO 98/46764, WO 00/12720 and WO 00/40705.

The choice of combination of cassettes used depends in part on the PUFA profile and/or desaturase/elongase profile of the oilseed plant cells to be transformed and the long-chain PUFA which is to be expressed.

In another aspect, this invention concerns a method for making long-chain PUFAs in a plant cell comprising:

(a) transforming a cell with the recombinant construct of the invention; and, (b) selecting those transformed cells that make long-chain PUFAs.

In still another aspect, this invention concerns a method for producing at least one PUFA in a soybean cell comprising:

(a) transforming a soybean cell with a first recombinant DNA construct comprising:

(i) an isolated polynucleotide encoding a delta-5 desaturase polypeptide, operably linked to at least one regulatory sequence; and, (ii) at least one additional recombinant DNA construct comprising an isolated polynucleotide, operably linked to at least one regulatory sequence, encoding a polypeptide selected from the group consisting of a delta-4 desaturase, a delta-5 desaturase, a delta-6 desaturase, a delta-8 desaturase, a delta-9 desaturase, a delta-9 elongase, a delta-12 desaturase, a delta-15 desaturase, a delta-17 desaturase, a $C_{14/16}$ elongase, a $C_{16/18}$ elongase, a $C_{18/20}$ elongase and a $C_{20/22}$ elongase;

(b) regenerating a soybean plant from the transformed cell of step (a); and, (c) selecting those seeds obtained from the plants of step (b) having an altered level of PUFAs when compared to the level in seeds obtained from a nontransformed soybean plant.

In other preferred embodiments, the at least one additional recombinant DNA construct encodes a polypeptide having delta-9 elongase activity, e.g., the delta-9 elongase isolated or derived from *Isochrysis galbana* (GenBank Accession No. AF390174; IgD9e) or the delta-9 elongase isolated or derived from *Euglena gracilis*.

In other preferred embodiments, the at least one additional recombinant DNA construct encodes a polypeptide having delta-8 desaturase activity. For example, PCT Publication No. WO 2005/103253 (published Apr. 22, 2005) discloses amino acid and nucleic acid sequences for a delta-8 desaturase enzyme from *Pavlova salina* (see also U.S. Publication No. 2005/0273885). Sayanova et al. (*FEBS Lett.* 580:1946-1952 (2006)) describes the isolation and characterization of a cDNA from the free living soil amoeba *Acanthamoeba castellanii* that, when expressed in *Arabidopsis*, encodes a $C_{20}$ delta-8 desaturase. Also, Applicants' Assignee's co-pending application having Provisional Application No. 60/795,810 filed Apr. 28, 2006 discloses amino acid and nucleic acid sequences for a delta-8 desaturase enzyme from *Pavlova lutheri* (CCMP459). U.S. Provisional Application No. 60/853,563 (filed Oct. 23, 2006) discloses amino acid and nucleic acid sequences for a delta-8 desaturase enzyme from *Tetruetreptia pomquetensis* CCMP1491, *Eutreptiella* sp. CCMP389 and *Eutreptiella cf_gymnastica* CCMP1594.

Microbial Expression Systems, Cassettes and Vectors, and Transformation

The delta-5 desaturase genes and gene products described herein (i.e., the *Peridinium* sp. CCMP626 delta-5 desaturase, or other mutant enzymes, codon-optimized enzymes or homologs thereof) may also be produced in heterologous microbial host cells, particularly in the cells of oleaginous yeasts (e.g., *Yarrowia lipolytica*).

Microbial expression systems and expression vectors containing regulatory sequences that direct high level expression of foreign proteins are well known to those skilled in the art. Any of these could be used to construct chimeric genes for production of any of the gene products of the instant sequences. These chimeric genes could then be introduced into appropriate microorganisms via transformation to provide high-level expression of the encoded enzymes.

Vectors or DNA cassettes useful for the transformation of suitable microbial host cells are well known in the art. The specific choice of sequences present in the construct is dependent upon the desired expression products (supra), the nature of the host cell and the proposed means of separating transformed cells versus non-transformed cells. Typically, however, the vector or cassette contains sequences directing transcription and translation of the relevant gene(s), a selectable marker and sequences allowing autonomous replication or chromosomal integration. Suitable vectors comprise a region 5' of the gene that controls transcriptional initiation (e.g., a promoter) and a region 3' of the DNA fragment that controls transcriptional termination (i.e., a terminator). It is most preferred when both control regions are derived from genes from the transformed microbial host cell, although it is to be understood that such control regions need not be derived from the genes native to the specific species chosen as a production host.

Initiation control regions or promoters which are useful to drive expression of the instant delta-5 desaturase ORFs in the desired microbial host cell are numerous and familiar to those skilled in the art. Virtually any promoter capable of directing expression of these genes in the selected host cell is suitable for the present invention. Expression in a microbial host cell can be accomplished in a transient or stable fashion. Transient expression can be accomplished by inducing the activity of a regulatable promoter operably linked to the gene of interest. Stable expression can be achieved by the use of a constitutive promoter operably linked to the gene of interest. As an example, when the host cell is yeast, transcriptional and translational regions functional in yeast cells are provided, particularly from the host species (e.g., see PCT Publication Nos. WO 2004/101757 and WO 2006/052870 for preferred transcriptional initiation regulatory regions for use in *Yarrowia lipolytica*). Any one of a number of regulatory sequences can be used, depending upon whether constitutive or induced transcription is desired, the efficiency of the promoter in expressing the ORF of interest, the ease of construction and the like.

Nucleotide sequences surrounding the translational initiation codon 'ATG' have been found to affect expression in yeast cells. If the desired polypeptide is poorly expressed in yeast, the nucleotide sequences of exogenous genes can be modified to include an efficient yeast translation initiation sequence to obtain optimal gene expression. For expression in yeast, this can be done by site-directed mutagenesis of an inefficiently expressed gene by fusing it in-frame to an endogenous yeast gene, preferably a highly expressed gene. Alternatively, one can determine the consensus translation initiation sequence in the host and engineer this sequence into heterologous genes for their optimal expression in the host of interest.

The termination region can be derived from the 3' region of the gene from which the initiation region was obtained or from a different gene. A large number of termination regions are known and function satisfactorily in a variety of hosts (when utilized both in the same and different genera and species from where they were derived). The termination region usually is selected more as a matter of convenience rather than because of any particular property. Preferably, when the microbial host is a yeast cell, the termination region is derived from a yeast gene (particularly *Saccharomyces*, *Schizosaccharomyces*, *Candida, Yarrowia* or *Kluyveromyces*). The 3'-regions of mammalian genes encoding γ-interferon and α-2 interferon are also known to function in yeast. Termination control regions may also be derived from various genes native to the preferred hosts. Optionally, a termination site may be unnecessary; however, it is most preferred if included. Although not intended to be limiting, termination regions useful in the disclosure herein include: ~100 bp of the 3' region of the *Yarrowia lipolytica* extracellular protease (XPR; GenBank Accession No. M17741); the acyl-coA oxidase (Aco3: GenBank Accession No. AJO01301 and No. CAA04661; Pox3: GenBank Accession No. XP_503244) terminators; the Pex20 (GenBank Accession No. AF054613) terminator; the Pex16 (GenBank Accession No. U75433) terminator; the Lip1 (GenBank Accession No. Z50020) terminator; the Lip2 (GenBank Accession No. AJ012632) terminator; and the 3-oxoacyl-coA thiolase (OCT; GenBank Accession No. X69988) terminator.

As one of skill in the art is aware, merely inserting a gene into a cloning vector does not ensure that it will be successfully expressed at the level needed. In response to the need for a high expression rate, many specialized expression vectors have been created by manipulating a number of different genetic elements that control aspects of transcription, translation, protein stability, oxygen limitation and secretion from the microbial host cell. More specifically, some of the molecular features that have been manipulated to control gene expression include: (1) the nature of the relevant transcriptional promoter and terminator sequences; (2) the number of copies of the cloned gene and whether the gene is plasmid-borne or integrated into the genome of the host cell; (3) the final cellular location of the synthesized foreign protein; (4) the efficiency of translation and correct folding of the protein in the host organism; (5) the intrinsic stability of the mRNA and protein of the cloned gene within the host cell; and (6) the codon usage within the cloned gene, such that its frequency approaches the frequency of preferred codon usage of the host cell. Each of these types of modifications are encompassed in the present invention, as means to further optimize expression of the delta-5 desaturase described herein.

Once the DNA encoding a polypeptide suitable for expression in an appropriate microbial host cell (e.g., oleaginous yeast) has been obtained (e.g., a chimeric gene comprising a promoter, ORF and terminator), it is placed in a plasmid vector capable of autonomous replication in a host cell, or it is directly integrated into the genome of the host cell. Integration of expression cassettes can occur randomly within the host genome or can be targeted through the use of constructs containing regions of homology with the host genome sufficient to target recombination within the host locus. Where constructs are targeted to an endogenous locus, all or some of the transcriptional and translational regulatory regions can be provided by the endogenous locus.

In the present invention, the preferred method of expressing genes in *Yarrowia lipolytica* is by integration of linear DNA into the genome of the host; and, integration into multiple locations within the genome can be particularly useful when high level expression of genes are desired [e.g., in the Ura3 locus (GenBank Accession No. AJ306421), the Leu2 gene locus (GenBank Accession No. AF260230), the Lys5 gene (GenBank Accession No. M34929), the Aco2 gene locus (GenBank Accession No. AJ001300), the Pox3 gene locus (Pox3: GenBank Accession No. XP_503244; or, Aco3: GenBank Accession No. AJ001301), the delta-12 desaturase gene locus (PCT Publication No. WO2004/104167), the Lip1 gene locus (GenBank Accession No. Z50020) and/or the Lip2 gene locus (GenBank Accession No. AJ012632)].

Advantageously, the Ura3 gene can be used repeatedly in combination with 5-fluoroorotic acid (5-fluorouracil-6-carboxylic acid monohydrate; "5-FOA") selection (infra), to readily permit genetic modifications to be integrated into the *Yarrowia* genome in a facile manner.

Where two or more genes are expressed from separate replicating vectors, it is desirable that each vector has a different means of selection and should lack homology to the other construct(s) to maintain stable expression and prevent reassortment of elements among constructs. Judicious choice of regulatory regions, selection means and method of propagation of the introduced construct(s) can be experimentally determined so that all introduced genes are expressed at the necessary levels to provide for synthesis of the desired products.

Constructs comprising the gene of interest may be introduced into a microbial host cell by any standard technique. These techniques include transformation (e.g., lithium acetate transformation [*Methods in Enzymology,* 194:186-187 (1991)]), protoplast fusion, bolistic impact, electroporation, microinjection, or any other method that introduces the gene of interest into the host cell. More specific teachings applicable for oleaginous yeasts (i.e., *Yarrowia lipolytica*) include U.S. Pat. No. 4,880,741 and U.S. Pat. No. 5,071,764 and Chen, D. C. et al. (*Appl. Microbiol. Biotechnol.,* 48(2): 232-235 (1997)).

For convenience, a host cell that has been manipulated by any method to take up a DNA sequence (e.g., an expression cassette) will be referred to as "transformed" or "recombinant" herein. Thus, the term "transformed" and "recombinant" are used interchangeably herein. The transformed host will have at least one copy of the expression construct and may have two or more, depending upon whether the gene is integrated into the genome, amplified or is present on an extrachromosomal element having multiple copy numbers.

The transformed host cell can be identified by various selection techniques, as described in PCT Publication Nos. WO 2004/101757 and WO 2006/052870. Preferred selection methods for use herein are resistance to kanamycin, hygromycin and the amino glycoside G418, as well as ability to grow on media lacking uracil, leucine, lysine, tryptophan or histidine. In alternate embodiments, 5-FOA is used for selection of yeast Ura− mutants. The compound is toxic to yeast cells that possess a functioning URA3 gene encoding orotidine 5'-monophosphate decarboxylase (OMP decarboxylase); thus, based on this toxicity, 5-FOA is especially useful for the selection and identification of Ura− mutant yeast strains (Bartel, P. L. and Fields, S., Yeast 2-Hybrid System, Oxford University: New York, v. 7, pp 109-147, 1997). More specifically, one can first knockout the native Ura3 gene to produce a strain having a Ura− phenotype, wherein selection occurs based on 5-FOA resistance. Then, a cluster of multiple chimeric genes and a new Ura3 gene can be integrated into a different locus of the *Yarrowia* genome to thereby produce a new strain having a Ura+ phenotype. Subsequent integration produces a new Ura3− strain (again identified using 5-FOA selection), when the introduced Ura3 gene is knocked out. Thus, the Ura3 gene (in combination with 5-FOA selection) can be used as a selection marker in multiple rounds of transformation.

Following transformation, substrates suitable for the instant delta-5 desaturase (and, optionally other PUFA enzymes that are co-expressed within the host cell) may be produced by the host either naturally or transgenically, or they may be provided exogenously.

Microbial host cells for expression of the instant genes and nucleic acid fragments may include hosts that grow on a variety of feedstocks, including simple or complex carbohydrates, fatty acids, organic acids, oils and alcohols, and/or hydrocarbons over a wide range of temperature and pH values. Based on the needs of the Applicants' Assignee, the genes described in the instant invention will be expressed in an oleaginous yeast (and in particular *Yarrowia lipolytica*); however, it is contemplated that because transcription, translation and the protein biosynthetic apparatus is highly conserved, any bacteria, yeast, algae and/or fungus will be a suitable microbial host for expression of the present nucleic acid fragments.

Preferred microbial hosts, however, are oleaginous yeasts. These organisms are naturally capable of oil synthesis and accumulation, wherein the oil can comprise greater than about 25% of the cellular dry weight, more preferably greater than about 30% of the cellular dry weight, and most preferably greater than about 40% of the cellular dry weight. Genera typically identified as oleaginous yeast include, but are not limited to: *Yarrowia*, *Candida*, *Rhodotorula*, *Rhodosporidium*, *Cryptococcus*, *Trichosporon* and *Lipomyces*. More specifically, illustrative oil-synthesizing yeasts include: *Rhodosporidium toruloides*, *Lipomyces starkeyii*, *L. lipoferus*, *Candida revkaufi*, *C. pulcherrima* , *C. tropicalis*, *C. utilis*, *Trichosporon pullans*, *T. cutaneum*, *Rhodotorula glutinus*, *R. graminis*, and *Yarrowia lipolytica* (formerly classified as *Candida lipolytica*).

Most preferred is the oleaginous yeast *Yarrowia lipolytica*; and, in a further embodiment, most preferred are the *Y. lipolytica* strains designated as ATCC #20362, ATCC #8862, ATCC #18944, ATCC #76982 and/or LGAM S(7)1 (Papanikolaou S., and Aggelis G., *Bioresour. Technol.* 82(1):43-9 (2002)).

Historically, various strains of *Y. lipolytica* have been used for the manufacture and production of: isocitrate lyase; lipases; polyhydroxyalkanoates; citric acid; erythritol; 2-oxoglutaric acid; γ-decalactone; γ-dodecalatone; and pyruvic acid. Specific teachings applicable for engineering ARA, EPA and DHA production in *Y. lipolytica* are provided in U.S. patent application Ser. No. 11/264,784 (WO 2006/055322), U.S. patent application Ser. No. 11/265,761 (WO 2006/052870) and U.S. patent application Ser. No. 11/264,737 (WO 2006/052871), respectively.

Other preferred microbial hosts include oleaginous bacteria, algae and other fungi; and, within this broad group of microbial hosts, of particular interest are microorganisms that synthesize omega-3/omega-6 fatty acids (or those that can be genetically engineered for this purpose [e.g., other yeast such as *Saccharomyces cerevisiae*]). Thus, for example, transformation of *Mortierella alpina* (which is commercially used for production of ARA) with any of the present delta-5 desaturase genes under the control of inducible or regulated promoters could yield a transformant organism capable of synthesizing increased quantities of DGLA. The method of transformation of *M. alpina* is described by Mackenzie et al. (*Appl. Environ. Microbiol.,* 66:4655 (2000)). Similarly, methods for transformation of Thraustochytriales microorganisms are disclosed in U.S. Pat. No. 7,001,772.

Based on the teachings described above, in one embodiment this invention is drawn to a method of producing either ARA or EPA, respectively, comprising:

(a) providing an oleaginous yeast comprising:

(i) a first recombinant DNA construct comprising an isolated polynucleotide encoding a delta-5 desaturase polypeptide, operably linked to at least one regulatory sequence; and, (ii) a source of desaturase substrate consisting of either DGLA or ETA, respectively; and, (b) growing the yeast of step (a) in the presence of a suitable fermentable carbon source wherein the gene encoding the delta-5 desaturase polypeptide is expressed and DGLA is converted to ARA or ETA is converted to EPA, respectively; and, (c) optionally recovering the ARA or EPA, respectively, of step (b).

Substrate feeding may be required.

Of course, since naturally produced PUFAs in oleaginous yeast are limited to 18:2 fatty acids (i.e., LA), and less commonly, 18:3 fatty acids (i.e., ALA), in more preferred embodiments of the present invention the oleaginous yeast will be genetically engineered to express multiple enzymes necessary for long-chain PUFA biosynthesis (thereby enabling production of e.g., ARA, EPA, DPA and DHA), in addition to the delta-5 desaturases described herein.

Specifically, in one embodiment this invention concerns an oleaginous yeast comprising:

(a) a first recombinant DNA construct comprising an isolated polynucleotide encoding a delta-5 desaturase polypeptide, operably linked to at least one regulatory sequence; and, (b) at least one additional recombinant DNA construct comprising an isolated polynucleotide, operably linked to at least one regulatory sequence, encoding a polypeptide selected from the group consisting of: a delta-4 desaturase, a delta-5 desaturase, delta-6 desaturase, a delta-9 desaturase, a delta-12 desaturase, a delta-15 desaturase, a delta-17 desaturase, a delta-9 elongase, a $C_{14/16}$ elongase, a $C_{16/18}$ elongase, a $C_{18/20}$ elongase and a $C_{20/22}$ elongase.

In particularly preferred embodiments, the at least one additional recombinant DNA construct encodes a polypeptide having delta-9 elongase activity, e.g., the delta-9 elongase isolated or derived from *Isochrysis galbana* (GenBank Accession No. AF390174; IgD9e or IgD9eS) or the delta-9 elongase isolated or derived from *Euglena gracilis*.

Metabolic Engineering of Omega-3 and/or Omega-6 Fatty Acid Biosynthesis in Microbes Methods for manipulating biochemical pathways are well known to those skilled in the art; and, it is expected that numerous manipulations will be possible to maximize omega-3 and/or omega-6 fatty acid biosynthesis in oleaginous yeasts, and particularly, in *Yarrowia lipolytica*. This manipulation may require metabolic engineering directly within the PUFA biosynthetic pathway or additional coordinated manipulation of various other metabolic pathways.

In the case of manipulations within the PUFA biosynthetic pathway, it may be desirable to increase the production of LA to enable increased production of omega-6 and/or omega-3 fatty acids. Introducing and/or amplifying genes encoding delta-9 and/or delta-12 desaturases may accomplish this. To maximize production of omega-6 unsaturated fatty acids, it is well known to one skilled in the art that production is favored in a host microorganism that is substantially free of ALA; thus, preferably, the host is selected or obtained by removing or inhibiting delta-15 or omega-3 type desaturase activity that permits conversion of LA to ALA. Alternatively, it may be desirable to maximize production of omega-3 fatty acids (and minimize synthesis of omega-6 fatty acids). In this example, one could utilize a host microorganism wherein the delta-12 desaturase activity that permits conversion of oleic acid to LA is removed or inhibited; subsequently, appropriate expression cassettes would be introduced into the host, along with appropriate substrates (e.g., ALA) for conversion to omega-3 fatty acid derivatives of ALA (e.g., STA, ETrA, ETA, EPA, DPA, DHA).

In alternate embodiments, biochemical pathways competing with the omega-3 and/or omega-6 fatty acid biosynthetic pathways for energy or carbon, or native PUFA biosynthetic pathway enzymes that interfere with production of a particular PUFA end-product, may be eliminated by gene disruption or down-regulated by other means (e.g., antisense mRNA).

Detailed discussion of manipulations within the PUFA biosynthetic pathway as a means to increase ARA, EPA or DHA (and associated techniques thereof) are presented in PCT Publication Nos. WO 2006/055322, WO 2006/052870 and WO 2006/052871, respectively, as are desirable manipulations in the TAG biosynthetic pathway and the TAG degradation pathway (and associated techniques thereof).

Within the context of the present invention, it may be useful to modulate the expression of the fatty acid biosynthetic pathway by any one of the strategies described above. For example, the present invention provides methods whereby genes encoding key enzymes in the delta-9 elongase/delta-8 desaturase biosynthetic pathway are introduced into oleaginous yeasts for the production of omega-3 and/or omega-6 fatty acids. It will be particularly useful to express the present the delta-5 desaturase genes in oleaginous yeasts that do not naturally possess omega-3 and/or omega-6 fatty acid biosynthetic pathways and coordinate the expression of these genes, to maximize production of preferred PUFA products using various means for metabolic engineering of the host organism.

Microbial Fermentation Processes for PUFA Production

The transformed host cell is grown under conditions that optimize expression of chimeric desaturase genes and produce the greatest and the most economical yield of desired PUFAs. In general, media conditions that may be optimized include the type and amount of carbon source, the type and amount of nitrogen source, the carbon-to-nitrogen ratio, the amount of different mineral ions, the oxygen level, growth temperature, pH, length of the biomass production phase, length of the oil accumulation phase and the time and method of cell harvest. *Yarrowia lipolytica* are generally grown in complex media (e.g., yeast extract-peptone-dextrose broth (YPD)) or a defined minimal media that lacks a component necessary for growth and thereby forces selection of the desired expression cassettes (e.g., Yeast Nitrogen Base (DIFCO Laboratories, Detroit, Mich.)).

Fermentation media in the present invention must contain a suitable carbon source. Suitable carbon sources are taught in PCT Publication No. WO 2004/101757. Although it is contemplated that the source of carbon utilized in the present invention may encompass a wide variety of carbon-containing sources, preferred carbon sources are sugars, glycerol, and/or fatty acids. Most preferred is glucose and/or fatty acids containing between 10-22 carbons.

Nitrogen may be supplied from an inorganic (e.g., $(NH_4)_2SO_4$) or organic (e.g., urea or glutamate) source. In addition to appropriate carbon and nitrogen sources, the fermentation media must also contain suitable minerals, salts, cofactors, buffers, vitamins and other components known to those skilled in the art suitable for the growth of the oleaginous host and promotion of the enzymatic pathways necessary for PUFA production. Particular attention is given to several metal ions (e.g., $Mn^{+2}$, $Co^{+2}$, $Zn^{+2}$, $Mg^{+2}$) that promote synthesis of lipids and PUFAs (Nakahara, T. et al., *Ind. Appl. Single Cell Oils*, D. J. Kyle and R. Colin, eds. pp 61-97 (1992)).

Preferred growth media in the present invention are common commercially prepared media, such as Yeast Nitrogen Base (DIFCO Laboratories, Detroit, Mich.). Other defined or synthetic growth media may also be used and the appropriate medium for growth of the transformant host cells will be known by one skilled in the art of microbiology or fermentation science. A suitable pH range for the fermentation is typically between about pH 4.0 to pH 8.0, wherein pH 5.5 to pH 7.5 is preferred as the range for the initial growth conditions. The fermentation may be conducted under aerobic or anaerobic conditions, wherein microaerobic conditions are preferred.

Typically, accumulation of high levels of PUFAs in oleaginous yeast cells requires a two-stage process, since the metabolic state must be "balanced" between growth and synthesis/storage of fats. Thus, most preferably, a two-stage fermentation process is necessary for the production of PUFAs in oleaginous yeast (e.g., *Yarrowia lipolytica*). This approach is described in PCT Publication No. WO 2004/101757, as are various suitable fermentation process designs (i.e., batch, fed-batch and continuous) and considerations during growth.

Purification and Processing of PUFA Oils

PUFAs may be found in the host microorganisms and plants as free fatty acids or in esterified forms such as acylglycerols, phospholipids, sulfolipids or glycolipids, and may be extracted from the host cells through a variety of means well-known in the art. One review of extraction techniques, quality analysis and acceptability standards for yeast lipids is that of Z. Jacobs (*Critical Reviews in Biotechnology,* 12(5/6): 463-491 (1992)). A brief review of downstream processing is also available by A. Singh and O. Ward (*Adv. Appl. Microbiol.,* 45:271-312 (1997)).

In general, means for the purification of PUFAs may include extraction with organic solvents, sonication, supercritical fluid extraction (e.g., using carbon dioxide), saponification and physical means such as presses, or combinations thereof. One is referred to the teachings of PCT Publication No. WO 2004/101757 for additional details. Methods of isolating seed oils are well known in the art: (Young et al., Processing of Fats and Oils, In *The Lipid Handbook*, Gunstone et al., eds., Chapter 5 pp 253-257; Chapman & Hall: London (1994)). For example, soybean oil is produced using a series of steps involving the extraction and purification of an edible oil product from the oil-bearing seed. Soybean oils and soybean byproducts are produced using the generalized steps shown in Table 3.

TABLE 3

Generalized Steps for Soybean Oil and Byproduct Production

| Process Step | Process | Impurities Removed and/or By-Products Obtained |
|---|---|---|
| # 1 | soybean seed | |
| # 2 | oil extraction | meal |
| # 3 | degumming | lecithin |
| # 4 | alkali or physical refining | gums, free fatty acids, pigments |
| # 5 | water washing | soap |
| # 6 | bleaching | color, soap, metal |
| # 7 | (hydrogenation) | |
| # 8 | (winterization) | stearine |
| # 9 | deodorization | free fatty acids, tocopherols, sterols, volatiles |
| # 10 | oil products | |

More specifically, soybean seeds are cleaned, tempered, dehulled and flaked, thereby increasing the efficiency of oil extraction. Oil extraction is usually accomplished by solvent (e.g., hexane) extraction but can also be achieved by a combination of physical pressure and/or solvent extraction. The resulting oil is called crude oil. The crude oil may be degummed by hydrating phospholipids and other polar and neutral lipid complexes that facilitate their separation from the nonhydrating, triglyceride fraction (soybean oil). The resulting lecithin gums may be further processed to make commercially important lecithin products used in a variety of food and industrial products as emulsification and release (i.e., antisticking) agents. Degummed oil may be further refined for the removal of impurities (primarily free fatty acids, pigments and residual gums). Refining is accomplished by the addition of a caustic agent that reacts with free fatty acid to form soap and hydrates phosphatides and proteins in the crude oil. Water is used to wash out traces of soap formed during refining. The soapstock byproduct may be used directly in animal feeds or acidulated to recover the free fatty acids. Color is removed through adsorption with a bleaching earth that removes most of the chlorophyll and carotenoid compounds. The refined oil can be hydrogenated, thereby resulting in fats with various melting properties and textures. Winterization (fractionation) may be used to remove stearine from the hydrogenated oil through crystallization under carefully controlled cooling conditions. Deodorization (principally via steam distillation under vacuum) is the last step and is designed to remove compounds which impart odor or flavor to the oil. Other valuable byproducts such as tocopherols and sterols may be removed during the deodorization process. Deodorized distillate containing these byproducts may be sold for production of natural vitamin E and other high-value pharmaceutical products. Refined, bleached, (hydrogenated, fractionated) and deodorized oils and fats may be packaged and sold directly or further processed into more specialized products. A more detailed reference to soybean seed processing, soybean oil production and byproduct utilization can be found in Erickson, Practical Handbook of Soybean Processing and Utilization, The American Oil Chemists' Society and United Soybean Board (1995). Soybean oil is liquid at room temperature because it is relatively low in saturated fatty acids when compared with oils such as coconut, palm, palm kernel and cocoa butter.

Plant and microbial oils containing PUFAs that have been refined and/or purified can be hydrogenated, to thereby result in fats with various melting properties and textures. Many processed fats (including spreads, confectionary fats, hard butters, margarines, baking shortenings, etc.) require varying degrees of solidity at room temperature and can only be produced through alteration of the source oil's physical properties. This is most commonly achieved through catalytic hydrogenation.

Hydrogenation is a chemical reaction in which hydrogen is added to the unsaturated fatty acid double bonds with the aid of a catalyst such as nickel. For example, high oleic soybean oil contains unsaturated oleic, LA and linolenic fatty acids and each of these can be hydrogenated. Hydrogenation has two primary effects. First, the oxidative stability of the oil is increased as a result of the reduction of the unsaturated fatty acid content. Second, the physical properties of the oil are changed because the fatty acid modifications increase the melting point resulting in a semi-liquid or solid fat at room temperature.

There are many variables which affect the hydrogenation reaction, which in turn alter the composition of the final product. Operating conditions including pressure, temperature, catalyst type and concentration, agitation and reactor design are among the more important parameters that can be controlled. Selective hydrogenation conditions can be used to hydrogenate the more unsaturated fatty acids in preference to the less unsaturated ones. Very light or brush hydrogenation is often employed to increase stability of liquid oils. Further hydrogenation converts a liquid oil to a physically solid fat. The degree of hydrogenation depends on the desired performance and melting characteristics designed for the particular end product. Liquid shortenings (used in the manufacture of baking products, solid fats and shortenings used for commercial frying and roasting operations) and base stocks for margarine manufacture are among the myriad of possible oil and fat products achieved through hydrogenation. A more detailed description of hydrogenation and hydrogenated products can be found in Patterson, H. B. W., Hydrogenation of Fats and Oils: Theory and Practice. The American Oil Chemists' Society (1994).

Hydrogenated oils have become somewhat controversial due to the presence of trans-fatty acid isomers that result from the hydrogenation process. Ingestion of large amounts of trans-isomers has been linked with detrimental health effects including increased ratios of low density to high density lipoproteins in the blood plasma and increased risk of coronary heart disease.

PUFA-Containing Oils for Use in Foodstuffs

The market place currently supports a large variety of food and feed products, incorporating omega-3 and/or omega-6 fatty acids (particularly ARA, EPA and DHA). It is contemplated that the plant/seed oils, altered seeds and microbial oils of the invention comprising PUFAs will function in food and feed products to impart the health benefits of current formulations. Compared to other vegetable oils, the oils of the invention are believed to function similarly to other oils in food applications from a physical standpoint (for example, partially hydrogenated oils such as soybean oil are widely used as ingredients for soft spreads, margarine and shortenings for baking and frying).

Plant/seed oils, altered seeds and microbial oils containing omega-3 and/or omega-6 fatty acids as described herein will be suitable for use in a variety of food and feed products including, but not limited to: food analogs, meat products, cereal products, baked foods, snack foods and dairy products. Additionally, the present plant/seed oils, altered seeds and microbial oils may be used in formulations to impart health benefit in medical foods including medical nutritionals, dietary supplements, infant formula as well as pharmaceutical products. One of skill in the art of food processing and food formulation will understand how the amount and composition of the plant and microbial oils may be added to the food or feed product. Such an amount will be referred to herein as an "effective" amount and will depend on the food or feed product, the diet that the product is intended to supplement or the medical condition that the medical food or medical nutritional is intended to correct or treat.

Food analogs can be made using processes well known to those skilled in the art. There can be mentioned meat analogs, cheese analogs, milk analogs and the like. Meat analogs made from soybeans contain soy protein or tofu and other ingredients mixed together to simulate various kinds of meats. These meat alternatives are sold as frozen, canned or dried foods. Usually, they can be used the same way as the foods they replace. Meat alternatives made from soybeans are excellent sources of protein, iron and B vitamins. Examples of meat analogs include, but are not limited to: ham analogs, sausage analogs, bacon analogs, and the like.

Food analogs can be classified as imitation or substitutes depending on their functional and compositional characteristics. For example, an imitation cheese need only resemble the cheese it is designed to replace. However, a product can generally be called a substitute cheese only if it is nutritionally equivalent to the cheese it is replacing and meets the minimum compositional requirements for that cheese. Thus, substitute cheese will often have higher protein levels than imitation cheeses and be fortified with vitamins and minerals.

Milk analogs or nondairy food products include, but are not limited to, imitation milks and nondairy frozen desserts (e.g., those made from soybeans and/or soy protein products).

Meat products encompass a broad variety of products. In the United States "meat" includes "red meats" produced from cattle, hogs and sheep. In addition to the red meats there are poultry items which include chickens, turkeys, geese, guineas, ducks and the fish and shellfish. There is a wide assortment of seasoned and processed meat products: fresh, cured and fried, and cured and cooked. Sausages and hot dogs are examples of processed meat products. Thus, the term "meat products" as used herein includes, but is not limited to, processed meat products.

A cereal food product is a food product derived from the processing of a cereal grain. A cereal grain includes any plant from the grass family that yields an edible grain (seed). The most popular grains are barley, corn, millet, oats, quinoa, rice, rye, sorghum, triticale, wheat and wild rice. Examples of a cereal food product include, but are not limited to: whole grain, crushed grain, grits, flour, bran, germ, breakfast cereals, extruded foods, pastas, and the like.

A baked goods product comprises any of the cereal food products mentioned above and has been baked or processed in a manner comparable to baking (i.e., to dry or harden by subjecting to heat). Examples of a baked good product include, but are not limited to: bread, cakes, doughnuts, bars, pastas, bread crumbs, baked snacks, mini-biscuits, mini-crackers, mini-cookies, and mini-pretzels. As was mentioned above, oils of the invention can be used as an ingredient.

A snack food product comprises any of the above or below described food products.

A fried food product comprises any of the above or below described food products that has been fried.

A health food product is any food product that imparts a health benefit. Many oilseed-derived food products may be considered as health foods.

A beverage can be in a liquid or in a dry powdered form.

For example, there can be mentioned non-carbonated drinks such as fruit juices, fresh, frozen, canned or concentrate; flavored or plain milk drinks, etc. Adult and infant nutritional formulas are well known in the art and commercially available (e.g., Similac®, Ensure®, Jevity®, and Alimentum® from Ross Products Division, Abbott Laboratories).

Infant formulas are liquids or reconstituted powders fed to infants and young children. "Infant formula" is defined herein as an enteral nutritional product which can be substituted for human breast milk in feeding infants and typically is composed of a desired percentage of fat mixed with desired percentages of carbohydrates and proteins in an aqueous solution (e.g., see U.S. Pat. No. 4,670,285). Based on the worldwide composition studies, as well as levels specified by expert groups, average human breast milk typically contains about 0.20% to 0.40% of total fatty acids (assuming about 50% of calories from fat); and, generally the ratio of DHA to ARA would range from about 1:1 to 1:2 (see, e.g., formulations of Enfamil LIPIL™ (Mead Johnson & Company) and Similac Advance™ (Ross Products Division, Abbott Laboratories)). Infant formulas have a special role to play in the diets of infants because they are often the only source of nutrients for infants; and, although breast-feeding is still the best nourishment for infants, infant formula is a close enough second that babies not only survive but thrive.

A dairy product is a product derived from milk. A milk analog or nondairy product is derived from a source other than milk, for example, soymilk as was discussed above. These products include, but are not limited to: whole milk, skim milk, fermented milk products such as yogurt or sour milk, cream, butter, condensed milk, dehydrated milk, coffee whitener, coffee creamer, ice cream, cheese, etc.

Additional food products into which the PUFA-containing oils of the invention could be included are, for example, chewing gums, confections and frostings, gelatins and puddings, hard and soft candies, jams and jellies, white granulated sugar, sugar substitutes, sweet sauces, toppings and syrups, and dry-blended powder mixes.

PUFA-Containing Oils for Use in Health Food Products and Pharmaceuticals

A health food product is any food product that imparts a health benefit and include functional foods, medical foods, medical nutritionals and dietary supplements. Additionally, the plant/seed oils, altered seeds and microbial oils of the invention may be used in standard pharmaceutical compositions (e.g., the long-chain PUFA containing oils could readily be incorporated into the any of the above mentioned food products, to thereby produce a functional or medical food). More concentrated formulations comprising PUFAs include capsules, powders, tablets, softgels, gelcaps, liquid concentrates and emulsions which can be used as a dietary supplement in humans or animals other than humans.

PUFA-Containing Oils for Use in Animal Feeds

Animal feeds are generically defined herein as products intended for use as feed or for mixing in feed for animals other than humans. The plant/seed oils, altered seeds and microbial oils of the invention can be used as an ingredient in various animal feeds.

More specifically, although not limited therein, it is expected that the oils of the invention can be used within pet food products, ruminant and poultry food products and aquacultural food products. Pet food products are those products intended to be fed to a pet (e.g., dog, cat, bird, reptile, rodent). These products can include the cereal and health food products above, as well as meat and meat byproducts, soy protein products, grass and hay products (e.g., alfalfa, timothy, oat or brome grass, vegetables). Ruminant and poultry food products are those wherein the product is intended to be fed to an animal (e.g., turkeys, chickens, cattle, swine). As with the pet foods above, these products can include cereal and health food products, soy protein products, meat and meat byproducts, and grass and hay products as listed above. Aquacultural food products (or "aquafeeds") are those products intended to be used in aquafarming, i.e., which concerns the propagation, cultivation or farming of aquatic organisms and/or animals in fresh or marine waters.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by: 1.) Sambrook, J., Fritsch, E. F. and Maniatis, T., *Molecular Cloning: A Laboratory Manual*; Cold Spring Harbor Laboratory: Cold Spring Harbor, N.Y. (1989) (Maniatis); 2.) T. J. Silhavy, M. L. Bennan, and L. W. Enquist, Experiments with Gene Fusions; Cold Spring Harbor Laboratory: Cold Spring Harbor, N.Y. (1984); and 3.) Ausubel, F. M. et al., Current Protocols in Molecular Biology, published by Greene Publishing Assoc. and Wiley-Interscience, Hoboken, N.J. (1987).

Materials and methods suitable for the maintenance and growth of microbial cultures are well known in the art. Techniques suitable for use in the following examples may be found as set out in Manual of Methods for General Bacteriology (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994)); or by Thomas D. Brock in Biotechnology: A Textbook of Industrial Microbiology, $2^{nd}$ ed., Sinauer Associates: Sunderland, Mass. (1989). All reagents, restriction enzymes and materials used for the growth and maintenance of microbial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.), unless otherwise specified. *E. coli* (XL1-Blue) competent cells were purchased from the Stratagene Company (San Diego, Calif.). *E. coli* strains were typically grown at 37° C. on Luria Bertani (LB) plates.

General molecular cloning was performed according to standard methods (Sambrook et al., supra). DNA sequence was generated on an ABI Automatic sequencer using dye terminator technology (U.S. Pat. No. 5,366,860; EP 272,007) using a combination of vector and insert-specific primers. Sequence editing was performed in Sequencher (Gene Codes Corporation, Ann Arbor, Mich.). All sequences represent coverage at least two times in both directions. Unless otherwise indicated herein comparisons of genetic sequences were accomplished using DNASTAR software (DNASTAR Inc., Madison, Wis.).

The meaning of abbreviations is as follows: "sec" means second(s), "min" means minute(s), "h" means hour(s), "d" means day(s), "μL" means microliter(s), "mL" means milliliter(s), "L" means liter(s), "μM" means micromolar, "mM" means millimolar, "M" means molar, "mmol" means millimole(s), "μmole" mean micromole(s), "g" means gram(s), "μg" means microgram(s), "ng" means nanogram(s), "U" means unit(s), "bp" means base pair(s) and "kB" means kilobase(s).

Transformation and Cultivation of *Yarrowia lipolytica*

*Yarrowia lipolytica* strain ATCC #20362 was purchased from the American Type Culture Collection (Rockville, Md.). *Y. lipolytica* strains were usually grown at 28° C. on YPD agar (1% yeast extract, 2% bactopeptone, 2% glucose, 2% agar).

Transformation of *Y. lipolytica* was performed according to the method of Chen, D. C. et al. (*Appl. Microbiol Biotechnol.,* 48(2):232-235 (1997)), unless otherwise noted. Briefly, *Yarrowia* was streaked onto a YPD plate and grown at 30° C. for approximately 18 hr. Several large loopfuls of cells were scraped from the plate and resuspended in 1 mL of transformation buffer containing: 2.25 mL of 50% PEG, average MW 3350; 0.125 mL of 2 M Li acetate, pH 6.0; 0.125 mL of 2 M DTT; and 50 μg sheared salmon sperm DNA. Then, approximately 500 ng of linearized plasmid DNA was incubated in 100 μl of resuspended cells, and maintained at 39° C. for 1 hr with vortex mixing at 15 min intervals. The cells were plated onto selection media plates and maintained at 30° C. for 2 to 3 days.

For selection of transformants, minimal medium ("MM") was generally used; the composition of MM is as follows:

0.17% yeast nitrogen base (DIFCO Laboratories, Detroit, Mich.) without ammonium sulfate or amino acids, 2% glucose, 0.1% proline, pH 6.1). Supplements of uracil were added as appropriate to a final concentration of 0.01% (thereby producing "MMU" selection media, prepared with 20 g/L agar).

Alternatively, transformants were selected on 5-fluoroorotic acid ("FOA"; also 5-fluorouracil-6-carboxylic acid monohydrate) selection media, comprising: 0.17% yeast nitrogen base (DIFCO Laboratories) without ammonium sulfate or amino acids, 2% glucose, 0.1% proline, 75 mg/L uracil, 75 mg/L uridine, 900 mg/L FOA (Zymo Research Corp., Orange, Calif.) and 20 g/L agar.

Fatty Acid Analysis of *Yarrowia lipolytica*

For fatty acid analysis, cells were collected by centrifugation and lipids were extracted as described in Bligh, E. G. & Dyer, W. J. (*Can. J. Biochem. Physiol.,* 37:911-917 (1959)). Fatty acid methyl esters were prepared by transesterification of the lipid extract with sodium methoxide (Roughan, G., and Nishida I., *Arch Biochem Biophys.,* 276(1):38-46 (1990)) and subsequently analyzed with a Hewlett-Packard 6890 GC fitted with a 30-m×0.25 mm (i.d.) HP-INNOWAX (Hewlett-Packard) column. The oven temperature was from 170° C. (25 min hold) to 185° C. at 3.5° C./min.

For direct base transesterification, *Yarrowia* culture (3 mL) was harvested, washed once in distilled water, and dried under vacuum in a Speed-Vac for 5-10 min. Sodium methoxide (100 μl of 1%) was added to the sample, and then the sample was vortexed and rocked for 20 min. After adding 3 drops of 1 M NaCl and 400 μl hexane, the sample was vortexed and spun. The upper layer was removed and analyzed by GC as described above.

Example 1

*Peridinium* sp. CCMP626 Lipid Profile and RNA Isolation

Figure 2:
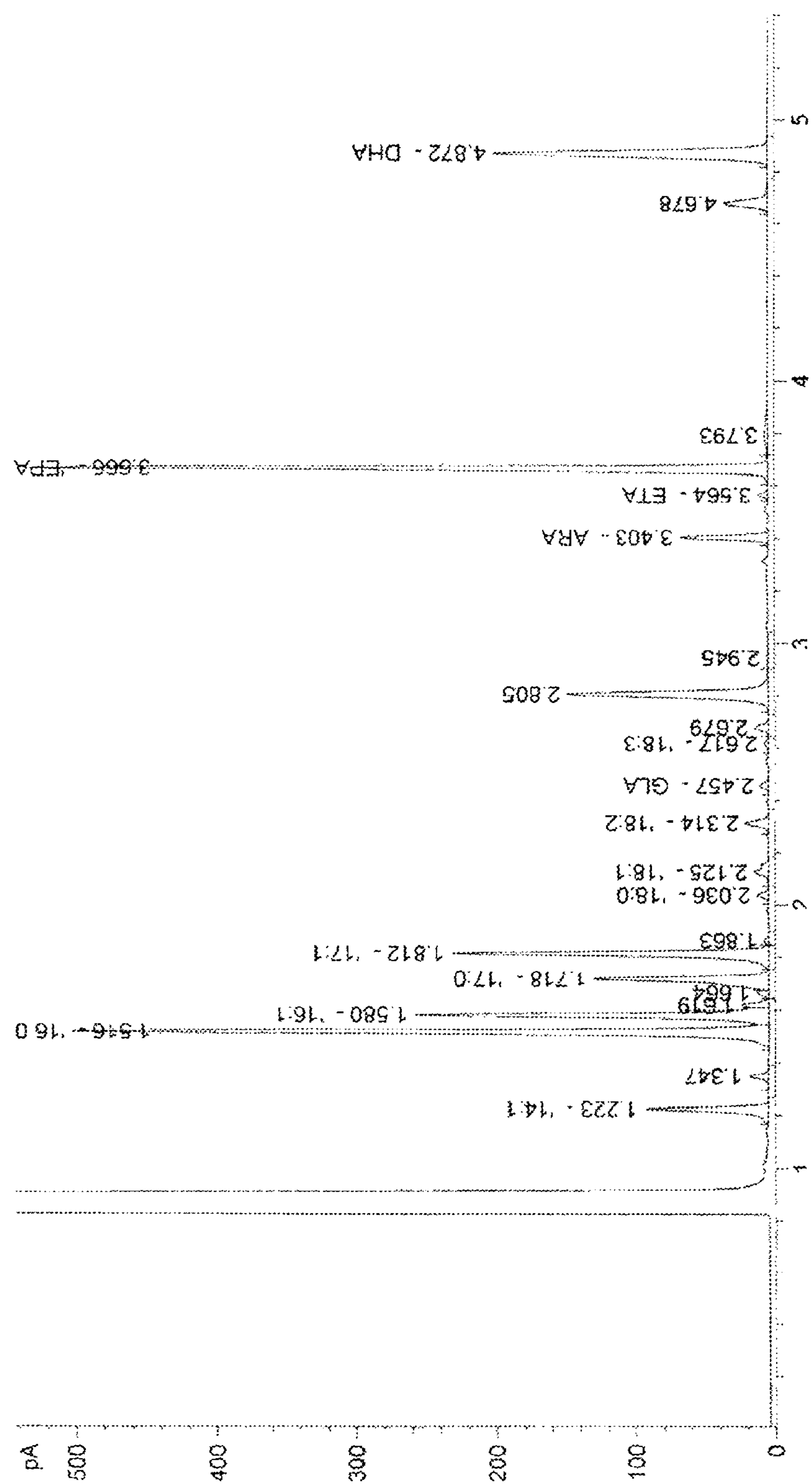
FIG. 2 shows a chromatogram of the lipid profile of a *Peridinium* sp. CCMP626 cell extract as described in Example 1.

*Peridinium* sp. CCMP626 (red algae) was purchased from The Provasoli-Guillard National Center for Culture of Marine Phytoplankton (Boothbay Harbor, Me.). About 200 mg cells were dried for 5 min under vacuum, resuspended in 100 μL of trimethylsulfonium hydroxide (TMSH) and incubated at room temperature for 15 min with shaking. After this, 0.5 mL of hexane was added and the vials were incubated for 15 min at room temperature with shaking. Fatty acid methyl esters (5 μL injected from hexane layer) were separated and quantified using a Hewlett-Packard 6890 Gas Chromatograph fitted with an Omegawax 320 fused silica capillary column (Catalog #24152, Supelco Inc., Bellefonte, Pa.). The oven temperature was programmed to hold at 220° C. for 2.7 min, increase to 240° C. at 20° C./min and then hold for an additional 2.3 min. Carrier gas was supplied by a Whatman hydrogen generator. Retention times were compared to those for methyl esters of standards commercially available (Catalog #U-99-A, Nu-Chek Prep, Inc., Elysian, Minn.) and the resulting chromatogram is shown in FIG. 2.

The GC profile demonstrated that *Peridinium* sp. CCMP626 cells produced large amounts of both ARA and EPA, thus suggesting the presence of a delta-5 desaturase with high efficiency. Since only a trace amount of GLA was detected, it was hypothesized that *Peridinium* sp. CCMP626 utilizes a delta-9 elongase/delta-8 desaturase pathway for PUFA production.

Total RNA was extracted from CCMP626 cells. Specifically, cells from 1 L of culture were collected by centrifugation, quick frozen in liquid $N_2$ and stored at −80° C. The cell pellet was resuspended in 1 mL of Trizol reagent (Invitrogen, Carlsbad, Calif.), mixed with 0.6 mL of glass beads (0.5 mm), and the mixture was homogenized at the highest setting on a Biospec Mini Beadbeater (Bartlesville, Okla.) for 3 min. Total RNA was then isolated, according to Invitrogen's protocol for Trizol. In this way, total RNA (34 μg) was obtained from 1 L culture. The total RNA sample was used for preparation of cDNA.

Example 2

*Peridinium* sp. CCMP626 cDNA Synthesis cDNA was synthesized directly from the *Peridinium* sp. CCMP626 total RNA as follows. Specifically, the total RNA was primered with adapter primer AP (SEQ ID NO:27) from Invitrogen's 3'-RACE kit (Carlsbad, Calif.), in the presence of the Smart IV oligonucleotide (SEQ ID NO:28) from the BD-Clontech Creator™ Smart™ cDNA library kit (Mississauga, ON, Canada). The reverse transcription was done with Superscript II reverse transcriptase from the 3'-RACE kit according to the protocol of the Creator™ Smart™ cDNA library kit.

The 1$^{st}$ strand cDNA synthesis mixture was used as template for PCR amplification, using primer AP (SEQ ID NO:27) as the 3' primer and CDSIII 5' primer (SEQ ID NO:29) as the 5' primer (supplied with the BD-Clontech Creator™ Smart™ cDNA library kit). Amplification was carried out with Clontech Advantage cDNA polymerase mix at 94° C. for 30 sec, followed by 20 cycles of 94° C. for 10 sec and 68° C. for 6 min. A final extension at 68° C. for 7 min was performed.

Example 3

Isolation of a Portion of the Coding Region of the *Peridinium* sp. CCMP626 Delta-5 Desaturase Gene The present Example describes the identification of a portion of the *Peridinium* sp. CCMP626 gene encoding delta-5 desaturase (designated herein as "RD5" [i.e., red algae D5] and corresponding to SEQ ID NOs:1 and 2), by use of primers derived from conserved regions of other known delta-5 and delta-8 desaturase sequences.

Various considerations were made when evaluating which desaturases might enable design of degenerate primers suitable to isolate the *Peridinium* sp. CCMP626 delta-5 desaturase. Specifically, the Applicants knew that only delta-5, delta-6 and delta-8 desaturase sequences comprise a conserved 'HPGG' motif at their N-terminus (wherein the 'HPGG' domain is part of the well-known cytochrome B5 domain); in contrast, delta-9 desaturases possess a 'HPGG' motif of the cytochrome B5 domain at their C-terminus, while both delta-17 and delta-12 desaturases lack the cytochrome B5 domain. Based on the GC results described in FIG. 2, it was assumed that a delta-9 elongase/delta-8 desaturase pathway operated in *Peridinium* sp. CCMP626; thus, among the desaturases sharing the N-terminal conserved 'HPGG' motif, only delta-5 and delta-8 desaturases were expected within the organism. Finally, although only a few delta-8 desaturase sequences are known, numerous delta-5 desaturase are publicly available. The Applicants selected those delta-5 desaturase sequences that possessed lower homology to "traditional" delta-5 desaturase genes and that also shared high homology to one another.

Based on the above, the four delta-5 desaturases and two delta-8 desaturases shown below in Table 3 were aligned, using the method of Clustal W (slow, accurate, Gonnet option; Thompson et al., *Nucleic Acids Res.,* 22:4673-4680 (1994)) of the MegAlign™ program of DNASTAR software.

TABLE 3

Delta-5 And Delta-8 Desaturases Aligned To Identify Regions Of Conserved Amino Acids

| Desaturase | Organism | Reference | SEQ ID NO: |
|---|---|---|---|
| delta-5 | *Pythium irregulare* | GenBank Accession No. AAL13311 | 12 |
| delta-5 | *Phytophthora megasperma* | GenBank Accession No. CAD53323 | 13 |
| delta-5 | *Phaeodactylum tricornutum* | GenBank Accession No. AAL92562 | 14 |
| delta-5 | *Dictyostelium discoideum* | GenBank Accession No. XP_640331 | 15 |
| delta-8 | *Euglena gracilis* | PCT Publications No. WO 2006/012325 and No. WO 2006/012326 | 16 |
| delta-8 | *Pavlova lutheri* | Example 12 (infra) | 18 |

FIG. 3 shows a portion of the resulting alignment, containing several stretches of conserved amino acid sequence among the 6 different organisms. Based on this alignment, two sets of degenerate oligonucleotides were designed to amplify a portion of the coding region of the delta-5 desaturase gene from *Peridinium* sp. CCMP626, corresponding to the regions of FIG. 3 that are labeled as "Conserved Region 1" and "Conserved Region 2". Specifically, the conserved amino acid sequence GHH(IN)YTN (SEQ ID NO:19) was designed to correspond to Conserved Region 1, while the conserved amino acid sequence NFQ(V/A)(S/N)HV (SEQ ID NO:20) was designed to correspond to Conserved Region 2. In order to reduce the degeneracy of the oligonucleotides, 4 sets of oligonucleotides (i.e., 5-1A, 5-1B, 5-1C and 5-1D) were designed to encode Conserved Region 1; and, 4 sets of oligonucleotides (i.e., 5-4AR, 5-4BR, 5-4CR and 5-4DR) were designed to encode the anti-sense strand of Conserved Region 2.

TABLE 4

Degenerate Oligonucleotides Used To Amplify The Delta-5 Desaturase Gene From *Peridinium* sp. CCMP626

| Oligonucleotide Name | Sequence | SEQ ID NO |
|---|---|---|
| 5-1A | GGHCAYCAYRTBTAYACAAA | SEQ ID NO: 30 |
| 5-1B | GGHCAYCAYRTBTAYACCAA | SEQ ID NO: 31 |
| 5-1C | GGHCAYCAYRTBTAYACGAA | SEQ ID NO: 32 |
| 5-1D | GGHCAYCAYRTBTAYACTAA | SEQ ID NO: 33 |
| 5-4AR | ACRTGRYTNACYTGRAAGTT | SEQ ID NO: 34 |
| 5-4BR | ACRTGRYTNACYTGRAAATT | SEQ ID NO: 35 |
| 5-4CR | ACRTGNGANACYTGRAAGTT | SEQ ID NO: 36 |
| 5-4DR | ACRTGNGANACYTGRAAATT | SEQ ID NO: 37 |

[Note:
The nucleic acid degeneracy code used for SEQ ID NOs: 30 to 37 was as follows: R = A/G; Y = C/T; B = G/T/C; and H = A/C/T.]

Based on the full-length sequences of the delta-5 sequences of FIG. 3, it was hypothesized that the *Peridinium* sp. CCMP626 delta-5 gene fragment amplified as described above would be about 630 bp in length (lacking about 210 amino acids at its N-terminal and 70 amino acids at its C-terminal).

A total of sixteen different PCR amplifications were conducted, as all combinations of the primers were tested (i.e., primer 5-1A was used with each of 5-4AR, 5-4BR, 5-4CR and 5-4DR, individually; similarly, primer 5-1B was used with each 5-4AR, 5-4BR, 5-4CR and 5-4DR; etc.). The PCR amplifications were carried out in a 50 µl total volume comprising: PCR buffer (containing 10 mM KCl, 10 mM $(NH_4)_2SO_4$, 20 mM Tris-HCl (pH 8.75), 2 mM $MgSO_4$, 0.1% Triton X-100), 100 µg/mL BSA (final concentration), 200 µM each deoxyribonucleotide triphosphate, 10 µmole of each primer, 10 ng cDNA of *Peridinium* sp. CCMP626 and 1 µl of Taq DNA polymerase (Epicentre Technologies, Madison, Wis.). The thermocycler conditions were set for 35 cycles at 95° C. for 1 min, 56° C. for 30 sec and 72° C. for 1 min, followed by a final extension at 72° C. for 10 min.

The PCR products were purified using a Qiagen PCR purification kit (Valencia, Calif.). One fragment of the approximate expected size was then further purified following gel electrophoresis in 1% (w/v) agarose and then cloned into the pGEM-T-easy vector (Promega, Madison, Wis.). The ligated DNA was used to transform cells of *E. coli* DH10B and transformants were selected on LB (1% bacto-tryptone, 0.5% bacto-yeast extract and 1% NaCl) agar containing ampicillin (100 µg/mL). Analysis of the plasmid DNA from a group of 12 transformants confirmed the presence of the insert with the expected size (plasmids were designated as "pT-12-D1", "pT-12-D2", "pT-12-D3", etc. to "pT-12-D12").

Sequence analyses showed that pT-12-D5 contained a 563 bp fragment (SEQ ID NO:4), which encoded 187 amino acids (SEQ ID NO:5) (including amino acids that corresponded to Conserved Region 1 and 2). Identity of the *Peridinium* sp. CCMP626 sequence was determined by conducting BLAST (Basic Local Alignment Search Tool; Altschul, S. F., et al., *J. Mol. Biol.,* 215:403-410 (1993)) searches for similarity to sequences contained in the BLAST "nr" database (comprising all non-redundant GenBank CDS translations, sequences derived from the 3-dimensional structure Brookhaven Protein Data Bank, the SWISS-PROT protein sequence database, EMBL and DDBJ databases). The sequence was analyzed for similarity to all publicly available DNA sequences contained in the "nr" database using the BLASTN algorithm provided by the National Center for Biotechnology Information (NCBI). SEQ ID NO:4 was compared for similarity to all publicly available protein sequences contained in the "nr" database, using the BLASTX algorithm (Gish, W. and States, D. J., *Nature Genetics,* 3:266-272 (1993)) provided by the NCBI.

The results of the BLASTX comparison summarizing the sequence to which SEQ ID NO:4 has the most similarity are reported according to the % identity, % similarity and Expectation value. "% Identity" is defined as the percentage of amino acids that are identical between the two proteins. "% Similarity" is defined as the percentage of amino acids that are identical or conserved between the two proteins. "Expectation value" estimates the statistical significance of the match, specifying the number of matches, with a given score, that are expected in a search of a database of this size absolutely by chance. Thus, the translated amino acid sequence of SEQ ID NO:4 (i.e., SEQ ID NO:5) had 64% identity and 78% similarity with the amino acid sequence of the delta-8-sphingolipid desaturase of *Thalassiosira pseudonana* (GenBank Accession No. AAX14502; SEQ ID NO:21), with an Expectation value of 2E-64; additionally, the partial fragment of SEQ ID NO:4 had 65% identity and 78% similarity with the delta-5 fatty acid desaturase of *Phaeodactylum tricornutum* (GenBank Accession No. AAL92562; SEQ ID NO:14), with an Expectation value of 7E-62.

Example 4

Isolation of the 5'Coding Region of the *Peridinium* sp. CCMP626 Delta-5 Desaturase Gene To isolate the N-terminal portion of the putative delta-5 desaturase identified in Example 3, a modified 5' RACE technique based on RACE protocols from two different companies (i.e., Invitrogen and BD-Clontech) was utilized.

Briefly, the double-stranded cDNA of *Peridinium* sp. CCMP626 (Example 2) was used as the template in a 5' RACE experiment, comprising two separate rounds of PCR amplification. In the first round of PCR amplification, the oligonucleotide primers consisted of a gene specific oligonucleotide (i.e., ODMW520; SEQ ID NO:38) and the generic oligonucleotide CDSIII 5' primer (SEQ ID NO:29) from the BD-Clontech Creator™ Smart™ cDNA library kit. The PCR amplifications were carried out in a 50 µl total volume, comprising: 25 µl of LA Taq™ pre-mix (TaKaRa Bio Inc., Otsu, Shiga, 520-2193, Japan), 10 pmole of each primer and 1 µl of Taq DNA polymerase (Epicentre Technologies, Madison, Wis.). The thermocycler conditions were set for 35 cycles at 95° C. for 1 min, 56° C. for 30 sec and 72° C. for 1 min, followed by a final extension at 72° C. for 10 min.

The second round of PCR amplification used 1 µl of the product from the first round PCR reaction as template. Primers consisted of a gene specific oligonucleotide (i.e., ODMW521; SEQ ID NO:39) and the generic oligonucleotide DNR CDS 5' (SEQ ID NO:40), supplied with BD-Clontech's Creator™ Smart™ cDNA library kit. Amplification was conducted as described above.

The products of the second round PCR reaction were electrophoresed in 1% (w/v) agarose. Products between 400 bp and 800 bp were then purified from the gel and cloned into the pGEM-T-easy vector (Promega, Madison, Wis.). The ligated DNA was used to transform *E. coli* DH10B and transformants were selected on LB agar containing ampicillin (100 µg/mL).

Analysis of the plasmid DNA from one transformant comprising the 5' region of the putative delta-5 desaturase gene confirmed the presence of the expected plasmid, designated pT-RD5-5'C2. Sequence analyses showed that pT-RD5-5'C2 contained a fragment of 693 bp (SEQ ID NO:6), which overlapped with 182 bp from the 5' end of the 563 bp fragment of pT-12-D5 (Example 3; SEQ ID NO:4) and additionally provided 511 bp of 5' upstream sequence (SEQ ID NO:7) (FIG. 4). The sequence of pT-RD5-5'C2 also corrected the sequence corresponding to Conserved Region 1, resulting from use of a degenerate oligonucleotide for initial PCR amplification of the 563 bp fragment in pT-12-D5 (Example 3). However, there was no translation initiation codon in the extended 693 bp fragment of SEQ ID NO:6.

A second round of the modified 5' RACE was carried out as described above, except that oligonucleotides ODMW541 (SEQ ID NO:41) and ODMW542 (SEQ ID NO:42) were used as gene-specific primers. Products between 200 bp and 400 bp were then purified from a gel and cloned into the pGEM-T-easy vector (Promega, Madison, Wis.). The ligated DNA was transformed into *E. coli* DH10B and transformants were selected on LB agar containing ampicillin (100 µg/mL).

Analysis of the plasmid DNA from one transformant comprising the 5' region of the putative delta-5 desaturase gene confirmed the presence of the expected plasmid, designated pT-RD5-5'2$^{nd}$. Sequence analyses showed that pT-RD5-5'2$^{nd}$ contained a fragment of 358 bp (SEQ ID NO:8), which overlapped with 197 bp of the 5' end of the DNA fragment in pT-RD5-5'C2 described above and additionally provided 161 bp of 5' upstream sequence (SEQ ID NO:9). One-hundred sixteen (116) bp of the 5' extended fragment encoded the N-terminal portion of the putative delta-5 desaturase gene, including the translation initiation codon, thus providing the complete 5' sequence of the gene.

Example 5

Isolation of the 3'Coding Region of the *Peridinium* sp. CCMP626 Delta-5 Desaturase Gene To isolate the C-terminal portion of the putative delta-5 desaturase identified in Example 3, a 3' RACE technique was utilized. The methodology was described above in Example 4; however, the primers used on both the first and second round of PCR amplification were as shown below in Table 5.

TABLE 5

Oligonucleotide Primers Used For 3' RACE

| PCR Amplification | Gene Specific Oligonucleotide | Generic Oligonucleotide |
|---|---|---|
| 1$^{st}$ Round | ODMW523 (SEQ ID NO: 43) | AUAP (SEQ ID NO: 44) |
| 2$^{nd}$ Round | ODMW524 (SEQ ID NO: 45) | AUAP (SEQ ID NO: 44) |

* Primer AUAP was supplied in Invitrogen's 3'-RACE kit (Carlsbad, CA).

Following isolation and purification of products (i.e., 200-500 bp), the fragments were cloned into the pGEM-T-easy vector (Promega) and transformed into *E. coli* DH10B, as in Example 4.

Analysis of the plasmid DNA from one transformant comprising the 3' region of the delta-5 desaturase gene confirmed the presence of the expected plasmid, designated pT-RD5-3'. Sequence analyses showed that pT-RD5-3' contained a fragment of 299 bp (SEQ ID NO:10), which over-lapped with 52 bp from the 3' end of the 563 bp fragment of pT-12-D5 (Example 3, SEQ ID NO:4) and provided 247 bp of additional 3' downstream sequence (SEQ ID NO:11). The first 202 bp of the extended 247 bp fragment included within pT-RD5-3' encoded the C-terminal coding region (including the translation stop codon) of the putative delta-5 desaturase gene. The sequence of pT-RD5-3' also corrected the sequence corresponding to Conserved Region 2, resulting from use of a degenerate oligonucleotide for initial PCR amplification of the 563 bp fragment in pT-12-D5 (Example 3).

After 2 rounds of 5' RACE and one round of 3' RACE, the DNA sequence of the entire putative *Peridinium* sp. CCMP626 delta-5 desaturase (RD5) coding region was determined. As shown in FIG. 4, the RD5 CDS was 1392 bp in length (SEQ ID NO:1) and encoded a polypeptide with 463 amino acids (SEQ ID NO:2), based on alignment of SEQ ID NOs:4, 6, 8 and 10. The results of BLASTP sequence analysis algorithms using the full length RD5 gene as the query sequence showed that it shared 67% identity and 81% similarity with the delta-5 fatty acid desaturase of *Phaeodactylum tricornutum* (GenBank Accession No. AAL92562; SEQ ID NO:14), with an Expectation value of 0.0. Additionally, the full length RD5 gene shared 64% identity and 76% similarity with the delta-8-sphingolipid desaturase of *Thalassiosira*

*pseudonana* (GenBank Accession No. AAX14502; SEQ ID NO:21), with an Expectation value of 2E-178.

Example 6

Generation of Construct pDMW368, Comprising RD5

The present Example describes the generation of pDMW368, comprising a chimeric FBAIN::RD5::Pex20 gene (FIG. 5C). This was designed to integrate the chimeric gene into the genome of *Yarrowia lipolytica* and then study the function of the *Peridinium* sp. CCMP626 delta-5 desaturase in *Yarrowia lipolytica*.

Based on the full length cDNA of RD5 (SEQ ID NO:1), oligonucleotides YL807 and YL810 (SEQ ID NOs:46 and 47, respectively) were used as primers to amplify the first portion of RD5 (FIG. 5A). Primer YL807 contained a NcoI site and primer YL810 contained a BamH1 site. Then, primers YL808 and YL809 (SEQ ID NOs:48 and 49, respectively) were used as primers to amplify the second portion of RD5. Primer YL809 contained a BamH1 site, while primer YL808 contained a NotI site. The PCR reactions, using primer pairs YL807/YL810 or YL808/YL809, with *Peridinium* sp. CCMP626 cDNA (Example 2) as template, were individually carried out in a 50 μl total volume comprising: PCR buffer (containing 10 mM KCl, 10 mM $(NH_4)_2SO_4$, 20 mM Tris-HCl (pH 8.75), 2 mM $MgSO_4$, 0.1% Triton X-100), 100 μg/mL BSA (final concentration), 200 μM each deoxyribonucleotide triphosphate, 10 pmole of each primer and 1 μl of Pfu DNA polymerase (Stratagene, San Diego, Calif.). The thermocycler conditions were set for 35 cycles at 95° C. for 1 min, 56° C. for 30 sec and 72° C. for 1 min, followed by a final extension at 72° C. for 10 min.

The individual PCR products were purified using a Qiagen PCR purification kit. The PCR products from the reaction amplified with primers YL807/YL810 were digested with NcoI and BamH1, while the PCR products from the reaction amplified with primers YL808/YL809 were digested with BamH1 and NotI. The NcoI/BamH1- and the BamH1/NotI-digested DNA fragments were purified following gel electrophoresis in 1% (w/v) agarose, and then directionally ligated with NcoI/NotI-digested pZUF17 (FIG. 5B; SEQ ID NO:22; comprising a synthetic delta-17 desaturase gene ["D17st"] derived from *Saprolegnia diclina* (U.S. Patent Publication No. 2003/0196217 A1), codon-optimized for expression in *Yarrowia lipolytica* (PCT Publication No. WO 2004/101757)). The product of this ligation was pDMW368 (FIG. 5C; SEQ ID NO:23, which thereby contained the following components:

TABLE 6

Components Of Plasmid pDMW368

| RE Sites And Nucleotides Within SEQ ID NO: 23 | Description Of Fragment And Chimeric Gene Components |
|---|---|
| EcoR I/BsiW I (6063-318) | FBAIN::RD5::Pex20, comprising: FBAIN: *Yarrowia lipolytica* FBAIN promoter (PCT Publication No. WO 2005/049805; U.S. Pat. No. 7,202,356) RD5: *Peridinium* sp. CCMP626 delta-5 desaturase (SEQ ID NO: 1 described herein) Pex20: Pex20 terminator sequence of *Yarrowia* Pex20 gene (GenBank Accession No. AF054613) |
| 1354-474 | ColE1 plasmid origin of replication |
| 2284-1424 | ampicillin-resistance gene ($Amp^R$) for selection in *E. colia* |
| 3183-4487 | *Yarrowia* autonomous replication sequence (ARS18; GenBank Accession No. A17608) |
| 6020-4533 | *Yarrowia* Ura 3 gene (GenBank Accession No. AJ306421) |

The term "FBAIN promoter" or "FBAIN promoter region" refers to the 5' upstream untranslated region in front of the 'ATG' translation initiation codon of the *Yarrowia lipolytica* fructose-bisphosphate aldolase enzyme (E.C. 4.1.2.13) encoded by the fba1 gene and that is necessary for expression, plus a portion of 5' coding region that has an intron of the fba1 gene.

Example 7

Generation of *Yarrowia lipolytica* Strain M4 to Produce About 8% DGLA of Total Lipids The present Example describes the construction of strain M4, derived from *Yarrowia lipolytica* ATCC #20362, capable of producing 8% DGLA relative to the total lipids. This strain was engineered to express the delta-6 desaturase/delta-6 elongase pathway, via introduction of construct pKUNF12T6E (FIG. 6A; SEQ ID NO:24). This construct was generated to integrate four chimeric genes (comprising a delta-12 desaturase, a delta-6 desaturase and two $C_{18/20}$ elongases) into the Ura3 loci of wild type *Yarrowia* strain ATCC #20362, to thereby enable production of DGLA. Thus, pKUNF12T6E contained the following components:

TABLE 7

Description of Plasmid pKUNF12T6E (SEQ ID NO: 24)

| RE Sites And Nucleotides Within SEQ ID NO: 24 | Description Of Fragment And Chimeric Gene Components |
|---|---|
| AscI/BsiWI (9420-8629) | 784 bp 5' portion of *Yarrowia* Ura3 gene (GenBank Accession No. AJ306421) |
| SphI/PacI (12128-1) | 516 bp 3' portion of *Yarrowia* Ura3 gene (GenBank Accession No. AJ306421) |
| SwaI/BsiWI (6380-8629) | FBAIN::EL1S::Pex20, comprising: FBAIN: *Yarrowia lipolytica* FBAIN promoter (PCT Publication No. WO 2005/049805; U.S. Pat. No. 7,202,356; labeled as "Fba1 + intron" in Figure) EL1S: codon-optimized elongase 1 gene (PCT Publication No. WO 2004/101753), derived from *Mortierella alpina* (GenBank Accession No. AX464731) Pex20: Pex20 terminator sequence from *Yarrowia* Pex20 gene (GenBank Accession No. AF054613) |
| BglII/SwaI (4221-6380) | TEF::delta-6S::Lip1, comprising: TEF: *Yarrowia lipolytica* TEF promoter (GenBank Accession No. AF054508) delta-6S: codon-optimized delta-6 desaturase gene (PCT Publication No. WO 2004/101753), derived from *Mortierella alpina* (GenBank Accession No. AF465281) Lip1: Lip1 terminator sequence from *Yarrowia* Lip1 gene (GenBank Accession No. Z50020) |
| PmeI/ClaI (4207-1459) | FBA::F.delta-12::Lip2, comprising: FBA: *Yarrowia lipolytica* FBA promoter (PCT Publication No. WO 2005/049805; U.S. Pat. No. 7,202,356; labeled as "FBA1" in Figure) |

TABLE 7-continued

Description of Plasmid pKUNF12T6E (SEQ ID NO: 24)

| RE Sites And Nucleotides Within SEQ ID NO: 24 | Description Of Fragment And Chimeric Gene Components |
|---|---|
| | F.delta-12: *Fusarium moniliforme* delta-12 desaturase gene (PCT Publication No. WO 2005/047485)<br>Lip2: Lip2 terminator sequence from *Yarrowia* Lip2 gene (GenBank Accession No. AJ012632) |
| ClaI/PacI (1459-1) | TEF::EL2Syn::XPR2, comprising:<br>TEF: *Yarrowia lipolytica* TEF promoter (GenBank Accession No. AF054508)<br>EL2Syn: codon-optimized elongase gene (SEQ ID NO: 25), derived from *Thraustochytrium aureum* (U.S. Pat. No. 6,677,145)<br>XPR2: ~100 bp of the 3' region of the *Yarrowia* Xpr gene (GenBank Accession No. M17741) |

Plasmid pKUNF12T6E was digested with AscI/SphI, and then used for transformation of wild type *Y. lipolytica* ATCC #20362 according to the General Methods. The transformant cells were plated onto FOA selection media plates and maintained at 30° C. for 2 to 3 days. The FOA resistant colonies were picked and streaked onto MM and MMU selection plates. The colonies that could grow on MMU plates but not on MM plates were selected as Ura− strains. Single colonies of Ura− strains were then inoculated into liquid MMU at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed the presence of DGLA in the transformants containing the 4 chimeric genes of pKUNF12T6E, but not in the wild type *Yarrowia* control strain. Most of the selected 32 Ura− strains produced about 6% DGLA of total lipids. There were 2 strains (i.e., strains M4 and 13-8) that produced about 8% DGLA of total lipids.

Example 8

Functional Analysis of RD5 Gene in *Yarrowia lipolytica* Strain M4

Plasmid pDMW368 (Example 6; comprising a chimeric FBAIN::RD5::Pex20 gene was transformed into strain M4 (Example 7), as described in the General Methods. The transformants were selected on MM plates. After 2 days grown at 30° C., 3 transformants grown on the MM plates were picked and re-streaked onto fresh MM plates. Once grown, these strains were individually inoculated into 3 mL liquid MM at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed that there were about 4.2% DGLA and 2.2% ARA of total lipids produced in all three transformants, wherein the conversion efficiency of DGLA to ARA in these three strains was determined to be about 35% (average). The conversion efficiency was measured according to the following formula: ([product]/[substrate+product])*100, where 'product' includes the immediate product and all products in the pathway derived from it. Thus, this experimental data demonstrated that the cloned *Peridinium* sp. CCMP626 delta-5 desaturase, described herein as SEQ ID NOs:1 and 2, efficiently desaturated DGLA to ARA.

Example 9

Synthesis of a Codon-Optimized Delta-5 Desaturase Gene ("RD5S") for Expression in *Yarrowia lipolytica*

The codon usage of the delta-5 desaturase gene of *Peridinium* sp. CCMP626 (SEQ ID NOs:1 and 2; RD5) was optimized for expression in *Yarrowia lipolytica*, in a manner similar to that described in PCT Publication No. WO 2004/101753 and U.S. Pat. No. 7,125,672. Specifically, a codon-optimized delta-5 desaturase gene (designated "RD5S", SEQ ID NO:3) was designed based on the coding sequence of the delta-5 desaturase gene of RD5 (SEQ ID NO:2), according to the *Yarrowia* codon usage pattern (PCT Publication No. WO 2004/101753), the consensus sequence around the 'ATG' translation initiation codon, and the general rules of RNA stability (Guhaniyogi, G. and J. Brewer, *Gene,* 265(1-2):11-23 (2001)). In addition to modification of the translation initiation site, 247 bp of the 1392 bp coding region was modified (17.7%, FIGS. 7A and 7B) and 229 codons were optimized (49.4%). The GC content was increased from 49.3% within the wild type gene (i.e., RD5) to 54.2% within the synthetic gene (i.e., RD5S). A NcoI site and NotI sites were incorporated around the translation initiation codon and after the stop codon of RD5S (SEQ ID NO:3), respectively. None of the modifications in the codon-optimized gene changed the amino acid sequence of the encoded protein (SEQ ID NO:2). The designed RD5S gene was synthesized by GenScript Corporation (Piscataway, N.J.) and cloned into pUC57 (GenBank Accession No. Y14837) to generate pRD5S (SEQ ID NO:50; FIG. 6B) (RD5S labeled as "RD5S (626)" in Figure).

Example 10

Generation of Construct pZURD5S, Comprising RD5S

The present Example describes the construction of plasmid pZURD5S comprising a chimeric FBAIN::RD5S::Pex20 gene. Plasmid pZURD5S (SEQ ID NO:51; FIG. 6C) was constructed by replacing the Nco I/Not I fragment of pZUF17 (FIG. 5B; SEQ ID NO:22) with the Nco I/Not I RD5S fragment from pRD5S (SEQ ID NO:50; FIG. 6B). The product of this ligation was pZURD5S (FIG. 6C; SEQ ID NO:51), which thereby contained the following components:

TABLE 8

Components Of Plasmid pZURD5S

| RE Sites And Nucleotides Within SEQ ID NO: 51 | Description Of Fragment And Chimeric Gene Components |
|---|---|
| EcoR I/BsiW I (7458-1713) | FBAIN::RD5S::Pex20, comprising:<br>FBAIN: *Yarrowia lipolytica* FBAIN promoter (PCT Publication No. WO 2005/049805; U.S. Pat. No. 7,202,356)<br>RD5S: codon-optimized delta-5 desaturase (SEQ ID NO: 3, described herein as RD5S), derived from *Peridinium* sp. CCMP626 (labeled as "RD5S(626)" in Figure)<br>Pex20: Pex20 terminator sequence of *Yarrowia* Pex20 gene (GenBank Accession No. AF054613) |
| 2749-1869 | ColE1 plasmid origin of replication |
| 3679-2819 | ampicillin-resistance gene ($Amp^R$) for selection in *E. coli* |
| 4578-5882 | *Yarrowia* autonomous replication sequence (ARS18; |

TABLE 8-continued

| Components Of Plasmid pZURD5S | |
|---|---|
| RE Sites And Nucleotides Within SEQ ID NO: 51 | Description Of Fragment And Chimeric Gene Components |
| | GenBank Accession No. A17608) |
| 7415-5928 | *Yarrowia* Ura 3 gene (GenBank Accession No. AJ306421) |

Example 11

Expression of the Codon-Optimized Delta-5 Desaturase ("RD5S") in *Yarrowia lipolytica* Strain M4

Plasmid pZURD5S (Example 10; comprising a chimeric FBAIN::RD5S::Pex20 gene) was used for transformation into strain M4 (Example 7), as described in the General Methods. Eight (8) transformants grown on the MM plates were picked and re-streaked onto fresh MM plates. Once grown, these strains were individually inoculated into 3 mL liquid MM at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

The GC results showed that there were about 5.4% DGLA and 3.3% ARA of total lipids produced in all 8 transformants. The conversion efficiency whereby RD5S converted DGLA to ARA in these 8 strains was at an average rate of about 38%. The conversion efficiency was measured according to the following formula: ([product]/[substrate+product])*100, where 'product' includes the immediate product and all products in the pathway derived from it. Thus, this experimental data demonstrated that the codon-optimized delta-5 desaturase gene (RD5S, as set forth in SEQ ID NO:3) derived from *Peridinium* sp. CCMP626 was about 8.9% more efficient converting DGLA to ARA than the wild type RD5 (Example 8).

Example 12

Isolation of a *Pavlova lutheri* (CCMP459) Delta-8 Desaturase

The present example describes the isolation of the *Pavlova lutheri* (CCMP459) delta-8 desaturase utilized in Example 3 and in FIG. 3 (also described in U.S. patent application Ser. No. 11/737,772, filed Apr. 20, 2007). This required: synthesis of *Pavlova lutheri* (CCMP459) cDNA; library construction and sequencing; identification of delta-8 desaturase homologs; and, cloning of a full-length delta-8 desaturase from genomic DNA.

*Pavlova lutheri* (CCMP459) cDNA Synthesis, Library Construction and Sequencing

A cDNA library of *Pavlova lutheri* (CCMP459) was synthesized as described in PCT Publication No. WO 2004/071467 (published Aug. 26, 2004). Briefly, frozen pellets of Pav459 were obtained from the Provasoli-Guillard National Center for Culture of Marine Phytoplankton (CCMP, West Boothbay Harbor, Me.). These pellets were crushed in liquid nitrogen and total RNA was extracted from Pav459 by using the Qiagen RNeasy® Maxi Kit (Qiagen, Valencia, Calif.), per the manufacturer's instructions. From this total RNA, mRNA was isolated using oligo dT cellulose resin, which was then used for the construction of a cDNA library using the pSport1 vector (Invitrogen, Carlsbad, Calif.). The cDNA thus produced was directionally cloned (5' SalI/3' NotI into pSport1 vector. The Pav459 library contained approximately $6.1\times10^5$ clones per mL, each with an average insert size of approximately 1200 bp. The *Pavlova lutheri* library was named eps1c.

For sequencing, clones first were recovered from archived glycerol cultures grown/frozen in 384-well freezing media plates, and inoculated with an automatic QPix® colony picker (Genetix) in 96-well deep-well plates containing LB+100 mg/mL ampicillin. After growing 20 hrs at 37° C., cells were pelleted by centrifugation and stored at −20° C. Plasmids then were isolated on an Eppendorf 5Prime robot, using a modified 96-well format alkaline lysis miniprep method (Eppendorf PerfectPrep®). Briefly, a filter and vacuum manifold was used to facilitate removal of cellular debris after acetate precipitation. Plasmid DNA was then bound on a second filter plate directly from the filtrate, washed, dried and eluted.

Plasmids were end-sequenced in 384-well plates, using vector-primed T7 primer (SEQ ID NO:52) and the ABI BigDye version 3 Prism sequencing kit. For the sequencing reaction, 100-200 ng of template and 6.4 pmol. of primer were used, and the following reaction conditions were repeated 25 times: 96° C. for 10 sec, 50° C. for 5 sec and 60° C. for 4 min. After ethanol-based cleanup, cycle sequencing reaction products were resolved and detected on Perkin-Elmer ABI 3700 automated sequencers.

Identification of Delta-8 Desaturase Enzyme Homologs from *Pavlova lutheri* cDNA Library eps1c cDNA clones encoding *Pavlova lutheri* delta-8 desaturase homologs (hereby called delta-8 desaturases) were identified by conducting BLAST searches for similarity to sequences contained in the BLAST "nr" database (as described in Example 3). The P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

The BLASTX search using the nucleotide sequence from clone eps1c.pk002.f22 revealed similarity of the protein encoded by the cDNA to the delta-6 desaturase from *Rhizopus stolonifer* (SEQ ID NO:53) (NCBI Accession No. AAX22052 (GI 60499699), locus AAX22052, CDS AY795076; Lu et al., unpublished). The sequence of a portion of the cDNA insert from clone eps1c.pk002.f22 is shown in SEQ ID NO:54 (5' end of cDNA insert). Subsequently, the full insert sequence (eps1c.pk002.f22:fis) was obtained and is shown in SEQ ID NO:55. Sequence for the deduced amino acid sequence (from nucleotide 1 of SEQ ID NO:55 to the first stop codon at nucleotide 864 of SEQ ID NO:55) is shown in SEQ ID NO:56. Full insert sequencing was carried out using a modified transposition protocol. Clones identified for full insert sequencing were recovered from archived glycerol stocks as single colonies, and plasmid DNA was isolated via alkaline lysis. Plasmid templates were transposed via the Template Generation System (TGS II) transposition kit (Finnzymes Oy, Espoo, Finland), following the manufacturer's protocol. The transposed DNA was transformed into EH10B electro-competent cells (Edge BioSystems, Gaithersburg, Md.) via electroporation. Multiple transformants were randomly selected from each transposition reaction, plasmid DNA was prepared, and templates were sequenced as above (ABI BigDye v3.1) outward from the transposition event site, utilizing unique primers SeqE (SEQ ID NO:57) and SeqW (SEQ ID NO:58).

Sequence data was collected (ABI Prism Collections software) and assembled using the Phrap sequence assembly program (P. Green, University of Washington, Seattle). Assemblies were viewed by the Consed sequence editor (D. Gordon, University of Washington, Seattle) for final editing.

The amino acid sequence set forth in SEQ ID NO:56 was evaluated by BLASTP, yielding a pLog value of 19.52 (E value of 3e-20) versus the delta-6 desaturase from *Mortierella alpina* (NCBI Accession No. BAC82361 (GI 34221934), locus BAC82361, CDS AB070557; Sakuradani and Shimizu, *Biosci. Biotechnol. Biochem.,* 67:704-711 (2003)). Based on the results from the BLASTP comparison to the *Mortierella alpina* and other fatty acid desaturases, the *Pavlova lutheri* delta-8 desaturase was not full length and was lacking sequence at the 5' end.

Cloning a Full-Length Delta-8 Desaturase from *Pavlova lutheri* Genomic DNA

Genomic DNA was isolated from *Pavlova lutheri* (CCMP459) using the Qiagen DNeasy® Plant Maxi Prep Kit according to the manufacturer's protocol. Using 1 maxi column per 1 gm of frozen cell pellet, a total of 122 μg of genomic DNA was isolated from 4 gm of *Pavlova lutheri* culture. The final concentration of genomic DNA was 22.8 ng/μL. GenomeWalker libraries were synthesized using the Universal GenomeWalker™ kit (BD Biosciences Clonetech, Palo Alto, Calif.) following the manufacturer's protocol (Prot #PT3042-1, version PRO3300). Briefly, four restriction digests were set up as per the protocol using 300 ng of genomic DNA per reaction. After phenol clean up, pellets were dissolved in 4 μL of water and adapters were ligated as per the protocol.

For the primary PCR, the Advantage®-GC Genomic PCR kit (BD Biosciences Clonetech) was used following the manufacturer's protocol (Prot #PT3090-1, version PR1X433). For each restriction digest, 1 μL of library was combined with 22.8 μL of PCR grade water, 10 μL of 5×GC Genomic PCR Reaction Buffer, 2.2 μL of 25 mM $Mg(CH_3CO_2)_2$, 10 μL of GC-Melt (5 M), 1 μL of 50×dNTP mix (10 mM each), 1 μL of Advantage-GC Genomic Pol. Mix (50×), 1 μL of Universal GenomeWalker™ primer AP1 (10 μM, SEQ ID NO:59) and 1 μL of GSP PvDES (10 μM, SEQ ID NO:60). After denaturation at 95° C., the following reaction conditions were repeated 35 times: 94° C. for 30 sec, 68° C. for 6 min. After these reaction conditions, an additional extension at 68° C. was carried out for 6 min followed by cooling to 15° C. until removed.

The primary PCR reaction for each library was analyzed by agarose gel electrophoresis and DNA bands with molecular weights around 6 kB, 3.5 kB, 2.5 kB and 1.2 kB were observed. DNA bands for each library were purified using the Zymoclean™ Gel DNA Recovery Kit (Zymo Research, Orange, Calif.) following the manufacturer's protocol. The resulting DNA was cloned into the pGEM®-T Easy Vector (Promega) following the manufacturer's protocol and inserts were sequenced using the T7 (SEQ ID NO:52) and M13-28Rev (SEQ ID NO:61) primers as described above. Additional sequence was then obtained using a gene-specific sequencing primer PavDES seq (SEQ ID NO:62) that was derived from the newly acquired sequence data. The full 5' end sequence obtained by genome walking is shown in SEQ ID NO:63. The sequence of the overlapping regions of the genomic sequence (SEQ ID NO:63) and the fully sequenced EST eps1c.pk002.f22:fis (SEQ ID NO:55) were aligned using Sequencher™ (Version 4.2, Gene Codes Corporation, Ann Arbor, Mich.) using the Large Gap assembly algorithm. Interestingly, the comparison showed that the EST that was originally sequenced (SEQ ID NO:55) was lacking 459 bp when compared to the genomic sequence (SEQ ID NO:63). This missing sequence in the EST appeared to be a deletion rather than an intron as no clear intron splice sites were identified in the genomic DNA at the 5' end of the gene. The genomic sequence for the 5' end (SEQ ID NO:63) was combined with the 3' end of the EST sequence (SEQ ID NO:55) to yield SEQ ID NO:64. Using Editseq™ 6.1 sequence analysis software (DNASTAR Inc., Madison, Wis.), an ORF was identified (SEQ ID NO:17). The amino acid sequence coded for by SEQ ID NO:17 is shown in SEQ ID NO:18.

The amino acid sequence set forth in SEQ ID NO:18 was evaluated by BLASTP, yielding a pLog value of 35.10 (E value of 8e-36) versus the delta-6 desaturase from *Rhizopus stolonifer* (SEQ ID NO:65) (NCBI Accession No. ABB96724 (GI 83027409), locus ABB96724, CDS DQ291156; Zhang et al., unpublished). Furthermore, the *Pavlova lutheri* delta-8 desaturase is 78.0% identical to the *Pavlova salina* delta-8 desaturase sequence (SEQ ID NO:66) disclosed in PCT Publication No. WO 2005/103253 (published Apr. 22, 2005) using the Jotun Hein method. Sequence percent identity calculations performed by the Jotun Hein method (Hein, J. J., *Meth. Enz.,* 183:626-645 (1990)) were done using the MegAlign™ v6.1 program of the LASERGENE bioinformatics computing suite (DNASTAR Inc., Madison, Wis.) with the default parameters for pairwise alignment (KTUPLE=2). The *Pavlova lutheri* delta-8 desaturase is 76.4% identical to the *Pavlova salina* delta-8 desaturase sequence using the Clustal V method. Sequence percent identity calculations performed by the Clustal V method (Higgins, D. G. and Sharp, P. M., *Comput. Appl. Biosci.,* 5:151-153 (1989); Higgins et al., *Comput Appl. Biosci.,* 8:189-191 (1992)) were done using the MegAlign™ v6.1 program of the LASERGENE bioinformatics computing suite (DNASTAR Inc.) with the default parameters for pairwise alignment (KTUPLE=1, GAP PENALTY=3, WINDOW=5, DIAGONALS SAVED=5 and GAP LENGTH PENALTY=10). BLAST scores and probabilities indicate that the fragment of SEQ ID NO:17 encodes an entire *Pavlova lutheri* delta-8 desaturase.

FIGS. 8A and 8B show a Clustal V alignment (with default parameters) of SEQ ID NO:18 (the amino acid sequence of the *Pavlova lutheri* delta-8 desaturase), SEQ ID NO:66 (the amino acid sequence of *Pavlova salina* delta-8 desaturase sequence, supra), SEQ ID NO:16 (the amino acid sequence of *Euglena gracilis* delta-8 desaturase sequence disclosed as SEQ ID NO:2 in PCT Publication No. WO 2006/012325; published Feb. 2, 2006), SEQ ID NO:65 (the amino acid sequence for the *Rhizopus stolonifer* delta-6 fatty acid desaturase (NCBI Accession No. ABB96724, supra)) and SEQ ID NO:53 (the amino acid sequence for the *Rhizopus stolonifer* delta-6 fatty acid desaturase (NCBI Accession No. AAX22052, supra)). The results of the Clustal V alignment show that SEQ ID NO:18 is 76.4%, 22.6%, 22.2% and 22.2% identical to SEQ ID NO:66, SEQ ID NO:16, SEQ ID NO:65 and SEQ ID NO:53, respectively.

Example 13

Transformation of Somatic Soybean Embryo Cultures

Culture Conditions:

Soybean embryogenic suspension cultures (cv. Jack) are maintained in 35 mL liquid medium SB196 (infra) on a rotary shaker, 150 rpm, 26° C. with cool white fluorescent lights on 16:8 hr day/night photoperiod at light intensity of 60-85 $\mu E/m^2/s$. Cultures are subcultured every 7 days to 2 weeks by inoculating approximately 35 mg of tissue into 35 mL of fresh liquid SB196 (the preferred subculture interval is every 7 days).

Soybean embryogenic suspension cultures are transformed with soybean expression plasmids by the method of particle gun bombardment (Klein et al., *Nature,* 327:70 (1987)) using a DuPont Biolistic PDS1000/HE instrument (helium retrofit) for all transformations.

Soybean Embryogenic Suspension Culture Initiation:

Soybean cultures are initiated twice each month with 5-7 days between each initiation. Pods with immature seeds from available soybean plants 45-55 days after planting are picked, removed from their shells and placed into a sterilized magenta box. The soybean seeds are sterilized by shaking them for 15 min in a 5% Clorox solution with 1 drop of ivory soap (i.e., 95 mL of autoclaved distilled water plus 5 mL Clorox and 1 drop of soap, mixed well). Seeds are rinsed using 2 1-liter bottles of sterile distilled water and those less than 4 mm are placed on individual microscope slides. The small end of the seed is cut and the cotyledons pressed out of the seed coat. Cotyledons are transferred to plates containing SB1 medium (25-30 cotyledons per plate). Plates are wrapped with fiber tape and stored for 8 weeks. After this time secondary embryos are cut and placed into SB196 liquid media for 7 days.

Preparation of DNA for Bombardment:

Either an intact plasmid or a DNA plasmid fragment containing the delta-5 desaturase genes of interest and the selectable marker gene are used for bombardment. Fragments from soybean expression plasmids comprising the delta-5 desaturase of the present invention are obtained by gel isolation of digested plasmids. The resulting DNA fragments are separated by gel electrophoresis on 1% SeaPlaque GTG agarose (BioWhitaker Molecular Applications) and the DNA fragments containing gene cassettes are cut from the agarose gel. DNA is purified from the agarose using the GELase digesting enzyme following the manufacturer's protocol.

A 50 μL aliquot of sterile distilled water containing 3 mg of gold particles is added to 5 μL of a 1 μg/μL DNA solution (either intact plasmid or DNA fragment prepared as described above), 50 μL 2.5 M $CaCl_2$ and 20 μL of 0.1 M spermidine. The mixture is shaken 3 min on level 3 of a vortex shaker and spun for 10 sec in a bench microfuge. After a wash with 400 μL of 100% ethanol, the pellet is suspended by sonication in 40 μL of 100% ethanol. DNA suspension (5 μL) is dispensed to each flying disk of the Biolistic PDS1000/HE instrument disk. Each 5 μL aliquot contains approximately 0.375 mg gold particles per bombardment (i.e., per disk).

Tissue Preparation and Bombardment with DNA:

Approximately 150-200 mg of 7 day old embryonic suspension cultures is placed in an empty, sterile 60×15 mm petri dish and the dish is covered with plastic mesh. Tissue is bombarded 1 or 2 shots per plate with membrane rupture pressure set at 1100 PSI and the chamber is evacuated to a vacuum of 27-28 inches of mercury. Tissue is placed approximately 3.5 inches from the retaining/stopping screen.

Selection of Transformed Embryos:

Transformed embryos ate selected using hygromycin as the selectable marker. Specifically, following bombardment, the tissue is placed into fresh SB196 media and cultured as described above. Six days post-bombardment, the SB196 is exchanged with fresh SB196 containing 30 mg/L hygromycin. The selection media is refreshed weekly. Four to six weeks post-selection, green, transformed tissue is observed growing from untransformed, necrotic embryogenic clusters. Isolated, green tissue is removed and inoculated into multi-well plates to generate new, clonally propagated, transformed embryogenic suspension cultures.

Embryo Maturation:

Embryos are cultured for 4-6 weeks at 26° C. in SB196 under cool white fluorescent (Phillips cool white Econowatt F40/CW/RS/EW) and Agro (Phillips F40 Agro) bulbs (40 watt) on a 16:8 hr photoperiod with light intensity of 90-120 $\mu E/m^2s$. After this time embryo clusters are removed to a solid agar media, SB166, for 1-2 weeks. Clusters are then subcultured to medium SB103 for 3 weeks. During this period, individual embryos are removed from the clusters and screened for alterations in their fatty acid compositions as described supra.

Media Recipes:

| SB 196 —FN Lite Liquid Proliferation Medium (per liter) | |
|---|---|
| MS FeEDTA - 100 × Stock 1 | 10 mL |
| MS Sulfate - 100 × Stock 2 | 10 mL |
| FN Lite Halides - 100 × Stock 3 | 10 mL |
| FN Lite P, B, Mo - 100 × Stock 4 | 10 mL |
| B5 vitamins (1 mL/L) | 1.0 mL |
| 2,4-D (10 mg/L final concentration) | 1.0 mL |
| $KNO_3$ | 2.83 gm |
| $(NH_4)_2SO_4$ | 0.463 gm |
| asparagine | 1.0 gm |
| sucrose (1%) | 10 gm |
| pH 5.8 | |

FN Lite Stock Solutions

| Stock Number | | 1000 mL | 500 mL |
|---|---|---|---|
| 1 | MS Fe EDTA 100x Stock | | |
| | $Na_2$ EDTA* | 3.724 g | 1.862 g |
| | $FeSO_4$—$7H_2O$ | 2.784 g | 1.392 g |
| *Add first, dissolve in dark bottle while stirring | | | |
| 2 | MS Sulfate 100x stock | | |
| | $MgSO_4$—$7H_2O$ | 37.0 g | 18.5 g |
| | $MnSO_4$—$H_2O$ | 1.69 g | 0.845 g |
| | $ZnSO_4$—$7H_2O$ | 0.86 g | 0.43 g |
| | $CuSO_4$—$5H_2O$ | 0.0025 g | 0.00125 g |
| 3 | FN Lite Halides 100x Stock | | |
| | $CaCl_2$—$2H_2O$ | 30.0 g | 15.0 g |
| | KI | 0.083 g | 0.0715 g |
| | $CoCl_2$—$6H_2O$ | 0.0025 g | 0.00125 g |
| 4 | FN Lite P, B, Mo 100x Stock | | |
| | $KH_2PO_4$ | 18.5 g | 9.25 g |
| | $H_3BO_3$ | 0.62 g | 0.31 g |
| | $Na_2MoO_4$—$2H_2O$ | 0.025 g | 0.0125 g |

| SB1 Solid Medium (per liter) |
|---|
| 1 package MS salts (Gibco/BRL - Cat. No. 11117-066) |
| 1 mL B5 vitamins 1000X stock |
| 31.5 g sucrose |
| 2 mL 2,4-D (20 mg/L final concentration) |
| pH 5.7 |
| 8 g TC agar |

| SB 166 Solid Medium (per liter) |
|---|
| 1 package MS salts (Gibco/BRL - Cat. No. 11117-066) |
| 1 mL B5 vitamins 1000X stock |
| 60 g maltose |
| 750 mg $MgCl_2$ hexahydrate |
| 5 g activated charcoal |
| pH 5.7 |
| 2 g gelrite |

| SB 103 Solid Medium (per liter) |
|---|
| 1 package MS salts (Gibco/BRL - Cat. No. 11117-066) |
| 1 mL B5 vitamins 1000X stock |
| 60 g maltose |

-continued

| |
|---|
| 750 mg $MgCl_2$ hexahydrate |
| pH 5.7 |
| 2 g gelrite |
| SB 71-4 Solid Medium (per liter) |
| 1 bottle Gamborg's B5 salts with sucrose (Gibco/BRL - Cat. No. 21153-036) |
| pH 5.7 |
| 5 g TC agar |
| 2,4-D Stock |
| Obtain premade from Phytotech Cat. No. D 295 - concentration 1 mg/mL |
| B5 Vitamins Stock (per 100 mL) |
| Store aliquots at −20° C. |
| 10 g myo-inositol |
| 100 mg nicotinic acid |
| 100 mg pyridoxine HCl |
| 1 g thiamine |

If the solution does not dissolve quickly enough, apply a low level of heat via the hot stir plate.

Example 14

Functional Analysis of Delta-5 Desaturase (SEQ ID NOs:1 and 2) in Somatic Soybean Embryos Mature somatic soybean embryos are a good model for zygotic embryos. While in the globular embryo state in liquid culture, somatic soybean embryos contain very low amounts of triacylglycerol (TAG) or storage proteins typical of maturing, zygotic soybean embryos. At this developmental stage, the ratio of total triacylglyceride to total polar lipid (phospholipids and glycolipid) is about 1:4, as is typical of zygotic soybean embryos at the developmental stage from which the somatic embryo culture was initiated. At the globular stage as well, the mRNAs for the prominent seed proteins, α'-subunit of β-conglycinin, kunitz trypsin inhibitor 3, and seed lectin are essentially absent. Upon transfer to hormone-free media to allow differentiation to the maturing somatic embryo state, TAG becomes the most abundant lipid class. As well, mRNAs for α'-subunit of β-conglycinin, kunitz trypsin inhibitor 3 and seed lectin become very abundant messages in the total mRNA population. On this basis, the somatic soybean embryo system behaves very similarly to maturing zygotic soybean embryos in vivo, and is thus a good and rapid model system for analyzing the phenotypic effects of modifying the expression of genes in the fatty acid biosynthesis pathway (see PCT Publication No. WO 2002/00904, Example 3). Most importantly, the model system is also predictive of the fatty acid composition of seeds from plants derived from transgenic embryos.

Transgenic somatic soybean embryos containing the delta-5 desaturase of the present invention are analyzed in the following way. Fatty acid methyl esters are prepared from single, matured, somatic soy embryos by transesterification. Individual embryos are placed in a vial containing 50 μL of trimethylsulfonium hydroxide (TMSH) and 0.5 mL of hexane and incubated for 30 min at room temperature while shaking. Fatty acid methyl esters (5 μL injected from hexane layer) are separated and quantified using a Hewlett-Packard 6890 Gas Chromatograph fitted with an Omegawax 320 fused silica capillary column (Catalog #24152, Supelco Inc.). The oven temperature are programmed to hold at 220° C. for 2.6 min, increase to 240° C. at 20° C./min and then hold for an additional 2.4 min. Carrier gas is supplied by a Whatman hydrogen generator. Retention times are compared to those for methyl esters of standards commercially available (Nu-Chek Prep, Inc.). Routinely, 5-10 embryos per event are analyzed by GC, using the methodology described above.

Example 15

Co-Expressing Other Promoter/Gene/Terminator Cassette Combinations in Somatic Soybean Embryos In addition to the genes, promoters, terminators and gene cassettes described herein, one skilled in the art can appreciate that other promoter/gene/terminator cassette combinations can be synthesized in a way similar to, but not limited to, that described herein. For instance, PCT Publications No. WO 2004/071467 and No. WO 2004/071178 describe the isolation of a number of promoter and transcription terminator sequences for use in embryo-specific expression in soybean. Furthermore, PCT Publications No. WO 2004/071467, No. WO 2005/047479 and No. WO 2006/012325 describe the synthesis of multiple promoter/gene/terminator cassette combinations by ligating individual promoters, genes and transcription terminators together in unique combinations. Generally, a NotI site flanked by the suitable promoter (e.g., those listed in, but not limited to, Table 9) and a transcription terminator (e.g., those listed in, but not limited to, Table 10) is used to clone the desired gene. NotI sites can be added to a gene of interest such as those listed in, but not limited to, Table 11 using PCR amplification with oligonucleotides designed to introduce NotI sites at the 5' and 3' ends of the gene. The resulting PCR product is then digested with NotI and cloned into a suitable promoter/NotI/terminator cassette.

In addition, PCT Publications No. WO 2004/071467, No. WO 2005/047479 and No. WO 2006/012325 describe the further linking together of individual gene cassettes in unique combinations, along with suitable selectable marker cassettes, in order to obtain the desired phenotypic expression. Although this is done mainly using different restriction enzymes sites, one skilled in the art can appreciate that a number of techniques can be utilized to achieve the desired promoter/gene/transcription terminator combination. In so doing, any combination of embryo-specific promoter/gene/transcription terminator cassettes can be achieved. One skilled in the art can also appreciate that these cassettes can be located on individual DNA fragments or on multiple fragments where co-expression of genes is the outcome of co-transformation of multiple DNA fragments.

TABLE 9

Seed-specific Promoters

| Promoter | Organism | Promoter Reference |
|---|---|---|
| β-conglycinin α'-subunit | soybean | Beachy et al., EMBO J., 4: 3047-3053 (1985) |
| kunitz trypsin inhibitor | soybean | Jofuku et al., Plant Cell, 1: 1079-1093 (1989) |
| Annexin | soybean | PCT Publication No. WO 2004/071467 |
| glycinin Gy1 | soybean | PCT Publication No. WO 2004/071467 |
| albumin 2S | soybean | U.S. Pat. No. 6,177,613 |
| legumin A1 | pea | Rerie et al., Mol. Gen. Genet., 225: 148-157 (1991) |
| β-conglycinin β-subunit | soybean | PCT Publication No. WO 2004/071467 |
| BD30 (also called P34) | soybean | PCT Publication No. WO 2004/071467 |
| legumin A2 | pea | Rerie et al., Mol. Gen. Genet., 225: 148-157 (1991) |

TABLE 10

| Transcription Terminators | | |
|---|---|---|
| Transcription Terminator | Organism | Reference |
| phaseolin 3' | bean | PCT Publication No. WO 2004/071467 |
| kunitz trypsin inhibitor 3' | soybean | PCT Publication No. WO 2004/071467 |
| BD30 (also called P34) 3' | soybean | PCT Publication No. WO 2004/071467 |
| legumin A2 3' | pea | PCT Publication No. WO 2004/071467 |
| albumin 2S 3' | soybean | PCT Publication No. WO 2004/071467 |

TABLE 11

| PUFA Biosynthetic Pathway Genes | | |
|---|---|---|
| Gene | Organism | Reference |
| delta-6 desaturase | *Saprolegnia diclina* | PCT Publication No. WO 2002/081668 |
| delta-6 desaturase | *Mortierella alpina* | U.S. Pat. No. 5,968,809 |
| elongase | *Mortierella alpina* | PCT Publication No. WO 2000/12720; U.S. Pat. No. 6,403,349 |
| delta-5 desaturase | *Mortierella alpina* | U.S. Pat. No. 6,075,183 |
| delta-5 desaturase | *Saprolegnia diclina* | PCT Publication No. WO 2002/081668 |
| delta-15 desaturase | *Fusarium moniliforme* | PCT Publication No. WO 2005/047479 |
| delta-17 desaturase | *Saprolegnia diclina* | PCT Publication No. WO 2002/081668 |
| elongase | *Thraustochytrium aureum* | PCT Publication No. WO 2002/08401; U.S. Pat. No. 6,677,145 |
| elongase | *Pavlova* sp. | Pereira et al., Biochem. J., 384: 357-366 (2004) |
| delta-4 desaturase | *Schizochytrium aggregatum* | PCT Publication No. WO 2002/090493 |
| delta-9 elongase | *Isochrysis galbana* | PCT Publication No. WO 2002/077213 |
| delta-9 elongase | *Euglena gracilis* | U.S. Patent Application No. 11/601563 |
| delta-8 desaturase | *Euglena gracilis* | PCT Publication No. WO 2000/34439; U.S. Pat. No. 6,825,017; PCT Publication No. WO 2004/057001; PCT Publication No. WO 2006/012325 |
| delta-8 desaturase | *Acanthamoeba castellanii* | Sayanova et al., FEBS Lett., 580: 1946-1952 (2006) |
| delta-8 desaturase | *Pavlova salina* | PCT Publication No. WO 2005/103253 |
| delta-8 desaturase | *Pavlova lutheri* | U.S. Patent Application No. 11/737,772 |

Example 16

Chlorsulfuron Selection (ALS) and Plant Regeneration

Chlorsulfuron (ALS) Selection:

Following bombardment, the plant tissue is divided between 2 flasks with fresh SB196 media and cultured as described in Example 13. Six to seven days post-bombardment, the SB196 is exchanged with fresh SB196 containing selection agent of 100 ng/mL chlorsulfuron. The selection media is refreshed weekly. Four to six weeks post selection, green, transformed tissue is observed growing from untransformed, necrotic embryogenic clusters. Isolated, green tissue is removed and inoculated into multiwell plates containing SB196 to generate new, clonally propagated, transformed embryogenic suspension cultures.

Regeneration of Soybean Somatic Embryos into Plants:

In order to obtain whole plants from embryogenic suspension cultures, the tissue must be regenerated. Embyros are matured as described in Example 13. After subculturing on medium SB103 for 3 weeks, individual embryos are removed from the clusters and screened for alterations in their fatty acid compositions as described in Example 14. It should be noted that any detectable phenotype, resulting from the expression of the genes of interest, can be screened at this stage. This would include, but not be limited to: alterations in fatty acid profile, protein profile and content, carbohydrate content, growth rate, viability, or the ability to develop normally into a soybean plant.

Matured individual embryos are desiccated by placing them into an empty, small petri dish (35×10 mm) for approximately 4 to 7 days. The plates are sealed with fiber tape (creating a small humidity chamber). Desiccated embryos are planted into SB71-4 medium where they are left to germinate under the same culture conditions described above. Germinated plantlets are removed from germination medium and rinsed thoroughly with water and then are planted in Redi-Earth in a 24-cell pack tray, covered with a clear plastic dome. After 2 weeks the dome is removed and plants hardened off for a further week. If plantlets look hardy, they are transplanted to 10" pots of Redi-Earth with up to 3 plantlets per pot. After 10 to 16 weeks, mature seeds are harvested, chipped and analyzed for fatty acids as described in Example 14.

Media recipes can be found in Example 13 and chlorsulfuron stock is 1 mg/mL in 0.01 N ammonium hydroxide.

Example 17

Comparing the Substrate Specificity of the *Mortierella alpina* Delta-5 Desaturase (MaD5) with the *Peridinium* sp. CCMP626 Delta-5 Desaturase (RD5) in *Yarrowia lipolytica*

The present Example describes comparison of the substrate specificity of a *Mortierella alpina* delta-5 desaturase (MaD5; SEQ ID NOs:67 and 68), which is described in U.S. Pat. No. 6,075,183 and PCT Publication Nos. WO 2004/071467 and No. WO 2005/047479) to that of RD5 (SEQ ID NO:2) in *Yarrowia lipolytica*.

This work included the following steps: (1) construction of *Yarrowia* expression vector pY98 comprising MaD5; (2) transformation of pY98 and pDMW368 into *Yarrowia* strain Y2224; and, 3.) comparison of lipid profiles within transformant organisms comprising pY98 or pDMW368 after feeding fatty acid substrates.

Construction of *Yarrowia* Expression Vector pY98, Comprising MaD5

Plasmid pY5-22 (SEQ ID NO:69) is a shuttle plasmid that can replicate both in *E. coli* and *Yarrowia lipolytica*, containing the following: a *Yarrowia* autonomous replication sequence (ARS18; GenBank Accession No. M91600); a ColE1 plasmid origin of replication; an ampicillin-resistance gene (AmpR) for selection in *E. coli*; a *Yarrowia* URA3 gene (GenBank Accession No. AJ306421) for selection in *Yarrowia*; and, a chimeric TEF::NcoI/NotI::XPR cassette, wherein "XPR" was ~100 bp of the 3' region of the *Yarrowia* Xpr gene (GenBank Accession No. M17741). Although the construction of plasmid pY5-22 is not described herein in detail, it was derived from pY5 (previously described in PCT Publication No. WO 2004/101757).

Plasmid pY5-22GPD (SEQ ID NO:70) was created from pY5-22 (SEQ ID NO:69), by replacing the TEF promoter with the *Yarrowia lipolytica* GPD promoter (SEQ ID NO:71) using techniques well known to one skilled in the art. The *Yarrowia* "GPD promoter" refers to the 5' upstream untranslated region in front of the 'ATG' translation initiation codon of a protein encoded by the *Yarrowia lipolytica* glyceraldehyde-3-phosphate dehydrogenase (GPD) gene and that is necessary for expression (PCT Publication No. WO 2005/003310). More specifically, the *Yarrowia lipolytica* GPD promoter was amplified from plasmid pYZDE2-S (SEQ ID NO:72; which was previously described in U.S. patent application Ser. No. 11/737,772 (the contents of which are hereby incorporated by reference)) using oligonucleotides GPDsense (SEQ ID NO:73) and GPDantisense (SEQ ID NO:74). The resulting DNA fragment was digested with SalI/NotI and cloned into the SalI/NotI fragment of pY5-22 (SEQ ID NO:69), thus replacing the TEF promoter and NcoI/NotI site with the GPD promoter and a unique NotI site, and thereby producing pY5-22GPD (SEQ ID NO:70).

The *Mortierella alpina* delta-5 desaturase gene (SEQ ID NO:67) was released from pKR136 (SEQ ID NO:75; which was previously described in PCT Publication No. WO 2004/071467 (the contents of which are hereby incorporated by reference)) by digestion with NotI and cloned into the NotI site of pY5-22GPD to produce pY98 (SEQ ID NO:76; FIG. 9).

Transformation of pY98 (Comprising MaD5) and pDMW368 (Comprising RD5) into *Yarrowia* Strain Y2224 and Comparison of Lipid Profiles Strain Y2224 was isolated in the following manner: *Yarrowia lipolytica* ATCC #20362 cells from a YPD agar plate (1% yeast extract, 2% bactopeptone, 2% glucose, 2% agar) were streaked onto a MM plate (75 mg/L each of uracil and uridine, 6.7 g/L YNB with ammonia sulfate, without amino acid, and 20 g/L glucose) containing 250 mg/L 5-FOA (Zymo Research). Plates were incubated at 28° C. and four of the resulting colonies were patched separately onto MM plates containing 200 mg/mL 5-FOA and MM plates lacking uracil and uridine to confirm uracil Ura3 auxotrophy.

Strain Y2224 was transformed with pY98 (SEQ ID NO:76, FIG. 9) and pDMW368 (SEQ ID NO:23; FIG. 5C; Example 6) as described in the General Methods.

Single colonies of transformant *Yarrowia lipolytica* containing pY98 (SEQ ID NO:76) or pDMW368 (SEQ ID NO:23) were grown in 3 mL MM lacking uracil supplemented with 0.2% tergitol at 30° C. for 1 day. After this, 0.1 mL was transferred to 3 mL of the same medium supplemented with either EDA, ETrA, DGLA, ETA or no fatty acid. These were incubated for 16 h at 30° C., 250 rpm and then pellets were obtained by centrifugation. Cells were washed once with water, pelleted by centrifugation and air dried. Pellets were transesterified (Roughan, G. and Nishida, I., *Arch. Biochem. Biophys.,* 276(1):38-46 (1990)) with 500 μL of 1% sodium methoxide for 30 min at 50° C. after which 500 μL of 1M NaCl and 100 μL of heptane were added. After thorough mixing and centrifugation, fatty acid methyl esters (FAMEs) were analyzed by GC.

FAMEs (5 μL injected from hexane layer) were separated and quantified using a Hewlett-Packard 6890 Gas Chromatograph fitted with an Omegawax 320 fused silica capillary column (Catalog No. 24152, Supelco Inc.). The oven temperature was programmed to hold at 220° C. for 2.6 min, increase to 240° C. at 20° C./min and then hold for an additional 2.4 min. Carrier gas was supplied by a Whatman hydrogen generator. Retention times were compared to those for methyl esters of standards commercially available (Nu-Chek Prep, Inc.).

The fatty acid profiles for *Yarrowia lipolytica* expressing pY98 (SEQ ID NO:76) or pDMW368 (SEQ ID NO:23) and fed various substrates are shown in FIG. 10A. In FIG. 10A shading indicates the substrates fed and products produced; fatty acids are identified as 16:0 (palmitate), 16:1, 18:0 (stearic acid), 18:1 (oleic acid), LA, GLA, ALA, STA, EDA, SCI (sciadonic acid or cis-5,11,14-eicosatrienoic acid; 20:3 omega-6), DGLA, ARA, ETrA, JUP (juniperonic acid or cis-5,11,14,17-eicosatrienoic acid; 20:4 omega-3), ETA and EPA. Fatty acid compositions were expressed as the weight percent (wt. %) of total fatty acids.

Percent delta-5 desaturation ("% delta-5 desat") of RD5 and MaD5 for each substrate is shown in FIG. 10B and was calculated by dividing the wt. % for product (either SCI, JUP, ARA or EPA) by the sum of the wt. % for the substrate and product (either EDA and SCI, ETrA and JUP, DGLA and ARA, or ETA and EPA, respectively) and multiplying by 100 to express as a %, depending on which substrate was fed.

The activities of MaD5 and RD5 are compared using the ratio of the percent delta-5 desaturation ("Ratio Desat R/Ma") in FIG. 10B and are calculated by dividing the percent delta-5 desaturation for RD5 on a particular substrate by the percent delta-5 desaturation for MaD5 on the same substrate.

The substrate specificity of RD5 and MaD5 for the correct omega-6 fatty acid substrate (i.e., DGLA) versus the by-product fatty acid (i.e., SCI) or the correct omega-3 fatty acid substrate (i.e., ETA) versus the by-product fatty acid (i.e., JUP) is also shown in FIG. 10B. Specifically, the substrate specificity ("Ratio Prod/By-Prod") for omega-6 substrates was calculated by dividing the percent delta-5 desaturation (% delta-5 desat) for DGLA by the percent delta-5 desaturation (% delta-5 desat) for EDA and is shown on the same lines as the results for DGLA. The substrate specificity ("Ratio Prod/By-Prod") for omega-3 substrates was calculated by dividing the percent delta-5 desaturation (% delta-5 desat) for ETA by the percent delta-5 desaturation (% delta-5 desat) for ETrA and is shown on the same lines as the results for ETA. Furthermore, the ratio of substrate specificity ("Ratio Prod/By-Prod R/Ma") for omega-6 substrates was determined by dividing the substrate specificity for RD5 on the omega-6 substrates (i.e., DGLA/EDA) by that for MaD5. The ratio of substrate specificity ("Ratio Prod/By-Prod R/Ma") for omega-3 substrates was calculated by dividing the substrate specificity for RD5 on the omega-3 substrates (i.e., ETA/ETrA) by that for MaD5.

The preference of RD5 and MaD5 for omega-6 or omega-3 substrates is compared using the ratio of the percent delta-5 desaturation ("Ratio n-6/n-3") in FIG. 10B and is calculated by dividing the percent delta-5 desaturation for RD5 and MaD5 on a particular omega-6 substrate (either DGLA or EDA) by the percent delta-5 desaturation on the corresponding omega-3 substrate (either ETA or ETrA, respectively).

From the results in FIG. 10B, it is clear that RD5 is approximately 3.0- to 9.7-fold more active in *Yarrowia* than MaD5 when DGLA, EDA, ETrA and ETA are used as substrates. The substrate specificity of RD5 compared to MaD5 (RD5/MaD5) for the correct omega-6 substrate (i.e., DGLA versus EDA) is approximately 0.4 and for the omega-3 substrate (i.e., ETA versus ETrA) is approximately 0.6. RD5 also has an approximate 1.4-fold preference for omega-6 substrates (i.e., EDA and DGLA) over the omega-3 substrates (i.e., ETrA and ETA), respectively.

Example 18

Construction of Soybean Expression Vector pKR916 for Co-Expression of the *Mortierella alpina* Delta-5 Desaturase (MaD5) with a Delta-9 Elongase Derived from *Euglena gracilis* (EgD9e) and a Delta-8 Desaturase Derived from *Euglena gracilis* (EgD8)

The present Example describes construction of a soybean vector for co-expression of MaD5 (SEQ ID NO:67, Example 17) with EgD9e (SEQ ID NO:77; which is described in U.S. application Ser. No. 11/601,563 (filed Nov. 16, 2006; and EgD8 (SEQ ID NO:78; described as Eg5 in PCT Publication No. WO 2006/012325).

*Euglena gracilis* delta-9 elongase (EgD9e):

A clone from the *Euglena* cDNA library (eeg1c), called eeg1c.pk001.n5f, containing the *Euglena gracilis* delta-9 elongase (EgD9e; SEQ ID NO:77) was used as template to amplify EgD9e with oligonucleotide primers oEugEL1-1 (SEQ ID NO:79) and oEugEL1-2 (SEQ ID NO:80) using the VentR® DNA Polymerase (Catalog No. M0254S, New England Biolabs Inc., Beverly, Mass.) following the manufacturer's protocol. The resulting DNA fragment was cloned into the pCR-Blunt® cloning vector using the Zero Blunt® PCR Cloning Kit (Invitrogen Corporation), following the manufacturer's protocol, to produce pKR906 (SEQ ID NO:81).

A starting plasmid pKR72 (ATCC Accession No. PTA-6019; SEQ ID NO:82, 7085 bp sequence), a derivative of pKS123 which was previously described in PCT Publication No. WO 02/008269 (the contents of which are hereby incorporated by reference), contains the hygromycin B phosphotransferase gene (HPT) (Gritz, L. and Davies, J., *Gene,* 25:179-188 (1983)), flanked by the T7 promoter and transcription terminator (i.e., a T7prom/HPT/T7term cassette), and a bacterial origin of replication (ori) for selection and replication in bacteria (e.g., *E. coli*). In addition, pKR72 also contains HPT, flanked by the 35S promoter (Odell et al., *Nature,* 313:810-812 (1985)) and NOS 3' transcription terminator (Depicker et al., *J. Mol. Appl. Genet.,* 1:561-570 (1982)) (i.e., a 35S/HPT/NOS3' cassette) for selection in plants such as soybean. pKR72 also contains a NotI restriction site, flanked by the promoter for the α' subunit of β-conglycinin (Beachy et al., *EMBO J.,* 4:3047-3053 (1985)) and the 3' transcription termination region of the phaseolin gene (Doyle et al., *J. Biol. Chem.,* 261:9228-9238 (1986)), thus allowing for strong tissue-specific expression in the seeds of soybean of genes cloned into the NotI site.

The AscI fragment from plasmid pKS102 (SEQ ID NO:83), previously described in PCT Publication No. WO 02/00905 (the contents of which are hereby incorporated by reference), containing a T7prom/hpt/T7term cassette and bacterial ori, was combined with the AscI fragment of plasmid pKR72 (SEQ ID NO:82), containing a βcon/NotI/Phas cassette to produce pKR197 (SEQ ID NO:84), previously described in PCT Publication No. WO 04/071467 (the contents of which are hereby incorporated by reference).

The gene for the *Euglena gracilis* delta-9 elongase was released from pKR906 (SEQ ID NO:81) by digestion with NotI and cloned into the NotI site of pKR197 (SEQ ID NO:84) to produce intermediate cloning vector pKR91 1 (SEQ ID NO:85).

*Euglena gracilis* Delta-8 Desaturase (EgD8):

Plasmid pKR680 (SEQ ID NO:86), which was previously described in PCT Publication No. WO 2006/012325 (the contents of which are hereby incorporated by reference), contains the *Euglena gracilis* delta-8 desaturase (EgD8; SEQ ID NO:78; described as Eg5 in WO 2006/012325) flanked by the Kunitz soybean Trypsin Inhibitor (KTi) promoter (Jofuku et al., *Plant Cell,* 1:1079-1093 (1989)) and the KTi 3' termination region, the isolation of which is described in U.S. Pat. No. 6,372,965, followed by the soy albumin transcription terminator, which was previously described in PCT Publication No. WO 2004/071467 (i.e., a Kti/NotI/Kti3'Salb3' cassette).

Plasmid pKR680 (SEQ ID NO:86) was digested with BsiWI and the fragment containing EgD8 was cloned into the BsiWI site of pKR911 (SEQ ID NO:85) to produce pKR913 (SEQ ID NO:87).

*Mortierella alpina* Delta-5 Desaturase (MaD5):

Plasmid pKR767 (SEQ ID NO:88), which was previously described in PCT Publication No. WO 2006/012325 (the contents of which are hereby incorporated by reference), contains the *Mortierella alpina* delta-5 desaturase (MaD5; SEQ ID NO:67) flanked by the promoter for the soybean glycinin Gy1 gene and the pea legumin A2 3' transcription termination region (i.e., a Gy1/MaD5/legA2 cassette; the construction of which is described in WO 2006/012325).

The Gy1/Mad5/legA2 cassette was released from pKR767 (SEQ ID NO:88) by digestion with SbfI and the resulting fragment was cloned into the SbfI site of pKR913 (SEQ ID NO:87) to produce pKR916 (SEQ ID NO:89). A schematic depiction of pKR916 is shown in FIG. 11A. In this way, the *Euglena gracilis* delta-9 elongase (labeled "eug el1" in FIG. 11A) was co-expressed with the *Euglena gracilis* delta-8 desaturase (labeled "eug d8-sq5" in FIG. 11A) and the *Mortierella alpina* delta-5 desaturase (labeled "DELTA 5 DESATURASE M ALPINA" in FIG. 11A) behind strong, seed specific promoters.

Example 19

Construction of Soybean Expression Vector pKR1038 for Co-Expression of the *Peridinium* sp. CCMP626 Delta-5 Desaturase (RD5) with a Delta-9 Elongase Derived from *Euglena gracilis* (EgD9e) and a Delta-8 Desaturase Derived from *Euglena gracilis* (EgD8)

The present Example describes construction of a soybean vector for co-expression of RD5 (SEQ ID NO:1, Example 5) with EgD9e (SEQ ID NO:77, Example 18) and EgD8 (SEQ ID NO:78, Example 18).

Starting plasmid pKR974 (SEQ ID NO:90) is identical to pKR767 (SEQ ID NO:88, Example 18) except the NotI fragment containing MaD5 was replaced with a NotI fragment containing the *Saprolegnia diclina* delta-5 desaturase (SdD5; SEQ ID NO:91, which is described in PCT Publication No. WO 2004/071467). In addition, a MfeI site in the legA2 terminator of pKR767 (SEQ ID NO:88) was removed by digestion with MfeI, filling the MfeI site and religating (i.e., CAATTG converted to CAATTAATTG) and therefore, the legA2 terminator of pKR974 (SEQ ID NO:90) is 770 bp versus 766 bp for pKR767 (SEQ ID NO:88).

In order to clone RD5 into a soybean expression vector, a NotI restriction site needed to be introduced at the 5' end of the gene. One skilled in the art will realized that there are many ways to introduce restriction sites into genes such as, but not limited to PCR or by subcloning into vectors containing the appropriate sites. In this case, in order to introduce a NotI site at the 5' end of RD5 (SEQ ID NO:1), pDMW368 (SEQ ID NO:23) was digested with MfeI and then partially digested with NcoI. The NcoI/MfeI fragment containing a full length RD5 (SEQ ID NO:1) was cloned into the NcoI/MfeI site of an intermediate cloning vector having a NotI site directly upstream of the NcoI site (i.e., GCGGCCGCAAACCATGG). The resulting plasmid was then digested with NotI and the fragment containing RD5 (SEQ ID NO:1) was cloned into the NotI site of pKR974 (SEQ ID NO:90) to produce pKR1033 (SEQ ID NO:92).

The Gy1/EgD5/legA2 cassette was released from pKR1033 (SEQ ID NO:92) by digestion with SbfI and the resulting fragment was cloned into the SbfI site of pKR913 (SEQ ID NO:87) to produce pKR1038 (SEQ ID NO:93). A schematic depiction of pKR1038 (SEQ ID NO:93) is shown in FIG. 11B. In this way, the *Euglena gracilis* delta-9 elongase (labeled "eug el1" in FIG. 11B) could be co-expressed with the *Euglena gracilis* delta-8 desaturase (labeled "eug d8-sq5" in FIG. 11B) and the *Peridinium* sp. CCMP626 delta-5 desaturase (labeled "CCMP626 d5 DS" in FIG. 11B) behind strong, seed specific promoters.

Example 20

Co-expression of the *Euglena gracilis* Delta-9 Elongase, the *Euglena gracilis* Delta-8 Desaturase and the *Saprolegnia diclina* Delta-17 Desaturase with Either the *Mortierella alpina* Delta-5 Desaturase (pKR916 & pKR328) or the *Peridinium* sp. CCMP626 Delta-5 Desaturase (pKR1038 & pKR328) in Soybean Somatic Embryos The present Example describes the transformation and expression in soybean somatic embryos of pKR916 (SEQ ID NO:89, Example 18; containing EgD9e, EgD8 and MaD5) with pKR328 (SEQ ID NO:94, FIG. 11C, previously described in PCT Publication No. WO 04/071467), containing the *Saprolegnia diclina* delta-17 desaturase (SdD17) and the hygromycin phosphotransferase gene for selection on hygromycin. The present Example further describes the transformation and expression in soybean somatic embryos of pKR1038 (SEQ ID NO:93, Example 19; containing EgD9e, EgD8 and RD5) with pKR328 (SEQ ID NO:94, FIG. 11C).

Soybean embryogenic suspension culture (cv. Jack) was transformed with the AscI fragment containing the expression cassette of pKR916 (SEQ ID NO:89) and intact plasmid pKR328 (SEQ ID NO:94), or with the AscI fragment containing the expression cassette of pK1038 (SEQ ID NO:93) and intact plasmid pKR328 (SEQ ID NO:94), as described in Example 13.

Embryos were matured in soybean histodifferentiation and maturation liquid medium (SHaM liquid media; Schmidt et al., *Cell Biology and Morphogenesis,* 24:393 (2005)) using a modified procedure. Briefly, after 4 weeks of selection in SB196 as described in Example 13, embryo clusters were removed to 35 mL of SB228 (SHaM liquid media) in a 250 mL Erlenmeyer flask. Tissue was maintained in SHaM liquid media on a rotary shaker at 130 rpm and 26° C. with cool white fluorescent lights on a 16:8 hr day/night photoperiod at a light intensity of 60-85 μE/m$^2$/s for 2 weeks as embryos matured. Embryos grown for 2 weeks in SHaM liquid media were equivalent in size and fatty acid content to embryos cultured on SB166/SB103 for 5-8 weeks as described in Example 13.

Media Recipes:

| SB 228-Soybean Histodifferentiation & Maturation (SHaM) (per liter) | |
|---|---|
| DDI $H_2O$ | 600 mL |
| FN-Lite Macro Salts for SHaM 10X | 100 mL |
| MS Micro Salts 1000x | 1 mL |
| MS FeEDTA 100x | 10 mL |
| CaCl 100x | 6.82 mL |
| B5 Vitamins 1000x | 1 mL |
| L-Methionine | 0.149 g |

-continued

| | |
|---|---|
| Sucrose | 30 g |
| Sorbitol | 30 g |
| Adjust volume to 900 mL | |
| pH 5.8 | |
| Autoclave | |
| Add to cooled media (≦30° C.): | |
| *Glutamine (final concentration 30 mM) 4% | 110 mL |

*Note:
Final volume will be 1010 mL after glutamine addition.

Since glutamine degrades relatively rapidly, it may be preferable to add immediately prior to using media. Expiration 2 weeks after glutamine is added; base media can be kept longer without glutamine.

| FN-lite Macro for SHAM 10X- Stock #1 (per liter) | |
|---|---|
| $(NH_4)_2SO_4$ (ammonium sulfate) | 4.63 g |
| $KNO_3$ (potassium nitrate) | 28.3 g |
| $MgSO_4$*$7H_20$ (magnesium sulfate heptahydrate) | 3.7 g |
| $KH_2PO_4$ (potassium phosphate, monobasic) | 1.85 g |
| Bring to volume | |
| Autoclave | |
| **MS Micro 1000X- Stock #2 (per 1 liter)** | |
| $H_3BO_3$ (boric acid) | 6.2 g |
| $MnSO_4$*$H_2O$ (manganese sulfate monohydrate) | 16.9 g |
| $ZnSO_4$*$7H_20$ (zinc sulfate heptahydrate) | 8.6 g |
| $Na_2MoO_4$*$2H_20$ (sodium molybdate dihydrate) | 0.25 g |
| $CuSO_4$*$5H_20$ (copper sulfate pentahydrate) | 0.025 g |
| $CoCl_2$*$6H_20$ (cobalt chloride hexahydrate) | 0.025 g |
| KI (potassium iodide) | 0.8300 g |
| Bring to volume | |
| Autoclave | |
| **FeEDTA 100X- Stock #3 (per liter)** | |
| $Na_2EDTA$* (sodium EDTA) | 3.73 g |
| $FeSO_4$*$7H_20$ (iron sulfate heptahydrate) | 2.78 g |
| *EDTA must be completely dissolved before adding iron. | |
| Bring to Volume | |
| Solution is photosensitive. Bottle(s) should be wrapped in foil to omit light. | |
| Autoclave | |
| **Ca 100X- Stock #4 (per liter)** | |
| $CaCl_2$*$2H_20$ (calcium chloride dihydrate) | 44 g |
| Bring to Volume | |
| Autoclave | |
| **B5 Vitamin 1000X- Stock #5 (per liter)** | |
| Thiamine*HCl | 10 g |
| Nicotinic Acid | 1 g |
| Pyridoxine*HCl | 1 g |
| Myo-Inositol | 100 g |
| Bring to Volume | |
| Store frozen | |
| **4% Glutamine- Stock #6 (per liter)** | |
| DDI water heated to 30° C. | 900 mL |
| L-Glutamine | 40 g |
| Gradually add while stirring and applying low heat. | |
| Do not exceed 35° C. | |
| Bring to Volume | |
| Filter Sterilize | |
| Store frozen* | |

*Note: Warm thawed stock in 31° C. bath to fully dissolve crystals.

After maturation in SHaM liquid media, individual embryos were removed from the clusters, dried and screened for alterations in their fatty acid compositions as described supra.

A subset of soybean embryos (i.e., six embryos per event) transformed with either pKR916 (SEQ ID NO:89) and pKR328 (SEQ ID NO:94), or pKR1038 (SEQ ID NO:93) and pKR328 (SEQ ID NO:94),were harvested and picked into glass GC vials and fatty acid methyl esters were prepared by transesterification. For transesterification, 50 μL of trimethylsulfonium hydroxide (TMSH) and 0.5 mL of hexane were added to the embryos in glass vials and incubated for 30 min at room temperature while shaking. Fatty acid methyl esters (5 μL injected from hexane layer) were separated and quantified using a Hewlett-Packard 6890 Gas Chromatograph fitted with an Omegawax 320 fused silica capillary column (Catalog No. 24152, Supelco Inc.). The oven temperature was programmed to hold at 220° C. for 2.6 min, increase to 240° C. at 20° C./min and then hold for an additional 2.4 min. Carrier gas was supplied by a Whatman hydrogen generator. Retention times were compared to those for methyl esters of standards commercially available (Nu-Chek Prep, Inc.).

In this way, 60 events transformed with pKR916 (SEQ ID NO:89) and pKR328 (SEQ ID NO:94) and 31 events transformed with pKR1038 (SEQ ID NO:93) and pKR328 (SEQ ID NO:94) were analyzed. The average fatty acid profiles for the ten events having the highest delta-5 desaturase activity for each transformation (pKR916 and pKR328, pKR1038 and pKR328) are shown in FIG. 12A and FIG. 12B, respectively.

In FIGS. 12A and 12B, fatty acids are identified as 16:0 (palmitate), 18:0 (stearic acid), 18:1 (oleic acid), LA, ALA, EDA, SCI, DGLA, ARA, ERA, JUP, ETA and EPA. Fatty acids listed as "others" include: 18:2 (5,9), GLA, STA, 20:0, 20:1(11), 20:2 (7,11) or 20:2 (8,11) and DPA. Each of these "other" fatty acids is present at a relative abundance of less than 3.0% of the total fatty acids. Fatty acid compositions for an individual embryo were expressed as the weight percent (wt. %) of total fatty acids and the average fatty acid composition is an average of six individual embryos for each event.

The activity of the delta-5 desaturase for the "correct" substrates (i.e., DGLA and ETA) is expressed as percent delta-5 desaturation ("Correct % delta-5 desat"), calculated according to the following formula: ([product]/[substrate+product])*100. More specifically, the percent delta-5 desaturation for the "correct" substrates was determined as: ([ARA+EPA]/[DGLA+ETA+ARA+EPA])*100.

The activity of the delta-5 desaturase for the "wrong" substrates (i.e., EDA and ERA) is also expressed as percent delta-5 desaturation ("Wrong % delta-5 desat"), calculated as: ([SCI+JUP]/[EDA+ERA+SCI+JUP])*100.

The substrate specificities of MaD5 and RD5 for the "correct" substrates (i.e., DGLA and ETA) versus the "wrong" substrates (i.e., EDA and ERA) were compared and the comparison is shown in FIG. 13. In FIG. 13, the activity of the delta-5 desaturase for the "correct" substrates ("Correct % delta-5 desat") is plotted on the x-axis and the activity of the delta-5 desaturase for the "wrong" substrates ("Wrong % delta-5 desat") is plotted on the y-axis for MaD5 (data from FIG. 12A) and RD5 (data from FIG. 12B).

What is claimed is:

1. An isolated polynucleotide comprising:

(a) a nucleotide sequence encoding a polypeptide having delta-5 desaturase activity, wherein the polypeptide has at least 80% amino acid identity, based on the Clustal W method of alignment, when compared to an amino acid sequence as set forth in SEQ ID NO:2;

(b) a nucleotide sequence encoding a polypeptide having delta-5 desaturase activity, wherein the nucleotide sequence has at least 80% sequence identity, based on the BLASTN method of alignment, when compared to a nucleotide sequence as set forth in SEQ ID NO:1 or SEQ ID NO:3;

(c) a nucleotide sequence encoding a polypeptide having delta-5 desaturase activity, wherein the nucleotide sequence selectively hybridizes to a nucleotide sequence as set forth in SEQ ID NO:1 or SEQ ID NO:3 under the following stringency conditions: 50% formamide, 1M sodium chloride and 1% SDS at 37° C. followed by a wash in 0.1×SSC at 60° C.; or (d) a complement of the nucleotide sequence of (a), (b) or (c), wherein the complement and the nucleotide sequence consist of the same number of nucleotides and are 100% complementary.

2. The polynucleotide of claim 1 wherein the nucleotide sequence comprises SEQ ID NO:1 or SEQ ID NO:3.

3. The polynucleotide of claim 1, wherein the amino acid sequence of the polypeptide of step (a) comprises (a) SEQ ID NO:2; or (b) an amino acid sequence that differs from the amino acid sequences in (a) by at least one conservative amino acid substitution.

4. A recombinant DNA construct comprising the polynucleotide of claim 1, 2, or 3 operably linked to at least one regulatory sequence.

5. A cell comprising in its genome the recombinant DNA construct of claim 4.

6. The cell of claim 5 wherein said cell is selected from the group consisting of plants and yeast.

7. A method for transforming a cell, comprising transforming a cell with the recombinant DNA construct of claim 4 and selecting those cell transformed with the recombinant DNA construct.

8. A method for producing a transformed plant comprising transforming a plant cell with the recombinant DNA construct of claim 4 and regenerating a plant from the transformed plant cell, wherein the transformed plant comprises the recombinant DNA construct.

9. The method of claim 8 wherein the plant is a soybean plant.

10. A transgenic seed comprising in its genome the recombinant DNA construct of claim 4.

11. A transgenic seed obtained from the transformed plant made by the method of claim 8, wherein the transgenic seed comprises the recombinant DNA construct.

12. A method for making long-chain polyunsaturated fatty acids in a plant cell comprising:

(a) transforming a cell with the recombinant DNA construct of claim 4; and (b) selecting those transformed cells that make long-chain polyunsaturated fatty acids.

13. An oilseed plant comprising in its genome the recombinant DNA construct of claim 4.

14. The oilseed plant of claim 13, wherein the oilseed plant is selected from the group consisting of soybean, *Brassica* species, sunflower, maize, cotton, flax and safflower.

15. Progeny plants obtained from the plant made by the method of claim 8, wherein the progeny plants comprise the recombinant DNA construct.

16. An isolated nucleic acid molecule which encodes a delta-5 desaturase as set forth in SEQ ID NO:2 wherein at least one codon is codon-optimized for expression in *Yarrowia* sp.

17. A method for producing at least one polyunsaturated fatty acid in an oilseed plant comprising:

(a) transforming an oilseed plant cell with the recombinant DNA construct of claim 4 and at least one additional recombinant DNA construct comprising an isolated polynucleotide, operably linked to at least one regulatory sequence, encoding a polypeptide selected from the group consisting of a delta-4 desaturase, a delta-5 desaturase, a delta-6 desaturase, a delta-8 desaturase, a delta-12 desaturase, a delta-15 desaturase, a delta-17 desaturase, a delta-9 desaturase, a delta-9 elongase, a C14/16 elongase, a C16/18 elongase, a C18/20 elongase and a C20/22 elongase;

(b) regenerating an oilseed plant from the transformed cell of step (a); and (c) selecting those seeds obtained from the plants of step (b) having an altered level of polyunsaturated fatty acids when compared to the level in seeds obtained from a nontransformed oilseed plant.

18. The method of claim 17 wherein the oilseed plant is selected from the group consisting of soybean, *Brassica* species, sunflower, maize, cotton, flax, and safflower.

19. An oilseed plant comprising:

(a) the recombinant DNA construct of claim 4; and (b) at least one additional recombinant DNA construct comprising an isolated polynucleotide, operably linked to at least one regulatory sequence, encoding a polypeptide selected from the group consisting of a delta-4 desaturase, a delta-5 desaturase, a delta-6 desaturase, a delta-8 desaturase, a delta-12 desaturase, a delta-15 desaturase, a delta-17 desaturase, a delta-9 desaturase, a delta-9 elongase, a C14/16 elongase, a C16/18 elongase, a C18/20 elongase and a C20/22 elongase.

20. The oilseed plant of claim 19, wherein the oilseed plant is selected from the group consisting of soybean, *Brassica* species, sunflower, maize, cotton, flax and safflower.

21. A transgenic seed obtained from the oilseed plant of claim 19, wherein the transgenic seed comprises the recombinant DNA construct.

22. A transgenic seed obtained from the oilseed plant of claim 20, wherein the transgenic seed comprises the recombinant DNA construct.

* * * * *